(12) United States Patent
De Fougerolles et al.

(10) Patent No.: US 8,344,127 B2
(45) Date of Patent: Jan. 1, 2013

(54) ORGANIC COMPOSITIONS TO TREAT BETA-ENAC-RELATED DISEASES

(75) Inventors: Antonin De Fougerolles, Cambridge, MA (US); John L. Diener, Cambridge, MA (US); Emma Hickman, Sutton (GB); Gregory Hinkle, Cambridge, MA (US); Stuart Milstein, Cambridge, MA (US); Anne-Marie Pulichino, Cambridge, MA (US); Andrew Sprague, Cambridge, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/090,580

(22) Filed: Apr. 20, 2011

(65) Prior Publication Data

US 2011/0263681 A1    Oct. 27, 2011

Related U.S. Application Data

(60) Provisional application No. 61/333,398, filed on May 11, 2010, provisional application No. 61/327,379, filed on Apr. 23, 2010.

(51) Int. Cl.
*C07H 21/04* (2006.01)
*C07H 21/02* (2006.01)
*A61K 48/00* (2006.01)

(52) U.S. Cl. ............... 536/24.5; 536/23.1; 536/24.2; 514/44

(58) Field of Classification Search ............ None
See application file for complete search history.

(56) References Cited

U.S. PATENT DOCUMENTS

| 7,718,632 B2 | 5/2010 | Van Heeke et al. |
| 7,939,508 B2 | 5/2011 | Van Heeke et al. |
| 7,943,592 B2 | 5/2011 | Van Heeke et al. |
| 2008/0113351 A1 | 5/2008 | Naito et al. |
| 2011/0054005 A1 | 3/2011 | Naito et al. |

FOREIGN PATENT DOCUMENTS

| EP | 1 752 536 A1 | 2/2007 |
| WO | WO 2008/152131 A2 | 12/2008 |

OTHER PUBLICATIONS

Caci et al.; "Epithelial Sodium Channel Inhibition in Primary Human Bronchial Epithelia by Transfected siRNA"; Am J Respir Cell Mol Biol; 40(2):211-216 & Supplemental Data (2009).
Partial International Search Report for PCT/EP2011/056299, dated: Jul. 22, 2011.
Jernigan et al.; "Myogenic vasoconstriction in mouse renal interlobar arteries: role of endogenous Beta and yENaC"; Am J Physiol Renal Physiol; 291:F 1184-F1191 [XP-002649088] (2006).
"WO 2005116204-A/596769"; Double strand polynucleotides generating RNA interference; XP002649089; retrieved from EBI accession No. EMBL:FZ190244; Database accession No. FZ190244 compound -& Database EMBL [Online] (2011).
"WO 2005116204-A/135974"; Double strand polynucleotides generating RNA interference; XP002649090; retrieved from EBI accession No. EMBL:FW729448; Database accession No. FW729448 compound [online] (2011).
Chu et al., RNA, 14:1714-1719 (2008).

*Primary Examiner* — Amy Bowman
(74) *Attorney, Agent, or Firm* — Frank Wu

(57) ABSTRACT

The present disclosure relates to RNAi agents useful in methods of treating Beta-ENaC-related diseases such as cystic fibrosis, pseudohypoaldosteronism type 1 (PHA1), Liddle's syndrome, hypertension, alkalosis, hypokalemia, and obesity-associated hypertension, using a therapeutically effective amount of a RNAi agent to Beta-ENaC.

21 Claims, 3 Drawing Sheets

ORGANIC COMPOSITIONS TO TREAT BETA-ENAC-RELATED DISEASES

This application claims benefit under 35 U.S.C. §119(a)-(d) of U.S. Provisional Application 61/327,379, filed Apr. 23, 2010, and U.S. Provisional Application 61/333,398, filed May 11, 2010, the contents of which are incorporated herein by reference in their entirety.

BACKGROUND OF THE INVENTION

The mucosal surface between the environment and the body has many protective mechanisms. One form of defense is cleansing the surface with liquid. The quantity of liquid reflects the balance between epithelial liquid secretion (which often reflects anion secretion coupled with water and a cation counter-ion) and liquid absorption (which often reflects $Na^+$ absorption, coupled with water and counter anion). Many diseases of mucosal surfaces are caused by too little liquid, as caused by an imbalance between secretion (too little) and absorption (too much). One method to balance the liquid layer is to decrease $Na^+$ channel-mediated liquid absorption.

Nonvoltage-gated, amiloride-sensitive sodium channels control fluid and electrolyte transport across epithelia in many organs. The apical membranes of many tight epithelia contain sodium channels that are primarily characterized by their high affinity to the diuretic blocker amiloride. These channels mediate the first step of active sodium reabsorption essential for the maintenance of body salt and water homeostasis. In vertebrates, the channels control reabsorption of sodium in the kidney, colon, lung and sweat glands; they also play a role in taste perception.

The rate-limiting step of $Na^+$ and liquid absorption is mediated by the epithelial sodium ($Na^+$) channel (ENaC). These sodium channels are heteromeric complexes consisting of 3 subunits: Alpha-ENaC, Beta-ENaC, and Gamma-ENaC.

Beta-ENaC (also known as SCNN1B) encodes the beta subunit of this sodium channel, and mutations in and/or altered expression of this gene have been associated with several diseases (and/or associated with treatments of diseases), including cystic fibrosis, pseudohypoaldosteronism type 1 (PHA1), Liddle's syndrome, hypertension, alkalosis, hypokalemia, and obesity-associated hypertension.

There exists the need for treatments related to Beta-ENaC-related diseases.

BRIEF SUMMARY OF THE INVENTION

The present disclosure encompasses RNAi agents to Beta-ENaC, which are useful in the treatment of Beta-ENaC-related diseases, such as cystic fibrosis, pseudohypoaldosteronism type 1 (PHA1), Liddle's syndrome, hypertension, alkalosis, hypokalemia, and obesity-associated hypertension. The present disclosure also encompasses a method of treating a human subject having a pathological state mediated at least in part by alpha-ENaC expression, the method comprising the step of administering to the subject a therapeutically effective amount of a RNAi agent Beta-ENaC.

The present disclosure provides specific RNAi agents and methods that are useful in reducing Beta-ENaC levels in a subject, e.g., a mammal, such as a human. The present disclosure specifically provides double-stranded RNAi agents comprising at least 15 or more contiguous nucleotides of Beta-ENaC. In particular, the present disclosure provides agents comprising sequences of 15 or more contiguous nucleotides differing by 0, 1, 2 or 3 from those of the RNAi agents provided, e.g., in Table 1. The RNAi agents particularly can in one embodiment comprise less than 30 nucleotides per strand, e.g., such as 18-23 nucleotides, and/or 19-21 nucleotides, and/or such as those provided, e.g., in Table 1.

The double-stranded RNAi agents can have blunt ends or overhangs of 1, 2, 3 or 4 nucleotides (i.e., 1-4 nt) from one or both 3' and/or 5' ends. The double-stranded RNAi agents can also optionally comprise one or two 3' caps and/or one or more modified nucleotides. Modified variants of sequences as provided herein include those that are otherwise identical but contain substitutions of a naturally occurring nucleotide for a corresponding modified nucleotide.

Further, the RNAi agent can either contain only naturally-occurring ribonucleotide subunits, or one or more modifications to the sugar, phosphate or base of one or more of the replacement nucleotide subunits, whether they comprise ribonucleotide subunits or deoxyribonucleotide subunits. In one embodiment, modified variants of the disclosed RNAi agents include RNAi agents with the same sequence, but with one or more modifications to one or more of the sugar, phosphate or base of one or more of the nucleotide subunits. In one embodiment, the modifications improve efficacy, stability and/or reduce immunogenicity of the RNAi agent. One aspect of the present disclosure relates to a double-stranded oligonucleotide comprising at least one non-natural nucleobase. In certain embodiments, the non-natural nucleobase is difluorotolyl, nitroindolyl, nitropyrrolyl, or nitroimidazolyl. In a particular embodiment, the non-natural nucleobase is difluorotolyl. In certain embodiments, only one of the two oligonucleotide strands contains a non-natural nucleobase. In certain embodiments, both of the oligonucleotide strands contain a non-natural nucleobase.

The RNAi agent(s) can optionally be attached to a ligand selected to improve one or more characteristic, such as, e.g., stability, distribution and/or cellular uptake of the agent, e.g., cholesterol or a derivative thereof. The RNAi agent(s) can be isolated or be part of a pharmaceutical composition used for the methods described herein. Particularly, the pharmaceutical composition can be formulated for delivery to the lungs or nasal passage or formulated for parental administration. The pharmaceutical compositions can optionally comprise two or more RNAi agents, each one directed to the same or a different segment of the Beta-ENaC mRNA. Optionally, the pharmaceutical compositions can further comprise or be used in conjunction with any known treatment for any Beta-ENaC-related disease.

The present disclosure further provides methods for reducing the level of Beta-ENaC mRNA in a cell, particularly in the case of a disease characterized by over-expression or hyperactivity of ENaC. The present disclosure also encompasses a method of treating a human subject having a pathological state mediated at least in part by Beta-ENaC expression, the method comprising the step of administering to the subject a therapeutically effective amount of a RNAi agent Beta-ENaC. Such methods comprise the step of administering one of the RNAi agents of the present disclosure to a subject, as further described below. The present methods utilize the cellular mechanisms involved in RNA interference to selectively degrade the target RNA in a cell and are comprised of the step of contacting a cell with one of the RNAi agents of the present disclosure. Such methods can be performed directly on a cell or can be performed on a mammalian subject by administering to a subject one of the RNAi agents/pharmaceutical compositions of the present disclosure. Reduction of target Beta-ENaC RNA in a cell results in a reduction in the amount of encoded Beta-ENaC protein produced. In an organism, this can result in reduction of epithelial potential difference, balanced fluid absorption and increased mucociliary clearance.

The methods and compositions of the present disclosure, e.g., the methods and Beta-ENaC RNAi agent compositions, can be used with any dosage and/or formulation described herein, as well as with any route of administration described herein.

The details of one or more embodiments of the present disclosure are set forth in the accompanying drawings and the description below. Other features, objects, and advantages of the present disclosure will be apparent from this description, the drawings, and from the claims.

DETAILED DESCRIPTION OF THE INVENTION

Figure 1:
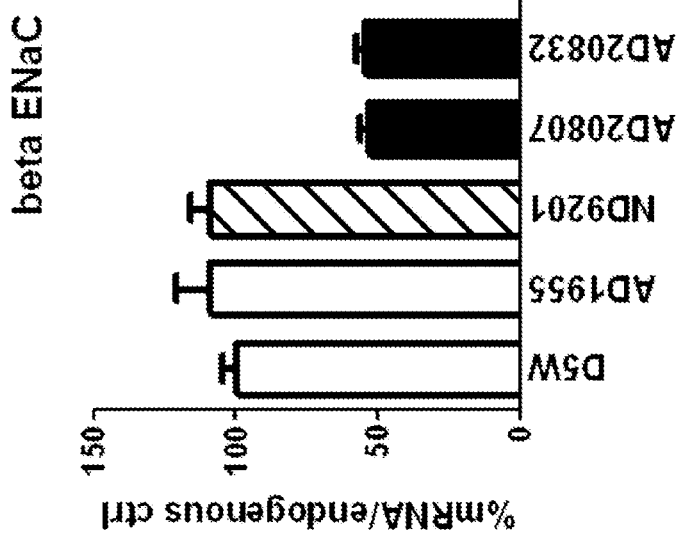
FIGS. 1A-1B depict the ability of RNAi agents AD20807, AD20826, AD20832, AS20834, AD20848, and AD20861 to knock-down Beta-ENaC activity in vivo.
Figure 1:
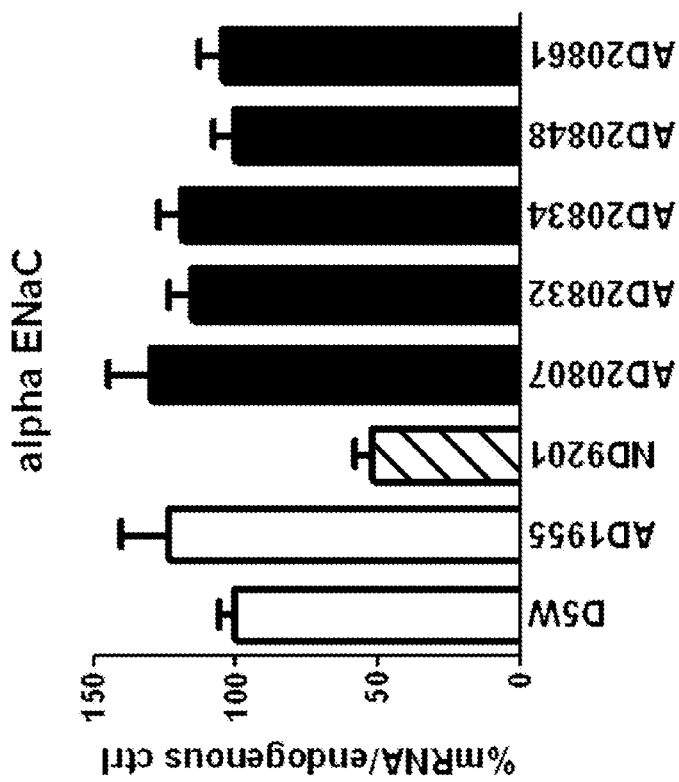

The present disclosure encompasses RNAi agents to Beta-ENaC, which are useful in treatment of Beta-ENaC-related diseases (e.g., diseases associated with mutations in and/or altered expression, level and/or activity of Beta-ENaC, and/or diseases treatable by modulating the expression, level and/or activity of Beta-ENaC), such as cystic fibrosis, pseudohypoaldosteronism type 1 (PHA1), Liddle's syndrome, hypertension, alkalosis, hypokalemia, and obesity-associated hypertension. The present disclosure also provides methods of treating a human subject having a pathological state mediated at least in part by Beta-ENaC expression, the method comprising the step of administering to the subject a therapeutically effective amount of a RNAi agent Beta-ENaC.

Various Embodiments of the Present Disclosure Include:

A RNAi Agent Comprising an Antisense Strand Described Herein.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of a RNAi agent specific to Beta-ENaC (or any set of overlapping RNAi agents specific to Beta-ENaC) provided, e.g., in Table 1. In another embodiment, the present disclosure relates to a composition comprising a RNAi agent comprising a sense and an anti-sense strand, wherein the anti-sense strand comprises at least 15 contiguous nucleotides differing by 0, 1, 2, or 3 nucleotides from the anti-sense strand of a RNAi agent from any sequence provided herein. In another embodiment, the present disclosure relates to a composition comprising a RNAi agent comprising a first strand and a second strand, wherein the first strand comprises at least 15 contiguous nucleotides differing by 0, 1, 2, or 3 nucleotides from the sequence of the first strand, and the second strand comprises at least 15 contiguous nucleotides differing by 0, 1, 2, or 3 nucleotides from the sequence of the second strand of any RNAi agent provided herein.

Particular duplexes include the following, wherein each duplex comprises a set of SEQ ID NOs, wherein the first SEQ ID NO corresponds to a first strand (e.g., a sense strand), and the second SEQ ID NO corresponds to a second strand (e.g., an anti-sense strand): AD-20805 (SEQ ID NOs. 111 and 112); AD-20806 (SEQ ID NOs. 113 and 114); AD-20807 (SEQ ID NOs. 115 and 116); AD-20808 (SEQ ID NOs. 117 and 118); AD-20809 (SEQ ID NOs. 119 and 120); AD-20810 (SEQ ID NOs. 121 and 122); AD-20811 (SEQ ID NOs. 123 and 124); AD-20812 (SEQ ID NOs. 125 and 126); AD-20813 (SEQ ID NOs. 127 and 128); AD-20814 (SEQ ID NOs. 129 and 130); AD-20815 (SEQ ID NOs. 131 and 132); AD-20816 (SEQ ID NOs. 133 and 134); AD-20817 (SEQ ID NOs. 135 and 136); AD-20818 (SEQ ID NOs. 137 and 138); AD-20819 (SEQ ID NOs. 139 and 140); AD-20820 (SEQ ID NOs. 141 and 142); AD-20821 (SEQ ID NOs. 143 and 144); AD-20822 (SEQ ID NOs. 145 and 146); AD-20823 (SEQ ID NOs. 147 and 148); AD-20824 (SEQ ID NOs. 149 and 150); AD-20825 (SEQ ID NOs. 151 and 152); AD-20826 (SEQ ID NOs. 153 and 154); AD-20827 (SEQ ID NOs. 155 and 156); AD-20828 (SEQ ID NOs. 157 and 158); AD-20829 (SEQ ID NOs. 159 and 160); AD-20830 (SEQ ID NOs. 161 and 162); AD-20831 (SEQ ID NOs. 163 and 164); AD-20832 (SEQ ID NOs. 165 and 166); AD-20833 (SEQ ID NOs. 167 and 168); AD-20834 (SEQ ID NOs. 169 and 170); AD-20835 (SEQ ID NOs. 171 and 172); AD-20836 (SEQ ID NOs. 173 and 174); AD-20837 (SEQ ID NOs. 175 and 176); AD-20838 (SEQ ID NOs. 177 and 178); AD-20839 (SEQ ID NOs. 179 and 180); AD-20840 (SEQ ID NOs. 181 and 182); AD-20841 (SEQ ID NOs. 183 and 184); AD-20842 (SEQ ID NOs. 185 and 186); AD-20843 (SEQ ID NOs. 187 and 188); AD-20844 (SEQ ID NOs. 189 and 190); AD-20845 (SEQ ID NOs. 191 and 192); AD-20846 (SEQ ID NOs. 193 and 194); AD-20847 (SEQ ID NOs. 195 and 196); AD-20848 (SEQ ID NOs. 197 and 198); AD-20849 (SEQ ID NOs. 199 and 200); AD-20850 (SEQ ID NOs. 201 and 202); AD-20851 (SEQ ID NOs. 203 and 204); AD-20852 (SEQ ID NOs. 205 and 206); AD-20861 (SEQ ID NOs. 207 and 208); AD-20862 (SEQ ID NOs. 209 and 210); AD-20863 (SEQ ID NOs. 211 and 212); AD-20864 (SEQ ID NOs. 213 and 214); AD-20865 (SEQ ID NOs. 215 and 216); AD-20866 (SEQ ID NOs. 217 and 218); and AD-20867 (SEQ ID NOs. 219 and 220), and modified variants thereof.

One embodiment provides modified variants of particular duplexes, wherein each duplex comprises a set of SEQ ID NOs, wherein the first SEQ ID NO corresponds to a first strand (e.g., a sense strand), and the second SEQ ID NO corresponds to a second strand (e.g., an anti-sense strand) that are selected from the group consisting of: AD-20805 (SEQ ID NOs. 1 and 2); AD-20806 (SEQ ID NOs. 3 and 4); AD-20807 (SEQ ID NOs. 5 and 6); AD-20808 (SEQ ID NOs. 7 and 8); AD-20809 (SEQ ID NOs. 9 and 10); AD-20810 (SEQ ID NOs. 11 and 12); AD-20811 (SEQ ID NOs. 13 and 14); AD-20812 (SEQ ID NOs. 15 and 16); AD-20813 (SEQ ID NOs. 17 and 18); AD-20814 (SEQ ID NOs. 19 and 20); AD-20815 (SEQ ID NOs. 21 and 22); AD-20816 (SEQ ID NOs. 23 and 24); AD-20817 (SEQ ID NOs. 25 and 26); AD-20818 (SEQ ID NOs. 27 and 28); AD-20819 (SEQ ID NOs. 29 and 30); AD-20820 (SEQ ID NOs. 31 and 32); AD-20821 (SEQ ID NOs. 33 and 34); AD-20822 (SEQ ID NOs. 35 and 36); AD-20823 (SEQ ID NOs. 37 and 38); AD-20824 (SEQ ID NOs. 39 and 40); AD-20825 (SEQ ID NOs. 41 and 42); AD-20826 (SEQ ID NOs. 43 and 44); AD-20827 (SEQ ID NOs. 45 and 46); AD-20828 (SEQ ID NOs. 47 and 48); AD-20829 (SEQ ID NOs. 49 and 50); AD-20830 (SEQ ID NOs. 51 and 52); AD-20831 (SEQ ID NOs. 53 and 54); AD-20832 (SEQ ID NOs. 55 and 56); AD-20833 (SEQ ID NOs. 57 and 58); AD-20834 (SEQ ID NOs. 59 and 60); AD-20835 (SEQ ID NOs. 61 and 62); AD-20836 (SEQ ID NOs. 63 and 64); AD-20837 (SEQ ID NOs. 65 and 66); AD-20838 (SEQ ID NOs. 67 and 68); AD-20839 (SEQ ID NOs. 69 and 70); AD-20840 (SEQ ID NOs. 71 and 72); AD-20841 (SEQ ID NOs. 73 and 74); AD-20842 (SEQ ID NOs. 75 and 76); AD-20843 (SEQ ID NOs. 77 and 78); AD-20844 (SEQ ID NOs. 79 and 80); AD-20845 (SEQ ID NOs. 81 and 82); AD-20846 (SEQ ID NOs. 83 and 84); AD-20847 (SEQ ID NOs. 85 and 86); AD-20848 (SEQ ID NOs. 87 and 88); AD-20849 (SEQ ID NOs. 89 and 90); AD-20850 (SEQ ID NOs. 91 and 92); AD-20851 (SEQ ID NOs. 93 and 94); AD-20852 (SEQ ID NOs. 95 and 96); AD-20861 (SEQ ID NOs. 97 and 98); AD-20862 (SEQ ID NOs. 99 and 100); AD-20863 (SEQ ID NOs. 101 and 102); AD-20864 (SEQ ID NOs. 103 and 104); AD-20865 (SEQ ID NOs. 105 and 106); AD-20866 (SEQ ID NOs. 107 and 108); and AD-20867 (SEQ ID NOs. 109 and 110).

Particular Compositions

In one embodiment, the present disclosure relates to a composition comprising a RNAi agent comprising an anti-sense strand, wherein the antisense strand comprises at least 15 contiguous nucleotides differing by 0, 1, 2, or 3 nucleotides from the antisense strand of a RNAi agent to Beta-ENaC selected from any sequence (or overlapping set of sequences) provided in a table here (e.g., Table 1). In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of a RNAi agent to Beta-ENaC selected from any sequence (or overlapping set of sequences) provided in a table here (e.g., Table 1). In another embodiment, the present disclosure relates to a composition comprising a RNAi agent comprising a sense and an anti-sense strand, wherein the anti-sense strand comprises at least 15 contiguous nucleotides differing by 0, 1, 2, or 3 nucleotides from the anti-sense strand of a RNAi agent from any sequence provided herein. In another embodiment, the present disclosure relates to a composition comprising a RNAi agent comprising a first strand and a second strand, wherein the first strand comprises at least 15 contiguous nucleotides differing by 0, 1, 2, or 3 nucleotides from the sequence of the first strand, and the second strand comprises at least 15 contiguous nucleotides differing by 0, 1, 2, or 3 nucleotides from the sequence of the second strand of any RNAi agent provided herein. Particular duplexes include those specific duplexes provided above and as listed in any one or more of Table 1. Additional modified sequences (e.g., sequences comprising one or more modified base) of each of the compositions above are also contemplated as part of the present disclosure.

Table A1, below, provides the SEQ ID NOs for the unmodified and an example modified sequence of the sense and an anti-sense strands of various RNAi agents to Beta-ENaC. The base composition of each is specific sequence represented by the SEQ ID NOs is provided in more detail in Table 1, and portions thereof are provided in Table 2.

TABLE A1

SEQ ID NOs for a first and a second strand (e.g., sense ("SS") and anti-sense ("AS") strand) for RNAi agents to Beta-ENaC

| RNAi agent - duplex name | | Modified sequence SEQ ID NO | Unmodified sequence SEQ ID NO |
|---|---|---|---|
| AD-20805 | Sense | 1 | 111 |
| | Anti-Sense | 2 | 112 |
| AD-20806 | Sense | 3 | 113 |
| | Anti-Sense | 4 | 114 |
| AD-20807 | Sense | 5 | 115 |
| | Anti-Sense | 6 | 116 |
| AD-20808 | Sense | 7 | 117 |
| | Anti-Sense | 8 | 118 |
| AD-20809 | Sense | 9 | 119 |
| | Anti-Sense | 10 | 120 |

TABLE A1-continued

SEQ ID NOs for a first and a second strand (e.g., sense ("SS") and anti-sense ("AS") strand) for RNAi agents to Beta-ENaC

| RNAi agent - duplex name | | Modified sequence SEQ ID NO | Unmodified sequence SEQ ID NO |
|---|---|---|---|
| AD-20810 | Sense | 11 | 121 |
| | Anti-Sense | 12 | 122 |
| AD-20811 | Sense | 13 | 123 |
| | Anti-Sense | 14 | 124 |
| AD-20812 | Sense | 15 | 125 |
| | Anti-Sense | 16 | 126 |
| AD-20813 | Sense | 17 | 127 |
| | Anti-Sense | 18 | 128 |
| AD-20814 | Sense | 19 | 129 |
| | Anti-Sense | 20 | 130 |
| AD-20815 | Sense | 21 | 131 |
| | Anti-Sense | 22 | 132 |
| AD-20816 | Sense | 23 | 133 |
| | Anti-Sense | 24 | 134 |
| AD-20817 | Sense | 25 | 135 |
| | Anti-Sense | 26 | 136 |
| AD-20818 | Sense | 27 | 137 |
| | Anti-Sense | 28 | 138 |
| AD-20819 | Sense | 29 | 139 |
| | Anti-Sense | 30 | 140 |
| AD-20820 | Sense | 31 | 141 |
| | Anti-Sense | 32 | 142 |
| AD-20821 | Sense | 33 | 143 |
| | Anti-Sense | 34 | 144 |
| AD-20822 | Sense | 35 | 145 |
| | Anti-Sense | 36 | 146 |
| AD-20823 | Sense | 37 | 147 |
| | Anti-Sense | 38 | 148 |
| AD-20824 | Sense | 39 | 149 |
| | Anti-Sense | 40 | 150 |
| AD-20825 | Sense | 41 | 151 |
| | Anti-Sense | 42 | 152 |
| AD-20826 | Sense | 43 | 153 |
| | Anti-Sense | 44 | 154 |
| AD-20827 | Sense | 45 | 155 |
| | Anti-Sense | 46 | 156 |
| AD-20828 | Sense | 47 | 157 |
| | Anti-Sense | 48 | 158 |
| AD-20829 | Sense | 49 | 159 |
| | Anti-Sense | 50 | 160 |
| AD-20830 | Sense | 51 | 161 |
| | Anti-Sense | 52 | 162 |
| AD-20831 | Sense | 53 | 163 |
| | Anti-Sense | 54 | 164 |
| AD-20832 | Sense | 55 | 165 |
| | Anti-Sense | 56 | 166 |
| AD-20833 | Sense | 57 | 167 |
| | Anti-Sense | 58 | 168 |
| AD-20834 | Sense | 59 | 169 |
| | Anti-Sense | 60 | 170 |
| AD-20835 | Sense | 61 | 171 |
| | Anti-Sense | 62 | 172 |
| AD-20836 | Sense | 63 | 173 |
| | Anti-Sense | 64 | 174 |
| AD-20837 | Sense | 65 | 175 |
| | Anti-Sense | 66 | 176 |
| AD-20838 | Sense | 67 | 177 |
| | Anti-Sense | 68 | 178 |
| AD-20839 | Sense | 69 | 179 |
| | Anti-Sense | 70 | 180 |
| AD-20840 | Sense | 71 | 181 |
| | Anti-Sense | 72 | 182 |
| AD-20841 | Sense | 73 | 183 |
| | Anti-Sense | 74 | 184 |
| AD-20842 | Sense | 75 | 185 |
| | Anti-Sense | 76 | 186 |
| AD-20843 | Sense | 77 | 187 |
| | Anti-Sense | 78 | 188 |
| AD-20844 | Sense | 79 | 189 |
| | Anti-Sense | 80 | 190 |
| AD-20845 | Sense | 81 | 191 |
| | Anti-Sense | 82 | 192 |

TABLE A1-continued

SEQ ID NOs for a first and a second strand (e.g., sense ("SS") and anti-sense ("AS") strand) for RNAi agents to Beta-ENaC

| RNAi agent - duplex name | | Modified sequence SEQ ID NO | Unmodified sequence SEQ ID NO |
|---|---|---|---|
| AD-20846 | Sense | 83 | 193 |
| | Anti-Sense | 84 | 194 |
| AD-20847 | Sense | 85 | 195 |
| | Anti-Sense | 86 | 196 |
| AD-20848 | Sense | 87 | 197 |
| | Anti-Sense | 88 | 198 |
| AD-20849 | Sense | 89 | 199 |
| | Anti-Sense | 90 | 200 |
| AD-20850 | Sense | 91 | 201 |
| | Anti-Sense | 92 | 202 |
| AD-20851 | Sense | 93 | 203 |
| | Anti-Sense | 94 | 204 |
| AD-20852 | Sense | 95 | 205 |
| | Anti-Sense | 96 | 206 |
| AD-20861 | Sense | 97 | 207 |
| | Anti-Sense | 98 | 208 |
| AD-20862 | Sense | 99 | 209 |
| | Anti-Sense | 100 | 210 |
| AD-20863 | Sense | 101 | 211 |
| | Anti-Sense | 102 | 212 |
| AD-20864 | Sense | 103 | 213 |
| | Anti-Sense | 104 | 214 |
| AD-20865 | Sense | 105 | 215 |
| | Anti-Sense | 106 | 216 |
| AD-20866 | Sense | 107 | 217 |
| | Anti-Sense | 108 | 218 |
| AD-20867 | Sense | 109 | 219 |
| | Anti-Sense | 110 | 220 |

For example, in Table A1, an exemplary modified sequence of RNAi agent AD-20805 is represented by SEQ ID NO: 1 (the sense strand) and SEQ ID NO: 2 (the anti-sense strand). The unmodified sequence of AD-20805 is represented by SEQ ID NO: 111 (the sense strand) and SEQ ID NO: 112 (the anti-sense strand). Thus, Table A1 presents the SEQ ID NO identifiers of a first and second strand of the unmodified sequence and at least one exemplary modified sequence for each of the various RNAi agents to Beta-ENaC.

An RNAi Agent Comprising an Anti-Sense Strand Described Herein

In one particular specific embodiment, the present disclosure relates to a composition comprising a RNAi agent comprising an anti-sense strand, wherein the anti-sense strand comprises at least 15 contiguous nucleotides differing by 0, 1, 2, or 3 nucleotides from the anti-sense strand of a RNAi agent to Beta-ENaC selected from those anti-sense strands in the specific duplexes provided herein and as listed, e.g., in Table 1.

Various specific embodiments of this embodiment are described below.

In one embodiment, the composition further comprises a second RNAi agent to Beta-ENaC. In various embodiments, the second RNAi agent is physically separate from the first, or the two are physically connected (e.g., covalently linked or otherwise conjugated).

In one embodiment, the antisense strand is about 30 or fewer nt in length.

In one embodiment, the sense strand and the antisense strand form a duplex region of about 15 to about 30 nucleotide pairs in length.

In one embodiment, the antisense strand is about 15 to about 36 nt in length, including about 18 to about 30 nt in length, and further including about 19 to about 23 nt in length. In one embodiment, the antisense strand has at least the length selected from about 15 nt, about 16 nt, about 17 nt, about 18 nt, about 19 nt, about 20 nt, about 21 nt, about 22 nt, about 23 nt, about 24 nt, about 25 nt, about 26 nt, about 27 nt, about 28 nt, about 29 nt and about 30 nt.

In one embodiment, the RNAi agent comprises a modification that causes the RNAi agent to have increased stability in a biological sample or environment, e.g., blood serum or intestinal lavage fluid.

In one embodiment, the RNAi agent comprises at least one sugar backbone modification (e.g., phosphorothioate linkage) and/or at least one 2'-modified nucleotide. In one embodiment, all the pyrimidines are 2' O-methyl-modified nucleotides.

In one embodiment, the RNAi agent comprises: at least one 5'-uridine-adenine-3' (5'-ua-3') dinucleotide, wherein the uridine is a 2'-modified nucleotide; and/or at least one 5'-uridine-guanine-3' (5'-ug-3') dinucleotide, wherein the 5'-uridine is a 2'-modified nucleotide; and/or at least one 5'-cytidine-adenine-3' (5'-ca-3') dinucleotide, wherein the 5'-cytidine is a 2'-modified nucleotide; and/or at least one 5'-uridine-uridine-3' (5'-uu-3') dinucleotide, wherein the 5'-uridine is a 2'-modified nucleotide.

In one embodiment, the RNAi agent comprises a 2'-modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA). In one embodiment, all the pyrimidines are 2' O-methyl-modified nucleotides.

In one embodiment, the RNAi agent comprises a blunt end.

In one embodiment, the RNAi agent comprises an overhang having 1 to 4 unpaired nucleotides.

In one embodiment, the RNAi agent comprises an overhang at the 3'-end of the antisense strand of the RNAi agent.

In one embodiment, the RNAi agent is ligated to one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

In one embodiment, the RNAi agent is capable of inhibiting expression of the Beta-ENaC gene by at least about 60% at a concentration of 10 nM in H441 cells in vitro.

In one embodiment, the RNAi agent is capable of inhibiting expression of the Beta-ENaC gene by at least about 70% at a concentration of 10 nM in H441 cells in vitro.

In one embodiment, the RNAi agent is capable of inhibiting expression of the Beta-ENaC gene by at least about 80% at a concentration of 10 nM in H441 cells in vitro.

In one embodiment, the RNAi agent is capable of inhibiting expression of the Beta-ENaC gene by at least about 90% at a concentration of 10 nM in H441 cells in vitro.

In one embodiment, the RNAi has an EC50 of no more than about 0.1 nM.

In one embodiment, the RNAi has an EC50 of no more than about 0.01 nM.

In one embodiment, the RNAi has an EC50 of no more than about 0.001 nM.

A RNAi Agent Comprising a First and a Second Strand Described Herein

In one particular specific embodiment, the present disclosure relates to a composition comprising a RNAi agent comprising a first strand and a second strand, wherein the first strand and second strand comprise at least 15 contiguous nucleotides, each differing by 0, 1, 2, or 3 nucleotides from the first and second strand, respectively, of a RNAi agent to Beta-ENaC selected from the specific duplexes provided herein and listed, e.g., in Table 1.

Various specific embodiments of this embodiment are described below.

In one embodiment, the composition further comprises a second RNAi agent to Beta-ENaC. In various embodiments, the second RNAi agent is physically separate from the first, or the two are physically connected (e.g., covalently linked or otherwise conjugated).

In one embodiment, the antisense strand is about 30 or fewer nt in length.

In one embodiment, the sense strand and the antisense strand form a duplex region of about 15 to about 30 nt pairs in length.

In one embodiment, the antisense strand is about 15 to about 36 nt in length, including about 18 to about 23 nt in length, and including about 19 to about 23 nt in length.

In one embodiment, the antisense strand has at least the length selected from about 15 nt, about 16 nt, about 17 nt, about 18 nt, about 19 nt, about 20 nt, about 21 nt, about 22 nt, about 23 nt, about 24 nt, about 25 nt, about 26 nt, about 27 nt, about 28 nt, about 29 nt and about 30 nt.

In one embodiment, the RNAi agent comprises a modification that causes the RNAi agent to have increased stability in a biological sample or environment, e.g., blood serum or intestinal lavage fluid.

In one embodiment, the RNAi agent comprises at least one sugar backbone modification (e.g., phosphorothioate linkage) and/or at least one 2'-modified nucleotide. In one embodiment, all the pyrimidines are 2' O-methyl-modified nucleotides.

In one embodiment, the RNAi agent comprises: at least one 5'-uridine-adenine-3' (5'-ua-3') dinucleotide, wherein the uridine is a 2'-modified nucleotide; and/or at least one 5'-uridine-guanine-3' (5'-ug-3') dinucleotide, wherein the 5'-uridine is a 2'-modified nucleotide; and/or at least one 5'-cytidine-adenine-3' (5'-ca-3') dinucleotide, wherein the 5'-cytidine is a 2'-modified nucleotide; and/or at least one 5'-uridine-uridine-3' (5'-uu-3') dinucleotide, wherein the 5'-uridine is a 2'-modified nucleotide.

In one embodiment, the RNAi agent comprises a 2'-modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).

In one embodiment, the RNAi agent comprises a blunt end.

In one embodiment, the RNAi agent comprises an overhang having 1 to 4 unpaired nucleotides.

In one embodiment, the RNAi agent comprises an overhang at the 3'-end of the antisense strand of the RNAi agent.

In one embodiment, the RNAi agent is ligated to one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

In one embodiment, the RNAi agent is capable of inhibiting expression of the Beta-ENaC gene by at least about 60% at a concentration of 10 nM in H441 cells in vitro.

In one embodiment, the RNAi agent is capable of inhibiting expression of the Beta-ENaC gene by at least about 70% at a concentration of 10 nM in H441 cells in vitro.

In one embodiment, the RNAi agent is capable of inhibiting expression of the Beta-ENaC gene by at least about 80% at a concentration of 10 nM in H441 cells in vitro.

In one embodiment, the RNAi agent is capable of inhibiting expression of the Beta-ENaC gene by at least about 90% at a concentration of 10 nM in H441 cells in vitro.

In one embodiment, the RNAi has an EC50 of no more than about 0.1 nM.

In one embodiment, the RNAi has an EC50 of no more than about 0.01 nM.

In one embodiment, the RNAi has an EC50 of no more than about 0.001 nM.

A Method of Treatment Using a RNAi Agent Described Herein

In one particular specific embodiment, the present disclosure relates to a method of treating a Beta-ENaC-related disease in an individual, comprising the step of administering to the individual a therapeutically effective amount of a composition comprising a RNAi agent comprising at least an antisense strand, wherein the antisense strand comprises at least 15 contiguous nucleotides differing by 0, 1, 2, or 3 nucleotides from the antisense strand of a RNAi agent to Beta-ENaC selected from the specific duplexes provided herein and as listed, e.g., in Table 1. In another embodiment, the present disclosure relates to such method, wherein the composition comprising a RNAi agent further comprises a sense strand, wherein the sense strand comprises at least 15 contiguous nucleotides differing by 0, 1, 2, or 3 nucleotides from the sense strand of a RNAi agent to Beta-ENaC selected from the specific duplexes provided herein and as listed, e.g., in Table 1.

Various particular specific embodiments of this embodiment are described below.

In one embodiment, the Beta-ENaC-related disease is cystic fibrosis, pseudohypoaldosteronism type 1 (PHA1), Liddle's syndrome, hypertension, alkalosis, hypokalemia, and/or obesity-associated hypertension.

In one embodiment, the Beta-ENaC-related disease is cystic fibrosis.

In one embodiment, the method further comprises the administration of an additional treatment. In one embodiment, the additional treatment is a therapeutically effective amount of a composition.

In one embodiment, the additional treatment is a method (or procedure).

In one embodiment, the additional treatment and the RNAi agent can be administered in any order, or can be administered simultaneously.

In one embodiment, the method further comprises the step of administering an additional treatment for cystic fibrosis, pseudohypoaldosteronism type 1 (PHA1), Liddle's syndrome, hypertension, alkalosis, hypokalemia, and/or obesity-associated hypertension.

In one embodiment, the method further comprises the step of administering an additional treatment or therapy selected from the list of an additional antagonist to ENaC, a potassium-sparing diuretic, amiloride, triamterene, regulation of dietary salt intake, antibiotics, DNase therapy, albutrol, N-acetylcysteine, breathing therapy, percussive therapy, and aerobic exercise.

In one embodiment, the composition comprises a second RNAi agent to Beta-ENaC. In various embodiments, the second RNAi agent is physically separate from the first, or the two are physically connected (e.g., covalently linked or otherwise conjugated).

In one embodiment, the method further comprises the step of administering an additional RNAi agent which comprises at least 15 contiguous nucleotides differing by 0, 1, 2, or 3 nucleotides from the antisense strand of a RNAi agent to Beta-ENaC selected from the specific duplexes provided herein and as listed, e.g., in Table 1.

A Method of Inhibiting the Expression of Beta-ENaC, Using a RNAi Agent Described Herein In one particular specific embodiment, the present disclosure relates to a method of inhibiting the expression of the Beta-ENaC gene in an individual, comprising the step of administering to the individual a therapeutically effective amount of a composition comprising a RNAi agent of the present disclosure. In one embodiment, the RNAi agent comprises at least an anti-sense strand, and/or comprises a sense and an anti-sense strand, wherein the anti-sense strand comprises at least 15 contiguous nucleotides differing by 0, 1, 2, or 3 nucleotides from the anti-sense strand of a RNAi agent to Beta-ENaC selected from those specific duplex provided herein and as listed, e.g., in Table 1.

Various embodiments of this aspect of the invention are described below.

In one embodiment, the individual is afflicted with or susceptible to a Beta-ENaC-related disease.

In one embodiment, the Beta-ENaC-related disease is cystic fibrosis, pseudohypoaldosteronism type 1 (PHA1), Liddle's syndrome, hypertension, alkalosis, hypokalemia, and/or obesity-associated hypertension.

In one embodiment, the Beta-ENaC-related disease is cystic fibrosis.

In one embodiment, the method further comprises the administration of an additional treatment. In one embodiment, the additional treatment is a therapeutically effective amount of a composition.

In one embodiment, the additional treatment is a method (or procedure).

In one embodiment, the additional treatment and the RNAi agent can be administered in any order or can be administered simultaneously.

In one embodiment, the method further comprises the step of administering an additional treatment for cystic fibrosis, pseudohypoaldosteronism type 1 (PHA1), Liddle's syndrome, hypertension, alkalosis, hypokalemia, and/or obesity-associated hypertension.

In one embodiment, the method further comprises the step of administering an additional treatment or therapy selected from the list of an additional antagonist to ENaC, a potassium-sparing diuretic, amiloride, triamterene, regulation of dietary salt intake, antibiotics, DNase therapy, albutrol, N-acetylcysteine, breathing therapy, percussive therapy, and aerobic exercise.

In one embodiment, the composition comprises a second RNAi agent to Beta-ENaC. In various embodiments, the second RNAi agent is physically separate from the first, or the two are physically connected (e.g., covalently linked or otherwise conjugated).

In one embodiment, the method further comprises the step of administering an additional RNAi agent which comprises at least 15 contiguous nucleotides differing by 0, 1, 2, or 3 nucleotides from the antisense strand of a RNAi agent to Beta-ENaC selected from the specific duplexes provided herein and as listed, e.g., in Table 1.

Pharmaceutical Formulations of a RNAi Agent to Beta-ENaC

In one particular specific embodiment, the present disclosure relates to a composition comprising a RNAi agent of the present disclosure. In one embodiment, the RNAi agent comprises at least an anti-sense strand, and/or comprises a sense and an anti-sense strand, wherein the anti-sense strand comprises at least 15 contiguous nucleotides differing by 0, 1, 2, or 3 nucleotides from the anti-sense strand of a RNAi agent to Beta-ENaC selected from those specific duplex provided herein and as listed, e.g., in Table 1, wherein the composition is in a pharmaceutically effective formulation.

In one embodiment, the present disclosure pertains to the use of a RNAi agent in the manufacture of a medicament for treatment of a Beta-ENaC-related disease, wherein the RNAi agent comprises a sense strand and an antisense strand, wherein the antisense strand comprises at least 15 contiguous nucleotides differing by 0, 1, 2, or 3 nucleotides from the antisense strand of a RNAi agent to Beta-ENaC selected from those specific duplex provided herein and as listed, e.g., in Table 1.

ENaC

By "ENaC" is meant the epithelial sodium channel, a membrane protein made of three different but homologous subunits (Alpha, Beta and Gamma).

ENaC is present in the apical membrane of epithelial cells of the distal nephron (cortical and medullary collecting tubule) and distal colon and in the airways and in the excretory ducts of several glands. ENaC is also expressed in placenta, brain and urinary bladder. It provides a controlled entry pathway for $Na^+$ from the lumen of these organs into the epithelial cells, and, together with the $Na^+/K^+$-ATPase located in the basolateral membrane of the same cells, and is responsible for the active, vectorial transport of $Na^+$ from the external medium through the epithelial cells into the extracellular fluid and toward the blood. ENaC is located on the apical membrane facing the lumen, and allows movement of sodium from the lumen into the epithelial cell. The sodium reabsorbed via ENaC is then extruded from the epithelial cell back into the bloodstream by the $Na^+/K^+$-ATPase. The reabsorption of sodium by the ENaC is accompanied by an osmotic uptake of water to maintain a constant extracellular $Na^+$ concentration. This changes blood volume and consequently affects blood pressure. Thus, ENaC plays an important role in electrolyte homeostasis and the control of blood volume and blood pressure. See, e.g., Saxena et al. 1998 Biochem. Biophys. Res. Comm. 252: 208-213.

ENaC has different functional roles in various organs in which it is expressed. In the kidney (collecting tubule), the modulated reabsorption of $Na^+$ through ENaC provides the primary mechanism of the regulation of urinary $Na^+$ excretion and thus allows the fine control of the whole organism $Na^+$ balance under the hormonal control of aldosterone. By its depolarizing effect on the apical membrane potential, the $Na^+$ channel also provides the driving force for tubular $K^+$ secretion.

Specific inhibitors of ENaC promote urinary $Na^+$ excretion and inhibit $K^+$ secretion; these drugs (including amiloride and triamterene), are therefore used as $K^+$-sparing diuretics. ENaC has a similar functional role in the distal colon, preventing excessive $Na^+$ loss in the stools. In airways, an important role is the reabsorption of the fluid that fills the airways at birth, promoting the shift from fluid secretion (before birth) to fluid reabsorption (postnatal).

With the cystic fibrosis transmembrane conductance regulator, it also participates in the delicate regulation of the fluid balance in the airways that maintains a thin mucosal fluid film necessary for mucus clearance. In the excretory ducts of the salivary and sweat glands, the activity of ENaC tends to decrease the luminal Na$^+$ concentration, allowing the excretion of a less salty saliva and preventing major loss of Na$^+$ in the sweat fluid. See, for example, Hummler et al. 1999 Am. J. Physiol. Gastrointest. Liver Physiol. 276: 567-571 and references cited therein.

Alterations and mutations in the sequence and/or expression of ENaC can lead to over-expression or hyper-activity of ENaC. Providing RNAi agents of this disclosure restores balance to the modulated reabsorption of Na$^+$ by reducing the level of the Beta-ENaC.

Beta-ENaC

By "Beta-ENaC" is meant the gene or protein amiloride-sensitive sodium channel subunit beta (or any nucleic acid encoding this protein), also variously designated: sodium channel, nonvoltage-gated 1, beta; SCNN1B; bENaC; ENaCb; ENaC-beta; SCNEB, or β-ENaC. Additional identifiers include: OMIM: 600760; MGI: 104696; HomoloGene: 284; and GeneCards: SCNN1B. Additional information can be found: Human: Entrez 6338; Ensembl ENSG00000168447; UniProt P51168; RefSeq (mRNA) NM_000336; RefSeq (protein) NP_000327; Location (UCSC) Chr 16: 23.22-23.3 Mb. Mouse: Entrez 20277; Ensembl ENSMUSG00000030873; UniProt Q3TP51; RefSeq (mRNA) NM_011325 RefSeq (protein) NP_035455; Location (UCSC) Chr 7: 121.66-121.71 Mb.

The amino acid sequence of human Beta-ENaC is provided in Saxena et al. 1998 Biochem. Biophys. Res. Comm. 252: 208-213.

The functional domains of Beta-ENaC have been delineated. The protein has an intracellular N-terminal domain [amino acids ("aa") 1 to 50], a first transmembrane domain (aa 51 to 71), an extracellular loop (aa 72 to 533), a second transmembrane domain (aa 534 to 553), and a C-terminal intracellular domain (aa 554 to 640).

The C-terminal intracellular domain contains two regions wherein mutations relate to Liddle's syndrome and other diseases: in the region from amino acid 564 to 595 and the "PY" motif [with the amino acid consensus sequence PPXY at aa (amino acids) 615 to 618]. See, e.g., Saxena et al. 1998.

The Beta-ENaC RNAi agent of the present disclosure can interact with a portion of the mRNA corresponding to a specific functional domain or domains of Beta-ENaC. In various embodiments, the RNAi agents herein specifically bind to Beta-ENaC mRNA, in a sequence corresponding to a functional domain, e.g., in the N-terminal intracellular domain, in the first transmembrane domain, in the extracellular loop, in the second transmembrane domain, or in the C-terminal intracellular domain, or, more specifically, in the region from amino acid 564 to 595, or in the PY motif (amino acids 615 to 618).

In various embodiments, the RNAi agents of the present disclosure bind to the 5' or 3' UTR (i.e., untranslated region(s)).

In various embodiments, the RNAi agents of the present disclosure bind to Beta-ENaC mRNA, but not in a sequence corresponding to a particular functional domain, e.g., not in the N-terminal intracellular domain, not in the first transmembrane domain, not in the extracellular loop, not in the second transmembrane domain, or not in the C-terminal intracellular domain, or, more specifically, not in the region from amino acid 564 to 595, or not in the PY motif (amino acids 615 to 618).

In embodiments herein, binding of a RNAi agent to a particular region of the Beta-ENaC mRNA leads to reduced expression, level and/or activity of Beta-ENaC.

The efficacy of a RNAi agent in reducing the level of Beta-ENaC can be measured directly, e.g., by measuring the levels of Beta-ENaC mRNA abundance or levels of the protein itself. Alternatively, the efficacy of the RNAi can be measured indirectly by measuring the level of any one or more of the known activities of Beta-ENaC or by measuring changes in the activities of pathway components downstream of Beta-ENaC.

The protein's chief activity is to form, along with Alpha-ENaC and Gamma-ENaC, and, possibly at times, Delta-ENaC, the sodium channel ENaC. Beta-ENaC, Gamma-ENaC and Delta-ENaC may also form a particular type of channel found in the pancreas, testes and ovaries. Beta-ENaC has also been shown to interact with WWP2 and NEDD4. See., e.g., McDonald et al. (2002). Am. J. Physiol. Renal Physiol. 283 (3): F431-6; Harvey et al. 2001. J. Biol. Chem. 276 (11): 8597-601; Farr et al. (2000). Biochem. J. 345 Pt 3: 503-9. The activity of Beta-ENaC can be measured, for example, by its ability to bind and form functional units with these other biological components. The efficacy of a RNAi agent can also be measured indirectly by measuring the amount of surface liquid on mucus membranes, and via histological studies of tissues expressing Beta-ENaC.

Beta-ENaC Sequences in Various Species

A RNAi agent specific to Beta-ENaC can be designed such that the sequence thereof completely matches that of the mRNA corresponding to the human Beta-ENaC gene and the homologous gene from a test animal. Thus, the exact same RNAi agent can be used in both test animals (e.g., rat, mouse, cynomolgus monkey, etc.) and humans. The sequences for the various ENaC genes have been determined in many species, including humans, mouse, rat, bovine and chicken, as described in, inter alia, Garty et al. 1997 Physiol. Rev. 77: 359-396; and Ahn et al. 1999 Am. J. Physiol. 277:F121-F129.

The Beta-ENaC sequence in cynomolgus monkey (*Macaca fascicularis*, or "cyno") has been determined.

The alignment of the cyno Beta-ENaC mRNA (SEQ ID NO: 221) and human Beta-ENaC mRNA (SEQ ID NO: 222) sequences is shown below.

```
Cyno Beta-ENaC   --------------------------------------------------
Human Beta-ENaC  GTGCTTCCCCGCCCCTGAACCTGCTCCCTCCCAGTCGGTCTCGCCGCGCT    50

Cyno Beta-ENaC   ----------------------------------GGTACCCAGCTTGCT     15
Human Beta-ENaC  CGCCGGGTGTCCCAGTGTCACCAACACTCGGCCGCCGCCGCCAGCTTGGC    100
                                                   *  *******

Cyno Beta-ENaC   TGTTCTTTTTGCAGAAGCTCAGAATAAACGCTCAACTTTGGCAGATCAAT    65
Human Beta-ENaC  GCGCACCGCCGCCTCCGCCACCGCCGACAGCGCGCATCCTCCGTGTCCCC    150
                    **    **      *  ** *     *     *   **
```

```
Cyno Beta-ENaC    TCCCCGGGGATCCGA-ATTCGCCACCATGCACGTGAAGAAGTACCTGCTG       114
Human Beta-ENaC   GCTCCGCCGCCCGAGCAGGTGCCACTATGCACGTGAAGAAGTACCTGCTG       200
                   *  ***   *     *     ****  ***********************

Cyno Beta-ENaC    AAGTGCCTGCACCGGCTGCAGAAGGGCCCCGGCTACACGTACAAGGAGCT       164
Human Beta-ENaC   AAGGGCCTGCATCGGCTGCAGAAGGGCCCCGGCTACACGTACAAGGAGCT       250
                  ***  ****** **************************************

Cyno Beta-ENaC    GCTGGTGTGGTACTGCGATAACACCAACACCCACGGCCCCAAGCGTATCA       214
Human Beta-ENaC   GCTGGTGTGGTACTGCGACAACACCAACACCCACGGCCCCAAGCGCATCA       300
                  ****************** ************************* ****

Cyno Beta-ENaC    TCTGCGAGGGGCCCAAGAAGAAAGCCGTGTGGTTCCTGCTCACCCTGCTC       264
Human Beta-ENaC   TCTGTGAGGGGCCCAAGAAGAAAGCCATGTGGTTCCTGCTCACCCTGCTC       350
                  **** ******************** ************************

Cyno Beta-ENaC    TTCACTGCTCTCGTCTGCTGGCAGTGGGGCATCTTCATCAGGACCTACTT       314
Human Beta-ENaC   TTCGCCGCCCTCGTCTGCTGGCAGTGGGGCATCTTCATCAGGACCTACTT       400
                  *** *  ** ****************************************

Cyno Beta-ENaC    GAGCTGGGAGGTCAGCGTCTCCCTCTCCGTAGGCTTCAAGACCATGGACT       364
Human Beta-ENaC   GAGCTGGGAGGTCAGCGTCTCCCTCTCCGTAGGCTTCAAGACCATGGACT       450
                  **************************************************

Cyno Beta-ENaC    TCCCCGCCGTCACCATCTGCAATGCTAGCCCCTTCAAGTATTCCAAAGTC       414
Human Beta-ENaC   TCCCTGCCGTCACCATCTGCAATGCTAGCCCCTTCAAGTATTCCAAAATC       500
                  **** ****************************************** **

Cyno Beta-ENaC    AAGCATTTGCTGAAGGACCTGGATGAGCTGATGGAAGCTGTCCTGGAGAG       464
Human Beta-ENaC   AAGCATTTGCTGAAGGACCTGGATGAGCTGATGGAAGCTGTCCTGGAGAG       550
                  **************************************************

Cyno Beta-ENaC    AATCCTGGCTCCTGAGCTAAGCCATGCCAATGCCACCAGGACCCTGAACT       514
Human Beta-ENaC   AATCCTGGCTCCTGAGCTAAGCCATGCCAATGCCACCAGGAACCTGAACT       600
                  *****************************************  *******

Cyno Beta-ENaC    CTTCCATCTGGAACCACACACCACTGGTCCTTATTGATGAACGGAACCCC       564
Human Beta-ENaC   TCTCCATCTGGAACCACACACCCCTGGTCCTTATTGATGAACGGAACCCC       650
                   * ******************* ***************************

Cyno Beta-ENaC    CACCACCCCATGGTCCTCGATCTCTTTGGAGATAACCACAATGGCTTAAC       614
Human Beta-ENaC   CACCACCCCATGGTCCTTGATCTCTTTGGAGACAACCACAATGGCTTAAC       700
                  ***************** ************** *****************

Cyno Beta-ENaC    AAACAGCTCAGCATCAGAAAAGATCTGTAATGCCCATGGGTGCAAAATGG       664
Human Beta-ENaC   AAGCAGCTCAGCATCAGAAAAGATCTGTAATGCCCACGGGTGCAAAATGG       750
                  ** ********************************* *************

Cyno Beta-ENaC    CCATGAGACTATGTAGCCTCAACGGGACCCAGTGCACCTTCCGGAACTTC       714
Human Beta-ENaC   CCATGAGACTATGTAGCCTCAACAGGACCCAGTGTACCTTCCGGAACTTC       800
                  *********************** ********** ***************

Cyno Beta-ENaC    ACCAGCGCTACCCAGGCAGTGACAGAGTGGTACAGCCTGCAGGCCACCAA       764
Human Beta-ENaC   ACCAGTGCTACCCAGGCATTGACAGAGTGGTACATCCTGCAGGCCACCAA       850
                  ***** ************  ************** ***************

Cyno Beta-ENaC    CATCTTTGCGCAGGTGCCGCAGCAGGAGCTGGTGGAGATGAGCTACCCCG       814
Human Beta-ENaC   CATCTTTGCACAGGTGCCACAGCAGGAGCTAGTAGAGATGAGCTACCCCG       900
                  ********* ******** ***********  ** ***************

Cyno Beta-ENaC    GCGAGCAGATGATCCTGGCCTGCCTGTTTGGAGCTGAGCCCTGCAACTAC       864
Human Beta-ENaC   GCGAGCAGATGATCCTGGCCTGCCTATTCGGAGCTGAGCCCTGCAACTAC       950
                  *************************  ** ********************

Cyno Beta-ENaC    CGGAACTTCACGTCCATCTTCTACCCTCACTATGGCAACTGTTACATCTT       914
Human Beta-ENaC   CGGAACTTCACGTCCATCTTCTACCCTCACTATGGCAACTGTTACATCTT      1000
                  **************************************************

Cyno Beta-ENaC    CAACTGGGGCATGACAGAGAAGGCACTTCCTTCGGCCAACCCTGGACCTG       964
Human Beta-ENaC   CAACTGGGGCATGACAGAGAAGGCACTTCCTTCGGCCAACCCTGGAACTG      1050
                  ***********************************************  *

Cyno Beta-ENaC    AATTTGGCCTGAAGTTGATCCTGGACATAGGCCAGGAAGACTACGTCCCC      1014
Human Beta-ENaC   AATTCGGCCTGAAGTTGATCCTGGACATAGGCCAGGAAGACTACGTCCCC      1100
                  ****  ********************************************

Cyno Beta-ENaC    TTCCTCGCGTCCACGGCTGGGGTCAGGCTGATGCTTCACGAGCAGAGGTC      1064
Human Beta-ENaC   TTCCTTGCGTCCACGGCCGGGGTCAGGCTGATGCTTCACGAGCAGAGGTC      1150
                  ***** *********** ********************************
```

```
                     -continued
Cyno Beta-ENaC   ATACCCCTTCATCAGAGACGAGGGCATCTATGCCATGTCGGGGACAGAGA   1114
Human Beta-ENaC  ATACCCCTTCATCAGAGATGAGGGCATCTACGCCATGTCGGGGACAGAGA   1200
                 ****************** ********** *******************

Cyno Beta-ENaC   CGTCCATCGGGGTACTCGTGGACAAGCTTCAGCGCATGGGGGAGCCCTAC   1164
Human Beta-ENaC  CGTCCATCGGGGTACTCGTGGACAAGCTTCAGCGCATGGGGGAGCCCTAC   1250
                 **************************************************

Cyno Beta-ENaC   AGCCCGTGCACCGTGAATGGCTCCGAGGTCCCCGTCCAAAACTTCTACAG   1214
Human Beta-ENaC  AGCCCGTGCACCGTGAATGGTTCTGAGGTCCCCGTCCAAAACTTCTACAG   1300
                 ******************** ** **************************

Cyno Beta-ENaC   TGACTACAACACGACCTACTCCATCCAGGCCTGTCTTCGCTCCTGCTTCC   1264
Human Beta-ENaC  TGACTACAACACGACCTACTCCATCCAGGCCTGTCTTCGCTCCTGCTTCC   1350
                 **************************************************

Cyno Beta-ENaC   AAGACCACATGATCCGTAGCTGCAAGTGTGGGCACTACCTCTACCCACTG   1314
Human Beta-ENaC  AAGACCACATGATCCGTAACTGCAACTGTGGCCACTACCTGTACCCACTG   1400
                 ****************** ****** ***** ******** *********

Cyno Beta-ENaC   CCCCGTGGGGAGAAATACTGCAACAACCGGGACTTCCCAGACTGGGCCCA   1364
Human Beta-ENaC  CCCCGTGGGGAGAAATACTGCAACAACCGGGACTTCCCAGACTGGGCCCA   1450
                 **************************************************

Cyno Beta-ENaC   TTGCTACTCAGATCTGCAGATGAGCGTGGCGCAGAGAGAGACCTGCATTG   1414
Human Beta-ENaC  TTGCTACTCAGATCTACAGATGAGCGTGGCGCAGAGAGAGACCTGCATTG   1500
                 *************** **********************************

Cyno Beta-ENaC   GCATGTGCAAGGAATCCTGCAATGACACCCAGTACAAGATGACTATCTCC   1464
Human Beta-ENaC  GCATGTGCAAGGAGTCCTGCAATGACACCCAGTACAAGATGACCATCTCC   1550
                 ************* ***************************** ******

Cyno Beta-ENaC   ATGGCTGACTGGCCTTCTGAGGCCTCTGAGGACTGGATTTTCCACGTCTT   1514
Human Beta-ENaC  ATGGCTGACTGGCCTTCTGAGGCCTCCGAGGACTGGATTTTCCACGTCTT   1600
                 ************************** ***********************

Cyno Beta-ENaC   GTCTCAGGAGCGGGACCAAAGCACCAATATCACCCTGAGCAGGAAGGGAA   1564
Human Beta-ENaC  GTCTCAGGAGCGGGACCAAAGCACCAATATCACCCTGAGCAGGAAGGGAA   1650
                 **************************************************

Cyno Beta-ENaC   TTGTCAAGCTCAACATCTACTTCCAAGAATTTAACTATCGCACCATTGAA   1614
Human Beta-ENaC  TTGTCAAGCTCAACATCTACTTCCAAGAATTTAACTATCGCACCATTGAA   1700
                 **************************************************

Cyno Beta-ENaC   GAATCAGCAGCCAATAACCTCGTCTGGCTGCTCTCAAATCTGGGTGGCCA   1664
Human Beta-ENaC  GAATCAGCAGCCAATAACATCGTCTGGCTGCTCTCGAATCTGGGTGGCCA   1750
                 ****************** **************** **************

Cyno Beta-ENaC   GTTTGGCTTCTGGATGGGGGGCTCTGTGCTGTGCCTCATCGAGTTTGGGG   1714
Human Beta-ENaC  GTTTGGCTTCTGGATGGGGGGCTCTGTGCTGTGCCTCATCGAGTTTGGGG   1800
                 **************************************************

Cyno Beta-ENaC   AGATCATCATCGACTTTGTGTGGATCACCATCATCAAGCTGGTGGCCTTG   1764
Human Beta-ENaC  AGATCATCATCGACTTTGTGTGGATCACCATCATCAAGCTGGTGGCCTTG   1850
                 **************************************************

Cyno Beta-ENaC   GCCAAGAGCCTCCGGCAGCGGCGAGCCCAAGCCAGCTACTCCGGCCCACC   1814
Human Beta-ENaC  GCCAAGAGCCTACGGCAGCGGCGAGCCCAAGCCAGCTACGCTGGCCCACC   1900
                 ********** ************************** *  ********

Cyno Beta-ENaC   GCCCACGGTGGCTGAGCTGGTGGAGGCCCACACCAACTTCGGCTACCAGC   1864
Human Beta-ENaC  GCCCACCGTGGCCGAGCTGGTGGAGGCCCACACCAACTTTGGCTTCCAGC   1950
                 ****** ***** ************************** **** *****

Cyno Beta-ENaC   CTGACACGGCCCCCGCAGCCCCAACACCGGGCCCTACCCCAGTGAGCAG   1914
Human Beta-ENaC  CTGACACGGCCCCCGCAGCCCCAACACTGGGCCCTACCCCAGTGAGCAG   2000
                 *************************** **********************

Cyno Beta-ENaC   GCCCTGCCCATCCCGGGCACCCCGCCCCCCAACTATGACTCCCTGCGTCT   1964
Human Beta-ENaC  GCCCTGCCCATCCCCAGGCACCCCGCCCCCCAACTATGACTCCCTGCGTCT   2050
                 **************  **********************************

Cyno Beta-ENaC   GCAGCCACTGGACGTCATCGAGTCTGACAGTGAGGGTGATGCCATCTAA-   2013
Human Beta-ENaC  GCAGCCGCTGGACGTCATCGAGTCTGACAGTGAGGGTGATGCCATCTAAC   2100
                 ****** ******************************************

Cyno Beta-ENaC   ---GCGGCCGCCTAG---AAATAGCTTGATCTGGTTA--CCACTAAACCA   2055
Human Beta-ENaC  CCTGCCCCTGCCCACCCCGGGCGGCTGAAACTCACTGAGCAGCCAAGACT   2150
                    ** * *** *       ***  * **       *  * * **   *
```

```
                     -continued
Cyno Beta-ENaC    GC--CTCAAGAACAC-CCGAATGGAGTCTCT----AAGCTACATAATACC     2098
Human Beta-ENaC   GTTGCCCGAGGCCTCACTGTATGGTGCCCTCTCCAAAGGGTCGGGAGGGT     2200
                    *   * * ** * * * **** * *         ***   *   *

Cyno Beta-ENaC    AACTTACACTTTACAAAATGTTGTCCCCCAA-AATGTAGCCATTCGTATC     2147
Human Beta-ENaC   AGCTCTCCAGGCCAGAGCTTGTGTCCTTCAACAGAGAGGCCAGCGGCAAC     2250
                  * **  *         *  *  ***** *** *  *  ****    * * *

Cyno Beta-ENaC    TGCTCCTAATAAAAAGAAAGTTTCTTCACATTCTAAAAAAAAAAAAAAAA     2197
Human Beta-ENaC   TGGTCCGTTACTGGCCAAGGGCTCTGTAGAATCACGGTGCTGGTACAGGA     2300
                  ** ***          ** *  ***  * **           *   *  *

Cyno Beta-ENaC    AAAAAAAAAAAAAAAAAACCCCCCCC--CCCCCCCCCCTGCAGAGATCTG     2245
Human Beta-ENaC   TGCAGGAATAAATTGTATCTTCACCTGGTTCCTACCCTCGTCCCTACCTG     2350
                    *  ** ***      * *  * **        ** ***  *    * ***

Cyno Beta-ENaC    CTAGCTTGAGTATTCTATAGAGTCACCTAAATACT---------------     2280
Human Beta-ENaC   TCCTGATCCTGGTCCTGAAGACCCCTCGGAACACCCTCTCCTGGTGGCAG     2400
                       *     * ** ***  *  *  ** **

Cyno Beta-ENaC    --------------------------------------------------
Human Beta-ENaC   GCCACTTCCCTCCCAGTGCCAGTCTCCATCCACCCCAGAGAGGAACAGGC     2450

Cyno Beta-ENaC    --------------------------------------------------
Human Beta-ENaC   GGGTGGGCCATGTGGTTTTCTCCTTCCTGGCCTTGGCTGGCCTCTGGGGC     2500

Cyno Beta-ENaC    --------------------------------------------------
Human Beta-ENaC   AGGGGTGGTGGAGAGATGGAAGGGCATCAGGTGTAGGGACCCTGCCAAGT     2550

Cyno Beta-ENaC    ----------------------------------------------
Human Beta-ENaC   GGCACCTGATTTACTCTAGAAAATAAAAGTAGAAAATACTGAGTCCA     2597

Cyno Beta-ENaC    (SEQ ID NO: 221)
Human Beta-ENaC   (SEQ ID NO: 222)
```

The start (ATG) and stop (TAA) codons of the cyno and human sequences are underlined. Nucleotides matching between the human and cyno sequences are marked with an asterick (*).

In one embodiment, the Beta-ENaC RNAi agent of the present disclosure comprises a sequence which is identical in the human, rat and cyno Beta-ENaC mRNAs.

This sequence identity facilitates animal testing prior to human testing. In another embodiment, the Beta-ENaC RNAi agent comprises a sequence which is identical in the human, mouse and cyno Beta-ENaC mRNAs.

Additional Embodiments of a RNAi Agent to Beta-ENaC

In one embodiment, the Beta-ENaC RNAi agent comprises a sequence which does not match that of any other mRNA or gene. In one embodiment, the Beta-ENaC RNAi agent comprises a sequence which differs from all other known non-Beta-ENaC mRNAs or genes by at least 0, 1, 2 or 3 nucleotides.

In one embodiment, the Beta-ENaC RNAi agent of the present disclosure is administered to a patient in need thereof (e.g., a patient suffering from cystic fibrosis, pseudohypoaldosteronism type 1 (PHA1), Liddle's syndrome, hypertension, alkalosis, hypokalemia, and obesity-associated hypertension).

The patient can also be administered more than one RNAi agent specific to Beta-ENaC. In one embodiment, the Beta-ENaC RNAi agent(s) of the present disclosure can optionally be administered along with one or more additional pharmaceutical agent appropriate for that disease. In one embodiment, the Beta-ENaC RNAi agent(s) of the present disclosure can be optionally administered along with any other appropriate additional treatment, wherein the additional treatment can be a composition or a method.

In the case of cystic fibrosis, pseudohypoaldosteronism type 1 (PHA1), Liddle's syndrome, hypertension, alkalosis, hypokalemia, and/or obesity-associated hypertension, the RNAi agent(s) and additional disease treatment(s) can be administered in any order, simultaneously or sequentially, or in one or multiple doses over time.

Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

RNAi Agent

In one embodiment, the present disclosure pertains to a Beta-ENaC RNAi agent or other composition comprising at least an antisense nucleic acid sequence complementary to a Beta-ENaC nucleic acid (or portion thereof), or pertains to a recombinant expression vector encoding the siRNA or composition comprising the antisense nucleic acid that can function as an RNAi as defined below. As used herein, an "antisense" nucleic acid comprises a nucleotide sequence complementary to a "sense" nucleic acid encoding the Beta-ENaC protein (e.g., complementary to the coding strand of a double-stranded DNA, complementary to an mRNA or complementary to the coding strand of a Beta-ENaC gene or nucleic acid).

As used herein, the term "RNAi agent to Beta-ENaC," "RNAi agent specific to Beta-ENaC," "iRNA agent to Beta-ENaC," "siRNA to Beta-ENaC", "Beta-ENaC siRNA" and the like refer to a siRNA (short inhibitory RNA), shRNA (short or small hairpin RNA), iRNA (interference RNA) agent, RNAi (RNA interference) agent, dsRNA (double-stranded RNA), microRNA, and the like, and refer to a composition which specifically targets, is specific to, and/or binds to a Beta-ENaC mRNA. As used herein, the term "antisense nucleic acid" or "composition comprising an anti-sense nucleic acid" and the like is broadly meant to encompass any composition comprising at least one nucleic acid strand which is anti-sense to its target; this includes, but is not limited to, any siRNA, shRNA, iRHA, dsRNA, microRNA, antisense oligonucleotide, and any other composition comprising an anti-sense nucleic acid. As used herein, the terms "iRNA" and "RNAi" refers to an agent that contains RNA (or a derivative thereof), and which mediates the targeted cleavage of another RNA transcript via an RNA-induced silencing complex (RISC) pathway. In one embodiment, the RNAi agent is an oligonucleotide composition that activates the RISC complex/pathway. In another embodiment, the RNAi agent comprises an antisense strand sequence (antisense oligonucleotide).

The RNAi agent(s) of the present disclosure target (e.g., bind to, anneal to, etc.) the Beta-ENaC mRNA. The use of the RNAi agent specific to Beta-ENaC results in a decrease of Beta-ENaC activity, level and/or expression, e.g., a "knockdown" or "knock-out" of the target gene or target sequence. Particularly in one embodiment, in the case of a disease state characterized by over-expression or hyper-activity of Beta-ENaC, administration of a RNAi agent to Beta-ENaC knocks down the Beta-ENaC target enough to restore a normal level of Beta-ENaC activity and/or a normal level of $Na^+$ reabsorption.

In one embodiment, the RNAi comprises a single strand (such as an shRNA, as described herein).

In various embodiments, one or both strands are nicked.

In one embodiment, a single-stranded RNAi agent oligonucleotide or polynucleotide can comprise the sense and/or antisense strand. See, e.g., Sioud 2005 J. Mol. Biol. 348: 1079-1090, and references cited therein. Thus the present disclosure encompasses RNAi agents with a single strand comprising either the sense or antisense strand of a RNAi agent described herein.

siRNAs that are particularly useful for this disclosure include those which can bind specifically to a region of the Beta-ENaC mRNA, and have one or more of the following qualities: binding in the coding segment of Beta-ENaC; binding at or near the junction of the 5' untranslated region and the start of the coding segment; binding at or near the translational start site of the mRNA; binding at, across or near junctions of exons and introns; little or no binding to the mRNAs or transcripts of other genes (little or no "off-target effects"); binding to the Beta-ENaC mRNA in or near a region or regions that is not double-stranded or a stem region, e.g., in a loop or single-stranded portion; eliciting little or no immunogenicity; binding in a segment of the Beta-ENaC mRNA sequence which is conserved among various animal species (including human, mouse, rat, cyno, etc.), as the presence of a conserved sequence facilitates testing using various laboratory animals; binding to double-stranded region(s) of the mRNA; binding to an AT-rich region (e.g., at least about 50, 51, 52, 53, 54, 55, 56, 57, 58, 59, or 60% AT-rich); and/or lacking particular sequences known or suspected to decrease siRNA activity, e.g., the presence of a GG sequence at the 5' end, which may decrease separation of the double-stranded portion of the siRNA. In one embodiment, the RNAi agent specific to Beta-ENaC can be a double-stranded RNA having any one or more of these qualities.

The term "double-stranded RNA" or "dsRNA," as used herein, refers to a RNAi agent comprising a first and a second strand; e.g., a composition that includes an RNA molecule or complex of molecules having a hybridized duplex region (i.e., a region where the nucleotide bases from the first strand and the second strand are paired) that comprises two anti-parallel and substantially complementary nucleic acid strands, which will be referred to as having "sense" and "antisense" orientations with respect to a target RNA. The antisense strand, with respect to the mRNA target, is also called the "guide" strand, and the sense strand is also called the "passenger" strand. The passenger strand can include at least one or more of the following: one or more extra nucleotides (e.g., a bulge or 1 nt loop) compared to the other strand, a nick, a gap, etc., compared to the other strand. In various embodiments, the RNAi agent comprises a first strand and a second strand. In various embodiments, the first strand is the sense strand and the second strand is the anti-sense strand. In other embodiments, the first strand is the anti-sense strand, and the second strand is the sense strand.

The duplex region can be of any length that permits specific degradation of a desired target RNA through a RISC pathway, but will typically range from 9 to 36 base pairs ("bp") in length, e.g., 15-30 bp in length. Considering a duplex between 9 and 36 bp, the duplex can be any length in this range, for example, 9, 10, 11, 12, 13, 14, 15, 16, 17, 18, 19, 20, 21, 22, 23, 24, 25, 26, 27, 28, 29, 30, 31, 32, 33, 34, 35, or 36 bp and any sub-range therebetween, including, but not limited to 15-30 bp, 15-26 bp, 15-23 bp, 15-22 bp, 15-21 bp, 15-20 bp, 15-19 bp, 15-18 bp, 15-17 bp, 18-30 bp, 18-26 bp, 18-23 bp, 18-22 bp, 18-21 bp, 18-20 bp, 19-30 bp, 19-26 bp, 19-23 bp, 19-22 bp, 19-21 bp, 19-20 bp, 19 bp, 20-30 bp, 20-26 bp, 20-25 bp, 20-24 bp, 20-23 bp, 20-22 bp, 20-21 bp, 20 basepairs, 21-30 bp, 21-26 bp, 21-25 bp, 21-24 bp, 21-23 bp, 21-22 bp, 21 bp, 22 bp, or 23 bp. The dsRNAs generated in the cell by processing with Dicer and similar enzymes are generally in the range of about 19 to about 22 bp in length. One strand of the duplex region of a dsRNA comprises a sequence that is substantially complementary to a region of a target RNA. The two strands forming the duplex structure can be from a single RNA molecule having at least one self-complementary duplex region, or can be formed from two or more separate RNA molecules that hybridize to form the duplex. Where the duplex region is formed from two self-complementary regions of a single molecule, the molecule can have a duplex region separated by a single-stranded chain of nucleotides (herein referred to as a "hairpin loop", e.g., such as found in an shRNA construct) between the 3'-end of one strand and the 5'-end of the respective other strand forming the duplex structure. The hairpin loop can comprise at least one unpaired nucleotide; in some embodiments the hairpin loop can comprise at least 3, at least 4, at least 5, at least 6, at least 7, at least 8, at least 9, at least 10, at least 20, at least 23 or more unpaired nucleotides. Where the two substantially complementary strands of a dsRNA are comprised by separate RNA molecules, those molecules need not, but can be covalently connected. Where the two strands are connected covalently by a hairpin loop, the construct is generally referred to herein and in the art as a "shRNA". Where the two strands are connected covalently by means other than a hairpin loop, the connecting structure is referred to as a "linker."

RNA Interference

RNA interference (RNAi) is a post-transcriptional, targeted gene-silencing technique that uses double-stranded RNA (dsRNA) to degrade messenger RNA (mRNA) containing the same sequence as the dsRNA. The process of RNAi occurs when ribonuclease III (Dicer) cleaves the longer dsRNA into shorter fragments called siRNAs. siRNAs (small interfering RNAs) are typically about 21 to 23 nucleotides long and comprise about 19 base pair duplexes. The smaller RNA segments then mediate the degradation of the target mRNA. Dicer has also been implicated in the excision of 21- and 22-nucleotide small temporal RNAs (stRNAs) from precursor RNA of conserved structure that are implicated in translational control. Hutvagner et al. 2001, Science, 293, 834. The RNAi response also features an endonuclease complex, commonly referred to as an RNA-induced silencing complex (RISC), which mediates cleavage of single-stranded mRNA complementary to the antisense strand of the siRNA. Cleavage of the target RNA takes place in the middle of the region complementary to the antisense strand of the siRNA duplex.

In one aspect, an RNA interference agent includes a single-stranded RNA that interacts with a target RNA sequence to direct the cleavage of the target RNA. Without wishing to be bound by theory, long double-stranded RNA introduced into plants and invertebrate cells is broken down into siRNA by a Type III endonuclease known as Dicer (Sharp et al., Genes Dev. 2001, 15:485). Dicer, a ribonuclease-III-like enzyme, processes the dsRNA into 19-23 base pair short interfering RNAs with characteristic two base 3' overhangs (Bernstein, et al., (2001) Nature 409:363). The siRNAs are then incorporated into an RNA-induced silencing complex (RISC) where one or more helicases unwind the siRNA duplex, enabling one of the now unpaired siRNA strands to act as a "guide" strand to guide target recognition (Nykanen, et al., (2001) Cell 107:309). Upon binding of the antisense guide strand to the appropriate target mRNA, one or more endonucleases within the RISC cleaves the target to induce silencing (Elbashir, et al., (2001) Genes Dev. 15:188). Thus, in one aspect the present disclosure relates to a single-stranded RNA that promotes the formation of a RISC complex to effect silencing of the target gene.

RNA interference has also been studied in a variety of systems. Work in *Drosophila* embryonic lysates (Elbashir et al. 2001 EMBO J. 20: 6877 and Tuschl et al. International PCT Publication No. WO 01/75164) has revealed certain requirements for siRNA length, structure, chemical composition, and sequence that are essential to mediate efficient RNAi activity in a variety of systems, including especially mammals. These studies have shown that 21-nucleotide siRNA duplexes are most active when containing 3'-terminal dinucleotide overhangs. Substitution of the 3'-terminal siRNA overhang nucleotides with 2'-deoxy nucleotides (2'-H) was tolerated. In addition, a 5'-phosphate on the target-complementary strand of a siRNA duplex is usually required for siRNA activity. Most importantly for therapeutic use, siRNA duplexes shorter than 50 bp or so do not activate the interferon response in mammalian cells. See, e.g., Tuschl et al., WO 01/752164.

The dsRNA molecules (RNAi agents) described herein are thus useful in RNA interference of Beta-ENaC.

Features of a RNAi Agent: Sense Strand, Antisense Strand and (Optional) Overhangs In various embodiments, the RNAi agents comprise a first strand and a second strand, e.g., a sense strand and an antisense strand and, optionally, one or both ends of the duplex containing unpaired nucleotides referred to herein as overhangs.

The term "antisense strand" refers to the strand of a RNAi agent which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches may be in the internal or terminal regions of the molecule. Generally, the most tolerated mismatches are in the terminal regions, e.g., within 5, 4, 3, or 2 nucleotides of the 5' and/or 3' terminus.

The term "sense strand," as used herein, refers to the strand of a RNAi agent that includes a region that is substantially complementary to a region of the antisense strand as that term is defined herein.

The sequence of a gene may vary from individual to individual, especially at wobble positions within the coding segment, or in the untranslated region; individuals may also differ from each other in coding sequence, resulting in additional differences in mRNA. The sequence of the sense and antisense strands of the RNAi agent can thus be designed to correspond to that of an individual patient, if and where needed. RNAi agents can also be modified in sequence to reduce immunogenicity, binding to undesired mRNAs (e.g., "off-target effects") or to increase stability in the blood. These sequence variants are independent of chemical modification of the bases or 5' or 3' or other end-caps of the RNAi agents.

The RNAi agents can also have overhangs of 0, 1, or 2 overhangs; in the case of a 0 nt overhang, they are blunt-ended. A RNAi agent can have 0, 1 or 2 blunt ends. In a "blunt-ended RNAi agent" both strands terminate in a base-pair; thus a blunt-ended molecule lacks either 3' or 5' single-stranded nucleotide overhangs.

As used herein, the term "overhang" or "nucleotide overhang" refer to at least one unpaired nucleotide that protrudes from the end of at least one of the two strands of the duplex structure of a RNAi agent. For example, when a 3'-end of one strand of a dsRNA extends beyond the 5'-end of the other strand, or vice versa, the unpaired nucleotide(s) form the overhang. A dsRNA can comprise an overhang of at least one nucleotide; alternatively the overhang can comprise at least two nucleotides, at least three nucleotides, at least four nucleotides, at least five nucleotides or more. An overhang can comprise or consist of a nucleotide/nucleoside analog, including a deoxynucleotide/nucleoside. The overhang(s) may be on the sense strand, the antisense strand or any combination thereof. Furthermore, the nucleotide(s) of an overhang can be present on the 5' end, 3' end or both ends of either an antisense or sense strand of a dsRNA.

The RNAi agent can also optionally comprise a cap. The term "cap" and the like include a chemical moiety attached to the end of a double-stranded nucleotide duplex, but is used herein to exclude a chemical moiety that is a nucleotide or nucleoside. A "3' Cap" is attached at the 3' end of a nucleotide or oligonucleotide. A "5' Cap" is attached at the 5' end of a nucleotide or oligonucleotide. In one embodiment, 3' end caps are as disclosed in, for example, WO 2005/021749 and WO 2007/128477.

The present disclosure thus contemplates a RNAi agent specific to Beta-ENaC comprising an antisense strand (which may be contiguous or connected via a linker or loop) in a RNAi agent. In a more specific embodiment, an RNAi agent comprises an antisense strand and a sense strand which together comprise a double-stranded or complementary region. In one embodiment, it can also optionally comprise one or two overhangs and/or one or two caps. The RNAi agent is used to induce RNA interference of Beta-ENaC.

Target and Complementary Sequences

The RNAi agents of the present disclosure target (e.g., specifically bind to, anneal to, etc.) the mRNA encoding the gene Beta-ENaC. The use of the RNAi agent specific to Beta-ENaC results in a decrease of Beta-ENaC activity, level and/or expression, e.g., a "knock-down" or "knock-out" of the target gene or target sequence. Particularly in one embodiment, in the case of a disease state characterized by over-expression or hyper-activity of Beta-ENaC, administration of a RNAi agent to Beta-ENaC knocks down the Beta-ENaC gene enough to restore a normal level of Beta-ENaC activity and/or a normal level of $Na^+$ reabsorption.

As used herein, "target sequence" or "target gene" refer to a contiguous portion of the nucleotide sequence of an mRNA molecule formed during the transcription of a gene, e.g., a Beta-ENaC gene, including mRNA that is a product of RNA processing of a primary transcription product. The target portion of the sequence will be at least long enough to serve as a substrate for iRNA-directed cleavage at or near that portion. For example, the target sequence will generally be from 9-36 nucleotides ("nt") in length, e.g., 15-30 nt in length, including all sub-ranges therebetween. As non-limiting examples, the target sequence can be from 15-30 nt, 15-26 nt, 15-23 nt, 15-22 nt, 15-21 nt, 15-20 nt, 15-19 nt, 15-18 nt, 15-17 nt, 18-30 nt, 18-26 nt, 18-23 nt, 18-22 nt, 18-21 nt, 18-20 nt, 19-30 nt, 19-26 nt, 19-23 nt, 19-22 nt, 19-21 nt, 19-20 nt, 19 nt, 20-30 nt, 20-26 nt, 20-25 nt, 20-24 nt, 20-23 nt, 20-22 nt, 20-21 nt, 20 nt, 21-30 nt, 21-26 nt, 21-25 nt, 21-24 nt, 21-23 nt, or 21-22 nt, 21 nt, 22 nt, or 23 nt. The sense and antisense strands of the RNAi comprise a sequence complementary to that of the target nucleic acid, Beta-ENaC.

As used herein, and unless otherwise indicated, the term "complementary" refers to the ability of an oligonucleotide or polynucleotide comprising a first nucleotide sequence to hybridize and form a duplex structure under certain conditions with an oligonucleotide or polynucleotide comprising a second nucleotide sequence. Such conditions can, for example, be stringent, e.g., 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but are not limited to, G:U Wobble or Hoogstein base pairing.

The terms "complementary," "fully complementary" and "substantially complementary" herein may furthermore be used with respect to the base matching between the sense strand and the antisense strand of a dsRNA, or between the antisense strand of a RNAi agent and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding Beta-ENaC). For example, a polynucleotide is complementary to at least a part of a Beta-ENaC mRNA if the sequence is substantially complementary to a non-interrupted portion of an mRNA encoding Beta-ENaC.

Complementary sequences within a RNAi agent, e.g., within a dsRNA as described herein, include base-paired oligonucleotides or polynucleotides comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they may form one or more, but generally not more than 5, 4, 3 or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single-stranded overhangs, such overhangs shall not be regarded as mismatches with regard to the determination of complementarity. For example, a duplex comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein. The term overhang describes an unpaired nucleotide at the 3' or 5' end of a double-stranded nucleotide duplex, as described above. In one embodiment, the overhang is 0 to 4 nt long and is on the 3' end.

Thus, the RNAi agent of the present disclosure is complimentary or substantially complimentary to a target sequence in the target Beta-ENaC and is double-stranded, comprising a sense and an antisense strand (which can be contiguous, linked via a loop, or otherwise joined), where the double-stranded region an be 9 to 36 bp long (particularly for example, 19-22 bp or 19-23 bp long), and can furthermore optionally comprise a 3' or 5' overhang, and the RNAi agent can furthermore comprise a 3' cap. The RNAi agent mediates RNA interference, down-regulating or inhibiting the level, expression and/or activity of Beta-ENaC, and/or establishing or re-establishing an approximately normal level of ENaC and/or Beta-ENaC activity, or other biological function related to ENaC.

RNAi Agents Lowering Beta-ENaC Level, Expression and/or Activity

RNAi agents for targeting Beta-ENaC include those which bind to a Beta-ENaC sequence provided herein and which work to reduce Beta-ENaC through a RNAi mechanism. Exemplary siRNAs to Beta-ENaC are provided, e.g., in Table 1.

The RNAi agents of the present disclosure silence, inhibit the expression of, down-regulate the expression of, and/or suppress the expression of the Beta-ENaC gene, such that an approximately normal level of Beta-ENaC activity, expression and/or level and/or $Na^+$ reabsorption is achieved.

In addition, in various embodiments, depending on the disease condition and biological context, it is acceptable to use the RNAi agents of the present disclosure to establish a level of Beta-ENaC expression, activity and/or level which is below the normal level, or above the normal level.

Any method known in the art can be use to measure changes in Beta-ENaC activity, level and/or expression induced by a Beta-ENaC siRNA. Measurements can be performed at multiple timepoints, prior to, during and after administration of the siRNA, to determine the effect of the siRNA.

The terms "silence," "inhibit the expression of," "down-regulate the expression of," "suppress the expression of," and the like, in so far as they refer to a Beta-ENaC gene, herein refer to the at least partial suppression of the expression of a Beta-ENaC gene, as manifested by a reduction of the amount of Beta-ENaC mRNA which may be isolated from or detected in a first cell or group of cells in which a Beta-ENaC gene is transcribed and which has or have been treated such that the expression of a Beta-ENaC gene is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\% \quad \text{Equation 1}$$

Alternatively, the degree of inhibition may be given in terms of a reduction of a parameter that is functionally linked to Beta-ENaC gene expression, e.g., the amount of protein encoded by a Beta-ENaC gene, alteration in lung fluid levels or mucus levels, etc. In principle, Beta-ENaC gene silencing may be determined in any cell expressing Beta-ENaC, either constitutively or by genomic engineering, and by any appropriate assay. However, when a reference or control is needed in order to determine whether a given RNAi agent inhibits the expression of the Beta-ENaC gene by a certain degree and therefore is encompassed by the instant disclosure, the assays provided in the Examples below shall serve as such reference.

For example, in certain instances, expression of a Beta-ENaC gene is suppressed by at least about 10%, 15%, 20%, 25%, 30%, 35%, 40%, 45%, or 50% by administration of a RNAi agent featured in the present disclosure. In some embodiments, a Beta-ENaC gene is suppressed by at least about 60%, 70%, or 80% by administration of a RNAi agent featured in the present disclosure. In some embodiments, a Beta-ENaC gene is suppressed by at least about 85%, 90%, or 95% or more by administration of a RNAi agent, as described herein.

The ability of a RNAi agent to suppress Beta-ENaC can be first tested in vitro (e.g., using test cells such as H441).

RNAi agents which can suppress Beta-ENaC in vitro can then be tested for immunostimulation using, for example, a PBMC (peripheral blood mononuclear cell) assay. RNAi agents can also be tested in animal tests. Test and control animals include those which over-express or under-express Beta-ENaC, as described in, for example, Hummer et al. 2005 J. Am. Soc. Nephrol. 16: 3160-3166; Randrianarison et al. 2007 Am. J. Physiol. Lung Cell. Mol. Physiol. 294: 409-416; Cao et al. 2006 Am. J. Physiol. Renal Physiol., and references cited therein. RNAi agents which suppress or alter the level, activity and/or expression of Beta-ENaC can be used in medicaments to treat various Beta-ENaC-related diseases.

By "lower" in the context of Beta-ENaC or a symptom of a Beta-ENaC-related disease is meant a statistically significant decrease in such level. The decrease can be, for example, at least 10%, at least 20%, at least 30%, at least 40% or more. If, for a particular disease, or for an individual suffering from a particular disease, the levels or expression of Beta-ENaC are elevated, treatment with a Beta-ENaC RNAi agent of the present disclosure can particularly reduce the level or expression of Beta-ENaC to a level considered in the literature as within the range of normal for an individual without such disorder. The level or expression of Beta-ENaC can be measured by evaluation of mRNA (e.g., via Northern blots or PCR), or protein (e.g., Western blots). The effect of a RNAi agent on Beta-ENaC expression can be determined by measuring Beta-ENaC gene transcription rates (e.g., via Northern blots; or reverse transcriptase polymerase chain reaction or real-time polymerase chain reaction). RT-PCR has been used to show that mRNA levels of Beta-ENaC are high in kidney, pancreas and prostate, and medium in liver and spleen. Brauner-Osborne et al. 2001. Biochim. Biophys. Acta 1518: 237-248. Direct measurements can be made of levels of Beta-ENaC (which is expressed by the cell surface), e.g. by Western blots of tissues in which Beta-ENaC is expressed.

As used herein, "down-regulates" refers to any statistically significant decrease in a biological activity and/or expression of Beta-ENaC, including full blocking of the activity (i.e., complete inhibition) and/or expression. For example, "down-regulation" can refer to a decrease of at least about 10, 20, 30, 40, 50, 60, 70, 80, 90 or 100% in Beta-ENaC level, activity and/or expression.

As used herein, the term "inhibit" or "inhibiting" Beta-ENaC refers to any statistically significant decrease in biological level, activity and/or expression of Beta-ENaC, including full blocking of the activity and/or expression. For example, "inhibition" can refer to a decrease of at least about 10, 20, 30, 40, 50, 60, 70, 80, 90 or 100% in Beta-ENaC level, activity and/or expression. As used herein, the term "inhibit" similarly refers to a significant decrease in level, activity and/or expression, while referring to any other biological agent or composition.

By "level", it is meant that the Beta-ENaC RNAi agent can alter the level of Beta-ENaC, e.g., the level of Beta-ENaC mRNA or the level of Beta-ENaC protein, or the level of activity of Beta-ENaC.

Some diseases, such as cystic fibrosis, are characterized by excessive ENaC-mediated $Na^+$ absorption. Particularly in one embodiment, in the case of a disease characterized by over-expression and/or hyper-activity of Beta-ENaC, administration of a RNAi agent to Beta-ENaC reduces the level, expression and/or activity of Beta-ENaC. However, excessively low levels of Beta-ENaC can also lead to impairment of lung fluid clearance and renal dysfunction. Randrianarison et al. 2007 Am. J. Physiol. Lung Cell. Mol. Physiol. 294: 409-416. Thus, in various embodiments, administration of a RNAi agent to Beta-ENaC particularly establishes or re-establishes a normal or approximately normal level of Beta-ENaC activity, expression and/or level.

By "normal" or "approximately normal" in terms of level, expression and/or activity, is meant at least: about 50%, about 60%, about 70%, about 80%, about 90%, and/or about 100%; and/or no more than: about 100%, about 120%, about 130%, about 140%, or about 150% of the level, expression or activity of Beta-ENaC in a healthy cell, tissue, or organ. This can be measured using, for example, lung or kidney homogenates, as described in Gambling et al. 2004 Kidney Intl. 65: 1774-1781. Particularly in one embodiment, administration of the appropriate amount of the appropriate Beta-ENaC RNAi agent restores Beta-ENaC level, activity and/or expression and/or $Na^+$ reabsorption levels to about 50% to about 150%, more particularly about 60% to about 140%, more particularly to about 70% to about 130%, more particularly to about 80% to about 120%, more particularly to about 90% to about 110%, and most particularly to about 100% of that of a healthy cell, tissue or organ. The level of Beta-ENaC activity can also be indirectly measured by lung fluid balance. Lung fluid balance can be estimated by calculating bloodless, wet-to-dry lung weight ratios, which reflect the amount of extra-vascular lung water. Randrianarison et al. 2007 Am. J. Physiol. Lung Cell. Mol. Physiol. 294: 409-416. The level of Beta-ENaC activity can also be indirectly measured by histological studies of the lung, particularly the bronchioles, alveolar ducts, alveolar epithelium, and blood vessels. Randrianarison et al. 2007; and Zhou et al. 2008 Am. J. Resp. Crit. Care Med. 178: 1245-1256. Administration of a Beta-ENaC RNAi to a patient with a Beta-ENaC-related disease thus particularly restores the level, activity, and/or expression of Beta-ENaC and the level of $Na^+$ reabsorption to an approximately normal level, as determined by direct measurements of Beta-ENaC mRNA or protein levels, or indirect determinations, such as analyses of histological samples or levels of lung fluid.

In addition, in various embodiments, depending on the disease condition and biological context, it is acceptable to use the RNAi agents of the present disclosure to establish a level of Beta-ENaC expression, activity and/or level which is below the normal level, or above the normal level.

Various factors are known to alter the level of ENaC or, specifically, Beta-ENaC. Hormones that increase the physiological activity of ENaC include aldosterone, vasopressin and insulin. Beta-ENaC is specifically up-regulated by vasopressin and water restriction, as well as during sodium-bicarbonate loading in rats. These various factors can be used as controls in determining the effect of a RNAi agent on Beta-ENaC level.

Types of RNAi Agents and Modification Thereof

The use of RNAi agents or compositions comprising an antisense nucleic acid to down-modulate the expression of a particular protein in a cell is well known in the art. A RNAi agent comprises a sequence complementary to, and is capable of hydrogen binding to, the coding strand of another nucleic acid (e.g., an mRNA). Thus, in various embodiments, the RNAi agents of the present disclosure encompass any RNAi agents which target (e.g., are complementary, capable of hydrogen binding to, etc.) any sequence presented, e.g., in Table 1.

Antisense sequences complementary to an mRNA can be complementary to the coding region, the 5' or 3' untranslated region of the mRNA, and/or a region bridging the coding and untranslated regions, and/or portions thereof. Furthermore, a RNAi agent or a portion thereof can be complementary to a regulatory region of the gene encoding the mRNA, for instance a transcription or translation initiation sequence or regulatory element. Particularly, a RNAi agent or a portion thereof can be complementary to a region preceding or spanning the initiation codon on the coding strand or in the 3' untranslated region of an mRNA.

RNAi agent molecules can be designed according to the rules of Watson and Crick base pairing. The RNAi agent can be complementary to the entire coding region of Beta-ENaC mRNA, but more particularly is an oligonucleotide which is antisense to only a portion of the coding or non-coding region of Beta-ENaC mRNA. For example, the antisense oligonucleotide can be complementary to the region surrounding the translation start site of Beta-ENaC mRNA. An antisense oligonucleotide can be, for example, about 5, 10, 15, 19, 20, 21, 22, 23, 24, 25, 30, 35, 40, 45 or 50 nucleotides in length.

The RNAi agent may have modifications internally, or at one or both ends. The modifications at the ends can help stabilize the RNAi agent, protecting it from degradation by nucleases in the blood. The RNAi agents may optionally be directed to regions of the Beta-ENaC mRNA known or predicted to be near or at splice sites of the gene; e.g., exon-intron junctions (as described in, for example, Saxena et al. 1998).

The RNAi agents can also optionally be designed to anneal to known or predicted exposed and/or single-stranded regions of the mRNA (e.g., loops).

A RNAi agent can be constructed using chemical synthesis and enzymatic ligation reactions using procedures known in the art. For example, RNAi agent can be chemically synthesized using naturally-occurring nucleotides or variously modified nucleotides designed to decrease off-target effects, and/or increase the biological stability of the molecules or to increase the physical stability of the duplex formed between the antisense and sense nucleic acids, e.g., phosphorothioate derivatives and acridine substituted nucleotides can be used.

"G," "C," "A," "T" and "U" each generally stand for a nucleotide that contains guanine, cytosine, adenine, thymidine and uracil as a base, respectively. However, the term "ribonucleotide" or "nucleotide" can also refer to a modified nucleotide or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of dsRNA featured in the present disclosure by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the present disclosure.

The skilled artisan will recognize that the term "RNA molecule" or "ribonucleic acid molecule" encompasses not only RNA molecules as expressed or found in nature (i.e., are naturally occurring), but also non-naturally occurring analogs and derivatives of RNA comprising one or more ribonucleotide/ribonucleoside analogs or derivatives as described herein or as known in the art. Strictly speaking, a "ribonucleoside" includes a nucleoside base and a ribose sugar, and a "ribonucleotide" is a ribonucleoside with one, two or three phosphate moieties. However, the terms "ribonucleoside" and "ribonucleotide" can be considered to be equivalent as used herein. The RNA can be modified in the nucleobase structure or in the ribose-phosphate backbone structure, e.g., as described herein below. However, the molecules comprising ribonucleoside analogs or derivatives must retain the ability to form a duplex. As non-limiting examples, an RNA molecule can also include at least one modified ribonucleoside, including but not limited to a 2'-O-methyl modified nucleotide, a nucleoside comprising a 5' phosphorothioate group, a terminal nucleoside linked to a cholesteryl derivative or dodecanoic acid bisdecylamide group, a locked nucleoside, an abasic nucleoside, a 2'-deoxy-2'-fluoro modified nucleoside, a 2'-amino-modified nucleoside, 2'-alkyl-modified nucleoside, morpholino nucleoside, an unlocked ribonucleotide (e.g., an acyclic nucleotide monomer, as described in WO 2008/147824), a phosphoramidate or a non-natural base comprising nucleoside, or any combination thereof. Alternatively, an RNA molecule can comprise at least two modified ribonucleosides, at least 3, at least 4, at least 5, at least 6, at least 7, at least 8, at least 9, at least 10, at least 15, at least 20 or more, up to the entire length of the dsRNA molecule. The modifications need not be the same for each of such a plurality of modified ribonucleosides in an RNA molecule. In one embodiment, modified RNAs contemplated for use in methods and compositions described herein are peptide nucleic acids (PNAs) that have the ability to form the required duplex structure and that permit or mediate the specific degradation of a target RNA via a RISC pathway.

Examples of modified nucleotides which can be used to generate the RNAi agent include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In one embodiment, the present disclosure encompasses modified any modified variant of any RNAi agent disclosed herein. The modified variant contains the same sequence, but can be modified to contain modifications in the phosphate, sugar, base, nucleotide, etc. For example, the modified variant can contain one or more of the modified nucleotides listed herein, for example a C replaced by a 2'-modified C.

In one aspect, a modified ribonucleoside includes a deoxyribonucleoside. In such an instance, a RNAi agent can comprise one or more deoxynucleosides, including, for example, a deoxynucleoside overhang(s), or one or more deoxynucleosides within the double-stranded portion of a dsRNA. However, it is self-evident that under no circumstances is a double-stranded DNA molecule encompassed by the term "RNAi agent."

Replacing the 3'-terminal nucleotide overhanging segments of a 21-mer siRNA duplex having two-nucleotide 3'-overhangs with deoxyribonucleotides does not have an adverse effect on RNAi activity. Replacing up to four nucleotides on each end of the siRNA with deoxyribonucleotides has been well tolerated, whereas complete substitution with deoxyribonucleotides results in no RNAi activity. International PCT Publication No. WO 00/44914, and Beach et al. International PCT Publication No. WO 01/68836 preliminarily suggest that siRNA may include modifications to either the phosphate-sugar backbone or the nucleoside to include at least one of a nitrogen or sulfur heteroatom. Kreutzer et al. Canadian Patent Application No. 2,359,180, also describe certain chemical modifications for use in dsRNA constructs in order to counteract activation of double-stranded RNA-dependent protein kinase PKR, specifically 2'-amino or 2'-O-methyl nucleotides, and nucleotides containing a 2'-0 or 4'-C methylene bridge. Additional 3'-terminal nucleotide overhangs include dT (deoxythimidine), 2'-O,4'-C-ethylene thymidine (eT), and 2-hydroxyethyl phosphate (hp).

Parrish et al. 2000 Molecular Cell 6: 1077-1087 tested certain chemical modifications targeting the unc-22 gene in C. elegans using long (>25 nt) siRNA transcripts. The authors describe the introduction of thiophosphate residues into these siRNA transcripts by incorporating thiophosphate nucleotide analogs with T7 and T3 RNA polymerase and observed that RNAs with two phosphorothioate modified bases also had substantial decreases in effectiveness as RNAi. Further, Parrish et al. reported that phosphorothioate modification of more than two residues greatly destabilized the RNAs in vitro such that interference activities could not be assayed. Id. at 1081. The authors also tested certain modifications at the 2'-position of the nucleotide sugar in the long siRNA transcripts and found that substituting deoxynucleotides for ribonucleotides produced a substantial decrease in interference activity, especially in the case of Uridine to Thymidine and/or Cytidine to deoxy-Cytidine substitutions. Id. In addition, the authors tested certain base modifications, including substituting, in sense and antisense strands of the siRNA, 4-thiouracil, 5-bromouracil, 5-iodouracil, and 3-(aminoallyl) uracil for uracil, and inosine for guanosine. Whereas 4-thiouracil and 5-bromouracil substitution appeared to be tolerated, Parrish reported that inosine produced a substantial decrease in interference activity when incorporated in either strand. Parrish also reported that incorporation of 5-iodouracil and 3-(aminoallyl)uracil in the antisense strand resulted in a substantial decrease in RNAi activity as well.

Those skilled in the art will appreciate that it is possible to synthesize and modify the siRNA as desired, using any conventional method known in the art (see Henschel et al. 2004 DEQOR: a web-based tool for the design and quality control of siRNAs. Nucleic Acids Research 32 (Web Server Issue): W113-W120). Further, it will be apparent to those skilled in the art that there are a variety of regulatory sequences (for example, constitutive or inducible promoters, tissue-specific promoters or functional fragments thereof, etc.) which are useful for the antisense oligonucleotide, siRNA, or shRNA expression construct/vector.

There are several examples in the art describing sugar, base, phosphate and backbone modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-fluoro, 2'-O-methyl, 2'-O-allyl, 2'-H, nucleotide base modifications (for a review see Usman and Cedergren 1992 TIBS. 17: 34; Usman et al. 1994 Nucleic Acids Symp. Ser. 31: 163; Burgin et al. 1996 Biochemistry 35: 14090). Sugar modification of nucleic acid molecules are extensively described in the art.

Additional modifications and conjugations of RNAi agents have been described. Soutschek et al. 2004 Nature 432: 173-178 presented conjugation of cholesterol to the 3'-end of the sense strand of a siRNA molecule by means of a pyrrolidine linker, thereby generating a covalent and irreversible conjugate. Chemical modifications (including conjugation with other molecules) of RNAi agents may also be made to improve the in vivo pharmacokinetic retention time and efficiency.

In various embodiments, the RNAi agent to Beta-ENaC comprises at least one 5'-uridine-adenine-3' (5'-ua-3') dinucleotide, wherein the uridine is a 2'-modified nucleotide; at least one 5'-uridine-guanine-3' (5'-ug-3') dinucleotide, wherein the 5'-uridine is a 2'-modified nucleotide; at least one 5'-cytidine-adenine-3' (5'-ca-3') dinucleotide, wherein the 5'-cytidine is a 2'-modified nucleotide; and/or at least one 5'-uridine-uridine-3' (5'-uu-3') dinucleotide, wherein the 5'-uridine is a 2'-modified nucleotide.

In various embodiments, the RNAi agent comprises a 2'-modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).

In another embodiment, the RNAi comprises a gap or missing base. For example, the phosphate-sugar backbone may be present, but the base missing.

In another embodiment, the RNAi agent has a single-stranded nick (e.g., a break or missing bond in the backbone). In various embodiments, a single-stranded nick can be in either the sense or anti-sense strand, or both.

This nick can be, for example, in the sense strand, producing a small internally segmented interfering RNA, or sisiRNA, which may have less off-target effects than the corresponding RNAi agent without a nick.

The antisense nucleic acid or RNAi agent can also have an alternative backbone such as locked nucleic acids (LNA), Morpholinos, peptidic nucleic acids (PNA), threose nucleic acid (TNA), or glycol nucleic acid (GNA), and/or it can be labeled (e.g., radiolabeled or otherwise tagged).

One or both strands can comprise an alternative backbone

In yet another embodiment, the RNAi agent employed by the methods of the present disclosure can include an α-anomeric nucleic acid molecule. An α-anomeric nucleic acid molecule forms specific double-stranded hybrids with complementary RNA in which, contrary to the usual β-units, the strands run parallel to each other. Gaultier et al. 1987 Nucleic Acids. Res. 15: 6625-6641.

The antisense nucleic acid molecule can also comprise a 2'-o-methylribonucleotide (Inoue et al. 1987 Nucleic Acids Res. 15: 6131-6148) or a chimeric RNA-DNA analogue (Inoue et al. 1987 FEBS Lett. 215: 327-330).

In still another embodiment, a RNAi agent is a ribozyme. Ribozymes are catalytic RNA molecules with ribonuclease activity which are capable of cleaving a single-stranded nucleic acid, such as an mRNA, to which they have a complementary region. Thus, ribozymes [e.g., hammerhead ribozymes (described in Haselhoff et al. 1988, Nature 334: 585-591)] can be used to catalytically cleave Beta-ENaC mRNA transcripts to thereby inhibit translation of Beta-ENaC mRNA.

Alternatively, gene expression can be inhibited by targeting nucleotide sequences complementary to the regulatory region of Beta-ENaC (e.g., the promoter and/or enhancers) to form triple helical structures that prevent transcription of the Beta-ENaC gene. See generally, Helene 1991 Anticancer Drug Des. 6(6): 569-84; Helene et al. 1992 Ann. N.Y. Acad. Sci. 660: 27-36; and Maher 1992, Bioassays 14(12): 807-15.

Production of RNAi Agents

The RNAi agent can be produced biologically using an expression vector into which a nucleic acid has been subcloned in an antisense orientation (i.e., RNA transcribed from the inserted nucleic acid will be in an antisense orientation to a target nucleic acid of interest). The RNAi agent can also be produced biologically using an expression vector into which a nucleic acid has been subcloned as an shRNA construct (i.e., RNA transcribed from the inserted nucleic acid will have a first region in an antisense orientation to a target nucleic acid of interest, a second region that comprises a loop or hinge, and a third region in a sense orientation to the target nucleic acid of interest, wherein the first and third regions of the transcript preferably hybridizes with itself, thereby forming a stem-and-loop structure).

Methods of producing RNAi agents are well-known in the art and available to persons of ordinary skill in the art.

Kits for synthesis of RNAi are commercially available from, e.g., New England Biolabs and Ambion.

Delivery of RNAi Agents

RNAi agents of the present disclosure can be delivered or introduced (e.g., to a cell in vitro, to a test animal, or to a human) by any means known in the art.

The RNAi agents of the present disclosure are typically administered to a subject or generated in situ such that they hybridize with cellular mRNA and/or genomic DNA encoding Beta-ENaC, and inhibit expression by inhibiting transcription and/or translation. An example of a route of administration of the RNAi agent includes direct injection at a tissue site. Alternatively, RNAi agents can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using vectors well known in the art and described in, for example, US20070111230, the entire contents of which are incorporated herein. To achieve sufficient intracellular concentrations of the antisense molecules, vector constructs in which the antisense nucleic acid molecule is placed under the control of a strong pol II or pol III promoter are preferred.

"Introducing into a cell," when referring to a RNAi agent, means facilitating or effecting uptake or absorption into the cell, as is understood by those skilled in the art. Absorption or uptake of a RNAi agent can occur through unaided diffusive or active cellular processes, or by auxiliary agents or devices. The meaning of this term is not limited to cells in vitro; a RNAi agent may also be "introduced into a cell," wherein the cell is part of a living organism. In such an instance, introduction into the cell will include the delivery to the organism. For example, for in vivo delivery, a RNAi agent can be injected into a tissue site or administered systemically. In vivo delivery can also be by a beta-glucan delivery system, such as those described in U.S. Pat. Nos. 5,032,401 and 5,607,677, and U.S. Publication No. 2005/0281781. In vitro introduction into a cell includes methods known in the art such as electroporation and lipofection. Further approaches are described herein or known in the art.

Delivery of RNAi agent to tissue is a problem both because the material must reach the target organ and must also enter the cytoplasm of target cells. RNA cannot penetrate cellular membranes, so systemic delivery of naked RNAi agent is unlikely to be successful. RNA is quickly degraded by RNAse activity in serum. For these reasons, other mechanisms to deliver RNAi agent to target cells has been devised. Methods known in the art include but are not limited to: viral delivery (retrovirus, adenovirus, lentivirus, baculovirus, AAV); liposomes (Lipofectamine, cationic DOTAP, neutral DOPC) or nanoparticles (cationic polymer, PEI), bacterial delivery (tkRNAi), and also chemical modification (LNA) of siRNA to improve stability. Xia et al. 2002 Nat. Biotechnol. 20 and Devroe et al. 2002. BMC Biotechnol. 2 1: 15, disclose incorporation of siRNA into a viral vector. Other systems for delivery of RNAi agents are contemplated and the RNAi agents of the present disclosure can be delivered by various methods yet to be found and/or approved by the FDA or other regulatory authorities. RNAi agents of the present disclosure can delivered in a suitable pharmaceutical composition.

Pharmaceutical Compositions of RNAi Agents

As used here, a "pharmaceutical composition" comprises a pharmaceutically effective amount of one or more Beta-ENaC RNAi agent, a pharmaceutically acceptable carrier, and, optionally, an additional disease treatment which works synergistically with the RNAi agent. As used herein, "pharmacologically effective amount," "therapeutically effective amount" or simply "effective amount" refers to that amount of a RNAi agent effective to produce the intended pharmacological, therapeutic or preventive result. For example, if a given clinical treatment is considered effective where there is at least a 10% reduction in a measurable parameter associated with a disease or disorder, a therapeutically effective amount of a drug for the treatment of that disease or disorder is the amount necessary to effect at least a 10% reduction in that parameter. In this embodiment, a therapeutically effective amount of a RNAi agent targeting Beta-ENaC can reduce Beta-ENaC protein levels by at least 10%. In additional embodiments, a given clinical treatment is considered effective where there is at least a 15, 20, 25, 30, 35, 40, 45, 50, 55, 60, 65, 70, 75, 80, 85, 90 or 95% reduction in a measurable parameter associated with a disease or disorder, and the therapeutically effective amount of a drug for the treatment of that disease or disorder is the amount necessary to effect at least a 15, 20, 25, 30, 35, 40, 45, 50, 55, 60, 65, 70, 75, 80, 85, 90 or 95% reduction, respectively, in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. Agents included in drug formulations are described further herein.

The pharmaceutical compositions comprising a Beta-ENaC RNAi agent can be in solid form, for example, powders, granules, tablets, pills, gelcaps, gelatin capsules, liposomes, suppositories, chewable forms, or patches. The pharmaceutical compositions comprising a Beta-ENaC RNAi agent can also be presented in liquid form, for example, solutions, emulsions, suspensions, elixirs, or syrups. Appropriate liquid supports can be, for example, water, organic solvents such as polyol, such as glycerol or glycols, including propylene glycol and polyethylene glycol, or ethanol, Cremophor EL, or mixtures thereof, in varying proportions, in water. The compositions can comprise nano-sized amorphous or crystalline granules coated with albumin or a surfactant.

Appropriate supports can include, for example, antibacterial and antifungal agents, buffering agents, calcium phosphate, cellulose, methyl cellulose, chlorobutanol, cocoa butter, colorings, dextrin, emulsifiers, enteric coatings, flavorings, gelatin, isotonic agents, lecithin, magnesium stearate, perfuming agents, polyalcohols such as mannitol, injectable organic esters such as ethyl oleate, paraben, phenol sorbic acid, polyethylene glycol, polyvinylpyrrolidine, phosphate buffered saline (PBS), preserving agents, propylene glycol, sodium carboxymethylcellulose, sodium chloride, sorbitol, various sugars (including, but not limited to, sucrose, fructose, galactose, lactose and trehalose), starch, suppository wax, talc, vegetable oils, such as olive oil and corn oil, vitamins, wax, and/or wetting agents. For Beta-ENaC RNAi agents, a preferred support comprises dextran and water, e.g. 5% dextrose in water (D5W).

The biologically inert portion of the pharmaceutical composition can optionally be erodible, allowing timed release of the RNAi agent.

The pharmaceutical composition can comprise additional components which aid in delivery, stability, efficacy, or reduction of immunogenicity.

Pharmaceutical Composition Comprising a RNAi Agent to Beta-ENaC

Additional components of a pharmaceutical composition comprising a RNAi Agent to Beta-ENaC can be added to aid in delivery, stability, efficacy, or reduction of immunogenicity.

Liposomes have been used previously for drug delivery (e.g., delivery of a chemotherapeutic). Liposomes (e.g., cationic liposomes) are described in PCT publications WO02/100435A1, WO03/015757A1, and WO04029213A2; U.S. Pat. Nos. 5,962,016; 5,030,453; and 6,680,068; and U.S. Patent Application 2004/0208921. A process of making liposomes is also described in WO04/002453A1. Furthermore, neutral lipids have been incorporated into cationic liposomes (e.g., Farhood et al. 1995).

Cationic liposomes have been used to deliver RNAi agent to various cell types (Sioud and Sorensen 2003; U.S. Patent Application 2004/0204377; Duxbury et al., 2004; Donze and Picard, 2002).

Use of neutral liposomes disclosed in Miller et al. 1998, and U.S. Patent Application 2003/0012812.

As used herein, the term "SNALP" refers to a stable nucleic acid-lipid particle. A SNALP represents a vesicle of lipids coating a reduced aqueous interior comprising a nucleic acid such as an iRNA or a plasmid from which an iRNA is transcribed. SNALPs are described, e.g., in U.S. Patent Application Publication Nos. 20060240093, 20070135372, and in International Application No. WO 2009082817.

Chemical transfection using lipid-based, amine-based and polymer-based techniques, is disclosed in products from Ambion Inc., Austin, Tex.; and Novagen, EMD Biosciences, Inc, an Affiliate of Merck KGaA, Darmstadt, Germany); Ovcharenko D (2003) "Efficient delivery of siRNAs to human primary cells." Ambion TechNotes 10 (5): 15-16). Additionally, Song et al. (Nat. Med. published online (Fete I 0, 2003) doi: 10.1038/nm828) and others [Caplen et al. 2001 Proc. Natl. Acad. Sci. (USA), 98: 9742-9747; and McCaffrey et al. Nature 414: 34-39] disclose that liver cells can be efficiently transfected by injection of the siRNA into a mammal's circulatory system.

A variety of molecules have been used for cell-specific RNAi agent delivery. For example, the nucleic acid-condensing property of protamine has been combined with specific antibodies to deliver siRNAs. Song et al. 2005 Nat. Biotech. 23: 709-717. The self-assembly PEGylated polycation polyethylenimine (PEI) has also been used to condense and protect siRNAs. Schiffelers et al. 2004 Nucl. Acids Res. 32: e149, 141-1 10.

The siRNA-containing nanoparticles were then successfully delivered to integrin-overexpressing tumor neovasculature. Hu-Lieskovan et al. 2005 Cancer Res. 65: 8984-8992.

The RNAi agents of the present disclosure can be delivered via, for example, Lipid nanoparticles (LNP); neutral liposomes (NL); polymer nanoparticles; double-stranded RNA binding motifs (dsRBMs); or via modification of the RNAi agent (e.g., covalent attachment to the dsRNA).

Lipid nanoparticles (LNP) are self-assembling cationic lipid based systems. These can comprise, for example, a neutral lipid (the liposome base); a cationic lipid (for siRNA loading); cholesterol (for stabilizing the liposomes); and PEG-lipid (for stabilizing the formulation, charge shielding and extended circulation in the bloodstream).

The cationic lipid can comprise, for example, a headgroup, a linker, a tail and a cholesterol tail. The LNP can have, for example, good tumor delivery, extended circulation in the blood, small particles (e.g., less than 100 nm), and stability in the tumor microenvironment (which has low pH and is hypoxic).

Neutral Liposomes (NL) are Non-Cationic Lipid Based Particles.

Polymer nanoparticles are self-assembling polymer-based particles.

Double-stranded RNA binding motifs (dsRBMs) are self-assembling RNA binding proteins, which will need modifications.

In various embodiments, the RNAi agent to Beta-ENaC is ligated to one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

The RNAi agents of the present disclosure can be prepared in a pharmaceutical composition comprising various components appropriate for the particular method of administration of the RNAi agent.

Administration of a RNAi Agent

The pharmaceutical composition comprising a Beta-ENaC can be administered by buccal, inhalation (including insufflation and deep inhalation), nasal, oral, parenteral, implant, injection or infusion via epidural, intra-arterial, intra-articular, intra-capsular, intra-cardiac, intra-cerebroventricular, intracranial, intradermal, intramuscular, intra-orbital, intraperitoneal, intra-spinal, intrasternal, intrathecal, intravenous, subarachnoid, sub-capsular, subcutaneous, sub-cuticular, transendothelial, transtracheal, transvascular, rectal, sublingual, topical, and/or vaginal routes. This may be by injection, infusion, dermal patch, or any other method known in the art. The formulation can be powdered, nebulized, aerosolized, granulized or otherwise appropriately prepared for delivery. The administration, if liquid, may be slow or via bolus, though, under some circumstances known in the art, bolus injections may lead to loss of material through the kidneys.

The pharmaceutical compositions comprising a Beta-ENaC RNAi agent can be administered with medical devices known in the art. For example, in a particular embodiment, a RNAi agent can be administered with a needle-less hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present disclosure include: U.S. Pat. No. 4,487,603, which discloses an implantable microinfusion pump for dispensing medication at a controlled rate; U.S. Pat. No. 4,486,194, which discloses a therapeutic device for administering medications through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the pharmaceutical compositions comprising a RNAi agent can be formulated to ensure proper distribution in vivo. Administration of a RNAi agent to Beta-ENaC can be systemic (whole-body) or, particularly, targeted to tissues or organs that express (or over-express or demonstrate a hyper-activity of) Beta-ENaC, such as lung, kidney, colon, and glands. Methods for targeting these particular tissues or organs are described herein, and/or are known in the art. For example, they can be formulated in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29: 685).

Example targeting moieties include folate or biotin (see, e.g., U.S. Pat. No. 5,416,016 to Low et al.); mannosides (Umezawa et al., (1988) Biochem. Biophys. Res. Commun. 153: 1038); antibodies (P. G. Bloeman et al. (1995) FEBS Lett. 357: 140; M. Owais et al. (1995) Antimicrob. Agents Chemother. 39: 180); surfactant protein A receptor (Briscoe et al. (1995) Am. J. Physiol. 1233: 134), different species of which may comprise the formulations of the present disclosures, as well as components of the invented molecules; p120 (Schreier et al. (1994) J. Biol. Chem. 269: 9090); see also K. Keinanen; M. L. Laukkanen (1994) FEBS Lett. 346: 123; J. J. Killion; I. J. Fidler (1994) Immunomethods 4: 273.

The present disclosure thus encompasses pharmaceutical compositions comprising one or more RNAi agents to Beta-ENaC, which can optionally comprise various modifications and/or additional components, for use in treatment of Beta-ENaC-related diseases.

Beta-ENaC-Related Diseases

The present disclosure encompasses RNAi agents to Beta-ENaC and administration of the RNAi agents to humans and non-human animals to treat various Beta-ENaC-related diseases.

By "Beta-ENaC-related disease" is meant any disease related to a dysfunction in the level, expression and/or activity of Beta-ENaC, and/or any disease which can be treated and/or ameliorated by modulating the level, expression and/or activity of Beta-ENaC. In particular, it includes cystic fibrosis, pseudohypoaldosteronism type 1 (PHA1), Liddle's syndrome, hypertension, alkalosis, hypokalemia, and obesity-associated hypertension.

By "cystic fibrosis" or "CF" is meant the common hereditary disease associated with mutations in the cystic fibrosis transmembrane conductance regulator (CFTR) gene. CFTR encodes a cAMP-dependent Cl-channel and regulates the ENaC. In CF airway epithelia, CFTR-mediated Cl-secretion is defective and ENaC-mediated $Na^+$ absorption is increased. These ion transport defects in CF airways cause airway surface liquid (ASL) volume depletion, defective mucus clearance, and mucus adhesion, suggesting that ASL volume depletion is a key mechanism in the pathogenesis of CF lung disease. In experimental mice, airway-specific over-expression of Beta-ENaC demonstrates that accelerated $Na^+$ transport alone is sufficient to produce ASL volume depletion and CF-like lung disease, including airway mucus obstruction, goblet cell metaplasia, chronic neutrophilic airway inflammation, impaired clearance of bacterial pathogens, and ultimately mortality. See Zhou et al. 2008, and references cited therein.

By "Liddle's syndrome" is meant an autosomal dominant hereditary form of hypertension, characterized by an early and severe hypertension, often accompanied by metabolic alkalosis and hypokalemia, all signs that are characteristic of an excess of aldosterone (Conn's syndrome).

The plasma levels of aldosterone are low, however. Thus, Liddle's syndrome is also called pseudoaldosteronism. This severe form of hypertension is responsive to treatment with a low-salt diet and $Na^+$ channel inhibitors ($K^+$-sparing diuretics), suggesting a primary defective regulation of the ENaC. The disease is related to mutations in Gamma-ENaC, and also several mutations in Beta-ENaC(P615S, P616L, and Y618H in the "PY" motif which has a consensus sequence of PPXY; and also R564st, W574st, 579de132, Q589st, T592fr, A593fr, and R595fr, where "fr" is a frameshift, "del" is a deletion, and "st" is a premature stop codon).

These mutations cause an overexpression of the $Na^+$ channels that are hyperactive compared to the wild-type ENaC. The mutations also prevent the downregulation of the channel that normally occurs with a rise in intracellular $Na^+$; ENaC channels with the Liddle's mutation remain in a highly active state despite a high intracellular $Na^+$ concentration. Thus, the level and/or activity of a mutated ENaC with Liddle's Syndrome can be modulated by a siRNA to Beta-ENaC, or such a siRNA in combination with known treatments for Liddle's syndrome, such as a low-salt diet, and $Na^+$ channel inhibitors ($K^+$-sparing diuretics).

For additional information on Beta-ENaC-related diseases, see, for example, Hummler et al. 1999. Am. J. Physiol. Gastrointest. Liver Physiol. 276: 567-571.

By "obesity-associated hypertension" is meant hypertension related or associated with obesity, and the like. Obesity is associated with hypertension. Multiple mechanisms have been proposed to explain this correlation, including (in the obese) increased sympathetic activity; increased activity of the renin-angiotensin-aldosterone system; increased cardiac output; and increased mechanical pressure from interstitial fat around organs, hyperinsulinemia, and/or insulin resistance. Sodium retention by the kidney could result from any of these mechanisms. In the connecting tubule and the collecting duct, sodium reabsorption occurs through the ENaC. Levels of Beta-ENaC were increased in the kidney in Zucker rats (a model animal for obesity).

Bickel et al. 2001 Am. J. Physiol. Renal Physiol. 281: 639-648. The relative increases in abundance of this and other sodium transporters, without decreases in the other sodium transporters, likely results in enhanced tubular sodium reabsorption. As a result, these alterations in renal sodium transporter abundance might play a role in the development and/or maintenance of elevated blood pressures in obese mammals, including humans.

By "pseudohypoaldosteronism type 1", "PHA1", "PHA-1" and the like is meant a heterologous clinical syndrome characterized by mineralocorticoid end organ resistance, i.e., urinary loss of $Na^+$ and reduced $K^+$ excretion despite an elevated level of aldosterone. A severe form of this syndrome is inherited as an autosomal recessive trait, resulting in sometimes lethal episodes of hyponatremia, hypotension, and hyperkalemia, and shows alteration of $Na^+$ transport in several organs, kidney, salivary glands, sweat glands, and colon. In several families showing this form of PHA-1, links to mutations in any one of the three ENaC subunits are found (including G37S in Beta-ENaC).

A less severe form of PHA-1 with an autosomal dominant mode of inheritance is symptomatic mostly during infancy and improves with age. See Hummler et al. 1999. Am. J. Physiol. Gastrointest. Liver Physiol. 276: 567-571.

RNAi agents to Beta-ENaC can be used to treat Beta-ENaC-related diseases, particularly those diseases associated with altered expression, activity and/or levels of Beta-ENaC.

Use of RNAi Agents for Treatment of Beta-ENaC-Related Diseases

The RNAi agents to Beta-ENaC described herein can be formulated into pharmaceutical compositions which can be administered to humans or non-human animals. These compositions can comprise one or more RNAi agents, and, optionally, additional treatments useful for treating Beta-ENaC-related diseases. They can be administered as part of an early/preventative treatment, and can be administered in a therapeutically-effective dosage. The pharmaceutical composition can comprise a pharmaceutical carrier and can be administered by any method known in the art. These various aspects of the present disclosure are described in additional detail below.

RNAi agents to Beta-ENaC can be administered to humans and non-human animals for treatment of Beta-ENaC-related diseases.

In one embodiment of the present disclosure, the compositions comprising a Beta-ENaC RNAi agent can be administered to non-human animals. For example, the compositions can be given to chickens, turkeys, livestock animals (such as sheep, pigs, horses, cattle, etc.), companion animals (e.g., cats and dogs) and can have efficacy in treatment of cystic fibrosis, pseudohypoaldosteronism type 1 (PHA1), Liddle's syndrome, hypertension, alkalosis, hypokalemia, and obesity-associated hypertension and similar diseases. In each case, the RNAi agent to Beta-ENaC would be selected to match the sequence of the Beta-ENaC of the genome of the animal, and to, particularly, contain at least 1 nt mismatch from all other genes in that animal's genome. The RNAi agents of the present disclosure can thus be used in treatment of Beta-ENaC-related diseases in humans and non-human animals.

As used herein in the context of Beta-ENaC expression, the terms "treat," "treatment," and the like, refer to relief from or alleviation of pathological processes mediated by Beta-ENaC expression. In the context of the present disclosure insofar as it relates to any of the other conditions recited herein below (other than pathological processes mediated by Beta-ENaC expression), the terms "treat," "treatment," and the like mean to relieve or alleviate at least one symptom associated with such condition, or to slow or reverse the progression or anticipated progression of such condition, such as slowing the progression of a lipid disorder, such as atherosclerosis.

By "treatment" is also meant prophylaxis, therapy, cure, or any other change in a patient's condition indicating improvement or absence of degradation of physical condition. By "treatment" is meant treatment of Beta-ENaC-related disease (e.g., cystic fibrosis, pseudohypoaldosteronism type 1 (PHA1), Liddle's syndrome, hypertension, alkalosis, hypokalemia, and obesity-associated hypertension), or any appropriate treatment of any other ailment the patient has. As used herein, the terms "treatment" and "treat" refer to both prophylactic and preventative treatment and curative or disease-modifying treatment, including treatment of patients at risk of contracting a disease or suspected of having a disease, as well as patients already ill or diagnosed as suffering from a condition. The terms "treatment" and "treat" also refer to the maintenance and/or promotion of health in an individual not suffering from a disease but who may be susceptible to developing an unhealthy condition, such as nitrogen imbalance or muscle loss. In one embodiment, "treatment" does not encompass prevention of a disease state. Thus, the present disclosure is useful for suppressing expression of the Beta-ENaC gene and/or treating a Beta-ENaC-related disease in an individual afflicted by a Beta-ENaC-related disease, or an individual susceptible to a Beta-ENaC-related disease. An individual "afflicted" by a Beta-ENaC-related disease has demonstrated detectable symptoms characteristics of the disease, or had otherwise been shown clinically to have been exposed to or to carry Beta-ENaC-related disease pathogens or markers. As non-limiting examples, an individual afflicted by a Beta-ENaC-related disease can show outward symptoms; or can show no outward symptoms but can be shown with a clinical test to carry protein markers associated with a Beta-ENaC-related disease, or proteins or genetic material associated with a pathogen in the blood.

Early treatment of some Beta-ENaC-related diseases may be more efficacious if administered early rather than later. Preventative early administration of amiloride (an ENaC inhibitor) was useful in treating CF model mice, while later administration was not. Similarly, early intervention with antimicrobial agents in CF was more effective than treatment after infection was established. Zhou et al. 2008. Thus, in one particular embodiment, the RNAi agent to Beta-ENaC is administered early, prior to disease manifestation, and/or as a preventative agent, rather than administered after disease establishment.

Treatments of Beta-ENaC-related diseases can comprise various treatments, comprising a Beta ENaC RNAi agent, and optionally further comprising an additional treatment, which can be a method (or procedure), or an additional composition (e.g., an agent or additional RNAi agent).

Dosages and Effective Amounts of RNAi Agents

The RNAi agents of the present disclosure are administered in a dosage of a therapeutically effective amount to a patient in need thereof.

An "effective amount" or a "therapeutically effective amount" is an amount that treats a disease or medical condition of an individual, or, more generally, provides a nutritional, physiological or medical benefit to an individual. As used herein, the phrases "therapeutically effective amount" and "prophylactically effective amount" refer to an amount that provides a therapeutic benefit in the treatment, prevention, or management of pathological processes mediated by Beta-ENaC expression or an overt symptom of pathological processes mediated by Beta-ENaC expression. The specific amount that is therapeutically effective can be readily determined by an ordinary medical practitioner, and may vary depending on factors known in the art, such as, for example, the type of pathological processes mediated by Beta-ENaC expression, the patient's history and age, the stage of pathological processes mediated by Beta-ENaC expression, and the administration of other agents that inhibit pathological processes mediated by Beta-ENaC expression.

In various embodiments of the present disclosure, the patient is at least about 1, 3, 6, or 9 months, or 1, 5, 10, 20, 30, 40, 50, 55, 60, 65, 70, or 75 years of age. In various embodiments, the patient is no more than about 1, 3, 6, or 9 months, or 1, 5, 10, 20, 30, 40, 50, 55, 60, 65, 70, 75, 80, 90, or 100 years of age. In various embodiments the patient has a body weight of at least about 5, 10, 15, 20, 30, 40, 50, 60, 70, 80, 90, 100, 120, 140, 160, 180, 200, 220, 240, 260, 280, 300, 320, 340, 360, 380 or 400 lbs. In various embodiments, the patient has a body weight of no more than about 5, 10, 15, 20, 30, 40, 50, 60, 70, 80, 90, 100, 120, 140, 160, 180, 200, 220, 240, 260, 280, 300, 320, 340, 360, 380 or 400 lbs.

In various embodiments of the present disclosure, the dosage [measuring only the active ingredient(s)] can be at least about 1, 5, 10, 25, 50, 100, 200, 250, 300, 250, 400, 450, 500, 550, 600, 650, 700, 750, 800, 850, 900, 950 or 1000 ng, 1, 5, 10, 25, 50, 100, 200, 250, 300, 250, 400, 450, 500, 550, 600, 650, 700, 750, 800, 850, 900, 950 or 1000 micrograms, 1, 5, 10, 25, 50, 100, 200, 250, 300, 250, 400, 450, 500, 550, 600, 650, 700, 750, 800, 850, 900, 950 or 1000 mg. In various embodiments, the dosage can be no more than about 10, 25, 50, 100, 200, 250, 300, 250, 400, 450, 500, 550, 600, 650, 700, 750, 800, 850, 900, 950 or 1000 mg. In various embodiments, the dosage can be administered at least more than once a day, daily, more than once a weekly, weekly, bi-weekly, monthly, and/or every 2, 3, 4, 5, 6, 7, 8, 9, 10, 11 or 12 months, or a combination thereof.

In various embodiments, the dosage is correlated to the body weight or body surface area of the individual. The actual dosage level can be varied to obtain an amount of active agent which is effective for a particular patient, composition and mode of administration, without being toxic to the patient. The selected dose will depend on a variety of pharmacokinetic factors, including the activity of the particular RNAi agent employed, the route of administration, the rate of excretion of the RNAi agent, the duration of the treatment, other drugs, compounds and/or materials used in combination with the RNAi agent, the age, sex, weight, condition, general health and prior medical history of the patient, and like factors well known in the medical arts. A physician or veterinarian having ordinary skill in the art can readily determine the effective amount of the RNAi agent required. A suitable dose will be that amount which is the lowest dose effective to produce a therapeutic effect, or a dose low enough to produce a therapeutic effect without causing side effects.

In addition to a therapeutically-effective dosage of one or more RNAi agents to Beta-ENaC, the pharmaceutical compositions of the present disclosure can comprise or be used in conjunction with an additional disease treatment which works synergistically with the RNAi agent. For example, the pharmaceutical composition can comprise an additional antagonist to ENaC, such as potassium-sparing diuretics, amiloride and triamterene. Additional treatments can be administered along with the pharmaceutical composition, including, as a non-limiting example, regulation of dietary salt intake. When used to treat cystic fibrosis, the pharmaceutical composition can be used in conjunction with various medicaments and therapies known in the art, including, but not limited to, antibiotics, DNase therapy, albutrol, N-acetylcysteine, breathing therapy, percussive therapy, aerobic exercise, and various medicaments and therapies to treat ailments associated with cystic fibrosis (e.g., diarrhea, osteoporosis, diabetes, bleeding, etc.).

Additional Embodiments of RNAi Agents to Beta-ENaC

In a particular embodiment, the present disclosure encompasses a composition comprising one or more Beta-ENaC RNAi agents. In one embodiment, the present disclosure comprises a RNAi agent comprising a sense strand and an antisense strand. In one embodiment, the antisense strand consists of, consists essentially of, or comprises the sequence of the antisense strand of a RNAi agent listed, e.g., in Table 1. In one embodiment, the antisense strand consists of, consists essentially of, or comprises a sequence with 0, 1, 2, or 3 mismatches from that of the antisense strand of any RNAi agent listed, e.g., in Table 1. In one embodiment, the antisense strand consists of the sequence of the antisense strand of a RNAi agent listed, e.g., in Table 1, and further comprises 0, 1, 2, 3, 4, 5, 6, 7, 8, 9, or 10 nucleotides. In one embodiment, the antisense strand consists of a sequence with 0, 1, 2, or 3 mismatches from that of the antisense strand of a RNAi agent listed, e.g., in Table 1, and further comprises 0, 1, 2, 3, 4, 5, 6, 7, 8, 9, or 10 nucleotides.

In another embodiment, the composition of the claimed disclosure does not comprise any particular individual RNAi agent listed, e.g., in Table 1. In another embodiment of the present disclosure, the RNAi agent to Beta-ENaC does not comprise a sequence of any Beta-ENaC RNAi agent disclosed in the patent or scientific literature, e.g., U.S. Patent App. No. 60/346,069 (PCT/US02/41850), and Hyde et al. 2009, The $23^{rd}$ North American Cystic Fibrosis Conference, Minneapolis, Oct. 14-17, 2009; or that available as sc-42418 (and related products) from Santa Cruz Biotechnology, Santa Cruz, Calif.

Specific Embodiments of RNAi Agents to Beta-ENaC

Various specific embodiments of a RNAi agent to Beta-ENaC are disclosed herein. Example duplex sequences are provided herein and, e.g., in Table 1. Specific embodiments of the present disclosure include RNAi agents which comprise sequences differing by 0, 1, 2, or 3 nt or by (e.g., with 0, 1, 2 or 3 mismatches) from those of the RNAi agents listed, e.g., in Table 1.

A mismatch is defined herein as a difference between the base sequence or length when two sequences are maximally aligned and compared. A mismatch is defined as a position wherein the base of one sequence does not match the base of the other sequence. Thus, a mismatch is counted, for example, if a position in one sequence has a particular base (e.g., A), and the corresponding position on the other sequence has a different base (e.g., G).

A mismatch is also counted, e.g., if a position in one sequence has a base (e.g., A), and the corresponding position on the other sequence has no base (e.g., that position is an abasic nucleotide which comprises a phosphate-sugar backbone but no base). A single-stranded nick in either sequence (or in the sense or antisense strand) is not counted as mismatch. Thus, as a non-limiting example, no mismatch would be counted if one sequence comprises the sequence AG, but the other sequence comprises the sequence AG with a single-stranded nick between the A and the G. A base modification is also not considered a mismatch. Thus, if one sequence comprises a C, and the other sequence comprises a modified C (e.g., 2'-modification) at the same position, no mismatch would be counted.

In one particular embodiment, the present disclosure comprises a RNAi agent comprising a antisense strand comprising at least 15 contiguous nucleotides differing by 0, 1, 2, or 3 nt from the antisense strand of: AD-20807 (SEQ ID NOs: 5 and 6, or SEQ ID NOs:115 and 116).

In another particular embodiment, the siRNA also further comprises a sense strand comprising at least 15 contiguous nucleotides differing by 0, 1, 2, or 3 nt from the sense strand of AD-20807.

In another particular embodiment, the siRNA comprises AD-20807.

In another particular embodiment, the siRNA has a sequence consisting of that of AD-20807.

In one particular embodiment, the present disclosure comprises a RNAi agent comprising a antisense strand comprising at least 15 contiguous nucleotides differing by 0, 1, 2, or 3 nt from the antisense strand of: AD-20826 (SEQ ID NOs: 43 and 44, or SEQ ID NOs:153 and 154).

In another particular embodiment, the siRNA also further comprises a sense strand comprising at least 15 contiguous nucleotides differing by 0, 1, 2, or 3 nt from the sense strand of AD-20826.

In another particular embodiment, the siRNA comprises AD-20826.

In another particular embodiment, the siRNA has a sequence consisting of that of AD-20626.

In one particular embodiment, the present disclosure comprises a RNAi agent comprising a antisense strand comprising at least 15 contiguous nucleotides differing by 0, 1, 2, or 3 nt from the antisense strand of: AD-20832, which comprises SEQ ID NOs: 55 and 56, or SEQ ID NOs:165 and 166.

In another particular embodiment, the siRNA also further comprises a sense strand comprising at least 15 contiguous nucleotides differing by 0, 1, 2, or 3 nt from the sense strand of AD-20832.

In another particular embodiment, the siRNA comprises AD-20832.

In another particular embodiment, the siRNA has a sequence consisting of that of AD-20832.

In one particular embodiment, the present disclosure comprises a RNAi agent comprising a antisense strand comprising at least 15 contiguous nucleotides differing by 0, 1, 2, or 3 nt from the antisense strand of: AD-20834, which comprises SEQ ID NOs: 59 and 60, or SEQ ID NOs:169 and 170.

In another particular embodiment, the siRNA also further comprises a sense strand comprising at least 15 contiguous nucleotides differing by 0, 1, 2, or 3 nt from the sense strand of AD-20834.

In another particular embodiment, the siRNA comprises AD-20834.

In another particular embodiment, the siRNA has a sequence consisting of that of AD-20834.

In one particular embodiment, the present disclosure comprises a RNAi agent comprising a antisense strand comprising at least 15 contiguous nucleotides differing by 0, 1, 2, or 3 nt from the antisense strand of: AD-20848, which comprises SEQ ID NOs: 87 and 88, or SEQ ID NOs:197 and 198.

In another particular embodiment, the siRNA also further comprises a sense strand comprising at least 15 contiguous nucleotides differing by 0, 1, 2, or 3 nt from the sense strand of AD-20848.

In another particular embodiment, the siRNA comprises AD-20848.

In another particular embodiment, the siRNA has a sequence consisting of that of AD-20848.

In one particular embodiment, the present disclosure comprises a RNAi agent comprising a antisense strand comprising at least 15 contiguous nucleotides differing by 0, 1, 2, or 3 nt from the antisense strand of: AD-20861, which comprises SEQ ID NOs: 97 and 98, or SEQ ID NOs:207 and 208.

In another particular embodiment, the siRNA also further comprises a sense strand comprising at least 15 contiguous nucleotides differing by 0, 1, 2, or 3 nt from the sense strand of AD-20861.

In another particular embodiment, the siRNA comprises AD-20861.

In another particular embodiment, the siRNA has a sequence consisting of that of AD-20861.

In one embodiment, the present disclosure comprises a RNAi agent demonstrating at least about 80% knockdown (no more than about 20% residual gene activity) of the Beta-ENaC gene at an in vitro concentration of 10 nM in H441 cells.

Thus, in one particular embodiment, the present disclosure comprises a RNAi agent comprising a antisense strand comprising at least 15 contiguous nucleotides differing by 0, 1, 2, or 3 nt from the antisense strand of: AD-20832; AD-20848; AD-20807; AD-20826; AD-20837; AD-20861; or AD-20834.

In another particular embodiment, the siRNA also further comprises a sense strand comprising at least 15 contiguous nucleotides differing by 0, 1, 2, or 3 nt from the sense strand of AD-20832; AD-20848; AD-20807; AD-20826; AD-20837; AD-20861; or AD-20834.

In another particular embodiment, the siRNA comprises AD-20832; AD-20848; AD-20807; AD-20826; AD-20837; AD-20861; or AD-20834.

In another particular embodiment, the siRNA has a sequence consisting of that of AD-20832; AD-20848; AD-20807; AD-20826; AD-20837; AD-20861; or AD-20834.

In one embodiment, the present disclosure comprises a RNAi agent demonstrating at least about 70% knockdown (no more than about 30% residual gene activity) of the Beta-ENaC gene at an in vitro concentration of 10 nM in H441 cells.

Thus, in one particular embodiment, the present disclosure comprises a RNAi agent comprising a antisense strand comprising at least 15 contiguous nucleotides differing by 0, 1, 2, or 3 nt from the antisense strand of: AD-20832; AD-20848; AD-20807; AD-20826; AD-20837; AD-20861; AD-20834;

AD-20806; AD-20851; AD-20865; AD-20811; AD-20819; AD-20839; AD-20835; AD-20825; or AD-20867.

In another particular embodiment, the siRNA also further comprises a sense strand comprising at least 15 contiguous nucleotides differing by 0, 1, 2, or 3 nt from the sense strand of AD-20832; AD-20848; AD-20807; AD-20826; AD-20837; AD-20861; AD-20834; AD-20806; AD-20851; AD-20865; AD-20811; AD-20819; AD-20839; AD-20835; AD-20825; or AD-20867.

In another particular embodiment, the siRNA comprises AD-20832; AD-20848; AD-20807; AD-20826; AD-20837; AD-20861; AD-20834; AD-20806; AD-20851; AD-20865; AD-20811; AD-20819; AD-20839; AD-20835; AD-20825; or AD-20867.

In another particular embodiment, the siRNA has a sequence consisting of that of AD-20832; AD-20848; AD-20807; AD-20826; AD-20837; AD-20861; AD-20834; AD-20806; AD-20851; AD-20865; AD-20811; AD-20819; AD-20839; AD-20835; AD-20825; or AD-20867.

In one embodiment, the present disclosure comprises a RNAi agent demonstrating at least about 60% knockdown (no more than about 40% residual gene activity) of the Beta-ENaC gene at an in vitro concentration of 10 nM in H441 cells.

Thus, in one particular embodiment, the present disclosure comprises a RNAi agent comprising a antisense strand comprising at least 15 contiguous nucleotides differing by 0, 1, 2, or 3 nt from the antisense strand of: AD-20832; AD-20848; AD-20807; AD-20826; AD-20837; AD-20861; AD-20834; AD-20806; AD-20851; AD-20865; AD-20811; AD-20819; AD-20839; AD-20835; AD-20825; AD-20867; AD-20813; AD-20823; AD-20805; AD-20831; AD-20862; AD-20808; or AD-20827.

In another particular embodiment, the siRNA also further comprises a sense strand comprising at least 15 contiguous nucleotides differing by 0, 1, 2, or 3 nt from the sense strand of AD-20832; AD-20848; AD-20807; AD-20826; AD-20837; AD-20861; AD-20834; AD-20806; AD-20851; AD-20865; AD-20811; AD-20819; AD-20839; AD-20835; AD-20825; AD-20867; AD-20813; AD-20823; AD-20805; AD-20831; AD-20862; AD-20808; or AD-20827.

In another particular embodiment, the siRNA comprises: AD-20832; AD-20848; AD-20807; AD-20826; AD-20837; AD-20861; AD-20834; AD-20806; AD-20851; AD-20865; AD-20811; AD-20819; AD-20839; AD-20835; AD-20825; AD-20867; AD-20813; AD-20823; AD-20805; AD-20831; AD-20862; AD-20808; or AD-20827.

In another particular embodiment, the siRNA has a sequence consisting of that of AD-20832; AD-20848; AD-20807; AD-20826; AD-20837; AD-20861; AD-20834; AD-20806; AD-20851; AD-20865; AD-20811; AD-20819; AD-20839; AD-20835; AD-20825; AD-20867; AD-20813; AD-20823; AD-20805; AD-20831; AD-20862; AD-20808; or AD-20827.

In one embodiment, the present disclosure comprises a RNAi agent demonstrating at least about 50% knockdown (no more than about 50% residual gene activity) of the Beta-ENaC gene at an in vitro concentration of 10 nM in H441 cells.

Thus, in one particular embodiment, the present disclosure comprises a RNAi agent comprising a antisense strand comprising at least 15 contiguous nucleotides differing by 0, 1, 2, or 3 nt from the antisense strand of: AD-20832; AD-20848; AD-20807; AD-20826; AD-20837; AD-20861; AD-20834; AD-20806; AD-20851; AD-20865; AD-20811; AD-20819; AD-20839; AD-20835; AD-20825; AD-20867; AD-20813; AD-20823; AD-20805; AD-20831; AD-20862; AD-20808; AD-20827; AD-20828; AD-20812; AD-20836; or AD-20822.

In another particular embodiment, the siRNA also further comprises a sense strand comprising at least 15 contiguous nucleotides differing by 0, 1, 2, or 3 nt from the sense strand of AD-20832; AD-20848; AD-20807; AD-20826; AD-20837; AD-20861; AD-20834; AD-20806; AD-20851; AD-20865; AD-20811; AD-20819; AD-20839; AD-20835; AD-20825; AD-20867; AD-20813; AD-20823; AD-20805; AD-20831; AD-20862; AD-20808; AD-20827; AD-20828; AD-20812; AD-20836; or AD-20822.

In another particular embodiment, the siRNA comprises AD-20832; AD-20848; AD-20807; AD-20826; AD-20837; AD-20861; AD-20834; AD-20806; AD-20851; AD-20865; AD-20811; AD-20819; AD-20839; AD-20835; AD-20825; AD-20867; AD-20813; AD-20823; AD-20805; AD-20831; AD-20862; AD-20808; AD-20827; AD-20828; AD-20812; AD-20836; or AD-20822.

In another particular embodiment, the siRNA has a sequence consisting of that of AD-20832; AD-20848; AD-20807; AD-20826; AD-20837; AD-20861; AD-20834; AD-20806; AD-20851; AD-20865; AD-20811; AD-20819; AD-20839; AD-20835; AD-20825; AD-20867; AD-20813; AD-20823; AD-20805; AD-20831; AD-20862; AD-20808; AD-20827; AD-20828; AD-20812; AD-20836; or AD-20822.

Various Embodiments of a RNAi Agent to Beta-ENaC

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20805.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20806.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20807.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20808.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20809.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20810.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20811.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20812.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20813.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20814.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20815.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20816.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20817.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20818.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20819.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20820.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20821.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20822.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20823.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20824.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20825.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20826.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20827.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20828.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20829.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20830.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20831.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20832.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20833.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20834.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20835.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20836.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20837.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20838.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20839.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20840.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20841.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20842.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20843.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20844.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20845.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20846.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20847.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20848.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20849.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20850.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20851.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20852.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20861.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20862.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20863.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20864.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20865.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20866.

In one embodiment, the present disclosure comprises a RNAi agent comprising a sense strand comprising at least 15 contiguous nucleotides differing by 0, 1, 2, or 3 nt from the sense strand and/or an antisense strand comprising at least 15 contiguous nucleotides differing by 0, 1, 2, or 3 nt from the antisense strand of AD-20867.

Various Embodiments of a RNAi Agent to Beta-ENaC

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20805, which comprises SEQ ID NOs. 111-112, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20806, which comprises SEQ ID NOs. 113-114, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20807, which comprises SEQ ID NOs. 115-116, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20808, which comprises SEQ ID NOs. 117-118, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20809, which comprises SEQ ID NOs. 119-120, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20810, which comprises SEQ ID NOs. 121-122, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20811, which comprises SEQ ID NOs. 123-124, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20812, which comprises SEQ ID NOs. 125-126, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20813, which comprises SEQ ID NOs. 127-128, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20814, which comprises SEQ ID NOs. 129-130, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20815, which comprises SEQ ID NOs. 131-132, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20816, which comprises SEQ ID NOs. 133-134, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20817, which comprises SEQ ID NOs. 135-136, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20818, which comprises SEQ ID NOs. 137-138, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20819, which comprises SEQ ID NOs. 139-140, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20820, which comprises SEQ ID NOs. 141-142, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20821, which comprises SEQ ID NOs. 143-144, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20822, which comprises SEQ ID NOs. 145-146, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20823, which comprises SEQ ID NOs. 147-148, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20824, which comprises SEQ ID NOs. 149-150, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20825, which comprises SEQ ID NOs. 151-152, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20826, which comprises SEQ ID NOs. 153-154, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20827, which comprises SEQ ID NOs. 155-156, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20828, which comprises SEQ ID NOs. 157-158, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20829, which comprises SEQ ID NOs. 159-160, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20830, which comprises SEQ ID NOs. 161-162, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20831, which comprises SEQ ID NOs. 163-164, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20832, which comprises SEQ ID NOs. 165-166, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20833, which comprises SEQ ID NOs. 167-168, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20834, which comprises SEQ ID NOs. 169-170, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20835, which comprises SEQ ID NOs. 171-172, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20836, which comprises SEQ ID NOs. 173-174, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20837, which comprises SEQ ID NOs. 175-176, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20838, which comprises SEQ ID NOs. 177-178, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20839, which comprises SEQ ID NOs. 179-180, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20840, which comprises SEQ ID NOs. 181-182, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20841, which comprises SEQ ID NOs. 183-184, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20842, which comprises SEQ ID NOs. 185-186, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20843, which comprises SEQ ID NOs. 187-188, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20844, which comprises SEQ ID NOs. 189-190, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20845, which comprises SEQ ID NOs. 191-192, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20846, which comprises SEQ ID NOs. 193-194, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20847, which comprises SEQ ID NOs. 195-196, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20848, which comprises SEQ ID NOs. 197-198, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20849, which comprises SEQ ID NOs. 199-200, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20850, which comprises SEQ ID NOs. 201-202, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20851, which comprises SEQ ID NOs. 203-204, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20852, which comprises SEQ ID NOs. 205-206, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20861, which comprises SEQ ID NOs. 207-208, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20862, which comprises SEQ ID NOs. 209-210, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20863, which comprises SEQ ID NOs. 211-212, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20864, which comprises SEQ ID NOs. 213-214, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20865, which comprises SEQ ID NOs. 215-216, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20866, which comprises SEQ ID NOs. 217-218, and modified variants thereof.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of: AD-20867, which comprises SEQ ID NOs. 219-220, and modified variants thereof.

Various Embodiments of a RNAi Agent to Beta-ENaC

In one embodiment, the composition comprises a RNAi agent comprising a sense strand and an antisense strand, wherein the antisense strand comprises at least 15 contiguous nucleotides differing by 0 nucleotides from the antisense strand of: AD-20805, which comprises SEQ ID NOs. 111 and 112.

In one embodiment, the composition comprises a RNAi agent comprising a sense strand and an antisense strand, wherein the antisense strand comprises at least 15 contiguous nucleotides differing by 0 nucleotides from the antisense strand of: AD-20806, which comprises SEQ ID NOs. 113 and 114

In one embodiment, the composition comprises a RNAi agent comprising a sense strand and an antisense strand, wherein the antisense strand comprises at least 15 contiguous nucleotides differing by 0 nucleotides from the antisense strand of: AD-20807, which comprises SEQ ID NOs. 115 and 116.

In one embodiment, the composition comprises a RNAi agent comprising a sense strand and an antisense strand, wherein the antisense strand comprises at least 15 contiguous nucleotides differing by 0 nucleotides from the antisense strand of: AD-20808, which comprises SEQ ID NOs. 117 and 118.

In one embodiment, the composition comprises a RNAi agent comprising a sense strand and an antisense strand, wherein the antisense strand comprises at least 15 contiguous nucleotides differing by 0 nucleotides from the antisense strand of: AD-20809, which comprises SEQ ID NOs. 119 and 120.

In one embodiment, the composition comprises a RNAi agent comprising a sense strand and an antisense strand, wherein the antisense strand comprises at least 15 contiguous nucleotides differing by 0 nucleotides from the antisense strand of: AD-20810, which comprises SEQ ID NOs. 121 and 122.

In one embodiment, the composition comprises a RNAi agent comprising a sense strand and an antisense strand, wherein the antisense strand comprises at least 15 contiguous nucleotides differing by 0 nucleotides from the antisense strand of: AD-20811, which comprises SEQ ID NOs. 123 and 124.

In one embodiment, the composition comprises a RNAi agent comprising a sense strand and an antisense strand, wherein the antisense strand comprises at least 15 contiguous nucleotides differing by 0 nucleotides from the antisense strand of: AD-20812, which comprises SEQ ID NOs. 125 and 126.

In one embodiment, the composition comprises a RNAi agent comprising a sense strand and an antisense strand, wherein the antisense strand comprises at least 15 contiguous nucleotides differing by 0 nucleotides from the antisense strand of: AD-20813, which comprises SEQ ID NOs. 127 and 128.

In one embodiment, the composition comprises a RNAi agent comprising a sense strand and an antisense strand, wherein the antisense strand comprises at least 15 contiguous nucleotides differing by 0 nucleotides from the antisense strand of: AD-20814, which comprises SEQ ID NOs. 129 and 130.

In one embodiment, the composition comprises a RNAi agent comprising a sense strand and an antisense strand, wherein the antisense strand comprises at least 15 contiguous nucleotides differing by 0 nucleotides from the antisense strand of: AD-20815, which comprises SEQ ID NOs. 131 and 132.

In one embodiment, the composition comprises a RNAi agent comprising a sense strand and an antisense strand, wherein the antisense strand comprises at least 15 contiguous nucleotides differing by 0 nucleotides from the antisense strand of: AD-20816, which comprises SEQ ID NOs. 133 and 134.

In one embodiment, the composition comprises a RNAi agent comprising a sense strand and an antisense strand, wherein the antisense strand comprises at least 15 contiguous nucleotides differing by 0 nucleotides from the antisense strand of: AD-20817, which comprises SEQ ID NOs. 135 and 136.

In one embodiment, the composition comprises a RNAi agent comprising a sense strand and an antisense strand, wherein the antisense strand comprises at least 15 contiguous nucleotides differing by 0 nucleotides from the antisense strand of: AD-20818, which comprises SEQ ID NOs. 137 and 138.

In one embodiment, the composition comprises a RNAi agent comprising a sense strand and an antisense strand, wherein the antisense strand comprises at least 15 contiguous nucleotides differing by 0 nucleotides from the antisense strand of: AD-20819, which comprises SEQ ID NOs. 139 and 140.

In one embodiment, the composition comprises a RNAi agent comprising a sense strand and an antisense strand, wherein the antisense strand comprises at least 15 contiguous nucleotides differing by 0 nucleotides from the antisense strand of: AD-20820, which comprises SEQ ID NOs. 141 and 142.

In one embodiment, the composition comprises a RNAi agent comprising a sense strand and an antisense strand, wherein the antisense strand comprises at least 15 contiguous nucleotides differing by 0 nucleotides from the antisense strand of: AD-20821, which comprises SEQ ID NOs. 143 and 144.

In one embodiment, the composition comprises a RNAi agent comprising a sense strand and an antisense strand, wherein the antisense strand comprises at least 15 contiguous nucleotides differing by 0 nucleotides from the antisense strand of: AD-20822, which comprises SEQ ID NOs. 145 and 146.

In one embodiment, the composition comprises a RNAi agent comprising a sense strand and an antisense strand, wherein the antisense strand comprises at least 15 contiguous nucleotides differing by 0 nucleotides from the antisense strand of: AD-20823, which comprises SEQ ID NOs. 147 and 148.

In one embodiment, the composition comprises a RNAi agent comprising a sense strand and an antisense strand, wherein the antisense strand comprises at least 15 contiguous nucleotides differing by 0 nucleotides from the antisense strand of: AD-20824, which comprises SEQ ID NOs. 149 and 150.

In one embodiment, the composition comprises a RNAi agent comprising a sense strand and an antisense strand, wherein the antisense strand comprises at least 15 contiguous nucleotides differing by 0 nucleotides from the antisense strand of: AD-20825, which comprises SEQ ID NOs. 151 and 152.

In one embodiment, the composition comprises a RNAi agent comprising a sense strand and an antisense strand, wherein the antisense strand comprises at least 15 contiguous nucleotides differing by 0 nucleotides from the antisense strand of: AD-20826, which comprises SEQ ID NOs. 153 and 154.

In one embodiment, the composition comprises a RNAi agent comprising a sense strand and an antisense strand, wherein the antisense strand comprises at least 15 contiguous nucleotides differing by 0 nucleotides from the antisense strand of: AD-20827, which comprises SEQ ID NOs. 155 and 156.

In one embodiment, the composition comprises a RNAi agent comprising a sense strand and an antisense strand, wherein the antisense strand comprises at least 15 contiguous nucleotides differing by 0 nucleotides from the antisense strand of: AD-20828, which comprises SEQ ID NOs. 157 and 158.

In one embodiment, the composition comprises a RNAi agent comprising a sense strand and an antisense strand, wherein the antisense strand comprises at least 15 contiguous nucleotides differing by 0 nucleotides from the antisense strand of: AD-20829, which comprises SEQ ID NOs. 159 and 160.

In one embodiment, the composition comprises a RNAi agent comprising a sense strand and an antisense strand, wherein the antisense strand comprises at least 15 contiguous nucleotides differing by 0 nucleotides from the antisense strand of: AD-20830, which comprises SEQ ID NOs. 161 and 162.

In one embodiment, the composition comprises a RNAi agent comprising a sense strand and an antisense strand, wherein the antisense strand comprises at least 15 contiguous nucleotides differing by 0 nucleotides from the antisense strand of: AD-20831, which comprises SEQ ID NOs. 163 and 164.

In one embodiment, the composition comprises a RNAi agent comprising a sense strand and an antisense strand, wherein the antisense strand comprises at least 15 contiguous nucleotides differing by 0 nucleotides from the antisense strand of: AD-20832, which comprises SEQ ID NOs. 165 and 166.

In one embodiment, the composition comprises a RNAi agent comprising a sense strand and an antisense strand, wherein the antisense strand comprises at least 15 contiguous nucleotides differing by 0 nucleotides from the antisense strand of: AD-20833, which comprises SEQ ID NOs. 167 and 168.

In one embodiment, the composition comprises a RNAi agent comprising a sense strand and an antisense strand, wherein the antisense strand comprises at least 15 contiguous nucleotides differing by 0 nucleotides from the antisense strand of: AD-20834, which comprises SEQ ID NOs. 169 and 170.

In one embodiment, the composition comprises a RNAi agent comprising a sense strand and an antisense strand, wherein the antisense strand comprises at least 15 contiguous nucleotides differing by 0 nucleotides from the antisense strand of: AD-20835, which comprises SEQ ID NOs. 171 and 172.

In one embodiment, the composition comprises a RNAi agent comprising a sense strand and an antisense strand, wherein the antisense strand comprises at least 15 contiguous nucleotides differing by 0 nucleotides from the antisense strand of: AD-20836, which comprises SEQ ID NOs. 173 and 174.

In one embodiment, the composition comprises a RNAi agent comprising a sense strand and an antisense strand, wherein the antisense strand comprises at least 15 contiguous nucleotides differing by 0 nucleotides from the antisense strand of: AD-20837, which comprises SEQ ID NOs. 175 and 176.

In one embodiment, the composition comprises a RNAi agent comprising a sense strand and an antisense strand, wherein the antisense strand comprises at least 15 contiguous nucleotides differing by 0 nucleotides from the antisense strand of: AD-20838, which comprises SEQ ID NOs. 177 and 178.

In one embodiment, the composition comprises a RNAi agent comprising a sense strand and an antisense strand, wherein the antisense strand comprises at least 15 contiguous nucleotides differing by 0 nucleotides from the antisense strand of: AD-20839, which comprises SEQ ID NOs. 179 and 180.

In one embodiment, the composition comprises a RNAi agent comprising a sense strand and an antisense strand, wherein the antisense strand comprises at least 15 contiguous nucleotides differing by 0 nucleotides from the antisense strand of: AD-20840, which comprises SEQ ID NOs. 181 and 182.

In one embodiment, the composition comprises a RNAi agent comprising a sense strand and an antisense strand, wherein the antisense strand comprises at least 15 contiguous nucleotides differing by 0 nucleotides from the antisense strand of: AD-20841, which comprises SEQ ID NOs. 183 and 184.

In one embodiment, the composition comprises a RNAi agent comprising a sense strand and an antisense strand, wherein the antisense strand comprises at least 15 contiguous nucleotides differing by 0 nucleotides from the antisense strand of: AD-20842, which comprises SEQ ID NOs. 185 and 186.

In one embodiment, the composition comprises a RNAi agent comprising a sense strand and an antisense strand, wherein the antisense strand comprises at least 15 contiguous nucleotides differing by 0 nucleotides from the antisense strand of: AD-20843, which comprises SEQ ID NOs. 187 and 188.

In one embodiment, the composition comprises a RNAi agent comprising a sense strand and an antisense strand, wherein the antisense strand comprises at least 15 contiguous nucleotides differing by 0 nucleotides from the antisense strand of: AD-20844, which comprises SEQ ID NOs. 189 and 190.

In one embodiment, the composition comprises a RNAi agent comprising a sense strand and an antisense strand, wherein the antisense strand comprises at least 15 contiguous nucleotides differing by 0 nucleotides from the antisense strand of: AD-20845, which comprises SEQ ID NOs. 191 and 192.

In one embodiment, the composition comprises a RNAi agent comprising a sense strand and an antisense strand, wherein the antisense strand comprises at least 15 contiguous nucleotides differing by 0 nucleotides from the antisense strand of: AD-20846, which comprises SEQ ID NOs. 193 and 194.

In one embodiment, the composition comprises a RNAi agent comprising a sense strand and an antisense strand, wherein the antisense strand comprises at least 15 contiguous nucleotides differing by 0 nucleotides from the antisense strand of: AD-20847, which comprises SEQ ID NOs. 195 and 196.

In one embodiment, the composition comprises a RNAi agent comprising a sense strand and an antisense strand, wherein the antisense strand comprises at least 15 contiguous nucleotides differing by 0 nucleotides from the antisense strand of: AD-20848, which comprises SEQ ID NOs. 197 and 198.

In one embodiment, the composition comprises a RNAi agent comprising a sense strand and an antisense strand, wherein the antisense strand comprises at least 15 contiguous nucleotides differing by 0 nucleotides from the antisense strand of: AD-20849, which comprises SEQ ID NOs. 199 and 200.

In one embodiment, the composition comprises a RNAi agent comprising a sense strand and an antisense strand, wherein the antisense strand comprises at least 15 contiguous nucleotides differing by 0 nucleotides from the antisense strand of: AD-20850, which comprises SEQ ID NOs. 201 and 202.

In one embodiment, the composition comprises a RNAi agent comprising a sense strand and an antisense strand, wherein the antisense strand comprises at least 15 contiguous nucleotides differing by 0 nucleotides from the antisense strand of: AD-20851, which comprises SEQ ID NOs. 203 and 204.

In one embodiment, the composition comprises a RNAi agent comprising a sense strand and an antisense strand, wherein the antisense strand comprises at least 15 contiguous nucleotides differing by 0 nucleotides from the antisense strand of: AD-20852, which comprises SEQ ID NOs. 205 and 206.

In one embodiment, the composition comprises a RNAi agent comprising a sense strand and an antisense strand, wherein the antisense strand comprises at least 15 contiguous nucleotides differing by 0 nucleotides from the antisense strand of: AD-20861, which comprises SEQ ID NOs. 207 and 208.

In one embodiment, the composition comprises a RNAi agent comprising a sense strand and an antisense strand, wherein the antisense strand comprises at least 15 contiguous nucleotides differing by 0 nucleotides from the antisense strand of: AD-20862, which comprises SEQ ID NOs. 209 and 210.

In one embodiment, the composition comprises a RNAi agent comprising a sense strand and an antisense strand, wherein the antisense strand comprises at least 15 contiguous nucleotides differing by 0 nucleotides from the antisense strand of: AD-20863, which comprises SEQ ID NOs. 211 and 212.

In one embodiment, the composition comprises a RNAi agent comprising a sense strand and an antisense strand, wherein the antisense strand comprises at least 15 contiguous nucleotides differing by 0 nucleotides from the antisense strand of: AD-20864, which comprises SEQ ID NOs. 213 and 214.

In one embodiment, the composition comprises a RNAi agent comprising a sense strand and an antisense strand, wherein the antisense strand comprises at least 15 contiguous nucleotides differing by 0 nucleotides from the antisense strand of: AD-20865, which comprises SEQ ID NOs. 215 and 216.

In one embodiment, the composition comprises a RNAi agent comprising a sense strand and an antisense strand, wherein the antisense strand comprises at least 15 contiguous nucleotides differing by 0 nucleotides from the antisense strand of: AD-20866, which comprises SEQ ID NOs. 217 and 218.

and In one embodiment, the composition comprises a RNAi agent comprising a sense strand and an antisense strand, wherein the antisense strand comprises at least 15 contiguous nucleotides differing by 0 nucleotides from the antisense strand of: AD-20867, which comprises SEQ ID NOs. 219 and 220.

Various Embodiments of a RNAi Agent to Beta-ENaC

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20805, which comprises SEQ ID NOs. 1 and 2.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20806, which comprises SEQ ID NOs. 3 and 4.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20807, which comprises SEQ ID NOs. 5 and 6.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20808, which comprises SEQ ID NOs. 7 and 8.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20809, which comprises SEQ ID NOs. 9 and 10.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20810, which comprises SEQ ID NOs. 11 and 12.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20811, which comprises SEQ ID NOs. 13 and 14.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20812, which comprises SEQ ID NOs. 15 and 16.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20813, which comprises SEQ ID NOs. 17 and 18.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20814, which comprises SEQ ID NOs. 19 and 20.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20815, which comprises SEQ ID NOs. 21 and 22.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20816, which comprises SEQ ID NOs. 23 and 24.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20817, which comprises SEQ ID NOs. 25 and 26.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20818, which comprises SEQ ID NOs. 27 and 28.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20819, which comprises SEQ ID NOs. 29 and 30.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20820, which comprises SEQ ID NOs. 31 and 32.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20821, which comprises SEQ ID NOs. 33 and 34.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20822, which comprises SEQ ID NOs. 35 and 36.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20823, which comprises SEQ ID NOs. 37 and 38.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20824, which comprises SEQ ID NOs. 39 and 40.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20825, which comprises SEQ ID NOs. 41 and 42.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20826, which comprises SEQ ID NOs. 43 and 44.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20827, which comprises SEQ ID NOs. 45 and 46.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20828, which comprises SEQ ID NOs. 47 and 48.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20829, which comprises SEQ ID NOs. 49 and 50.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20830, which comprises SEQ ID NOs. 51 and 52.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20831, which comprises SEQ ID NOs. 53 and 54.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20832, which comprises SEQ ID NOs. 55 and 56.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20833, which comprises SEQ ID NOs. 57 and 58.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20834, which comprises SEQ ID NOs. 59 and 60.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20835, which comprises SEQ ID NOs. 61 and 62.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20836, which comprises SEQ ID NOs. 63 and 64.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20837, which comprises SEQ ID NOs. 65 and 66.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20838, which comprises SEQ ID NOs. 67 and 68.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20839, which comprises SEQ ID NOs. 69 and 70.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20840, which comprises SEQ ID NOs. 71 and 72.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20841, which comprises SEQ ID NOs. 73 and 74.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20842, which comprises SEQ ID NOs. 75 and 76.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20843, which comprises SEQ ID NOs. 77 and 78.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20844, which comprises SEQ ID NOs. 79 and 80.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20845, which comprises SEQ ID NOs. 81 and 82.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20846, which comprises SEQ ID NOs. 83 and 84.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20847, which comprises SEQ ID NOs. 85 and 86.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20848, which comprises SEQ ID NOs. 87 and 88.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20849, which comprises SEQ ID NOs. 89 and 90.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20850, which comprises SEQ ID NOs. 91 and 92.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20851, which comprises SEQ ID NOs. 93 and 94.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20852, which comprises SEQ ID NOs. 95 and 96.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20861, which comprises SEQ ID NOs. 97 and 98.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20862, which comprises SEQ ID NOs. 99 and 100.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20863, which comprises SEQ ID NOs. 101 and 102.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20864, which comprises SEQ ID NOs. 103 and 104.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20865, which comprises SEQ ID NOs. 105 and 106.

In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20866, which comprises SEQ ID NOs. 107 and 108.

and In one embodiment, the composition comprises a modified variant of a RNAi agent, wherein the variant comprises a sense strand and an antisense strand, wherein the antisense strand comprises at least 15 contiguous nucleotides differing by 0, 1, 2, or 3 nucleotides from the antisense sequence of: AD-20867, which comprises SEQ ID NOs. 109 and 110.

Various Embodiments of a RNAi Agent to Beta-ENaC

In one embodiment, the present disclosure comprises AD-20805 (SEQ ID NOs: 1 and 2, or SEQ ID NOs: 111 and 112).

In one embodiment, the present disclosure comprises AD-20806 (SEQ ID NOs: 3 and 4, or SEQ ID NOs: 113 and 114).

In one embodiment, the present disclosure comprises AD-20807 (SEQ ID NOs: 5 and 6, or SEQ ID NOs: 115 and 116).

In one embodiment, the present disclosure comprises AD-20808 (SEQ ID NOs: 7 and 8, or SEQ ID NOs: 117 and 118).

In one embodiment, the present disclosure comprises AD-20809 (SEQ ID NOs: 9 and 10, or SEQ ID NOs: 119 and 120).

In one embodiment, the present disclosure comprises AD-20810 (SEQ ID NOs: 11 and 12, or SEQ ID NOs: 121 and 122).

In one embodiment, the present disclosure comprises AD-20811 (SEQ ID NOs: 13 and 14, or SEQ ID NOs: 123 and 124).

In one embodiment, the present disclosure comprises AD-20812 (SEQ ID NOs: 15 and 16, or SEQ ID NOs: 125 and 126).

In one embodiment, the present disclosure comprises AD-20813 (SEQ ID NOs: 17 and 18, or SEQ ID NOs: 127 and 128).

In one embodiment, the present disclosure comprises AD-20814 (SEQ ID NOs: 19 and 20, or SEQ ID NOs: 129 and 130).

In one embodiment, the present disclosure comprises AD-20815 (SEQ ID NOs: 21 and 22, or SEQ ID NOs: 131 and 132).

In one embodiment, the present disclosure comprises AD-20816 (SEQ ID NOs: 23 and 24, or SEQ ID NOs: 133 and 134).

In one embodiment, the present disclosure comprises AD-20817 (SEQ ID NOs: 25 and 26, or SEQ ID NOs: 135 and 136).

In one embodiment, the present disclosure comprises AD-20818 (SEQ ID NOs: 27 and 28, or SEQ ID NOs: 137 and 138).

In one embodiment, the present disclosure comprises AD-20819 (SEQ ID NOs: 29 and 30, or SEQ ID NOs: 139 and 140).

In one embodiment, the present disclosure comprises AD-20820 (SEQ ID NOs: 31 and 32, or SEQ ID NOs: 141 and 142).

In one embodiment, the present disclosure comprises AD-20821 (SEQ ID NOs: 33 and 34, or SEQ ID NOs: 143 and 144).

In one embodiment, the present disclosure comprises AD-20822 (SEQ ID NOs: 35 and 36, or SEQ ID NOs: 145 and 146).

In one embodiment, the present disclosure comprises AD-20823 (SEQ ID NOs: 37 and 38, or SEQ ID NOs: 147 and 148).

In one embodiment, the present disclosure comprises AD-20824 (SEQ ID NOs: 39 and 40, or SEQ ID NOs: 149 and 150).

In one embodiment, the present disclosure comprises AD-20825 (SEQ ID NOs: 41 and 42, or SEQ ID NOs: 151 and 152).

In one embodiment, the present disclosure comprises AD-20826 (SEQ ID NOs: 43 and 44, or SEQ ID NOs: 153 and 154).

In one embodiment, the present disclosure comprises AD-20827 (SEQ ID NOs: 45 and 46, or SEQ ID NOs: 155 and 156).

In one embodiment, the present disclosure comprises AD-20828 (SEQ ID NOs: 47 and 48, or SEQ ID NOs: 157 and 158).

In one embodiment, the present disclosure comprises AD-20829 (SEQ ID NOs: 49 and 50, or SEQ ID NOs: 159 and 160).

In one embodiment, the present disclosure comprises AD-20830 (SEQ ID NOs: 51 and 52, or SEQ ID NOs: 161 and 162).

In one embodiment, the present disclosure comprises AD-20831 (SEQ ID NOs: 53 and 54, or SEQ ID NOs: 163 and 164).

In one embodiment, the present disclosure comprises AD-20832 (SEQ ID NOs: 55 and 56, or SEQ ID NOs: 165 and 166).

In one embodiment, the present disclosure comprises AD-20833 (SEQ ID NOs: 57 and 58, or SEQ ID NOs: 167 and 168).

In one embodiment, the present disclosure comprises AD-20834 (SEQ ID NOs: 59 and 60, or SEQ ID NOs: 169 and 170).

In one embodiment, the present disclosure comprises AD-20835 (SEQ ID NOs: 61 and 62, or SEQ ID NOs: 171 and 172).

In one embodiment, the present disclosure comprises AD-20836 (SEQ ID NOs: 63 and 64, or SEQ ID NOs: 173 and 174).

In one embodiment, the present disclosure comprises AD-20837 (SEQ ID NOs: 65 and 66, or SEQ ID NOs: 175 and 176).

In one embodiment, the present disclosure comprises AD-20838 (SEQ ID NOs: 67 and 68, or SEQ ID NOs: 177 and 178).

In one embodiment, the present disclosure comprises AD-20839 (SEQ ID NOs: 69 and 70, or SEQ ID NOs: 179 and 180).

In one embodiment, the present disclosure comprises AD-20840 (SEQ ID NOs: 71 and 72, or SEQ ID NOs: 181 and 182).

In one embodiment, the present disclosure comprises AD-20841 (SEQ ID NOs: 73 and 74, or SEQ ID NOs: 183 and 184).

In one embodiment, the present disclosure comprises AD-20842 (SEQ ID NOs: 75 and 76, or SEQ ID NOs: 185 and 186).

In one embodiment, the present disclosure comprises AD-20843 (SEQ ID NOs: 77 and 78, or SEQ ID NOs: 187 and 188).

In one embodiment, the present disclosure comprises AD-20844 (SEQ ID NOs: 79 and 80, or SEQ ID NOs: 189 and 190).

In one embodiment, the present disclosure comprises AD-20845 (SEQ ID NOs: 81 and 82, or SEQ ID NOs: 191 and 192).

In one embodiment, the present disclosure comprises AD-20846 (SEQ ID NOs: 83 and 84, or SEQ ID NOs: 193 and 194).

In one embodiment, the present disclosure comprises AD-20847 (SEQ ID NOs: 85 and 86, or SEQ ID NOs: 195 and 196).

In one embodiment, the present disclosure comprises AD-20848 (SEQ ID NOs: 87 and 88, or SEQ ID NOs: 197 and 198).

In one embodiment, the present disclosure comprises AD-20849 (SEQ ID NOs: 89 and 90, or SEQ ID NOs: 199 and 200).

In one embodiment, the present disclosure comprises AD-20850 (SEQ ID NOs: 91 and 92, or SEQ ID NOs: 201 and 202).

In one embodiment, the present disclosure comprises AD-20851 (SEQ ID NOs: 93 and 94, or SEQ ID NOs: 203 and 204).

In one embodiment, the present disclosure comprises AD-20852 (SEQ ID NOs: 95 and 96, or SEQ ID NOs: 205 and 206).

In one embodiment, the present disclosure comprises AD-20861 (SEQ ID NOs: 97 and 98, or SEQ ID NOs: 207 and 208).

In one embodiment, the present disclosure comprises AD-20862 (SEQ ID NOs: 99 and 100, or SEQ ID NOs: 209 and 210).

In one embodiment, the present disclosure comprises AD-20863 (SEQ ID NOs: 101 and 102, or SEQ ID NOs: 211 and 212).

In one embodiment, the present disclosure comprises AD-20864 (SEQ ID NOs: 103 and 104, or SEQ ID NOs: 213 and 214).

In one embodiment, the present disclosure comprises AD-20865 (SEQ ID NOs: 105 and 106, or SEQ ID NOs: 215 and 216).

In one embodiment, the present disclosure comprises AD-20866 (SEQ ID NOs: 107 and 108, or SEQ ID NOs: 217 and 218).

In one embodiment, the present disclosure comprises AD-20867 (SEQ ID NOs: 109 and 110, or SEQ ID NOs: 219 and 220).

In one embodiment, the RNAi agent comprises an antisense strand that is the exact sequence and length of the antisense strand of AD-20805.

In one embodiment, the RNAi agent comprises an antisense strand that is the exact sequence and length of the antisense strand of AD-20806.

In one embodiment, the RNAi agent comprises an antisense strand that is the exact sequence and length of the antisense strand of AD-20807.

In one embodiment, the RNAi agent comprises an antisense strand that is the exact sequence and length of the antisense strand of AD-20808.

In one embodiment, the RNAi agent comprises an antisense strand that is the exact sequence and length of the antisense strand of AD-20809.

In one embodiment, the RNAi agent comprises an antisense strand that is the exact sequence and length of the antisense strand of AD-20810.

In one embodiment, the RNAi agent comprises an antisense strand that is the exact sequence and length of the antisense strand of AD-20811.

In one embodiment, the RNAi agent comprises an antisense strand that is the exact sequence and length of the antisense strand of AD-20812.

In one embodiment, the RNAi agent comprises an antisense strand that is the exact sequence and length of the antisense strand of AD-20813.

In one embodiment, the RNAi agent comprises an antisense strand that is the exact sequence and length of the antisense strand of AD-20814.

In one embodiment, the RNAi agent comprises an antisense strand that is the exact sequence and length of the antisense strand of AD-20815.

In one embodiment, the RNAi agent comprises an antisense strand that is the exact sequence and length of the antisense strand of AD-20816.

In one embodiment, the RNAi agent comprises an antisense strand that is the exact sequence and length of the antisense strand of AD-20817.

In one embodiment, the RNAi agent comprises an antisense strand that is the exact sequence and length of the antisense strand of AD-20818.

In one embodiment, the RNAi agent comprises an antisense strand that is the exact sequence and length of the antisense strand of AD-20819.

In one embodiment, the RNAi agent comprises an antisense strand that is the exact sequence and length of the antisense strand of AD-20820.

In one embodiment, the RNAi agent comprises an antisense strand that is the exact sequence and length of the antisense strand of AD-20821.

In one embodiment, the RNAi agent comprises an antisense strand that is the exact sequence and length of the antisense strand of AD-20822.

In one embodiment, the RNAi agent comprises an antisense strand that is the exact sequence and length of the antisense strand of AD-20823.

In one embodiment, the RNAi agent comprises an antisense strand that is the exact sequence and length of the antisense strand of AD-20824.

In one embodiment, the RNAi agent comprises an antisense strand that is the exact sequence and length of the antisense strand of AD-20825.

In one embodiment, the RNAi agent comprises an antisense strand that is the exact sequence and length of the antisense strand of AD-20826.

In one embodiment, the RNAi agent comprises an antisense strand that is the exact sequence and length of the antisense strand of AD-20827.

In one embodiment, the RNAi agent comprises an antisense strand that is the exact sequence and length of the antisense strand of AD-20828.

In one embodiment, the RNAi agent comprises an antisense strand that is the exact sequence and length of the antisense strand of AD-20829.

In one embodiment, the RNAi agent comprises an antisense strand that is the exact sequence and length of the antisense strand of AD-20830.

In one embodiment, the RNAi agent comprises an antisense strand that is the exact sequence and length of the antisense strand of AD-20831.

In one embodiment, the RNAi agent comprises an antisense strand that is the exact sequence and length of the antisense strand of AD-20832.

In one embodiment, the RNAi agent comprises an antisense strand that is the exact sequence and length of the antisense strand of AD-20833.

In one embodiment, the RNAi agent comprises an antisense strand that is the exact sequence and length of the antisense strand of AD-20834.

In one embodiment, the RNAi agent comprises an antisense strand that is the exact sequence and length of the antisense strand of AD-20835.

In one embodiment, the RNAi agent comprises an antisense strand that is the exact sequence and length of the antisense strand of AD-20836.

In one embodiment, the RNAi agent comprises an antisense strand that is the exact sequence and length of the antisense strand of AD-20837.

In one embodiment, the RNAi agent comprises an antisense strand that is the exact sequence and length of the antisense strand of AD-20838.

In one embodiment, the RNAi agent comprises an antisense strand that is the exact sequence and length of the antisense strand of AD-20839.

In one embodiment, the RNAi agent comprises an antisense strand that is the exact sequence and length of the antisense strand of AD-20840.

In one embodiment, the RNAi agent comprises an antisense strand that is the exact sequence and length of the antisense strand of AD-20841.

In one embodiment, the RNAi agent comprises an antisense strand that is the exact sequence and length of the antisense strand of AD-20842.

In one embodiment, the RNAi agent comprises an antisense strand that is the exact sequence and length of the antisense strand of AD-20843.

In one embodiment, the RNAi agent comprises an antisense strand that is the exact sequence and length of the antisense strand of AD-20844.

In one embodiment, the RNAi agent comprises an antisense strand that is the exact sequence and length of the antisense strand of AD-20845.

In one embodiment, the RNAi agent comprises an antisense strand that is the exact sequence and length of the antisense strand of AD-20846.

In one embodiment, the RNAi agent comprises an antisense strand that is the exact sequence and length of the antisense strand of AD-20847.

In one embodiment, the RNAi agent comprises an antisense strand that is the exact sequence and length of the antisense strand of AD-20848.

In one embodiment, the RNAi agent comprises an antisense strand that is the exact sequence and length of the antisense strand of AD-20849.

In one embodiment, the RNAi agent comprises an antisense strand that is the exact sequence and length of the antisense strand of AD-20850.

In one embodiment, the RNAi agent comprises an antisense strand that is the exact sequence and length of the antisense strand of AD-20851.

In one embodiment, the RNAi agent comprises an antisense strand that is the exact sequence and length of the antisense strand of AD-20852.

In one embodiment, the RNAi agent comprises an antisense strand that is the exact sequence and length of the antisense strand of AD-20861.

In one embodiment, the RNAi agent comprises an antisense strand that is the exact sequence and length of the antisense strand of AD-20862.

In one embodiment, the RNAi agent comprises an antisense strand that is the exact sequence and length of the antisense strand of AD-20863.

In one embodiment, the RNAi agent comprises an antisense strand that is the exact sequence and length of the antisense strand of AD-20864.

In one embodiment, the RNAi agent comprises an antisense strand that is the exact sequence and length of the antisense strand of AD-20865.

In one embodiment, the RNAi agent comprises an antisense strand that is the exact sequence and length of the antisense strand of AD-20866.

In one embodiment, the RNAi agent comprises an antisense strand that is the exact sequence and length of the antisense strand of AD-20867. In these various embodiments, a RNAi agent comprising an antisense strand that is the exact sequence and length of a recited antisense strand of a recited RNAi agent can comprise modified nucleotides, 3'-end caps, and/or other modifications which do not alter the sequence or length of the RNAi agent.

Various Embodiments of a RNAi Agent to Beta-ENaC

In one embodiment, the RNAi agent comprises an antisense strand consisting of a sequence with 0, 1, 2, or 3 mismatches from that of the antisense strand of AD-20805.

In one embodiment, the RNAi agent comprises an antisense strand consisting of a sequence with 0, 1, 2, or 3 mismatches from that of the antisense strand of AD-20806.

In one embodiment, the RNAi agent comprises an antisense strand consisting of a sequence with 0, 1, 2, or 3 mismatches from that of the antisense strand of AD-20807.

In one embodiment, the RNAi agent comprises an antisense strand consisting of a sequence with 0, 1, 2, or 3 mismatches from that of the antisense strand of AD-20808.

In one embodiment, the RNAi agent comprises an antisense strand consisting of a sequence with 0, 1, 2, or 3 mismatches from that of the antisense strand of AD-20809.

In one embodiment, the RNAi agent comprises an antisense strand consisting of a sequence with 0, 1, 2, or 3 mismatches from that of the antisense strand of AD-20810.

In one embodiment, the RNAi agent comprises an antisense strand consisting of a sequence with 0, 1, 2, or 3 mismatches from that of the antisense strand of AD-20811.

In one embodiment, the RNAi agent comprises an antisense strand consisting of a sequence with 0, 1, 2, or 3 mismatches from that of the antisense strand of AD-20812.

In one embodiment, the RNAi agent comprises an antisense strand consisting of a sequence with 0, 1, 2, or 3 mismatches from that of the antisense strand of AD-20813.

In one embodiment, the RNAi agent comprises an antisense strand consisting of a sequence with 0, 1, 2, or 3 mismatches from that of the antisense strand of AD-20814.

In one embodiment, the RNAi agent comprises an antisense strand consisting of a sequence with 0, 1, 2, or 3 mismatches from that of the antisense strand of AD-20815.

In one embodiment, the RNAi agent comprises an antisense strand consisting of a sequence with 0, 1, 2, or 3 mismatches from that of the antisense strand of AD-20816.

In one embodiment, the RNAi agent comprises an antisense strand consisting of a sequence with 0, 1, 2, or 3 mismatches from that of the antisense strand of AD-20817.

In one embodiment, the RNAi agent comprises an antisense strand consisting of a sequence with 0, 1, 2, or 3 mismatches from that of the antisense strand of AD-20818.

In one embodiment, the RNAi agent comprises an antisense strand consisting of a sequence with 0, 1, 2, or 3 mismatches from that of the antisense strand of AD-20819.

In one embodiment, the RNAi agent comprises an antisense strand consisting of a sequence with 0, 1, 2, or 3 mismatches from that of the antisense strand of AD-20820.

In one embodiment, the RNAi agent comprises an antisense strand consisting of a sequence with 0, 1, 2, or 3 mismatches from that of the antisense strand of AD-20821.

In one embodiment, the RNAi agent comprises an antisense strand consisting of a sequence with 0, 1, 2, or 3 mismatches from that of the antisense strand of AD-20822.

In one embodiment, the RNAi agent comprises an antisense strand consisting of a sequence with 0, 1, 2, or 3 mismatches from that of the antisense strand of AD-20823.

In one embodiment, the RNAi agent comprises an antisense strand consisting of a sequence with 0, 1, 2, or 3 mismatches from that of the antisense strand of AD-20824.

In one embodiment, the RNAi agent comprises an antisense strand consisting of a sequence with 0, 1, 2, or 3 mismatches from that of the antisense strand of AD-20825.

In one embodiment, the RNAi agent comprises an antisense strand consisting of a sequence with 0, 1, 2, or 3 mismatches from that of the antisense strand of AD-20826.

In one embodiment, the RNAi agent comprises an antisense strand consisting of a sequence with 0, 1, 2, or 3 mismatches from that of the antisense strand of AD-20827.

In one embodiment, the RNAi agent comprises an antisense strand consisting of a sequence with 0, 1, 2, or 3 mismatches from that of the antisense strand of AD-20828.

In one embodiment, the RNAi agent comprises an antisense strand consisting of a sequence with 0, 1, 2, or 3 mismatches from that of the antisense strand of AD-20829.

In one embodiment, the RNAi agent comprises an antisense strand consisting of a sequence with 0, 1, 2, or 3 mismatches from that of the antisense strand of AD-20830.

In one embodiment, the RNAi agent comprises an antisense strand consisting of a sequence with 0, 1, 2, or 3 mismatches from that of the antisense strand of AD-20831.

In one embodiment, the RNAi agent comprises an antisense strand consisting of a sequence with 0, 1, 2, or 3 mismatches from that of the antisense strand of AD-20832.

In one embodiment, the RNAi agent comprises an antisense strand consisting of a sequence with 0, 1, 2, or 3 mismatches from that of the antisense strand of AD-20833.

In one embodiment, the RNAi agent comprises an antisense strand consisting of a sequence with 0, 1, 2, or 3 mismatches from that of the antisense strand of AD-20834.

In one embodiment, the RNAi agent comprises an antisense strand consisting of a sequence with 0, 1, 2, or 3 mismatches from that of the antisense strand of AD-20835.

In one embodiment, the RNAi agent comprises an antisense strand consisting of a sequence with 0, 1, 2, or 3 mismatches from that of the antisense strand of AD-20836.

In one embodiment, the RNAi agent comprises an antisense strand consisting of a sequence with 0, 1, 2, or 3 mismatches from that of the antisense strand of AD-20837.

In one embodiment, the RNAi agent comprises an antisense strand consisting of a sequence with 0, 1, 2, or 3 mismatches from that of the antisense strand of AD-20838.

In one embodiment, the RNAi agent comprises an antisense strand consisting of a sequence with 0, 1, 2, or 3 mismatches from that of the antisense strand of AD-20839.

In one embodiment, the RNAi agent comprises an antisense strand consisting of a sequence with 0, 1, 2, or 3 mismatches from that of the antisense strand of AD-20840.

In one embodiment, the RNAi agent comprises an antisense strand consisting of a sequence with 0, 1, 2, or 3 mismatches from that of the antisense strand of AD-20841.

In one embodiment, the RNAi agent comprises an antisense strand consisting of a sequence with 0, 1, 2, or 3 mismatches from that of the antisense strand of AD-20842.

In one embodiment, the RNAi agent comprises an antisense strand consisting of a sequence with 0, 1, 2, or 3 mismatches from that of the antisense strand of AD-20843.

In one embodiment, the RNAi agent comprises an antisense strand consisting of a sequence with 0, 1, 2, or 3 mismatches from that of the antisense strand of AD-20844.

In one embodiment, the RNAi agent comprises an antisense strand consisting of a sequence with 0, 1, 2, or 3 mismatches from that of the antisense strand of AD-20845.

In one embodiment, the RNAi agent comprises an antisense strand consisting of a sequence with 0, 1, 2, or 3 mismatches from that of the antisense strand of AD-20846.

In one embodiment, the RNAi agent comprises an antisense strand consisting of a sequence with 0, 1, 2, or 3 mismatches from that of the antisense strand of AD-20847.

In one embodiment, the RNAi agent comprises an antisense strand consisting of a sequence with 0, 1, 2, or 3 mismatches from that of the antisense strand of AD-20848.

In one embodiment, the RNAi agent comprises an antisense strand consisting of a sequence with 0, 1, 2, or 3 mismatches from that of the antisense strand of AD-20849.

In one embodiment, the RNAi agent comprises an antisense strand consisting of a sequence with 0, 1, 2, or 3 mismatches from that of the antisense strand of AD-20850.

In one embodiment, the RNAi agent comprises an antisense strand consisting of a sequence with 0, 1, 2, or 3 mismatches from that of the antisense strand of AD-20851.

In one embodiment, the RNAi agent comprises an antisense strand consisting of a sequence with 0, 1, 2, or 3 mismatches from that of the antisense strand of AD-20852.

In one embodiment, the RNAi agent comprises an antisense strand consisting of a sequence with 0, 1, 2, or 3 mismatches from that of the antisense strand of AD-20861.

In one embodiment, the RNAi agent comprises an antisense strand consisting of a sequence with 0, 1, 2, or 3 mismatches from that of the antisense strand of AD-20862.

In one embodiment, the RNAi agent comprises an antisense strand consisting of a sequence with 0, 1, 2, or 3 mismatches from that of the antisense strand of AD-20863.

In one embodiment, the RNAi agent comprises an antisense strand consisting of a sequence with 0, 1, 2, or 3 mismatches from that of the antisense strand of AD-20864.

In one embodiment, the RNAi agent comprises an antisense strand consisting of a sequence with 0, 1, 2, or 3 mismatches from that of the antisense strand of AD-20865.

In one embodiment, the RNAi agent comprises an antisense strand consisting of a sequence with 0, 1, 2, or 3 mismatches from that of the antisense strand of AD-20866.

In one embodiment, the RNAi agent comprises an antisense strand consisting of a sequence with 0, 1, 2, or 3 mismatches from that of the antisense strand of AD-20867.

Various Embodiments of a RNAi Agent to Beta-ENaC

In one embodiment, the RNAi agent comprises an antisense strand consisting of a sequence with 0, 1, 2, or 3 mismatches from that of the antisense strand of AD-20805, wherein the antisense strand optionally further comprises 0, 1, 2, 3, 4, 5, 6, 7, 8, 9, or 10 nt (or any range thereof, e.g., 0-1, 1-2, 1-3, 1-4, 1-5, 1-6, 1-7, 1-8, 1-9, 1-10, 2-3, 2-4, or 2-5 nt, etc.).

In one embodiment, the RNAi agent comprises an antisense strand consisting of a sequence with 0, 1, 2, or 3 mismatches from that of the antisense strand of AD-20806, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20807, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20808, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20809, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20810, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20811, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20812, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20813, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20814, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20815, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20816, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20817, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20818, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20819, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20820, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20821, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20822, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20823, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20824, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20825, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20826, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20827, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20828, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20829, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20830, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20831, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20832, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20833, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20834, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20835, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20836, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20837, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20838, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20839, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20840, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20841, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20842, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20843, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20844, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20845, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20846, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20847, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20848, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20849, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20850, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20851, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20852, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20861, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20862, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20863, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20864, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20865, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20866, wherein the antisense strand optionally further comprises 0, 1, 2, 3, 4, 5, 6, 7, 8, 9, or 10 nt (or any range thereof).

In one embodiment, the RNAi agent comprises an antisense strand consisting of a sequence with 0, 1, 2, or 3 mismatches from that of the antisense strand of AD-20867, wherein the antisense strand optionally further comprises 0, 1, 2, 3, 4, 5, 6, 7, 8, 9, or 10 nt (or any range thereof).

Additional Particular Specific Embodiments

In various embodiments, the disclosure comprises a RNAi agent comprising a sense and an antisense strand, wherein the antisense strand comprises at least 15 contiguous nucleotides differing by 0, 1, 2, or 3 nt from the antisense strand of any RNAi agent disclosed herein.

Thus, in various embodiments:

The disclosure comprises a RNAi agent comprising a sense and an antisense strand, wherein the antisense strand comprises at least 15 contiguous nucleotides differing by 0, 1, 2, or 3 nt from the antisense strand of any one or more of the following duplexes, or modified or unmodified variants thereof: AD-20832; AD-20848; AD-20807; AD-20826; AD-20837; AD-20861; AD-20834, AD-20805, AD-20806, AD-20808, AD-20809, AD-20810, AD-20811, AD-20812, AD-20813, AD-20814, AD-20815, AD-20816, AD-20817, AD-20818, AD-20819, AD-20820, AD-20821, AD-20822, AD-20823, AD-20824, AD-20825, AD-20827, AD-20828, AD-20829, AD-20830, AD-20831, AD-20833, AD-20835, AD-20836, AD-20838, AD-20839, AD-20840, AD-20841, AD-20842, AD-20843, AD-20844, AD-20845, AD-20846, AD-20847, AD-20849, AD-20850, AD-20851, AD-20852, AD-20862, AD-20863, AD-20864, AD-20865, AD-20866, AD-20867, or modified or unmodified variants thereof.

Additional Particular Specific Embodiments

In various embodiments, the disclosure comprises a RNAi agent comprising a first and a second strand, wherein the sequence of the first strand comprises at least 15 contiguous nucleotides differing by 0, 1, 2, or 3 nt from the sequence of the first strand of, and the sequence of the second strand comprises at least 15 contiguous nucleotides differing by 0, 1, 2, or 3 nucleotides from the sequence of the second strand, of any RNAi agent, disclosed herein.

Thus, in various embodiments:

The disclosure comprises a RNAi agent comprising a sense and an antisense strand, wherein the sequence of the first strand comprises at least 15 contiguous nucleotides differing by 0, 1, 2, or 3 nt from the sequence of the first strand of, and the sequence of the second strand comprises at least 15 contiguous nucleotides differing by 0, 1, 2, or 3 nucleotides from the sequence of the second strand, of any one or more of the following duplexes, or modified or unmodified variants thereof: AD-20832; AD-20848; AD-20807; AD-20826; AD-20837; AD-20861; AD-20834, AD-20805, AD-20806, AD-20808, AD-20809, AD-20810, AD-20811, AD-20812, AD-20813, AD-20814, AD-20815, AD-20816, AD-20817, AD-20818, AD-20819, AD-20820, AD-20821, AD-20822, AD-20823, AD-20824, AD-20825, AD-20827, AD-20828, AD-20829, AD-20830, AD-20831, AD-20833, AD-20835, AD-20836, AD-20838, AD-20839, AD-20840, AD-20841, AD-20842, AD-20843, AD-20844, AD-20845, AD-20846, AD-20847, AD-20849, AD-20850, AD-20851, AD-20852, AD-20862, AD-20863, AD-20864, AD-20865, AD-20866, AD-20867, or modified or unmodified variants thereof.

Additional Particular Embodiments

In various embodiments, the disclosure comprises a RNAi agent comprising a sense and an antisense strand, wherein the antisense strand comprises or consists of the antisense strand of any RNAi agent disclosed herein.

Thus, the following are provided as examples of the various embodiments.

The disclosure comprises a RNAi agent comprising a sense and an antisense strand, wherein the antisense strand comprises or consists of the antisense strand of: AD-20832; AD-20848; AD-20807; AD-20826; AD-20837; AD-20861; AD-20834, AD-20805, AD-20806, AD-20808, AD-20809, AD-20810, AD-20811, AD-20812, AD-20813, AD-20814, AD-20815, AD-20816, AD-20817, AD-20818, AD-20819, AD-20820, AD-20821, AD-20822, AD-20823, AD-20824, AD-20825, AD-20827, AD-20828, AD-20829, AD-20830, AD-20831, AD-20833, AD-20835, AD-20836, AD-20838, AD-20839, AD-20840, AD-20841, AD-20842, AD-20843, AD-20844, AD-20845, AD-20846, AD-20847, AD-20849, AD-20850, AD-20851, AD-20852, AD-20862, AD-20863, AD-20864, AD-20865, AD-20866, AD-20867, or modified or unmodified variants thereof.

In various embodiments, the disclosure comprises a RNAi agent comprising a sense and an antisense strand, wherein the antisense strand comprises at least 15 contiguous nucleotides differing by 0, 1, 2, or 3 nt from the antisense strand of any RNAi agent disclosed herein, or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

Thus, in various embodiments, the disclosure comprises a RNAi agent comprising a sense and an antisense strand, wherein the antisense strand comprises at least 15 contiguous nucleotides differing by 0, 1, 2, or 3 nt from the antisense strand of: AD-20832; AD-20848; AD-20807; AD-20826; AD-20837; AD-20861; AD-20834, AD-20805, AD-20806, AD-20808, AD-20809, AD-20810, AD-20811, AD-20812, AD-20813, AD-20814, AD-20815, AD-20816, AD-20817, AD-20818, AD-20819, AD-20820, AD-20821, AD-20822, AD-20823, AD-20824, AD-20825, AD-20827, AD-20828, AD-20829, AD-20830, AD-20831, AD-20833, AD-20835, AD-20836, AD-20838, AD-20839, AD-20840, AD-20841, AD-20842, AD-20843, AD-20844, AD-20845, AD-20846, AD-20847, AD-20849, AD-20850, AD-20851, AD-20852, AD-20862, AD-20863, AD-20864, AD-20865, AD-20866, AD-20867, or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

In various embodiments, the disclosure comprises a RNAi agent comprising a first and a second strand, wherein the sequence of the first strand comprises or consists of the sequence of the first strand of, and the sequence of the second strand comprises or consists of the sequence of the second strand of any RNAi agent disclosed herein, or modified or unmodified variants thereof.

Thus, in various embodiments, the disclosure comprises a RNAi agent comprising a first and a second strand, wherein the sequence of the first strand comprises or consists of the sequence of the first strand of, and the sequence of the second strand comprises or consists of the sequence of the second strand of: AD-20832; AD-20848; AD-20807; AD-20826; AD-20837; AD-20861; AD-20834, AD-20805, AD-20806, AD-20808, AD-20809, AD-20810, AD-20811, AD-20812, AD-20813, AD-20814, AD-20815, AD-20816, AD-20817, AD-20818, AD-20819, AD-20820, AD-20821, AD-20822, AD-20823, AD-20824, AD-20825, AD-20827, AD-20828, AD-20829, AD-20830, AD-20831, AD-20833, AD-20835, AD-20836, AD-20838, AD-20839, AD-20840, AD-20841, AD-20842, AD-20843, AD-20844, AD-20845, AD-20846, AD-20847, AD-20849, AD-20850, AD-20851, AD-20852, AD-20862, AD-20863, AD-20864, AD-20865, AD-20866, AD-20867.

In one embodiment, the disclosure comprises any one or more RNAi agent listed herein.

Overlapping Sets of RNAi Agents to Beta-ENaC

In various embodiments, the present disclosure relates to groups of RNAi agents to Beta-ENaC with overlapping sequences. Thus, the present disclosure encompasses groups of RNAi agents wherein each RNAi agent in the group overlaps with each other RNAi agent in the same group by at least 5, 6, 7, 8, 9, 10, 11, 12, 13, 14, 15, 16, 17, 18, 19 or more nucleotides. Particularly, in one embodiment, the overlap is at least 12 nt.

Some of the RNAi agents listed herein overlap each other in sequence. Table 2 presents a compilation of some of these groups of overlapping RNAi agents, wherein each member of a group overlaps with each other member of the same group by at least 12 nt. A 12-nt portion of the overlap of the sense and anti-sense strand are presented.

Thus, for example, as shown in Table 2, the sequences of RNAi agents AD-20807 and AD-20832 overlap, wherein the overlap in the sense strand comprises the sequence UGAAGAAGUACC (SEQ ID NO: 223); these RNAi agents also overlap in the anti-sense strand sequence, wherein the overlap comprises the sequence GGUACUUCUUCA (SEQ ID NO: 224). The RNAi agents AD-20807, AD-20862 and AD-20832 all overlap in the sense strand, wherein the overlap comprises the sequence GAAGAAGUACCU (SEQ ID NO: 225); these RNAi agents also overlap in the anti-sense strand, wherein the overlap comprises the sequence AGGUACUUCUUC (SEQ ID NO: 226). Thus, these and other various sets of overlapping RNAi agents presented in Table 2 share common technical features, for example, the overlap in the sense and anti-sense strand.

Particular sets of overlapping RNAi agents to Beta-ENaC are provided below in Table 2.

The present disclosure thus encompasses any group or subgroup of RNAi agents comprising a common technical feature, wherein the common technical feature is an overlap (e.g., of at least 12 nt) of a sequence in the sense or anti-sense strand.

Thus:

The present disclosure encompasses a RNAi agent comprising: an antisense strand comprising at least 15 contiguous nucleotides differing by 0, 1, 2, or 3 nt from the antisense strand, and/or a sense strand comprising at least 15 contiguous nucleotides differing by 0, 1, 2, or 3 nt from the sense strand, of any of the group of: AD-20807 and AD-20832 (or any other group presented in Table 2).

The present disclosure encompasses a RNAi agent comprising a first and a second strand, wherein the first strand comprises at least 15 contiguous nucleotides differing by 0, 1, 2, or 3 nt from the first strand of, and/or the second strand comprises at least 15 contiguous nucleotides differing by 0, 1, 2, or 3 nt from the second strand, of any of the group of: AD-20807 and AD-20832 (or any other group presented in Table 2).

The present disclosure encompasses a RNAi agent comprising a first and a second strand, wherein the first strand comprises or consists of the sequence of a first strand of, and/or the second strand comprises or consists of the sequence of, any of the group of: AD-20807 and AD-20832 (or any other group presented in Table 2).

The disclose encompasses a RNAi agent comprising a first and a second strand (wherein the first and second strand may optionally be covalently linked, linked via a loop or linker, or contiguous), and wherein the first and/or second strand comprise, consist essentially of, or consist of sequences with 0, 1, 2, or 3 nt or by mismatches of any of the group of: AD-20807 and AD-20832 (or any other group presented in Table 2), optionally further comprising 0-10 nt or bp.

The present disclosure similarly encompasses various embodiments encompassing groups of overlapping RNAi agents presented in Table 2.

Additional Definitions

The articles "a" and "an" as used herein and in the claims refer to one or more than one (at least one) of the grammatical object of the article.

The terms "RNAi agent," "RNAi agents", "RNAi agent(s)" and the like all refer without limitation to one or more RNAi agents of the present disclosure.

The designations of particular example duplexes of RNAi agents to Beta-ENaC disclosed herein on occasion have the suffix "b" followed by a number. This indicates a batch number. Thus, the suffix "b1" indicates "batch 1." Thus, a RNAi duplex designated, for example, "AD-20807-b1" is specifically from batch 1 and has the same sequence as any RNAi agent designated "AD-20807".

Unless defined otherwise, the technical and scientific terms used herein have the same meaning as that usually understood by a specialist familiar with the field to which the present disclosure belongs.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein.

Claims to the present disclosure are non-limiting and are provided below.

Although particular embodiments and claims have been disclosed herein in detail, this has been done by way of example for purposes of illustration only, and is not intended to be limiting with respect to the scope of the appended claims, or the scope of subject matter of claims of any corresponding future application. In particular, it is contemplated by the inventors that various substitutions, alterations, and modifications may be made to the present disclosure without departing from the spirit and scope of the present disclosure as defined by the claims. The choice of nucleic acid starting material, clone of interest, or library type is believed to be a matter of routine for a person of ordinary skill in the art with knowledge of the embodiments described herein. Other aspects, advantages, and modifications considered to be within the scope of the following claims. Redrafting of claim scope in later-filed corresponding applications may be due to limitations by the patent laws of various countries and should not be interpreted as giving up subject matter of the claims.

Various additional formulations and obvious variants of the described RNAi agents to Beta-ENaC can be devised by those of ordinary skill in the art. Non-limiting example RNAi agents to Beta-ENaC are described in the Examples below, which do not limit the scope of the present disclosure as described in the claims.

EXAMPLES

Example 1

Bioinformatics and Beta-ENaC RNAi Agent (siRNA) Sequences

Beta-ENaC oligonucleotide design is carried out to identify siRNAs targeting mRNAs encoding the Beta-ENaC gene ["sodium channel, nonvoltage-gated 1 beta" from human (NCBI human symbol SCNN1B) and the orthologous sequences from cynomolgus monkey (*Macaca fascicularis*) and rat (*Rattus norvegicus*)]. The design process uses the SCNNB1 transcripts NM_000336.2 from human (NCBI Geneld 6338), NM_012648.1 from rat (NCBI Geneld 24767), and a full length cynomolgus monkey sequence (described herein).

All siRNA duplexes are designed to have 100% identity to all three SCNNB1 transcripts. All sequences are from Transcript NM_000336.

Unmodified and modified sequences are listed in Table 1. Unmodified sequences include both the sense and antisense sequences which are listed as SEQ ID NO: 111 to 220. The relative positions of the first residue as compared to the human Beta-ENaC transcript in SEQ ID NO: 222 are also provided.

As described below, Table 1 also provides example modified variants of these sequences (SEQ ID NO: 1 to 110). For the Table 1 columns, "S" represents the sense strand, "AS" represents the antisense strand, and "Pos'n" represents the position of the first nucleotide. Modified nucleotides, as indicated by lower case letters (e.g., "c" and "u") are as described in Table 1A, below.

In the sequences in Table 1, the modified and unmodified sequences can optionally comprise the sequence "dTsdT" at the 3' end. Thus, for example, AD-20805 can optionally have the modified sequence cAGuGAcuAcAAcAcGAccdTsdT (SEQ ID NO: 429) in the sense strand and GGUCGUGUU-GuAGUcACUGdTsdT (SEQ ID NO: 430) in the anti-sense strand. As noted in Table 1A, below, dT is 2'-deoxy-thymidine-5'-phosphate and sdT is 2'-deoxy Thymidine 5'-phosphorothioate.

TABLE 1

Beta-ENaC sequences

| Duplex ID | | SEQ ID | Modified sequence | SEQ ID | Unmodified sequence | Pos'n |
|---|---|---|---|---|---|---|
| AD-20805 | S | 1 | cAGuGAcuAcAAcAcGAcc | 111 | CAGUGACUACAACACGACC | 1298 |
| | AS | 2 | GGUCGUGUUGuAGUcACUG | 112 | GGUCGUGUUGUAGUCACUG | 1298 |
| AD-20806 | S | 3 | AuGAcAGAGAAGGcAcuuc | 113 | AUGACAGAGAAGGCACUUC | 1011 |
| | AS | 4 | GAAGUGCCUUCUCUGUcAU | 114 | GAAGUGCCUUCUCUGUCAU | 1011 |
| AD-20807 | S | 5 | GuGAAGAAGuAccuGcuGA | 115 | GUGAAGAAGUACCUGCUGA | 183 |
| | AS | 6 | UcAGcAGGuACUUCUUcAC | 116 | UCAGCAGGUACUUCUUCAC | 183 |
| AD-20808 | S | 7 | GuGAcuAcAAcAcGAccuA | 117 | GUGACUACAACACGACCUA | 1300 |
| | AS | 8 | uAGGUCGUGUUGuAGUcAC | 118 | UAGGUCGUGUUGUAGUCAC | 1300 |
| AD-20809 | S | 9 | GGuGGAGGcccAcAccAAc | 119 | GGUGGAGGCCCACACCAAC | 1919 |
| | AS | 10 | GUUGGUGUGGGCCUCcACC | 120 | GUUGGUGUGGGCCUCCACC | 1919 |
| AD-20810 | S | 11 | uGGuGGAGGcccAcAccAA | 121 | UGGUGGAGGCCCACACCAA | 1918 |
| | AS | 12 | UUGGUGUGGGCCUCcACcA | 122 | UUGGUGUGGGCCUCCACCA | 1918 |
| AD-20811 | S | 13 | uuccAAGAccAcAuGAucc | 123 | UUCCAAGACCACAUGAUCC | 1347 |
| | AS | 14 | GGAUcAUGUGGUCUUGGAA | 124 | GGAUCAUGUGGUCUUGGAA | 1347 |
| AD-20812 | S | 15 | AGcuGGGAGGucAGcGucu | 125 | AGCUGGGAGGUCAGCGUCU | 402 |
| | AS | 16 | AGACGCUGACCUCCcAGCU | 126 | AGACGCUGACCUCCCAGCU | 402 |
| AD-20813 | S | 17 | GGGAGAAAuAcUGcAAcAA | 127 | GGGAGAAAUACUGCAACAA | 1408 |
| | AS | 18 | UUGUUGcAGuAUUUCUCCC | 128 | UUGUUGCAGUAUUUCUCCC | 1408 |
| AD-20814 | S | 19 | ccAGuuuGGcuucuGGAuG | 129 | CCAGUUUGGCUUCUGGAUG | 1748 |
| | AS | 20 | cAUCcAGAAGCcAAACUGG | 130 | CAUCCAGAAGCCAAACUGG | 1748 |
| AD-20815 | S | 21 | AGuGAcuAcAAcAcGAccu | 131 | AGUGACUACAACACGACCU | 1299 |
| | AS | 22 | AGGUCGUGUUGuAGUcACU | 132 | AGGUCGUGUUGUAGUCACU | 1299 |
| AD-20816 | S | 23 | AAuAucAcccuGAGcAGGA | 133 | AAUAUCACCCUGAGCAGGA | 1626 |
| | AS | 24 | UCCUGCUcAGGGUGAuAUU | 134 | UCCUGCUCAGGGUGAUAUU | 1626 |
| AD-20817 | S | 25 | ccuGcAGGccAccAAcAuc | 135 | CCUGCAGGCCACCAACAUC | 836 |
| | AS | 26 | GAUGUUGGUGGCCUGcAGG | 136 | GAUGUUGGUGGCCUGCAGG | 836 |
| AD-20818 | S | 27 | AucAcccuGAGcAGGAAGG | 137 | AUCACCCUGAGCAGGAAGG | 1629 |
| | AS | 28 | CCUUCCUGCUcAGGGUGAU | 138 | CCUUCCUGCUCAGGGUGAU | 1629 |

TABLE 1-continued

Beta-ENaC sequences

| Duplex ID | | SEQ ID | Modified sequence | SEQ ID | Unmodified sequence | Pos'n |
|---|---|---|---|---|---|---|
| AD-20819 | S | 29 | GcuGGGAGGucAGcGucuc | 139 | GCUGGGAGGUCAGCGUCUC | 403 |
| | AS | 30 | GAGACGCUGACCUCCcAGC | 140 | GAGACGCUGACCUCCCAGC | 403 |
| AD-20820 | S | 31 | GAGcuGGGAGGucAGcGuc | 141 | GAGCUGGGAGGUCAGCGUC | 401 |
| | AS | 32 | GACGCUGACCUCCcAGCUC | 142 | GACGCUGACCUCCCAGCUC | 401 |
| AD-20821 | S | 33 | GuGGccAGuuuGGcuucuG | 143 | GUGGCCAGUUUGGCUUCUG | 1744 |
| | AS | 34 | cAGAAGCcAAACUGGCcAC | 144 | CAGAAGCCAAACUGGCCAC | 1744 |
| AD-20822 | S | 35 | cAGuuuGGcuucuGGAuGG | 145 | CAGUUUGGCUUCUGGAUGG | 1749 |
| | AS | 36 | CCAUCCAGAAGCCAAACUG | 146 | CCAUCCAGAAGCCAAACUG | 1749 |
| AD-20823 | S | 37 | GGccAGuuuGGcuucuGGA | 147 | GGCCAGUUUGGCUUCUGGA | 1746 |
| | AS | 38 | UCcAGAAGCcAAACUGGCC | 148 | UCCAGAAGCCAAACUGGCC | 1746 |
| AD-20824 | S | 39 | cuGGGuGGccAGuuuGGcu | 149 | CUGGGUGGCCAGUUUGGCU | 1740 |
| | AS | 40 | AGCcAAACUGGCcACCcAG | 150 | AGCCAAACUGGCCACCCAG | 1740 |
| AD-20825 | S | 41 | ucuAcAGuGAcuAcAAcAc | 151 | UCUACAGUGACUACAACAC | 1294 |
| | AS | 42 | GUGUUGuAGUcACUGuAGA | 152 | GUGUUGUAGUCACUGUAGA | 1294 |
| AD-20826 | S | 43 | GcAuGAcAGAGAAGGcAcu | 153 | GCAUGACAGAGAAGGCACU | 1009 |
| | AS | 44 | AGUGCCUUCUCUGUcAUGC | 154 | AGUGCCUUCUCUGUCAUGC | 1009 |
| AD-20827 | S | 45 | AuAucAcccuGAGcAGGAA | 155 | AUAUCACCCUGAGCAGGAA | 1627 |
| | AS | 46 | UUCCUGCUcAGGGUGAuAU | 156 | UUCCUGCUCAGGGUGAUAU | 1627 |
| AD-20828 | S | 47 | cuAcAGuGAcuAcAAcAcG | 157 | CUACAGUGACUACAACACG | 1295 |
| | AS | 48 | CGUGUUGuAGUcACUGuAG | 158 | CGUGUUGUAGUCACUGUAG | 1295 |
| AD-20829 | S | 49 | uAucAcccuGAGcAGGAAG | 159 | UAUCACCCUGAGCAGGAAG | 1628 |
| | AS | 50 | CUUCCUGCUcAGGGUGAuA | 160 | CUUCCUGCUCAGGGUGAUA | 1628 |
| AD-20830 | S | 51 | uGcAGGccAccAAcAucuu | 161 | UGCAGGCCACCAACAUCUU | 838 |
| | AS | 52 | AAGAUGUUGGUGGCCUGcA | 162 | AAGAUGUUGGUGGCCUGCA | 838 |
| AD-20831 | S | 53 | cAuGAcAGAGAAGGcAcuu | 163 | CAUGACAGAGAAGGCACUU | 1010 |
| | AS | 54 | AAGUGCCUUCUCUGUcAUG | 164 | AAGUGCCUUCUCUGUCAUG | 1010 |
| AD-20832 | S | 55 | uGAAGAAGuAccUGcuGAA | 165 | UGAAGAAGUACCUGCUGAA | 184 |
| | AS | 56 | UUcAGcAGGuACUUCUUcA | 166 | UUCAGCAGGUACUUCUUCA | 184 |
| AD-20833 | S | 57 | GcuGGuGGAGGcccAcAcc | 167 | GCUGGUGGAGGCCCACACC | 1916 |
| | AS | 58 | GGUGUGGGCCUCcACcAGC | 168 | GGUGUGGGCCUCCACCAGC | 1916 |
| AD-20834 | S | 59 | uAcAGuGAcuAcAAcAcGA | 169 | UACAGUGACUACAACACGA | 1296 |
| | AS | 60 | UCGUGUUGuAGUcACUGuA | 170 | UCGUGUUGUAGUCACUGUA | 1296 |
| AD-20835 | S | 61 | AcAGAGAAGGcAcuuccuu | 171 | ACAGAGAAGGCACUUCCUU | 1014 |
| | AS | 62 | AAGGAAGUGCCUUCUCUGU | 172 | AAGGAAGUGCCUUCUCUGU | 1014 |
| AD-20836 | S | 63 | AcAGuGAcuAcAAcAcGAc | 173 | ACAGUGACUACAACACGAC | 1297 |
| | AS | 64 | GUCGUGUUGuAGUcACUGU | 174 | GUCGUGUUGUAGUCACUGU | 1297 |
| AD-20837 | S | 65 | uGAGcuGGGAGGucAGcGu | 175 | UGAGCUGGGAGGUCAGCGU | 400 |
| | AS | 66 | ACGCUGACCUCCcAGCUcA | 176 | ACGCUGACCUCCCAGCUCA | 400 |

TABLE 1-continued

Beta-ENaC sequences

| Duplex ID | | SEQ ID | Modified sequence | SEQ ID | Unmodified sequence | Pos'n |
|---|---|---|---|---|---|---|
| AD-20838 | S | 67 | uGGccAGuuuGGcuucuGG | 177 | UGGCCAGUUUGGCUUCUGG | 1745 |
| | AS | 68 | CcAGAAGCcAAACUGGCcA | 178 | CCAGAAGCCAAACUGGCCA | 1745 |
| AD-20839 | S | 69 | uGucucAGGAGcGGGAccA | 179 | UGUCUCAGGAGCGGGACCA | 1600 |
| | AS | 70 | UGGUCCCGCUCCUGAGAcA | 180 | UGGUCCCGCUCCUGAGACA | 1600 |
| AD-20840 | S | 71 | GuGGAGGcccAcAccAAcu | 181 | GUGGAGGCCCACACCAACU | 1920 |
| | AS | 72 | AGUUGGUGUGGGCCUCcAC | 182 | AGUUGGUGUGGGCCUCCAC | 1920 |
| AD-20841 | S | 73 | GGGuGGccAGuuuGGcuuc | 183 | GGGUGGCCAGUUUGGCUUC | 1742 |
| | AS | 74 | GAAGCcAAACUGGCcACCC | 184 | GAAGCCAAACUGGCCACCC | 1742 |
| AD-20842 | S | 75 | GGuGGccAGuuuGGcuucu | 185 | GGUGGCCAGUUUGGCUUCU | 1743 |
| | AS | 76 | AGAAGCcAAACUGGCcACC | 186 | AGAAGCCAAACUGGCCACC | 1743 |
| AD-20843 | S | 77 | ucAcccuGAGcAGGAAGGG | 187 | UCACCCUGAGCAGGAAGGG | 1630 |
| | AS | 78 | CCCUUCCUGCUcAGGGUGA | 188 | CCCUUCCUGCUCAGGGUGA | 1630 |
| AD-20844 | S | 79 | GccAGuuuGGcuucuGGAu | 189 | GCCAGUUUGGCUUCUGGAU | 1747 |
| | AS | 80 | AUCcAGAAGCcAAACUGGC | 190 | AUCCAGAAGCCAAACUGGC | 1747 |
| AD-20845 | S | 81 | AGcuGGuGGAGGcccAcAc | 191 | AGCUGGUGGAGGCCCACAC | 1915 |
| | AS | 82 | GUGUGGGCCUCcAccAGCU | 192 | GUGUGGGCCUCCACCAGCU | 1915 |
| AD-20846 | S | 83 | AucuccAuGGcuGAcuGGc | 193 | AUCUCCAUGGCUGACUGGC | 1545 |
| | AS | 84 | GCcAGUcAGCcAUGGAGAU | 194 | GCCAGUCAGCCAUGGAGAU | 1545 |
| AD-20847 | S | 85 | GGcAuGAcAGAGAAGGcAc | 195 | GGCAUGACAGAGAAGGCAC | 1008 |
| | AS | 86 | GUGCCUUCUCUGUcAUGCC | 196 | GUGCCUUCUCUGUCAUGCC | 1008 |
| AD-20848 | S | 87 | GGAGAAAuAcuGcAAcAAc | 197 | GGAGAAAUACUGCAACAAC | 1409 |
| | AS | 88 | GUUGUUGcAGuAUUUCUCC | 198 | GUUGUUGCAGUAUUUCUCC | 1409 |
| AD-20849 | S | 89 | uGGGuGGccAGuuuGGcuu | 199 | UGGGUGGCCAGUUUGGCUU | 1741 |
| | AS | 90 | AAGCcAAACUGGCcACCcA | 200 | AAGCCAAACUGGCCACCCA | 1741 |
| AD-20850 | S | 91 | GAGcuGGuGGAGGcccAcA | 201 | GAGCUGGUGGAGGCCCACA | 1914 |
| | AS | 92 | UGUGGGCCUCcAccAGCUC | 202 | UGUGGGCCUCCACCAGCUC | 1914 |
| AD-20851 | S | 93 | GAcAGAGAAGGcAcuuccu | 203 | GACAGAGAAGGCACUUCCU | 1013 |
| | AS | 94 | AGGAAGUGCCUUCUCUGUC | 204 | AGGAAGUGCCUUCUCUGUC | 1013 |
| AD-20852 | S | 95 | AGuuuGGcuucuGGAuGGG | 205 | AGUUUGGCUUCUGGAUGGG | 1750 |
| | AS | 96 | CCcAUCcAGAAGCcAAACU | 206 | CCCAUCCAGAAGCCAAACU | 1750 |
| AD-20861 | S | 97 | uGAcAGAGAAGGcAcuucc | 207 | UGACAGAGAAGGCACUUCC | 1012 |
| | AS | 98 | GGAAGUGCCUUCUCUGUcA | 208 | GGAAGUGCCUUCUCUGUCA | 1012 |
| AD-20862 | S | 99 | GAAGAAGuAccuGcuGAAG | 209 | GAAGAAGUACCUGCUGAAG | 185 |
| | AS | 100 | CUUcAGcAGGuACUUCUUC | 210 | CUUCAGCAGGUACUUCUUC | 185 |
| AD-20863 | S | 101 | ucuccAuGGcuGAcuGGcc | 211 | UCUCCAUGGCUGACUGGCC | 1546 |
| | AS | 102 | GGCcAGUcAGCcAUGGAGA | 212 | GGCCAGUCAGCCAUGGAGA | 1546 |

TABLE 1-continued

Beta-ENaC sequences

| Duplex ID | | SEQ ID | Modified sequence | SEQ ID | Unmodified sequence | Pos'n |
|---|---|---|---|---|---|---|
| AD-20864 | S | 103 | cuGGuGGAGGcccAcAccA | 213 | CUGGUGGAGGCCCACACCA | 1917 |
| | AS | 104 | UGGUGUGGGCCUCcACcAG | 214 | UGGUGUGGGCCUCCACCAG | 1917 |
| AD-20865 | S | 105 | cAGAGAAGGcAcuuccuuc | 215 | CAGAGAAGGCACUUCCUUC | 1015 |
| | AS | 106 | GAAGGAAGUGCCUUCUCUG | 216 | GAAGGAAGUGCCUUCUCUG | 1015 |
| AD-20866 | S | 107 | cuGcAGGccAccAAcAucu | 217 | CUGCAGGCCACCAACAUCU | 837 |
| | AS | 108 | AGAUGUUGGUGGCCUGcAG | 218 | AGAUGUUGGUGGCCUGCAG | 837 |
| AD-20867 | S | 109 | GGGcAuGAcAGAGAAGGcA | 219 | GGGCAUGACAGAGAAGGCA | 1007 |
| | AS | 110 | UGCCUUCUCUGUcAUGCCC | 220 | UGCCUUCUCUGUCAUGCCC | 1007 |

Modifications of the sequences of RNAi agents of SEQ ID NO: 111 to 220 are easily conceived by one of skill in the art. Examples and non-limiting modifications of these sequences are conceived and are also listed in Table 1, e.g., the sense and antisense (AS) sequences in SEQ ID NO: 1 to 110.

Some modifications are placed at sites predicted to be sensitive to endonucleases. Some modifications are designed to eliminate an immune response to the siRNA while preserving activity. In general, the sense strand is heavily modified, and the antisense strand lightly modified. Some modifications serve more than one purpose.

The sequences in Table 1 and other tables are represented by these abbreviations:

TABLE 1A

ABBREVIATIONS

| Abbreviation | Nucleotide(s) |
|---|---|
| A | adenosine-5'-phosphate |
| C | cytidine-5'-phosphate |
| G | guanosine-5'-phosphate |
| dT | 2'-deoxy-thymidine-5'-phosphate |
| U | uridine-5'-phosphate |
| c | 2'-O-methylcytidine-5'-phosphate |
| u | 2'-O-methyluridine-5'-phosphate |
| sdT | 2'-deoxy Thymidine 5'-phosphorothioate | siRNA Sequence Selection

A total of 55 sense and 55 antisense human SCNNB1-derived siRNA oligos (RNAi agents to Beta-ENaC) are synthesized, as described in Example 2. The sense and their respective antisense oligos are annealed into duplexes.

Example 1A

Overlapping Sets of Beta-ENaC RNAi Agents

The present disclosure also relates to groups of RNAi agents to Beta-ENaC with overlapping sequences. Thus, the present disclosure encompasses groups of RNAi agents wherein each RNAi agent in the group overlaps with each other RNAi agent in the same group by at least 5, 6, 7, 8, 9, 10, 11, 12, 13, 14, 15, 16, 17, 18, 19 or more nucleotides. Particularly, in one embodiment, the overlap is at least 12 nt.

Some of the RNAi agents listed herein overlap each other in sequence. Table 2 presents a compilation of some of these groups of overlapping RNAi agents, wherein each member of a group overlaps with each other member of the same group by at least 12 nt. A 12-nt portion of the overlap of the sense and anti-sense strand are presented.

Thus, for example, as shown in Table 2, the sequences of RNAi agents AD-20807 and AD-20832 overlap, wherein the overlap in the sense strand comprises the sequence UGAAGAAGUACC (SEQ ID NO: 223); these RNAi agents also overlap in the anti-sense strand sequence, wherein the overlap comprises the sequence GGUACUUCUUCA (SEQ ID NO: 224). The RNAi agents AD-20807, AD-20862 and AD-20832 all overlap in the sense strand, wherein the overlap comprises the sequence GAAGAAGUACCU (SEQ ID NO: 225); these RNAi agents also overlap in the anti-sense strand, wherein the overlap comprises the sequence AGGUACUUCUUC (SEQ ID NO: 226). Thus, these and other various sets of overlapping RNAi agents presented in Table 2 share common technical features, for example, the overlap in the sense and anti-sense strand.

Particular sets of overlapping RNAi agents to Beta-ENaC are provided below in Table 2.

The present disclosure thus encompasses any group or subgroup of RNAi agents comprising a common technical feature, wherein the common technical feature is an overlap (e.g., of at least 12 nt) of a sequence in the sense or anti-sense strand.

TABLE 2

| Pos | Sense overlap | SEQ ID | Anti-sense overlap | SEQ ID | Overlapping RNAi agents to Beta-ENaC |
|---|---|---|---|---|---|
| 183 | UGAAGAAGUACC | 223 | GGUACUUCUUCA | 224 | AD-20807, AD-20832 |
| 184 | GAAGAAGUACCU | 225 | AGGUACUUCUUC | 226 | AD-20807, AD-20862, AD-20832 |

TABLE 2-continued

| Pos | Sense overlap | SEQ ID | Anti-sense overlap | SEQ ID | Overlapping RNAi agents to Beta-ENaC |
|---|---|---|---|---|---|
| 185 | AAGAAGUACCUG | 227 | CAGGUACUUCUU | 228 | AD-20807, AD-20862, AD-20832 |
| 186 | AGAAGUACCUGC | 229 | GCAGGUACUUCU | 230 | AD-20807, AD-20862, AD-20832 |
| 187 | GAAGUACCUGCU | 231 | AGCAGGUACUUC | 232 | AD-20807, AD-20862, AD-20832 |
| 188 | AAGUACCUGCUG | 233 | CAGCAGGUACUU | 234 | AD-20807, AD-20862, AD-20832 |
| 189 | AGUACCUGCUGA | 235 | UCAGCAGGUACU | 236 | AD-20807, AD-20862, AD-20832 |
| 190 | GUACCUGCUGAA | 237 | UUCAGCAGGUAC | 238 | AD-20862, AD-20832 |
| 400 | GAGCUGGGAGGU | 239 | ACCUCCCAGCUC | 240 | AD-20820, AD-20837 |
| 401 | AGCUGGGAGGUC | 241 | GACCUCCCAGCU | 242 | AD-20820, AD-20812, AD-20837 |
| 402 | GCUGGGAGGUCA | 243 | UGACCUCCCAGC | 244 | AD-20820, AD-20819, AD-20812, AD-20837 |
| 403 | CUGGGAGGUCAG | 245 | CUGACCUCCCAG | 246 | AD-20819, AD-20812, AD-20837 |
| 404 | UGGGAGGUCAGC | 247 | GCUGACCUCCCA | 248 | AD-20820, AD-20819, AD-20837 |
| 405 | GGGAGGUCAGCG | 249 | CGCUGACCUCCC | 250 | AD-20820, AD-20819, AD-20812, AD-20837 |
| 406 | GGAGGUCAGCGU | 251 | ACGCUGACCUCC | 252 | AD-20819, AD-20837 |
| 407 | GAGGUCAGCGUC | 253 | GACGCUGACCUC | 254 | AD-20820, AD-20819, AD-20812 |
| 408 | AGGUCAGCGUCU | 255 | AGACGCUGACCU | 256 | AD-20819, AD-20812 |
| 836 | CUGCAGGCCACC | 257 | GGUGGCCUGCAG | 258 | AD-20866, AD-20817 |
| 837 | UGCAGGCCACCA | 259 | UGGUGGCCUGCA | 260 | AD-20866, AD-20830, AD-20817 |
| 838 | GCAGGCCACCAA | 261 | UUGGUGGCCUGC | 262 | AD-20866, AD-20830, AD-20817 |
| 839 | CAGGCCACCAAC | 263 | GUUGGUGGCCUG | 264 | AD-20866, AD-20830, AD-20817 |
| 840 | AGGCCACCAACA | 265 | UGUUGGUGGCCU | 266 | AD-20866, AD-20830, AD-20817 |
| 841 | GGCCACCAACAU | 267 | AUGUUGGUGGCC | 268 | AD-20866, AD-20830, AD-20817 |
| 842 | GCCACCAACAUC | 269 | GAUGUUGGUGGC | 270 | AD-20866, AD-20830, AD-20817 |
| 843 | CCACCAACAUCU | 271 | AGAUGUUGGUGG | 272 | AD-20866, AD-20830 |
| 1007 | GGCAUGACAGAG | 273 | CUCUGUCAUGCC | 274 | AD-20847, AD-20867 |
| 1008 | GCAUGACAGAGA | 275 | UCUCUGUCAUGC | 276 | AD-20826, AD-20867 |
| 1009 | CAUGACAGAGAA | 277 | UUCUCUGUCAUG | 278 | AD-20826, AD-20831, AD-20867 |
| 1010 | AUGACAGAGAAG | 279 | CUUCUCUGUCAU | 280 | Aa20826, AD-20831, AD-20867, AD-20806 |
| 1011 | UGACAGAGAAGG | 281 | CCUUCUCUGUCA | 282 | AD-20826, AD-20831, AD-20867, AD-20806, AD-20861 |

TABLE 2-continued

| Pos | Sense overlap | SEQ ID | Anti-sense overlap | SEQ ID | Overlapping RNAi agents to Beta-ENaC |
|---|---|---|---|---|---|
| 1012 | GACAGAGAAGGC | 283 | GCCUUCUCUGUC | 284 | AD-20851, AD-20847, AD-20826, AD-20831, AD-20867, AD-20806, AD-20861 |
| 1013 | ACAGAGAAGGCA | 285 | UGCCUUCUCUGU | 286 | AD-20851, AD-20835, AD-20847, AD-20826, AD-20831, AD-20867, AD-20806, AD-20861 |
| 1014 | CAGAGAAGGCAC | 287 | GUGCCUUCUCUG | 288 | AD-20851, AD-20835, AD-20865, AD-20826, AD-20831, AD-20806, AD-20861 |
| 1015 | AGAGAAGGCACU | 289 | AGUGCCUUCUCU | 290 | AD-20851, AD-20835, AD-20865, AD-20826, AD-20831, AD-20806, AD-20861 |
| 1016 | GAGAAGGCACUU | 291 | AAGUGCCUUCUC | 292 | AD-20851, AD-20835, AD-20865, AD-20831, AD-20806, AD-20861 |
| 1017 | AGAAGGCACUUC | 293 | GAAGUGCCUUCU | 294 | AD-20851, AD-20835, AD-20865, AD-20806, AD-20861 |
| 1018 | GAAGGCACUUCC | 295 | GGAAGUGCCUUC | 296 | AD-20851, AD-20835, AD-20865, AD-20861 |
| 1019 | AAGGCACUUCCU | 297 | AGGAAGUGCCUU | 298 | AD-20851, AD-20835, AD-20865 |
| 1020 | AGGCACUUCCUU | 299 | AAGGAAGUGCCU | 300 | AD-20835, AD-20865 |
| 1294 | CUACAGUGACUA | 301 | UAGUCACUGUAG | 302 | AD-20828, AD-20825 |
| 1295 | UACAGUGACUAC | 303 | GUAGUCACUGUA | 304 | AD-20834, AD-20825 |
| 1296 | ACAGUGACUACA | 305 | UGUAGUCACUGU | 306 | AD-20828, AD-20834, AD-20825, AD-20836 |
| 1297 | CAGUGACUACAA | 307 | UUGUAGUCACUG | 308 | AD-20834, AD-20805, AD-20825 |
| 1298 | AGUGACUACAAC | 309 | GUUGUAGUCACU | 310 | AD-20828, AD-20834, AD-20805, AD-20825, AD-20836 |
| 1299 | GUGACUACAACA | 311 | UGUUGUAGUCAC | 312 | AD-20834, AD-20805, AD-20808, AD-20825 |
| 1300 | UGACUACAACAC | 313 | GUGUUGUAGUCA | 314 | AD-20828, AD-20834, AD-20805, AD-20808, AD-20825, AD-20815, AD-20836 |
| 1301 | GACUACAACACG | 315 | CGUGUUGUAGUC | 316 | AD-20828, AD-20834, AD-20805, AD-20808, AD-20836 |
| 1302 | ACUACAACACGA | 317 | UCGUGUUGUAGU | 318 | AD-20834, AD-20805, AD-20808 |
| 1303 | CUACAACACGAC | 319 | GUCGUGUUGUAG | 320 | AD-20805, AD-20808, AD-20815, AD-20836 |
| 1304 | UACAACACGACC | 321 | GGUCGUGUUGUA | 322 | AD-20805, AD-20808 |
| 1305 | ACAACACGACCU | 323 | AGGUCGUGUUGU | 324 | AD-20808, AD-20815 |
| 1408 | GGAGAAAUACUG | 325 | CAGUAUUUCUCC | 326 | AD-20813, AD-20848 |
| 1409 | GAGAAAUACUGC | 327 | GCAGUAUUUCUC | 328 | AD-20813, AD-20848 |
| 1410 | AGAAAUACUGCA | 329 | UGCAGUAUUUCU | 330 | AD-20813, AD-20848 |
| 1411 | GAAAUACUGCAA | 331 | UUGCAGUAUUUC | 332 | AD-20813, AD-20848 |
| 1412 | AAAUACUGCAAC | 333 | GUUGCAGUAUUU | 334 | AD-20813, AD-20848 |
| 1413 | AAUACUGCAACA | 335 | UGUUGCAGUAUU | 336 | AD-20813, AD-20848 |

TABLE 2-continued

| Pos | Sense overlap | SEQ ID | Anti-sense overlap | SEQ ID | Overlapping RNAi agents to Beta-ENaC |
|---|---|---|---|---|---|
| 1414 | AUACUGCAACAA | 337 | UUGUUGCAGUAU | 338 | AD-20813, AD-20848 |
| 1545 | UCUCCAUGGCUG | 339 | CAGCCAUGGAGA | 340 | AD-20846, AD-20863 |
| 1546 | CUCCAUGGCUGA | 341 | UCAGCCAUGGAG | 342 | AD-20846, AD-20863 |
| 1547 | UCCAUGGCUGAC | 343 | GUCAGCCAUGGA | 344 | AD-20846, AD-20863 |
| 1548 | CCAUGGCUGACU | 345 | AGUCAGCCAUGG | 346 | AD-20846, AD-20863 |
| 1549 | CAUGGCUGACUG | 347 | CAGUCAGCCAUG | 348 | AD-20846, AD-20863 |
| 1550 | AUGGCUGACUGG | 349 | CCAGUCAGCCAU | 350 | AD-20846, AD-20863 |
| 1551 | UGGCUGACUGGC | 351 | GCCAGUCAGCCA | 352 | AD-20846, AD-20863 |
| 1626 | AUAUCACCCUGA | 353 | UCAGGGUGAUAU | 354 | AD-20816, AD-20827 |
| 1627 | UAUCACCCUGAG | 355 | CUCAGGGUGAUA | 356 | AD-20816, AD-20827, AD-20829 |
| 1628 | AUCACCCUGAGC | 357 | GCUCAGGGUGAU | 358 | AD-20816, AD-20827, AD-20829, AD-20818 |
| 1629 | UCACCCUGAGCA | 359 | UGCUCAGGGUGA | 360 | AD-20816, AD-20827, AD-20829, AD-20843, AD-20818 |
| 1630 | CACCCUGAGCAG | 361 | CUGCUCAGGGUG | 362 | AD-20816, AD-20827, AD-20829, AD-20843, AD-20818 |
| 1631 | ACCCUGAGCAGG | 363 | CCUGCUCAGGGU | 364 | AD-20816, AD-20827, AD-20829, AD-20843, AD-20818 |
| 1632 | CCCUGAGCAGGA | 365 | UCCUGCUCAGGG | 366 | AD-20816, AD-20827, AD-20829, AD-20843, AD-20818 |
| 1633 | CCUGAGCAGGAA | 367 | UUCCUGCUCAGG | 368 | AD-20827, AD-20829, AD-20843, AD-20818 |
| 1634 | CUGAGCAGGAAG | 369 | CUUCCUGCUCAG | 370 | AD-20829, AD-20843, AD-20818 |
| 1635 | UGAGCAGGAAGG | 371 | CCUUCCUGCUCA | 372 | AD-20843, AD-20818 |
| 1740 | UGGGUGGCCAGU | 373 | ACUGGCCACCCA | 374 | AD-20824, AD-20849 |
| 1741 | GGGUGGCCAGUU | 375 | AACUGGCCACCC | 376 | AD-20824, AD-20841, AD-20849 |
| 1742 | GGUGGCCAGUUU | 377 | AAACUGGCCACC | 378 | AD-20824, AD-20842, AD-20841, AD-20849 |
| 1743 | GUGGCCAGUUUG | 379 | CAAACUGGCCAC | 380 | AD-20824, AD-20842, AD-20821, AD-20841, AD-20849 |
| 1744 | UGGCCAGUUUGG | 381 | CCAAACUGGCCA | 382 | AD-20824, AD-20842, AD-20821, AD-20838, AD-20841, AD-20849 |
| 1745 | GGCCAGUUUGGC | 383 | GCCAAACUGGCC | 384 | AD-20824, AD-20842, AD-20821, AD-20838, AD-20841, AD-20823, AD-20849 |
| 1746 | GCCAGUUUGGCU | 385 | AGCCAAACUGGC | 386 | AD-20844, AD-20824, AD-20842, AD-20821, AD-20838, AD-20841, AD-20823, AD-20849 |
| 1747 | CCAGUUUGGCUU | 387 | AAGCCAAACUGG | 388 | AD-20814, AD-20844, AD-20842, AD-20821, AD-20838, AD-20841, AD-20823, AD-20849 |
| 1748 | CAGUUUGGCUUC | 389 | GAAGCCAAACUG | 390 | AD-20814, AD-20844, AD-20842, AD-20821, AD-20838, AD-20841, AD-20822, AD-20823 |

TABLE 2-continued

| Pos | Sense overlap | SEQ ID | Anti-sense overlap | SEQ ID | Overlapping RNAi agents to Beta-ENaC |
|---|---|---|---|---|---|
| 1749 | AGUUUGGCUUCU | 391 | AGAAGCCAAACU | 392 | AD-20814, AD-20844, AD-20842, AD-20821, AD-20852, AD-20838, AD-20822, AD-20823 |
| 1750 | GUUUGGCUUCUG | 393 | CAGAAGCCAAAC | 394 | AD-20814, AD-20844, AD-20821, AD-20852, AD-20838, AD-20822, AD-20823 |
| 1751 | UUUGGCUUCUGG | 395 | CCAGAAGCCAAA | 396 | AD-20814, AD-20844, AD-20852, AD-20838, AD-20822, AD-20823 |
| 1752 | UUGGCUUCUGGA | 397 | UCCAGAAGCCAA | 398 | AD-20814, AD-20844, AD-20852, AD-20822, AD-20823 |
| 1753 | UGGCUUCUGGAU | 399 | AUCCAGAAGCCA | 400 | AD-20814, AD-20844, AD-20852, AD-20822 |
| 1754 | GGCUUCUGGAUG | 401 | CAUCCAGAAGCC | 402 | AD-20814, AD-20852, AD-20822 |
| 1755 | GCUUCUGGAUGG | 403 | CCAUCCAGAAGC | 404 | AD-20852, AD-20822 |
| 1914 | AGCUGGUGGAGG | 405 | CCUCCACCAGCU | 406 | AD-20850, AD-20845 |
| 1915 | GCUGGUGGAGGC | 407 | GCCUCCACCAGC | 408 | AD-20850, AD-20845, AD-20833 |
| 1916 | CUGGUGGAGGCC | 409 | GGCCUCCACCAG | 410 | AD-20850, AD-20845, AD-20833, AD-20864 |
| 1917 | UGGUGGAGGCCC | 411 | GGGCCUCCACCA | 412 | AD-20810, AD-20850, AD-20845, AD-20833, AD-20864 |
| 1918 | GGUGGAGGCCCA | 413 | UGGGCCUCCACC | 414 | AD-20809, AD-20810, AD-20850, AD-20845, AD-20833, AD-20864 |
| 1919 | GUGGAGGCCCAC | 415 | GUGGGCCUCCAC | 416 | AD-20809, AD-20810, AD-20850, AD-20845, AD-20833, AD-20864, AD-20840 |
| 1920 | UGGAGGCCCACA | 417 | UGUGGGCCUCCA | 418 | AD-20809, AD-20810, AD-20850, AD-20845, AD-20833, AD-20864, AD-20840 |
| 1921 | GGAGGCCCACAC | 419 | GUGUGGGCCUCC | 420 | AD-20809, AD-20810, AD-20845, AD-20833, AD-20864, AD-20840 |
| 1922 | GAGGCCCACACC | 421 | GGUGUGGGCCUC | 422 | AD-20809, AD-20810, AD-20833, AD-20864, AD-20840 |
| 1923 | AGGCCCACACCA | 423 | UGGUGUGGGCCU | 424 | AD-20809, AD-20810, AD-20864, AD-20840 |
| 1924 | GGCCCACACCAA | 425 | UUGGUGUGGGCC | 426 | AD-20809, AD-20810, AD-20840 |
| 1925 | GCCCACACCAAC | 427 | GUUGGUGUGGGC | 428 | AD-20809, AD-20840 |

The position ("Pos") in NM_000336.2 is indicated. 12 exemplary nt of the overlap in the sense and anti-sense strand are presented; in many cases, the overlap is actually longer.

Example 2

Synthesis of Beta-ENaC RNAi Agent Sequences

The modified Beta-ENaC RNAi agent sequences listed as SEQ ID NO: 1 to 110 in Table 1 are synthesized on MerMade 192 synthesizer at 1 µmol scale.

For all the sequences in the list, 'endolight' chemistry is applied as detailed below.

All pyrimidines (cytosine and uridine) in the sense strand contain 2'-O-Methyl bases (2' O-Methyl C and 2'-O-Methyl U).

In the antisense strand, pyrimidines adjacent to (i.e., towards the 5' position) ribo A nucleoside are replaced with their corresponding 2-O-Methyl nucleosides.

A two-base dTsdT extension at 3' end of both sense and anti sense sequences is introduced.

The sequence file is converted to a text file to make it compatible for loading in the MerMade 192 synthesis software.

Synthesis, Cleavage and Deprotection:

The synthesis of Beta-ENaC sequences uses solid supported oligonucleotide synthesis using phosphoramidite chemistry.

The synthesis of the above sequences is performed at 1 um scale in 96 well plates. The amidite solutions are prepared at 0.1M concentration and ethyl thio tetrazole (0.6M in Acetonitrile) is used as activator.

The synthesized sequences are cleaved and de-protected in 96 well plates, using methylamine in the first step and fluoride reagent in the second step. The crude sequences are precipitated using acetone:ethanol (80:20) mix and the pellets are re-suspended in 0.2M sodium acetate buffer. Samples from each sequence are analyzed by LC-MS to confirm the identity, UV for quantification and a selected set of samples by IEX chromatography to determine purity.

Purification and Desalting:

Beta-ENaC sequences are purified on AKTA explorer purification system using Source 15Q column. A column temperature of 65 C is maintained during purification. Sample injection and collection is performed in 96 well (1.8 mL-deep well) plates. A single peak corresponding to the full length sequence is collected in the eluent. The purified sequences are desalted on a Sephadex G25 column using AKTA purifier. The desalted Beta-ENaC sequences are analyzed for concentration (by UV measurement at A260) and purity (by ion exchange HPLC).

The single strands are then submitted for annealing.

A detailed list of Beta-ENaC single strands and duplexes are shown in Table 1, above. The duplexes are used in in vitro screening to test their ability to knock down Beta-ENaC gene level.

Example 3

In Vitro Screening of Beta-ENaC RNAi Agents

The Beta-ENaC RNAi agents are screened in vitro to determine their ability to knock down Beta-ENaC gene level.

Cell Culture and Transfections:

H441 (ATCC, Manassas, Va.) cells are grown to near confluence at 37° C. in an atmosphere of 5% $CO_2$ in RPMI 1640 (ATCC) supplemented with 10% FBS, streptomycin, and glutamine (ATCC) before being released from the plate by trypsinization. Reverse transfection is carried out by adding 5 µl of Opti-MEM to 5 µl of siRNA duplexes per well into a 96-well plate along with 10 µl of Opti-MEM plus 0.2 µl of Lipofectamine RNAiMax per well (Invitrogen, Carlsbad Calif. cat #13778-150) and incubated at room temperature for 15 minutes. 80 µl of complete growth media without antibiotic containing $2.0 \times 10^4$ H441 cells are then added. Cells are incubated for 24 hours prior to RNA purification. Experiments are performed at 0.1 or 10 nM final duplex concentration for single dose screens with each of the 55 Beta-ENaC duplexes. Each siRNA is transfected 3 times at each of the doses tested. The results are shown in Table 3.

A subset of duplexes that shows robust silencing in the 10 nM and 0.1 nM screens is assayed over a range of concentrations from 10 nM to 10 fM using serial dilutions to determine their IC50. The results are shown in Table 4.

Total RNA Isolation:

Cells are harvested and lysed in 140 µl of Lysis/Binding Solution then mixed for 1 minute at 850 rpm using an Eppendorf Thermomixer (the mixing speed was the same throughout the process).

A MagMAX-96 Total RNA Isolation Kit (Applied Biosystem, Foster City Calif., part #: AM1830) is used to isolate total RNA. Twenty micro liters of magnetic beads and Lysis/Binding Enhancer mixture are added into cell-lysate and mixed for 5 minutes. Magnetic beads are captured using magnetic stand and the supernatant is removed without disturbing the beads. After removing supernatant, magnetic beads are washed with Wash Solution 1 (isopropanol added) and mixed for 1 minute. Beads are capture again and supernatant removed. Beads are then washed with 150 µl Wash Solution 2 (Ethanol added), captured and supernatant is removed. 50 ul of DNase mixture (MagMax turbo DNase Buffer and Turbo DNase) is then added to the beads and they are mixed for 10 to 15 minutes. After mixing, 100 µl of RNA Rebinding Solution is added and mixed for 3 minutes. Supernatant is removed and magnetic beads are washed again with 150 µl Wash Solution 2 and mixed for 1 minute and supernatant is removed completely. The magnetic beads are mixed for 2 minutes to dry before RNA is eluted with 50 µl of water.

cDNA Synthesis:

ABI High capacity cDNA reverse transcription kit (Applied Biosystems, Foster City, Calif., Cat #4368813) is used for cDNA synthesis. A master mix of 2 µl 10× Buffer, 0.8 µl 25×dNTPs, 2 µl Random primers, 1 µl. Reverse Transcriptase, 1 µl RNase inhibitor and 3.2 µl of $H_2O$ per reaction are added into 10 µl total RNA. cDNA is generated using a Bio-Rad C-1000 or S-1000 thermal cycler (Hercules, Calif.) through the following steps: 25° C. 10 min, 37° C. 120 min, 85° C. 5 sec, 4° C. hold.

Real time PCR:

2 µl of cDNA are added to a master mix containing 0.5 ul GAPDH TaqMan Probe (Applied Biosystems. Cat # 4326317E), 0.5 µl Beta-ENaC TaqMan probe (Applied Biosystems cat #Hs00165722_ml) and 5 µl Roche Probes Master Mix (Roche Cat # 04887301001) in a total of 10 piper well in a LightCycler 480 384 well plate (Roche cat #0472974001). Real time PCR is done in a LightCycler 480 Real Time PCR machine (Roche). Each duplex is tested in two independent transfections and each transfections is assayed in duplicate.

Real time data are analyzed using the ΔΔCt method. Each sample is normalized to GAPDH expression and knockdown is assessed relative to cells transfected with the non-targeting duplex AD-1955. IC50s are defined using a 4 parameter fit model in XLfit.

The results are shown below. Table 3 shows the results of experiments performed at 0.1 nM or 10 nM final duplex concentrations for single dose screens with each of the 55 Beta-ENaC duplexes. The "Fraction message remaining" indicates the residual gene level, at 10 nm or 0.1 nM. Thus "0.17" in the second column for AD-20832-b1 indicates that, at a concentration of 10 nM, there was 17% residual gene level, or 83% knockdown of expression. Note also that the suffix "b1" indicates "batch 1." Thus, for example, a RNAi agent with the designation "AD-20832-b1" has the same sequence as a RNAi agent designated "AD-20832".

TABLE 3

10 nM and 0.1 nM knockdown of Beta-ENaC

| | Fraction message remaining At 10 nM | Fraction message remaining At 0.1 nM | Standard deviation At 10 nM | Standard deviation At 0.1 nM |
|---|---|---|---|---|
| AD-20832-b1 | 0.17 | 0.33 | 0.04 | 0.03 |
| AD-20848-b1 | 0.17 | 0.49 | 0.01 | 0.04 |
| AD-20807-b1 | 0.18 | 0.26 | 0.02 | 0.05 |

TABLE 3-continued 10 nM and 0.1 nM knockdown of Beta-ENaC

| | Fraction message remaining At 10 nM | Fraction message remaining At 0.1 nM | Standard deviation At 10 nM | Standard deviation At 0.1 nM |
|---|---|---|---|---|
| AD-20826-b1 | 0.19 | 0.49 | 0.02 | 0.22 |
| AD-20837-b1 | 0.19 | 0.51 | 0.04 | 0.04 |
| AD-20861-b1 | 0.19 | 0.71 | 0.02 | 0.29 |
| AD-20834-b1 | 0.20 | 0.34 | 0.06 | 0.05 |
| AD-20806-b1 | 0.22 | 0.60 | 0.02 | 0.15 |
| AD-20851-b1 | 0.23 | 0.55 | 0.04 | 0.07 |
| AD-20865-b1 | 0.24 | 0.64 | 0.02 | 0.05 |
| AD-20811-b1 | 0.25 | 0.52 | 0.17 | 0.23 |
| AD-20819-b1 | 0.27 | 0.60 | 0.01 | 0.07 |
| AD-20839-b1 | 0.27 | 0.55 | 0.06 | 0.05 |
| AD-20835-b1 | 0.28 | 0.63 | 0.07 | 0.21 |
| AD-20825-b1 | 0.30 | 0.72 | 0.11 | 0.15 |
| AD-20867-b1 | 0.30 | 0.68 | 0.00 | 0.20 |
| AD-20813-b1 | 0.34 | 0.56 | 0.17 | 0.36 |
| AD-20823-b1 | 0.34 | 0.75 | 0.05 | 0.05 |
| AD-20805-b1 | 0.36 | 0.86 | 0.02 | 0.09 |
| AD-20831-b1 | 0.36 | 0.60 | 0.01 | 0.21 |
| AD-20862-b1 | 0.38 | 0.93 | 0.02 | 0.29 |
| AD-20808-b1 | 0.40 | 0.81 | 0.13 | 0.16 |
| AD-20827-b1 | 0.40 | 2.55 | 0.07 | 1.44 |
| AD-20828-b1 | 0.42 | 0.89 | 0.11 | 0.25 |
| AD-20812-b1 | 0.47 | 0.74 | 0.32 | 0.36 |
| AD-20836-b1 | 0.48 | 1.07 | 0.11 | 0.27 |
| AD-20822-b1 | 0.49 | 0.94 | 0.11 | 0.09 |
| AD-20810-b1 | 0.53 | 0.87 | 0.25 | 0.20 |
| AD-20824-b1 | 0.54 | 1.12 | 0.08 | 0.33 |
| AD-20844-b1 | 0.55 | 0.98 | 0.07 | 0.28 |
| AD-20814-b1 | 0.60 | 1.30 | 0.09 | 0.12 |
| AD-20838-b1 | 0.65 | 1.18 | 0.07 | 0.18 |
| AD-20816-b1 | 0.66 | 1.38 | 0.05 | 0.17 |
| AD-20845-b1 | 0.72 | 1.18 | 0.01 | 0.27 |
| AD-20820-b1 | 0.75 | 0.89 | 0.06 | 0.14 |
| AD-20830-b1 | 0.75 | 0.94 | 0.04 | 0.24 |
| AD-20866-b1 | 0.77 | 1.24 | 0.03 | 0.57 |
| AD-20809-b1 | 0.78 | 1.05 | 0.05 | 0.03 |
| AD-20833-b1 | 0.79 | 0.99 | 0.01 | 0.35 |
| AD-20821-b1 | 0.80 | 0.99 | 0.07 | 0.14 |
| AD-20846-b1 | 0.83 | 1.13 | 0.10 | 0.15 |
| AD-20818-b1 | 0.88 | 1.36 | 0.04 | 0.62 |
| AD-20817-b1 | 0.89 | 1.11 | 0.11 | 0.19 |
| AD-20843-b1 | 0.92 | 1.64 | 0.11 | 0.16 |
| AD-20840-b1 | 0.93 | 1.13 | 0.15 | 0.30 |
| AD-20847-b1 | 0.94 | 0.99 | 0.64 | 0.12 |
| AD-20815-b1 | 0.96 | 2.06 | 0.23 | 0.99 |
| AD-20842-b1 | 0.96 | 1.37 | 0.16 | 0.28 |
| AD-20852-b1 | 0.96 | 1.30 | 0.17 | 0.17 |
| AD-20863-b1 | 0.99 | 0.84 | 0.24 | 0.11 |
| AD-20864-b1 | 0.99 | 1.36 | 0.05 | 0.74 |
| AD-20850-b1 | 1.00 | 1.22 | 0.14 | 0.14 |
| AD-20829-b1 | 1.08 | 1.39 | 0.26 | 0.70 |
| AD-20849-b1 | 1.11 | 1.31 | 0.27 | 0.17 |
| AD-20841-b1 | 1.12 | 1.37 | 0.10 | 0.48 |

All the RNAi agents to Beta-ENaC used in these experiments were the modified sequences (SEQ ID NO: 1 to 110) listed in Table 1.

Table 4 shows the results of experiments wherein a subset of duplexes that show robust silencing in the 10 nM and 0.1 nM screens is assayed over a range of concentrations from 10 nM to 10 fM using serial dilutions to determine their IC50.

TABLE 4

Beta-ENaC dose response screen

| Duplex_ID | H441 New (Average of 4 replicates) | | H441 Old (Average of 8 replicates) | |
|---|---|---|---|---|
| | IC50 nM | IC50 Standard deviation | IC50 nM | IC50 Standard deviation |
| AD-20807 | 0.05 | 0.03 | 0.04 | 0.06 |
| AD-20826 | 0.14 | 0.05 | 0.05 | 0.07 |
| AD-20832 | 0.05 | 0.02 | 0.04 | 0.05 |
| AD-20834 | 0.06 | 0.03 | 0.03 | 0.06 |
| AD-20848 | 0.25 | 0.14 | 0.13 | 0.17 |
| AD-20861 | 0.13 | 0.08 | 0.09 | 0.06 |

Example 4

In Vivo Analysis of Beta-ENaC RNAi Agents AD-20807 and AD-20832

In in vivo experiments, two Beta-ENaC RNAi agents, AD-20807 and AD-20832, are tested for the ability to knock down Beta-ENaC gene level in whole lungs in rats. The purpose is to determine the dose responses. Immunostimulation is also measured.

The Rat strain used is Sprague-Dawley; individuals have an approximate weight of 280-300 grams. Rats are dosed once a day for two days. They are then sacrificed about 24 hrs after the second dose. The left lung is taken and ground for qPCR determination of Beta-ENaC levels; the right lung frozen and stored.

TABLE 5

| Group | Rat Numbers | Formulation | Concentration | Rats per group |
|---|---|---|---|---|
| 1 | 1-5 | D5W | NA | 5 |
| 2 | 6-10 | AD1955 | 10 mg/kg | 5 |
| 3 | 11-15 | AD20191 | 10 mg/kg | 5 |
| 4 | 16-20 | AD20807 | 10 mg/kg | 5 |
| 5 | 12-25 | AD20807 | 3 mg/kg | 5 |
| 6 | 26-30 | AD20807 | 1 mg/kg | 5 |
| 7 | 31-35 | AD20832 | 10 mg/kg | 4* |
| 8 | 36-40 | AD20832 | 3 mg/kg | 5 |
| 9 | 41-45 | AD20832 | 1 mg/kg | 5 |

*In the group of 4, 5 rats are initially dosed, but 1 in each group does not survive the experiment and is not included in the final data.

Both RNAi agents to Beta-ENaC, AD20807 and AD20832, show reductions in Beta-ENaC levels in a dose-dependent manner. For AD20807, the level of Beta-ENaC is reduced by approximately 30%, 40%, and 50% at dosages of 1, 3 and 10 mg/kg, respectively.

In contrast, the Beta-ENaC (bENaC) RNAi agents do not decrease the level of Alpha-ENaC (aENaC). There is, however, an increase in Alpha-ENaC with administration of AD20832.

Negative Controls Include:

D5W: a solution of 5% dextrose in water; it is the vehicle used to dilute the siRNA when dosing; AD1955: a siRNA which does not specifically target either Alpha- or Beta-ENaC, but targets firefly luciferase; and AD20191: a siRNA which does not bind to Beta-ENaC, but targets rat Alpha-ENaC; and AD-9201, which targets Alpha-ENaC (not used in this particular example).

Thus, specific knock-down of Beta-ENaC is seen with RNAi agent AD20807 and AD20832 in this experiment.

Example 5

In Vivo Analysis of Beta-ENaC AD-20834

In in vivo experiments, Beta-ENaC RNAi agent AD20834 is tested for its ability to knock down Beta-ENaC gene level in whole lungs in rats. The purpose is to determine the dosage responses. Immunostimulation is also measured.

The rat strain is Sprague-Dawley; individuals have an approximate weight of 280-300 grams. Rats are dosed once a day for two days. They are then sacrificed about 24 hours after the second dose. The left lung is taken and ground for qPCR determination of Beta-ENaC levels; the right lung is frozen and stored.

TABLE 6

| Group | rat #s | Formulation | concentration | rats per group |
|-------|--------|-------------|---------------|----------------|
| 1 | 1-5 | D5W | NA | 5 |
| 2 | 6-10 | AD1955 | 10 mg/kg | 4* |
| 3 | 11-15 | AD20191 | 10 mg/kg | 5 |
| 4 | 16-20 | AD20834 | 10 mg/kg | 5 |
| 5 | 21-25 | AD20834 | 3 mg/kg | 5 |
| 6 | 26-30 | AD20834 | 1 mg/kg | 4* |

*In the groups of 4, 5 rats are initially dosed, but 1 in each group does not survive the experiment and is not included in the final data.

Assuming a weight of 300 grams (0.3 kg) the following dilutions are made:
10 mg/kg=3 mg of siRNA in a 200 uL volume=15 mg/mL
3 mg/kg=1 mg of siRNA in a 200 uL volume=5 mg/mL
1 mg/kg=0.3 mg of siRNA in a 200 uL volume=1.5 mg/mL The data are normalized to PPIB [Peptidyl-prolyl cis-trans isomerase B, used as a housekeeping (normalization) gene].

The experiments show that Beta-ENaC RNAi agent AD20834 demonstrates an approximately 40% reduction in Beta-ENaC level in Sprague-Dawley rats. This effect is specific to Beta-ENaC.

The controls are as follows: D5W (5% dextrose in water) is a negative control, not showing an effect on Alpha-ENaC or Beta-ENaC levels. AD1955, a control siRNA which does not bind to Alpha- or Beta-ENaC, also showing little effect on Alpha- or Beta-ENaC level. The positive control siRNA AD20191, which targets Alpha- but not Beta-ENaC, demonstrates an approximately 50% reduction in Alpha-ENaC level, but not Beta-ENaC.

Thus, a dosage of 10 mg/kg of Beta-ENaC RNAi agent AD20834 demonstrates at least about 40% inhibition of Beta-ENaC gene expression in Sprague-Dawley rats.

Example 6

Analysis of Beta-ENaC RNAi Agents

Additional experimentation is done with Beta-ENaC RNAi agents AD20807, AD20832, AD20834, AD20848, and AD20861 in vivo in Sprague-Dawley rats. Rats are dosed at 10 mg/kg in D5W on day 1 and day 2, and are sacrificed on day 3, and the lungs are collected.

The results are shown in FIG. 1. The results show qPCR data from the left lung, normalized to the control gene PPIB.

The controls in FIG. 1 are as follows: D5W (5% dextrose in water) is a negative control, not showing an effect on Alpha-ENaC or Beta-ENaC levels. The positive control is AD-9201, which targets Alpha-ENaC (aENaC).

The results, shown in FIG. 1, show a statistically significant and specific knock-down of Beta-ENaC (bENaC) by AD20807, AD20832, AD20834, AD20848, and AD20861. The expression of the Beta-ENaC gene is inhibited by at least about 40% at a concentration of 10 mg/kg of these RNAi agents in Sprague-Dawley rats.

Example 7

Figure 2:
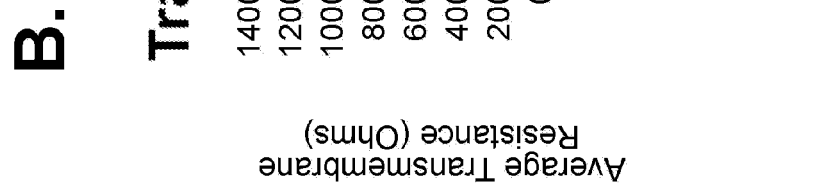
FIGS. 2A-2C depict the in vitro effect of Beta-ENaC RNAi Agent AD20832 on ENaC channel functional activity in human bronchial epithelial cells.
Figure 2:
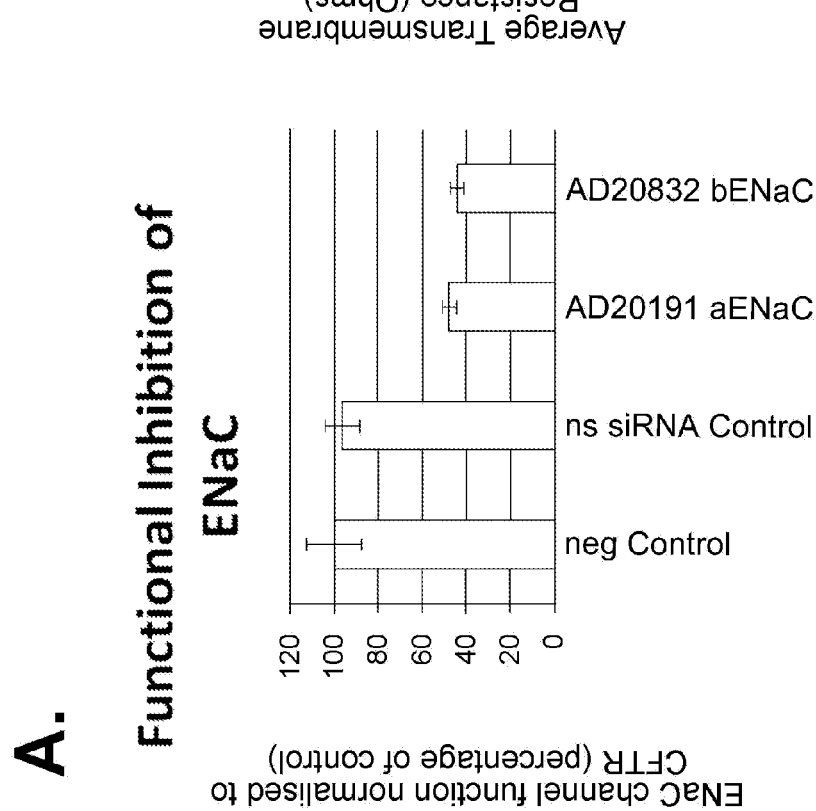
Figure 2:
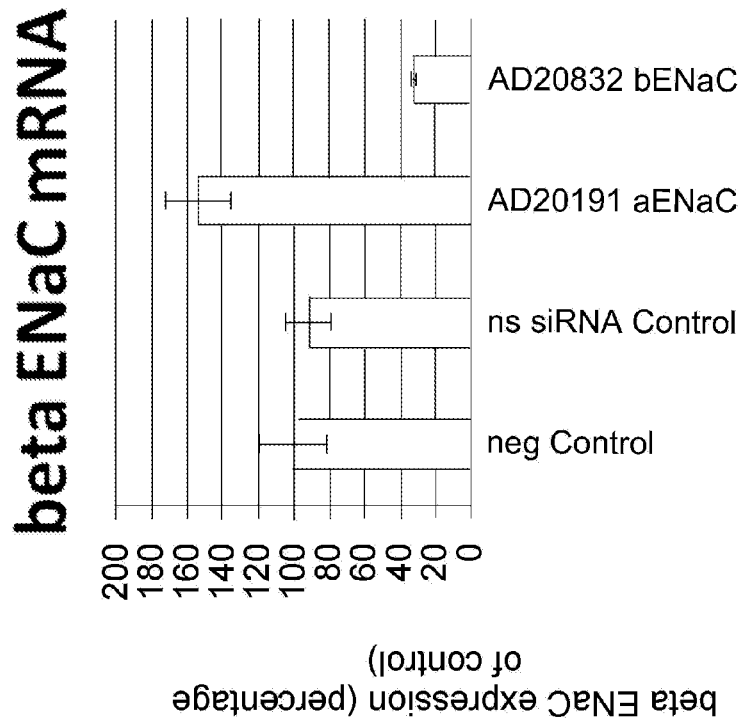
Figure 2:
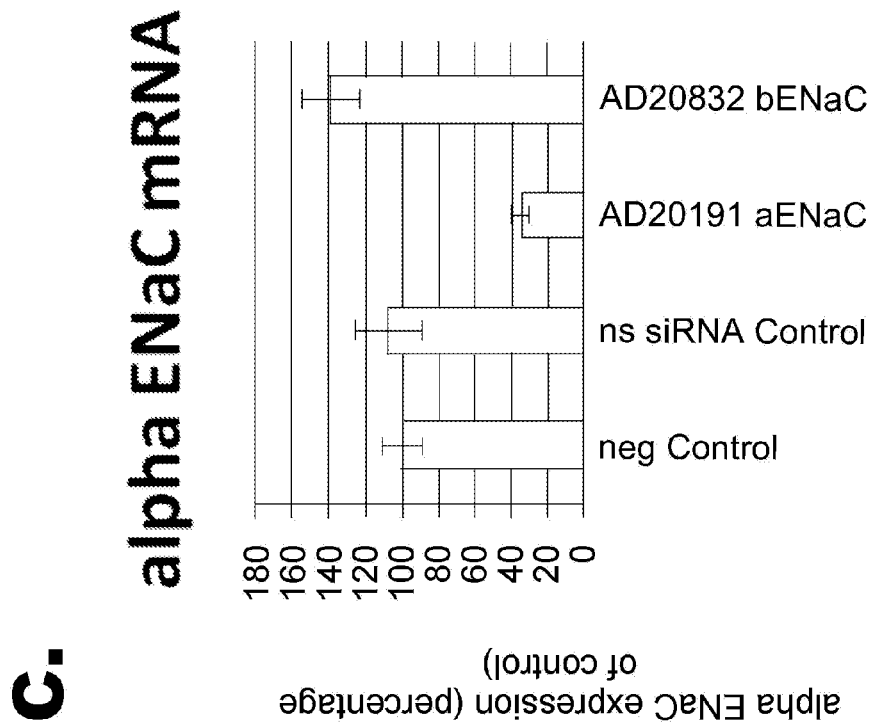

In Vitro Effect of Beta-ENaC RNAi Agent AD20832 on ENaC Channel Functional Activity in Human Bronchial Epithelial Cells Human Bronchial Epithelial Cells (HBEC) are transfected with the indicated siRNA, including Beta-ENaC RNAi agent AD20832. Transfected cells are seeded onto Snapwell inserts and cultured for 24 hours. Subsequently, the apical culture medium is removed from each insert and the cells cultured at Air Liquid Interface (ALI). Cells are assayed for ENaC and CFTR activity at Day 8 post-ALI as described. To control for cell viability, ENaC function is normalized to CFTR activity and the data presented as a percentage relative to the untransfected control (FIG. 2A). As an additional viability control, trans-membrane resistance is also measured (FIG. 2B). Expression analysis of alpha and beta ENaC subunit mRNA is performed for each insert and normalized to GAPDH expression. (FIG. 2C). The data demonstrate that a 70% inhibition of mRNA expression is sufficient to generate a 50% functional inhibition of ENaC channel. This is true for knockdown of either alpha or beta subunits, where each is compared to untransfected (neg) and non-specific (ns) siRNA controls. The data also show that beta ENaC siRNA does not inhibit alpha ENaC mRNA expression and vice versa.

Methods: ENaC Functional Activity in Human Bronchial Epithelial Cells

Human Bronchial Epithelial Cells (HBEC) are purchased from Lonza and passaged once before freezing in growth media (BEGM plus singlequots—Lonza). Subsequently, cells are thawed, expanded to confluence and split 1:10 for transfection. Once at 80% confluence, each flask of cells is transfected with the indicated siRNA at 30 nM, using 2 µL/mL Lipofectamine 2000 in a total volume of 30 mL transfection media (1:1 mix of BEGM (Lonza) and DMEM high glucose (Gibco) with no additives). At 24 hours post-transfection, cells are seeded onto 6 well Snapwell inserts (Costar) at $2.5 \times 10^5$ cells/insert in differentiation medium (50:50 mix of BEBM and DMEM/high glucose with singlequots (minus the tri-iodothreonine and retinoic acid supplements, with all-trans retinoic acid added separately at 50 nM). Cells are supplemented with 0.5 mL differentiation media apically and 2.5 mL differentiation media basolaterally. Following a further 24 hours of culture on the inserts the basolateral media is replaced and the apical media is removed, thus taking the cells to Air Liquid Interface (ALI) culture. Cells are assayed for ENaC and CFTR activity at Day 8 (D8) Post-ALI.

To assess the ion transport phenotype of the transfected cells the Snapwell inserts are mounted in Vertical Diffusion Chambers (Costar) and are bathed continuously with gassed Ringer solution (5% $CO_2$ in $O_2$; pH 7.4) maintained at 37° C. containing (in mM): 120 NaCl, 25 $NaHCO_3$, 3.3 $KH_2PO_4$, 0.8 $K_2HPO_4$, 1.2 $CaCl_2$, 1.2 $MgCl_2$, and 10 glucose (Osmolarity maintained between 280 and 300 mosmol/l). Cells are voltage clamped to 0 mV (model EVC4000; WPI). Trans-membrane resistance (TM res) is measured by applying a 2-mV pulse at 30-s intervals and calculating TM res using Ohm's law. Short circuit current data are recorded using a PowerLab workstation (ADI Instruments). Activity of the ENaC channel in each group is assessed by the change in short-circuit current following the apical addition of 10 µM of the ENaC blocker Amiloride (Amiloride-sensitive current). Chloride secretion via CFTR is assessed by the change in short circuit current following apical and basolateral addition of 0.6 μM Forskolin which is known to activate CFTR (Forskolin response). For each insert the Amiloride-sensitive current is normalized to the Forskolin response and the data presented as a percentage relative to the untransfected control. At the end of the study each insert is lysed for RNA analysis (300 μL RLT Buffer—Qiagen) and samples retained for subsequent analysis of mRNA knockdown by rtPCR as described.

Abbreviations:
ALI Air-Liquid Interface
BEGM Bronchial Epithelial Growth Medium
D6, D8 Day 6, Day 8
DMEM Dulbecco's Modified Eagle Medium
HBEC Human Bronchial Epithelial Cells
TM res Trans-membrane resistance Equivalents A composition comprising a RNAi agent comprising a sense strand and an antisense strand, wherein the antisense strand comprises at least 15 contiguous nucleotides differing by 0, 1, 2, or 3 nucleotides from the antisense strand of a RNAi agent specific to Beta-ENaC provided in Table 1.

The composition of paragraph [00879], wherein the composition further comprises a second RNAi agent to Beta-ENaC.

The composition of paragraph [00879], wherein the antisense strand is 30 or fewer nucleotides in length.

The composition of paragraph [00879], wherein the sense strand and the antisense strand form a duplex region 15 to 30 nucleotide pairs in length.

The composition of paragraph [00879], wherein the antisense strand and the sense strand are independently 19 to 23 nucleotides in length.

The composition of paragraph [00879], wherein the RNAi agent comprises a modification that causes the RNAi agent to have increased stability in a biological sample or environment.

The composition of paragraph [00879], wherein the RNAi agent comprises at least one modified backbone and/or at least one 2'-modified nucleotide.

The composition of paragraph [00879], wherein the RNAi agent comprises:
a) at least one 5'-uridine-adenine-3' (5'-ua-3') dinucleotide, wherein the uridine is a 2'-modified nucleotide; and/or
b) at least one 5'-uridine-guanine-3' (5'-ug-3') dinucleotide, wherein the 5'-uridine is a 2'-modified nucleotide; and/or
c) at least one 5'-cytidine-adenine-3' (5'-ac-3') dinucleotide, wherein the 5'-cytidine is a 2'-modified nucleotide; and/or
d) at least one 5'-uridine-uridine-3' (5'-uu-3') dinucleotide, wherein the 5'-uridine is a 2'-modified nucleotide.

The composition of paragraph [00879], wherein the RNAi agent comprises a 2'-modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).

The composition of cla paragraph [00879]1, wherein the RNAi agent comprises a blunt end.

The composition of paragraph [00879], wherein the RNAi agent comprises an overhang having 1 to 4 unpaired nucleotides.

The composition of paragraph [00879], wherein the RNAi agent comprises an overhang at the 3'-end of the antisense strand of the RNAi agent.

The composition of paragraph [00879], wherein the RNAi agent is ligated to one or more agent selected from: diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

The composition of paragraph [00879], wherein the RNAi agent is capable of inhibiting expression of the Beta-ENaC gene by at least about 60% at a concentration of 10 nM in H441 cells in vitro.

The composition of paragraph [00879], wherein the RNAi agent is capable of inhibiting expression of the Beta-ENaC gene by at least about 70% at a concentration of 10 nM in H441 cells in vitro.

The composition of paragraph [00879], wherein the RNAi agent is capable of inhibiting expression of the Beta-ENaC gene by at least about 80% at a concentration of 10 nM in H441 cells in vitro.

The composition of paragraph [00879], wherein the RNAi agent is capable of inhibiting expression of the Beta-ENaC gene by at least about 90% at a concentration of 10 nM in H441 cells in vitro.

The composition of paragraph [00879], wherein the RNAi has an EC50 of no more than about 0.1 nM.

The composition of paragraph [00879], wherein the RNAi has an EC50 of no more than about 0.01 nM.

The composition of paragraph [00879], wherein the RNAi has an EC50 of no more than about 0.001 nM.

A composition comprising a RNAi agent comprising a first strand and a second strand, wherein the first strand and second strand comprise at least 15 contiguous nucleotides differing by 0, 1, 2, or 3 nucleotides from the first and second strand, respectively, of a RNAi agent specific to Beta-ENaC provided in Table 1.

The composition of paragraph [00899], wherein the composition comprises a second RNAi agent to Beta-ENaC.

The composition of paragraph [00899], wherein the second strand is 30 or fewer nucleotides in length.

The composition of paragraph [00899], wherein the first strand and the second strand form a duplex region 15 to 30 nucleotide pairs in length.

The composition of paragraph [00899], wherein the first strand and the second strand are independently 19 to 23 nucleotides in length.

The composition of paragraph [00899], wherein the RNAi agent comprises a modification that causes the RNAi agent to have increased stability in a biological sample or environment.

The composition of paragraph [00899], wherein the RNAi agent comprises a phosphorothioate and/or a 2'-modified nucleotide.

The composition of paragraph [00899], wherein the RNAi agent comprises:
at least one 5'-uridine-adenine-3' (5'-ua-3') dinucleotide, wherein the uridine is a 2'-modified nucleotide; and/or at least one 5'-uridine-guanine-3' (5'-ug-3') dinucleotide, wherein the 5'-uridine is a 2'-modified nucleotide;

and/or at least one 5'-cytidine-adenine-3' (5'-ac-3') dinucleotide, wherein the 5'-cytidine is a 2'-modified nucleotide;

and/or at least one 5'-uridine-uridine-3' (5'-uu-3') dinucleotide, wherein the 5'-uridine is a 2'-modified nucleotide.

The composition of paragraph [00899], wherein the RNAi agent comprises one or more 2'-modifications selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).

The composition of paragraph [00899], wherein the RNAi agent comprises a blunt end.

The composition of paragraph [00899], wherein the RNAi agent comprises an overhang having 1 to 4 unpaired nucleotides.

The composition of paragraph [00899], wherein the RNAi agent comprises an overhang at the 3'-end of the antisense strand.

The composition of paragraph [00899], wherein the RNAi agent is ligated to one or more agents, the agent selected from a: diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

The composition of paragraph [00899], wherein the RNAi agent is capable of inhibiting expression of the Beta-ENaC gene by at least about 60% at a concentration of 10 nM in H441 cells in vitro.

The composition of paragraph [00899], wherein the RNAi agent is capable of inhibiting expression of the Beta-ENaC gene by at least about 70% at a concentration of 10 nM in H441 cells in vitro.

The composition of paragraph [00899], wherein the RNAi agent is capable of inhibiting expression of the Beta-ENaC gene by at least about 80% at a concentration of 10 nM in H441 cells in vitro.

The composition of paragraph [00899], wherein the RNAi agent is capable of inhibiting expression of the Beta-ENaC gene by at least about 90% at a concentration of 10 nM in H441 cells in vitro.

The composition of paragraph [00899], wherein the RNAi has an EC50 of no more than about 0.1 nM.

The composition of paragraph [00899], wherein the RNAi has an EC50 of no more than about 0.01 nM.

The composition of paragraph [00899], wherein the RNAi has an EC50 of no more than about 0.001 nM.

A method of treating a Beta-ENaC-related disease in an individual, comprising the step of administering to the individual a therapeutically effective amount of a composition comprising a RNAi agent comprising a sense strand and an antisense strand, wherein the antisense strand comprises at least 15 contiguous nucleotides differing by 0, 1, 2, or 3 nucleotides from the antisense strand of a RNAi agent specific to Beta-ENaC provided in Table 1.

The method of paragraph [00919], wherein the Beta-ENaC-related disease is cystic fibrosis, pseudohypoaldosteronism type 1 (PHA1), Liddle's syndrome, hypertension, alkalosis, hypokalemia, and/or obesity-associated hypertension.

The method of paragraph [00919], wherein the Beta-ENaC-related disease is cystic fibrosis.

The method of paragraph [00919], wherein the method further comprises the step of administering an additional treatment for cystic fibrosis, pseudohypoaldosteronism type 1 (PHA1), Liddle's syndrome, hypertension, alkalosis, hypokalemia, and/or obesity-associated hypertension.

The method of paragraph [00919], wherein the composition comprises a second RNAi agent to Beta-ENaC.

The method of paragraph [00919], wherein the method further comprises the step of administering an additional RNAi agent to Beta-ENaC.

The method of paragraph [00919], further comprising the administration of an additional treatment.

The method of paragraph [00919], wherein the additional treatment is a composition.

The method of paragraph [00919], wherein the additional treatment is a method.

The method of paragraph [00919], wherein the additional treatment and the RNAi agent can be administered in any order.

A method of inhibiting the expression of the Beta-ENaC gene in an individual, comprising the step of administering to the individual a therapeutically effective amount of a composition comprising a RNAi agent comprising a sense strand and an antisense strand, wherein the antisense strand comprises at least 15 contiguous nucleotides differing by 0, 1, 2, or 3 nucleotides from the antisense strand of a RNAi agent specific to Beta-ENaC provided in Table 1.

The method of paragraph [00929], wherein the individual is afflicted with or susceptible to a Beta-ENaC-related disease.

The method of paragraph [00929], wherein the Beta-ENaC-related disease is cystic fibrosis, pseudohypoaldosteronism type 1 (PHA1), Liddle's syndrome, hypertension, alkalosis, hypokalemia, and/or obesity-associated hypertension.

The method of paragraph [00929], wherein the Beta-ENaC-related disease is cystic fibrosis.

The method of paragraph [00932], further comprising the administration of an additional treatment.

The method of paragraph [00933], wherein the additional treatment is a composition.

The method of paragraph [00933], wherein the additional treatment is a method.

The method of paragraph [00933], wherein the additional treatment and the RNAi agent can be administered in any order.

A medicament for use in an RNAi formulation comprising a RNAi agent comprising a sense strand and an antisense strand, wherein the antisense strand comprises at least 15 contiguous nucleotides differing by 0, 1, 2, or 3 nucleotides from the antisense strand of a RNAi agent specific to Beta-ENaC provided in Table 1.

Any composition above in a pharmaceutically effective formulation.

The composition according to paragraph [00879], for use in a method of treating a Beta-ENaC-related disease in an individual, the method comprising the step of administering to the individual a therapeutically effective amount of a composition according to paragraph [00879].

The use of a composition according to paragraph [00879], in the manufacture of a medicament for the treatment of a Beta-ENaC-related disease.

The use of paragraph [00940], wherein the Beta-ENaC-related disease is cystic fibrosis, pseudohypoaldosteronism type 1 (PHA1), Liddle's syndrome, hypertension, alkalosis, hypokalemia, and/or obesity-associated hypertension.

The composition of paragraph [00879], wherein all the pyrimidines are 2' O-methyl-modified nucleotides.

The composition of paragraph [00899], wherein all the pyrimidines are 2' O-methyl-modified nucleotides.

We claim:

1. A composition comprising a RNAi agent comprising a first strand and a second strand, wherein:
   a. the sequence of first strand comprises at least 15 contiguous nucleotides differing by 0, 1, 2, or 3 nucleotides from the sequence of SEQ ID NO: 116, or
   b. the sequence of the first strand comprises at least 15 contiguous nucleotides differing by 0, 1, 2 or 3 nucleotides from the sequence of SEQ ID NO: 166;
   wherein the length of the first and second strand are each at least about 15 nucleotides and no more than about 30 nucleotides; and
   wherein the first and/or the second strand are modified or unmodified.

2. The composition of claim 1, wherein the composition further comprises a second RNAi agent to Beta-ENaC.

3. The composition of claim 1, wherein the RNAi agent comprises at least one modified backbone and/or at least one 2'-modified nucleotide.

4. The composition of claim 1, wherein the RNAi agent is ligated to one or more agents, wherein the one or more agents are selected from: diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and transferrin.

5. A composition comprising a RNAi agent comprising a first strand and a second strand, wherein:
   a. the sequence of the first strand comprises the sequence of SEQ ID NO: 116, or
   b. the sequence of the first strand comprises the sequence of SEQ ID NO: 166;
   wherein the length of the first and second strand are each no more than about 30 nucleotides, and
   wherein the first and/or the second strand are modified or unmodified.

6. The composition of claim 5, wherein the composition further comprises a second RNAi agent to Beta-ENaC.

7. The composition of claim 5, wherein the RNAi agent comprises a phosphorothioate and/or a 2'-modified nucleotide.

8. The composition of claim 5, wherein the RNAi agent is ligated to one or more agents, wherein the one or more agents are selected from: diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and transferrin.

9. A method of reducing the level and/or expression of Beta-ENaC in an individual, the method comprising the step of administering to the individual a composition comprising a pharmaceutically acceptable carrier and a RNAi agent comprising a first strand and a second strand, wherein:
 a. the sequence of the first strand comprises at least 15 contiguous nucleotides differing by 0, 1, 2, or 3 nucleotides from the sequence of SEQ ID NO: 116, or,
 b. the sequence of the first strand comprises at least 15 contiguous nucleotides differing by 0, 1, 2, or 3 nucleotides from the sequence of SEQ ID NO: 166; and wherein the length of the first and second strand are each at least about 15 nucleotides and no more than about 30 nucleotides; and wherein the first and/or the second strand are modified or unmodified.

10. The method of claim 9, wherein the method further comprises the step of administering an additional RNAi agent to Beta-ENaC.

11. A composition comprising a RNAi agent comprising a first strand and a second strand, wherein:
 a. the sequence of the first strand is the sequence of SEQ ID NO: 116, and/or the sequence of the second strand is the sequence of SEQ ID NO:115, or
 b. the sequence of the first strand is the sequence of SEQ ID NO: 166, and/or the sequence of the second strand is the sequence of SEQ ID NO: 165; and
 wherein the first and/or the second strand are modified or unmodified.

12. The composition of claim 11, wherein the RNAi agent comprises one or more 2'-modifications selected from the group consisting of:
 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O-N-methylacetamido (2'-O-NMA).

13. The composition of claim 11, wherein the RNAi agent is ligated to one or more agents, wherein the one or more agents are selected from:
 diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and transferrin.

14. The composition of claim 11, wherein the composition comprises a second RNAi agent to Beta-ENaC.

15. The composition of claim 11, wherein the RNAi agent comprises a phosphorothioate and/or a 2'-modified nucleotide.

16. A composition comprising a therapeutically effective amount of a composition of claim 1 and a pharmaceutically acceptable carrier.

17. A composition comprising a therapeutically effective amount of a composition of claim 5 and a pharmaceutically acceptable carrier.

18. A composition comprising a therapeutically effective amount of a composition of claim 11 and a pharmaceutically acceptable carrier.

19. A composition comprising a RNAi agent comprising a first strand and a second strand, wherein:
 a. the sequence of the first strand is the sequence of SEQ ID NO: 116, or
 b. the sequence of the first strand is the sequence of SEQ ID NO: 166; and
 wherein the first and/or the second strand are modified or unmodified.

20. A composition comprising a RNAi agent comprising a first strand and a second strand, wherein:
 a. the sequence of first strand comprises at least 15 contiguous nucleotides from the sequence of SEQ ID NO: 116, or
 b. the sequence of the first strand comprises at least 15 contiguous nucleotides from the sequence of SEQ ID NO: 166; and
 wherein the length of the first and second strand are each at least about 19 nucleotides and no more than about 30 nucleotides; and
 wherein the first and/or the second strand are modified or unmodified.

21. A composition comprising a RNAi agent comprising a first strand and a second strand, wherein:
 a. the sequence of the first strand comprises the sequence of SEQ ID NO: 116, or,
 b. the sequence of the first strand comprises the sequence of SEQ ID NO: 166; and wherein the length of the first and second strand are each at least about 19 nucleotides and no more than about 30 nucleotides; and wherein the first and/or the second strand are modified or unmodified.

* * * * *

```
                        SEQUENCE LISTING

<160> NUMBER OF SEQ ID NOS: 430

<210> SEQ ID NO 1
<211> LENGTH: 19
<212> TYPE: RNA
<213> ORGANISM: Artificial
<220> FEATURE:
<223> OTHER INFORMATION: RNAi Agent

<400> SEQUENCE: 1
cagugacuac aacacgacc                                                  19

<210> SEQ ID NO 2
<211> LENGTH: 19
<212> TYPE: RNA
<213> ORGANISM: Artificial
<220> FEATURE:
<223> OTHER INFORMATION: RNAi Agent

<400> SEQUENCE: 2
ggucguguug uagucacug                                                  19

<210> SEQ ID NO 3
<211> LENGTH: 19
<212> TYPE: RNA
<213> ORGANISM: Artificial
<220> FEATURE:
<223> OTHER INFORMATION: RNAi Agent

<400> SEQUENCE: 3
augacagaga aggcacuuc                                                  19

<210> SEQ ID NO 4
<211> LENGTH: 19
<212> TYPE: RNA
<213> ORGANISM: Artificial
<220> FEATURE:
<223> OTHER INFORMATION: RNAi Agent

<400> SEQUENCE: 4
gaagugccuu cucugucau                                                  19

<210> SEQ ID NO 5
<211> LENGTH: 19
<212> TYPE: RNA
<213> ORGANISM: Artificial
<220> FEATURE:
<223> OTHER INFORMATION: RNAi Agent

<400> SEQUENCE: 5
gugaagaagu accugcuga                                                  19

<210> SEQ ID NO 6
<211> LENGTH: 19
<212> TYPE: RNA
<213> ORGANISM: Artificial
<220> FEATURE:
<223> OTHER INFORMATION: RNAi Agent

<400> SEQUENCE: 6
```
ucagcaggua cuucuucac    19

<210> SEQ ID NO 7
<211> LENGTH: 19
<212> TYPE: RNA
<213> ORGANISM: Artificial
<220> FEATURE:
<223> OTHER INFORMATION: RNAi Agent

<400> SEQUENCE: 7
gugacuacaa cacgaccua    19

<210> SEQ ID NO 8
<211> LENGTH: 19
<212> TYPE: RNA
<213> ORGANISM: Artificial
<220> FEATURE:
<223> OTHER INFORMATION: RNAi Agent

<400> SEQUENCE: 8
uaggucgugu uguagucac    19

<210> SEQ ID NO 9
<211> LENGTH: 19
<212> TYPE: RNA
<213> ORGANISM: Artificial
<220> FEATURE:
<223> OTHER INFORMATION: RNAi Agent

<400> SEQUENCE: 9
gguggaggcc cacaccaac    19

<210> SEQ ID NO 10
<211> LENGTH: 19
<212> TYPE: RNA
<213> ORGANISM: Artificial
<220> FEATURE:
<223> OTHER INFORMATION: RNAi Agent

<400> SEQUENCE: 10
guuggugugg gccuccacc    19

<210> SEQ ID NO 11
<211> LENGTH: 19
<212> TYPE: RNA
<213> ORGANISM: Artificial
<220> FEATURE:
<223> OTHER INFORMATION: RNAi Agent

<400> SEQUENCE: 11
ugguggaggc ccacaccaa    19

<210> SEQ ID NO 12
<211> LENGTH: 19
<212> TYPE: RNA
<213> ORGANISM: Artificial
<220> FEATURE:
<223> OTHER INFORMATION: RNAi Agent

<400> SEQUENCE: 12 uuggguguggg ccuccacca   19

<210> SEQ ID NO 13
<211> LENGTH: 19
<212> TYPE: RNA
<213> ORGANISM: Artificial
<220> FEATURE:

```
<223> OTHER INFORMATION: RNAi Agent

<400> SEQUENCE: 13
uuccaagacc acaugaucc                                              19

<210> SEQ ID NO 14
<211> LENGTH: 19
<212> TYPE: RNA
<213> ORGANISM: Artificial
<220> FEATURE:
<223> OTHER INFORMATION: RNAi Agent

<400> SEQUENCE: 14
ggaucaugug gucuuggaa                                              19

<210> SEQ ID NO 15
<211> LENGTH: 19
<212> TYPE: RNA
<213> ORGANISM: Artificial
<220> FEATURE:
<223> OTHER INFORMATION: RNAi Agent

<400> SEQUENCE: 15
agcugggagg ucagcgucu                                              19

<210> SEQ ID NO 16
<211> LENGTH: 19
<212> TYPE: RNA
<213> ORGANISM: Artificial
<220> FEATURE:
<223> OTHER INFORMATION: RNAi Agent

<400> SEQUENCE: 16
agacgcugac cucccagcu                                              19

<210> SEQ ID NO 17
<211> LENGTH: 19
<212> TYPE: RNA
<213> ORGANISM: Artificial
<220> FEATURE:
<223> OTHER INFORMATION: RNAi Agent

<400> SEQUENCE: 17
gggagaaaua cugcaacaa                                              19

<210> SEQ ID NO 18
<211> LENGTH: 19
<212> TYPE: RNA
<213> ORGANISM: Artificial
<220> FEATURE:
<223> OTHER INFORMATION: RNAi Agent

<400> SEQUENCE: 18
uuguugcagu auuucuccc                                              19

<210> SEQ ID NO 19
<211> LENGTH: 19
<212> TYPE: RNA
<213> ORGANISM: Artificial
<220> FEATURE:
<223> OTHER INFORMATION: RNAi Agent

<400> SEQUENCE: 19
ccaguuuggc uucuggaug                                              19

<210> SEQ ID NO 20
```

```
<211> LENGTH: 19
<212> TYPE: RNA
<213> ORGANISM: Artificial
<220> FEATURE:
<223> OTHER INFORMATION: RNAi Agent

<400> SEQUENCE: 20
cauccagaag ccaaacugg                                                   19

<210> SEQ ID NO 21
<211> LENGTH: 19
<212> TYPE: RNA
<213> ORGANISM: Artificial
<220> FEATURE:
<223> OTHER INFORMATION: RNAi Agent

<400> SEQUENCE: 21
agugacuaca acacgaccu                                                   19

<210> SEQ ID NO 22
<211> LENGTH: 19
<212> TYPE: RNA
<213> ORGANISM: Artificial
<220> FEATURE:
<223> OTHER INFORMATION: RNAi Agent

<400> SEQUENCE: 22
aggucguguu guagucacu                                                   19

<210> SEQ ID NO 23
<211> LENGTH: 19
<212> TYPE: RNA
<213> ORGANISM: Artificial
<220> FEATURE:
<223> OTHER INFORMATION: RNAi Agent

<400> SEQUENCE: 23
aauaucaccc ugagcagga                                                   19

<210> SEQ ID NO 24
<211> LENGTH: 19
<212> TYPE: RNA
<213> ORGANISM: Artificial
<220> FEATURE:
<223> OTHER INFORMATION: RNAi Agent

<400> SEQUENCE: 24
uccugcucag ggugauauu                                                   19

<210> SEQ ID NO 25
<211> LENGTH: 19
<212> TYPE: RNA
<213> ORGANISM: Artificial
<220> FEATURE:
<223> OTHER INFORMATION: RNAi Agent

<400> SEQUENCE: 25
ccugcaggcc accaacauc                                                   19

<210> SEQ ID NO 26
<211> LENGTH: 19
<212> TYPE: RNA
<213> ORGANISM: Artificial
<220> FEATURE:
<223> OTHER INFORMATION: RNAi Agent

<400> SEQUENCE: 26
```

-continued

| | |
|---|---|
| gauguuggug gccugcagg | 19 |

<210> SEQ ID NO 27
<211> LENGTH: 19
<212> TYPE: RNA
<213> ORGANISM: Artificial
<220> FEATURE:
<223> OTHER INFORMATION: RNAi Agent

<400> SEQUENCE: 27

| | |
|---|---|
| aucacccuga gcaggaagg | 19 |

<210> SEQ ID NO 28
<211> LENGTH: 19
<212> TYPE: RNA
<213> ORGANISM: Artificial
<220> FEATURE:
<223> OTHER INFORMATION: RNAi Agent

<400> SEQUENCE: 28

| | |
|---|---|
| ccuuccugcu cagggugau | 19 |

<210> SEQ ID NO 29
<211> LENGTH: 19
<212> TYPE: RNA
<213> ORGANISM: Artificial
<220> FEATURE:
<223> OTHER INFORMATION: RNAi Agent

<400> SEQUENCE: 29

| | |
|---|---|
| gcugggaggu cagcgucuc | 19 |

<210> SEQ ID NO 30
<211> LENGTH: 19
<212> TYPE: RNA
<213> ORGANISM: Artificial
<220> FEATURE:
<223> OTHER INFORMATION: RNAi Agent

<400> SEQUENCE: 30

| | |
|---|---|
| gagacgcuga ccucccagc | 19 |

<210> SEQ ID NO 31
<211> LENGTH: 19
<212> TYPE: RNA
<213> ORGANISM: Artificial
<220> FEATURE:
<223> OTHER INFORMATION: RNAi Agent

<400> SEQUENCE: 31

| | |
|---|---|
| gagcugggag gucagcguc | 19 |

<210> SEQ ID NO 32
<211> LENGTH: 19
<212> TYPE: RNA
<213> ORGANISM: Artificial
<220> FEATURE:
<223> OTHER INFORMATION: RNAi Agent

<400> SEQUENCE: 32

| | |
|---|---|
| gacgcugacc ucccagcuc | 19 |

<210> SEQ ID NO 33
<211> LENGTH: 19
<212> TYPE: RNA
<213> ORGANISM: Artificial
<220> FEATURE:

```
<223> OTHER INFORMATION: RNAi Agent

<400> SEQUENCE: 33
guggccaguu uggcuucug                                            19

<210> SEQ ID NO 34
<211> LENGTH: 19
<212> TYPE: RNA
<213> ORGANISM: Artificial
<220> FEATURE:
<223> OTHER INFORMATION: RNAi Agent

<400> SEQUENCE: 34
cagaagccaa acuggccac                                            19

<210> SEQ ID NO 35
<211> LENGTH: 19
<212> TYPE: RNA
<213> ORGANISM: Artificial
<220> FEATURE:
<223> OTHER INFORMATION: RNAi Agent

<400> SEQUENCE: 35
caguuuggcu ucuggaugg                                            19

<210> SEQ ID NO 36
<211> LENGTH: 19
<212> TYPE: RNA
<213> ORGANISM: Artificial
<220> FEATURE:
<223> OTHER INFORMATION: RNAi Agent

<400> SEQUENCE: 36
ccauccagaa gccaaacug                                            19

<210> SEQ ID NO 37
<211> LENGTH: 19
<212> TYPE: RNA
<213> ORGANISM: Artificial
<220> FEATURE:
<223> OTHER INFORMATION: RNAi Agent

<400> SEQUENCE: 37
ggccaguuug gcuucugga                                            19

<210> SEQ ID NO 38
<211> LENGTH: 19
<212> TYPE: RNA
<213> ORGANISM: Artificial
<220> FEATURE:
<223> OTHER INFORMATION: RNAi Agent

<400> SEQUENCE: 38
uccagaagcc aaacuggcc                                            19

<210> SEQ ID NO 39
<211> LENGTH: 19
<212> TYPE: RNA
<213> ORGANISM: Artificial
<220> FEATURE:
<223> OTHER INFORMATION: RNAi Agent

<400> SEQUENCE: 39
cuggguggcc aguuuggcu                                            19

<210> SEQ ID NO 40
```

-continued

```
<211> LENGTH: 19
<212> TYPE: RNA
<213> ORGANISM: Artificial
<220> FEATURE:
<223> OTHER INFORMATION: RNAi Agent

<400> SEQUENCE: 40
agccaaacug gccacccag                                                    19

<210> SEQ ID NO 41
<211> LENGTH: 19
<212> TYPE: RNA
<213> ORGANISM: Artificial
<220> FEATURE:
<223> OTHER INFORMATION: RNAi Agent

<400> SEQUENCE: 41
ucuacaguga cuacaacac                                                    19

<210> SEQ ID NO 42
<211> LENGTH: 19
<212> TYPE: RNA
<213> ORGANISM: Artificial
<220> FEATURE:
<223> OTHER INFORMATION: RNAi Agent

<400> SEQUENCE: 42
guguuguagu cacuguaga                                                    19

<210> SEQ ID NO 43
<211> LENGTH: 19
<212> TYPE: RNA
<213> ORGANISM: Artificial
<220> FEATURE:
<223> OTHER INFORMATION: RNAi Agent

<400> SEQUENCE: 43
gcaugacaga gaaggcacu                                                    19

<210> SEQ ID NO 44
<211> LENGTH: 19
<212> TYPE: RNA
<213> ORGANISM: Artificial
<220> FEATURE:
<223> OTHER INFORMATION: RNAi Agent

<400> SEQUENCE: 44
agugccuucu cugucaugc                                                    19

<210> SEQ ID NO 45
<211> LENGTH: 19
<212> TYPE: RNA
<213> ORGANISM: Artificial
<220> FEATURE:
<223> OTHER INFORMATION: RNAi Agent

<400> SEQUENCE: 45
auaucacccu gagcaggaa                                                    19

<210> SEQ ID NO 46
<211> LENGTH: 19
<212> TYPE: RNA
<213> ORGANISM: Artificial
<220> FEATURE:
<223> OTHER INFORMATION: RNAi Agent

<400> SEQUENCE: 46
```
uuccugcuca gggugauau 19

<210> SEQ ID NO 47
<211> LENGTH: 19
<212> TYPE: RNA
<213> ORGANISM: Artificial
<220> FEATURE:
<223> OTHER INFORMATION: RNAi Agent

<400> SEQUENCE: 47
cuacagugac uacaacacg 19

<210> SEQ ID NO 48
<211> LENGTH: 19
<212> TYPE: RNA
<213> ORGANISM: Artificial
<220> FEATURE:
<223> OTHER INFORMATION: RNAi Agent

<400> SEQUENCE: 48
cguguuguag ucacuguag 19

<210> SEQ ID NO 49
<211> LENGTH: 19
<212> TYPE: RNA
<213> ORGANISM: Artificial
<220> FEATURE:
<223> OTHER INFORMATION: RNAi Agent

<400> SEQUENCE: 49
uaucacccug agcaggaag 19

<210> SEQ ID NO 50
<211> LENGTH: 19
<212> TYPE: RNA
<213> ORGANISM: Artificial
<220> FEATURE:
<223> OTHER INFORMATION: RNAi Agent

<400> SEQUENCE: 50
cuuccugcuc agggugaua 19

<210> SEQ ID NO 51
<211> LENGTH: 19
<212> TYPE: RNA
<213> ORGANISM: Artificial
<220> FEATURE:
<223> OTHER INFORMATION: RNAi Agent

<400> SEQUENCE: 51
ugcaggccac caacaucuu 19

<210> SEQ ID NO 52
<211> LENGTH: 19
<212> TYPE: RNA
<213> ORGANISM: Artificial
<220> FEATURE:
<223> OTHER INFORMATION: RNAi Agent

<400> SEQUENCE: 52
aagauguugg uggccugca 19

<210> SEQ ID NO 53
<211> LENGTH: 19
<212> TYPE: RNA
<213> ORGANISM: Artificial
<220> FEATURE:

<223> OTHER INFORMATION: RNAi Agent

<400> SEQUENCE: 53
caugacagag aaggcacuu                                                        19

<210> SEQ ID NO 54
<211> LENGTH: 19
<212> TYPE: RNA
<213> ORGANISM: Artificial
<220> FEATURE:
<223> OTHER INFORMATION: RNAi Agent

<400> SEQUENCE: 54
aagugccuuc ucugucaug                                                        19

<210> SEQ ID NO 55
<211> LENGTH: 19
<212> TYPE: RNA
<213> ORGANISM: Artificial
<220> FEATURE:
<223> OTHER INFORMATION: RNAi Agent

<400> SEQUENCE: 55
ugaagaagua ccugcugaa                                                        19

<210> SEQ ID NO 56
<211> LENGTH: 19
<212> TYPE: RNA
<213> ORGANISM: Artificial
<220> FEATURE:
<223> OTHER INFORMATION: RNAi Agent

<400> SEQUENCE: 56
uucagcaggu acuucuuca                                                        19

<210> SEQ ID NO 57
<211> LENGTH: 19
<212> TYPE: RNA
<213> ORGANISM: Artificial
<220> FEATURE:
<223> OTHER INFORMATION: RNAi Agent

<400> SEQUENCE: 57
gcugguggag gcccacacc                                                        19

<210> SEQ ID NO 58
<211> LENGTH: 19
<212> TYPE: RNA
<213> ORGANISM: Artificial
<220> FEATURE:
<223> OTHER INFORMATION: RNAi Agent

<400> SEQUENCE: 58
ggugugggcc uccaccagc                                                        19

<210> SEQ ID NO 59
<211> LENGTH: 19
<212> TYPE: RNA
<213> ORGANISM: Artificial
<220> FEATURE:
<223> OTHER INFORMATION: RNAi Agent

<400> SEQUENCE: 59
uacagugacu acaacacga                                                        19

<210> SEQ ID NO 60

```
<211> LENGTH: 19
<212> TYPE: RNA
<213> ORGANISM: Artificial
<220> FEATURE:
<223> OTHER INFORMATION: RNAi Agent

<400> SEQUENCE: 60
ucguguugua gucacugua                                            19

<210> SEQ ID NO 61
<211> LENGTH: 19
<212> TYPE: RNA
<213> ORGANISM: Artificial
<220> FEATURE:
<223> OTHER INFORMATION: RNAi Agent

<400> SEQUENCE: 61
acagagaagg cacuuccuu                                            19

<210> SEQ ID NO 62
<211> LENGTH: 19
<212> TYPE: RNA
<213> ORGANISM: Artificial
<220> FEATURE:
<223> OTHER INFORMATION: RNAi Agent

<400> SEQUENCE: 62
aaggaagugc cuucucugu                                            19

<210> SEQ ID NO 63
<211> LENGTH: 19
<212> TYPE: RNA
<213> ORGANISM: Artificial
<220> FEATURE:
<223> OTHER INFORMATION: RNAi Agent

<400> SEQUENCE: 63
acagugacua caacacgac                                            19

<210> SEQ ID NO 64
<211> LENGTH: 19
<212> TYPE: RNA
<213> ORGANISM: Artificial
<220> FEATURE:
<223> OTHER INFORMATION: RNAi Agent

<400> SEQUENCE: 64
gucguguugu agucacugu                                            19

<210> SEQ ID NO 65
<211> LENGTH: 19
<212> TYPE: RNA
<213> ORGANISM: Artificial
<220> FEATURE:
<223> OTHER INFORMATION: RNAi Agent

<400> SEQUENCE: 65
ugagcuggga ggucagcgu                                            19

<210> SEQ ID NO 66
<211> LENGTH: 19
<212> TYPE: RNA
<213> ORGANISM: Artificial
<220> FEATURE:
<223> OTHER INFORMATION: RNAi Agent

<400> SEQUENCE: 66
```
acgcugaccu cccagcuca                                                     19

<210> SEQ ID NO 67
<211> LENGTH: 19
<212> TYPE: RNA
<213> ORGANISM: Artificial
<220> FEATURE:
<223> OTHER INFORMATION: RNAi Agent

<400> SEQUENCE: 67
uggccaguuu ggcuucugg                                                     19

<210> SEQ ID NO 68
<211> LENGTH: 19
<212> TYPE: RNA
<213> ORGANISM: Artificial
<220> FEATURE:
<223> OTHER INFORMATION: RNAi Agent

<400> SEQUENCE: 68
ccagaagcca aacuggcca                                                     19

<210> SEQ ID NO 69
<211> LENGTH: 19
<212> TYPE: RNA
<213> ORGANISM: Artificial
<220> FEATURE:
<223> OTHER INFORMATION: RNAi Agent

<400> SEQUENCE: 69
ugucucagga gcgggacca                                                     19

<210> SEQ ID NO 70
<211> LENGTH: 19
<212> TYPE: RNA
<213> ORGANISM: Artificial
<220> FEATURE:
<223> OTHER INFORMATION: RNAi Agent

<400> SEQUENCE: 70
uggucccgcu ccugagaca                                                     19

<210> SEQ ID NO 71
<211> LENGTH: 19
<212> TYPE: RNA
<213> ORGANISM: Artificial
<220> FEATURE:
<223> OTHER INFORMATION: RNAi Agent

<400> SEQUENCE: 71
guggaggccc acaccaacu                                                     19

<210> SEQ ID NO 72
<211> LENGTH: 19
<212> TYPE: RNA
<213> ORGANISM: Artificial
<220> FEATURE:
<223> OTHER INFORMATION: RNAi Agent

<400> SEQUENCE: 72
aguuggugug ggccuccac                                                     19

<210> SEQ ID NO 73
<211> LENGTH: 19
<212> TYPE: RNA
<213> ORGANISM: Artificial
<220> FEATURE:

<223> OTHER INFORMATION: RNAi Agent

<400> SEQUENCE: 73
ggguggccag uuuggcuuc                                                        19

<210> SEQ ID NO 74
<211> LENGTH: 19
<212> TYPE: RNA
<213> ORGANISM: Artificial
<220> FEATURE:
<223> OTHER INFORMATION: RNAi Agent

<400> SEQUENCE: 74
gaagccaaac uggccaccc                                                        19

<210> SEQ ID NO 75
<211> LENGTH: 19
<212> TYPE: RNA
<213> ORGANISM: Artificial
<220> FEATURE:
<223> OTHER INFORMATION: RNAi Agent

<400> SEQUENCE: 75
gguggccagu uggcuucu                                                         19

<210> SEQ ID NO 76
<211> LENGTH: 19
<212> TYPE: RNA
<213> ORGANISM: Artificial
<220> FEATURE:
<223> OTHER INFORMATION: RNAi Agent

<400> SEQUENCE: 76
agaagccaaa cuggccacc                                                        19

<210> SEQ ID NO 77
<211> LENGTH: 19
<212> TYPE: RNA
<213> ORGANISM: Artificial
<220> FEATURE:
<223> OTHER INFORMATION: RNAi Agent

<400> SEQUENCE: 77
ucacccugag caggaaggg                                                        19

<210> SEQ ID NO 78
<211> LENGTH: 19
<212> TYPE: RNA
<213> ORGANISM: Artificial
<220> FEATURE:
<223> OTHER INFORMATION: RNAi Agent

<400> SEQUENCE: 78
cccuuccugc ucaggguga                                                        19

<210> SEQ ID NO 79
<211> LENGTH: 19
<212> TYPE: RNA
<213> ORGANISM: Artificial
<220> FEATURE:
<223> OTHER INFORMATION: RNAi Agent

<400> SEQUENCE: 79
gccaguuugg cuucuggau                                                        19

<210> SEQ ID NO 80

```
<211> LENGTH: 19
<212> TYPE: RNA
<213> ORGANISM: Artificial
<220> FEATURE:
<223> OTHER INFORMATION: RNAi Agent

<400> SEQUENCE: 80
auccagaagc caaacuggc                                                 19

<210> SEQ ID NO 81
<211> LENGTH: 19
<212> TYPE: RNA
<213> ORGANISM: Artificial
<220> FEATURE:
<223> OTHER INFORMATION: RNAi Agent

<400> SEQUENCE: 81
agcuggugga ggcccacac                                                 19

<210> SEQ ID NO 82
<211> LENGTH: 19
<212> TYPE: RNA
<213> ORGANISM: Artificial
<220> FEATURE:
<223> OTHER INFORMATION: RNAi Agent

<400> SEQUENCE: 82
gugugggccu ccaccagcu                                                 19

<210> SEQ ID NO 83
<211> LENGTH: 19
<212> TYPE: RNA
<213> ORGANISM: Artificial
<220> FEATURE:
<223> OTHER INFORMATION: RNAi Agent

<400> SEQUENCE: 83
aucuccaugg cugacuggc                                                 19

<210> SEQ ID NO 84
<211> LENGTH: 19
<212> TYPE: RNA
<213> ORGANISM: Artificial
<220> FEATURE:
<223> OTHER INFORMATION: RNAi Agent

<400> SEQUENCE: 84
gccagucagc cauggagau                                                 19

<210> SEQ ID NO 85
<211> LENGTH: 19
<212> TYPE: RNA
<213> ORGANISM: Artificial
<220> FEATURE:
<223> OTHER INFORMATION: RNAi Agent

<400> SEQUENCE: 85
ggcaugacag agaaggcac                                                 19

<210> SEQ ID NO 86
<211> LENGTH: 19
<212> TYPE: RNA
<213> ORGANISM: Artificial
<220> FEATURE:
<223> OTHER INFORMATION: RNAi Agent

<400> SEQUENCE: 86
```
gugccuucuc ugucaugcc                                              19

<210> SEQ ID NO 87
<211> LENGTH: 19
<212> TYPE: RNA
<213> ORGANISM: Artificial
<220> FEATURE:
<223> OTHER INFORMATION: RNAi Agent

<400> SEQUENCE: 87
ggagaaauac ugcaacaac                                              19

<210> SEQ ID NO 88
<211> LENGTH: 19
<212> TYPE: RNA
<213> ORGANISM: Artificial
<220> FEATURE:
<223> OTHER INFORMATION: RNAi Agent

<400> SEQUENCE: 88
guuguugcag uauuucucc                                              19

<210> SEQ ID NO 89
<211> LENGTH: 19
<212> TYPE: RNA
<213> ORGANISM: Artificial
<220> FEATURE:
<223> OTHER INFORMATION: RNAi Agent

<400> SEQUENCE: 89
uggguggcca guuuggcuu                                              19

<210> SEQ ID NO 90
<211> LENGTH: 19
<212> TYPE: RNA
<213> ORGANISM: Artificial
<220> FEATURE:
<223> OTHER INFORMATION: RNAi Agent

<400> SEQUENCE: 90
aagccaaacu ggccaccca                                              19

<210> SEQ ID NO 91
<211> LENGTH: 19
<212> TYPE: RNA
<213> ORGANISM: Artificial
<220> FEATURE:
<223> OTHER INFORMATION: RNAi Agent

<400> SEQUENCE: 91
gagcuggugg aggcccaca                                              19

<210> SEQ ID NO 92
<211> LENGTH: 19
<212> TYPE: RNA
<213> ORGANISM: Artificial
<220> FEATURE:
<223> OTHER INFORMATION: RNAi Agent

<400> SEQUENCE: 92
ugugggccuc caccagcuc                                              19

<210> SEQ ID NO 93
<211> LENGTH: 19
<212> TYPE: RNA
<213> ORGANISM: Artificial
<220> FEATURE:

```
<223> OTHER INFORMATION: RNAi Agent

<400> SEQUENCE: 93
gacagagaag gcacuuccu                                                    19

<210> SEQ ID NO 94
<211> LENGTH: 19
<212> TYPE: RNA
<213> ORGANISM: Artificial
<220> FEATURE:
<223> OTHER INFORMATION: RNAi Agent

<400> SEQUENCE: 94
aggaagugcc uucucuguc                                                    19

<210> SEQ ID NO 95
<211> LENGTH: 19
<212> TYPE: RNA
<213> ORGANISM: Artificial
<220> FEATURE:
<223> OTHER INFORMATION: RNAi Agent

<400> SEQUENCE: 95
aguuuggcuu cuggaugggg                                                   19

<210> SEQ ID NO 96
<211> LENGTH: 19
<212> TYPE: RNA
<213> ORGANISM: Artificial
<220> FEATURE:
<223> OTHER INFORMATION: RNAi Agent

<400> SEQUENCE: 96
cccauccaga agccaaacu                                                    19

<210> SEQ ID NO 97
<211> LENGTH: 19
<212> TYPE: RNA
<213> ORGANISM: Artificial
<220> FEATURE:
<223> OTHER INFORMATION: RNAi Agent

<400> SEQUENCE: 97
ugacagagaa ggcacuucc                                                    19

<210> SEQ ID NO 98
<211> LENGTH: 19
<212> TYPE: RNA
<213> ORGANISM: Artificial
<220> FEATURE:
<223> OTHER INFORMATION: RNAi Agent

<400> SEQUENCE: 98
ggaagugccu ucucuguca                                                    19

<210> SEQ ID NO 99
<211> LENGTH: 19
<212> TYPE: RNA
<213> ORGANISM: Artificial
<220> FEATURE:
<223> OTHER INFORMATION: RNAi Agent

<400> SEQUENCE: 99
gaagaaguac cugcugaag                                                    19

<210> SEQ ID NO 100
```

```
<211> LENGTH: 19
<212> TYPE: RNA
<213> ORGANISM: Artificial
<220> FEATURE:
<223> OTHER INFORMATION: RNAi Agent

<400> SEQUENCE: 100
cuucagcagg uacuucuuc                                                     19

<210> SEQ ID NO 101
<211> LENGTH: 19
<212> TYPE: RNA
<213> ORGANISM: Artificial
<220> FEATURE:
<223> OTHER INFORMATION: RNAi Agent

<400> SEQUENCE: 101
ucuccauggc ugacuggcc                                                     19

<210> SEQ ID NO 102
<211> LENGTH: 19
<212> TYPE: RNA
<213> ORGANISM: Artificial
<220> FEATURE:
<223> OTHER INFORMATION: RNAi Agent

<400> SEQUENCE: 102
ggccagucag ccauggaga                                                     19

<210> SEQ ID NO 103
<211> LENGTH: 19
<212> TYPE: RNA
<213> ORGANISM: Artificial
<220> FEATURE:
<223> OTHER INFORMATION: RNAi Agent

<400> SEQUENCE: 103
cugguggagg cccacacca                                                     19

<210> SEQ ID NO 104
<211> LENGTH: 19
<212> TYPE: RNA
<213> ORGANISM: Artificial
<220> FEATURE:
<223> OTHER INFORMATION: RNAi Agent

<400> SEQUENCE: 104
uggugugggc cuccaccag                                                     19

<210> SEQ ID NO 105
<211> LENGTH: 19
<212> TYPE: RNA
<213> ORGANISM: Artificial
<220> FEATURE:
<223> OTHER INFORMATION: RNAi Agent

<400> SEQUENCE: 105
cagagaaggc acuuccuuc                                                     19

<210> SEQ ID NO 106
<211> LENGTH: 19
<212> TYPE: RNA
<213> ORGANISM: Artificial
<220> FEATURE:
<223> OTHER INFORMATION: RNAi Agent

<400> SEQUENCE: 106
```

```
gaaggaagug ccuucucug                                              19

<210> SEQ ID NO 107
<211> LENGTH: 19
<212> TYPE: RNA
<213> ORGANISM: Artificial
<220> FEATURE:
<223> OTHER INFORMATION: RNAi Agent

<400> SEQUENCE: 107
cugcaggcca ccaacaucu                                              19

<210> SEQ ID NO 108
<211> LENGTH: 19
<212> TYPE: RNA
<213> ORGANISM: Artificial
<220> FEATURE:
<223> OTHER INFORMATION: RNAi Agent

<400> SEQUENCE: 108
agauguuggu ggccugcag                                              19

<210> SEQ ID NO 109
<211> LENGTH: 19
<212> TYPE: RNA
<213> ORGANISM: Artificial
<220> FEATURE:
<223> OTHER INFORMATION: RNAi Agent

<400> SEQUENCE: 109
gggcaugaca gagaaggca                                              19

<210> SEQ ID NO 110
<211> LENGTH: 19
<212> TYPE: RNA
<213> ORGANISM: Artificial
<220> FEATURE:
<223> OTHER INFORMATION: RNAi Agent

<400> SEQUENCE: 110
ugccuucucu gucaugccc                                              19

<210> SEQ ID NO 111
<211> LENGTH: 19
<212> TYPE: RNA
<213> ORGANISM: Artificial
<220> FEATURE:
<223> OTHER INFORMATION: RNAi Agent

<400> SEQUENCE: 111
cagugacuac aacacgacc                                              19

<210> SEQ ID NO 112
<211> LENGTH: 19
<212> TYPE: RNA
<213> ORGANISM: Artificial
<220> FEATURE:
<223> OTHER INFORMATION: RNAi Agent

<400> SEQUENCE: 112
ggucguguug uagucacug                                              19

<210> SEQ ID NO 113
<211> LENGTH: 19
<212> TYPE: RNA
<213> ORGANISM: Artificial
<220> FEATURE:
```

<223> OTHER INFORMATION: RNAi Agent

<400> SEQUENCE: 113
augacagaga aggcacuuc                                                      19

<210> SEQ ID NO 114
<211> LENGTH: 19
<212> TYPE: RNA
<213> ORGANISM: Artificial
<220> FEATURE:
<223> OTHER INFORMATION: RNAi Agent

<400> SEQUENCE: 114
gaagugccuu cucugucau                                                      19

<210> SEQ ID NO 115
<211> LENGTH: 19
<212> TYPE: RNA
<213> ORGANISM: Artificial
<220> FEATURE:
<223> OTHER INFORMATION: RNAi Agent

<400> SEQUENCE: 115
gugaagaagu accugcuga                                                      19

<210> SEQ ID NO 116
<211> LENGTH: 19
<212> TYPE: RNA
<213> ORGANISM: Artificial
<220> FEATURE:
<223> OTHER INFORMATION: RNAi Agent

<400> SEQUENCE: 116
ucagcaggua cuucuucac                                                      19

<210> SEQ ID NO 117
<211> LENGTH: 19
<212> TYPE: RNA
<213> ORGANISM: Artificial
<220> FEATURE:
<223> OTHER INFORMATION: RNAi Agent

<400> SEQUENCE: 117
gugacuacaa cacgaccua                                                      19

<210> SEQ ID NO 118
<211> LENGTH: 19
<212> TYPE: RNA
<213> ORGANISM: Artificial
<220> FEATURE:
<223> OTHER INFORMATION: RNAi Agent

<400> SEQUENCE: 118
uaggucgugu uguagucac                                                      19

<210> SEQ ID NO 119
<211> LENGTH: 19
<212> TYPE: RNA
<213> ORGANISM: Artificial
<220> FEATURE:
<223> OTHER INFORMATION: RNAi Agent

<400> SEQUENCE: 119
gguggaggcc cacaccaac                                                      19

<210> SEQ ID NO 120

```
<211> LENGTH: 19
<212> TYPE: RNA
<213> ORGANISM: Artificial
<220> FEATURE:
<223> OTHER INFORMATION: RNAi Agent

<400> SEQUENCE: 120
guuguguggg gccuccacc                                                      19

<210> SEQ ID NO 121
<211> LENGTH: 19
<212> TYPE: RNA
<213> ORGANISM: Artificial
<220> FEATURE:
<223> OTHER INFORMATION: RNAi Agent

<400> SEQUENCE: 121 uggguggaggc ccacaccaa                                                     19

<210> SEQ ID NO 122
<211> LENGTH: 19
<212> TYPE: RNA
<213> ORGANISM: Artificial
<220> FEATURE:
<223> OTHER INFORMATION: RNAi Agent

<400> SEQUENCE: 122
uugguguggg ccuccacca                                                      19

<210> SEQ ID NO 123
<211> LENGTH: 19
<212> TYPE: RNA
<213> ORGANISM: Artificial
<220> FEATURE:
<223> OTHER INFORMATION: RNAi Agent

<400> SEQUENCE: 123
uuccaagacc acaugaucc                                                      19

<210> SEQ ID NO 124
<211> LENGTH: 19
<212> TYPE: RNA
<213> ORGANISM: Artificial
<220> FEATURE:
<223> OTHER INFORMATION: RNAi Agent

<400> SEQUENCE: 124
ggaucaugug gucuuggaa                                                      19

<210> SEQ ID NO 125
<211> LENGTH: 19
<212> TYPE: RNA
<213> ORGANISM: Artificial
<220> FEATURE:
<223> OTHER INFORMATION: RNAi Agent

<400> SEQUENCE: 125
agcugggagg ucagcgucu                                                      19

<210> SEQ ID NO 126
<211> LENGTH: 19
<212> TYPE: RNA
<213> ORGANISM: Artificial
<220> FEATURE:
<223> OTHER INFORMATION: RNAi Agent

<400> SEQUENCE: 126
```
agacgcugac cucccagcu                                                    19

<210> SEQ ID NO 127
<211> LENGTH: 19
<212> TYPE: RNA
<213> ORGANISM: Artificial
<220> FEATURE:
<223> OTHER INFORMATION: RNAi Agent

<400> SEQUENCE: 127
gggagaaaua cugcaacaa                                                    19

<210> SEQ ID NO 128
<211> LENGTH: 19
<212> TYPE: RNA
<213> ORGANISM: Artificial
<220> FEATURE:
<223> OTHER INFORMATION: RNAi Agent

<400> SEQUENCE: 128
uuguugcagu auuucuccc                                                    19

<210> SEQ ID NO 129
<211> LENGTH: 19
<212> TYPE: RNA
<213> ORGANISM: Artificial
<220> FEATURE:
<223> OTHER INFORMATION: RNAi Agent

<400> SEQUENCE: 129
ccaguuuggc uucuggaug                                                    19

<210> SEQ ID NO 130
<211> LENGTH: 19
<212> TYPE: RNA
<213> ORGANISM: Artificial
<220> FEATURE:
<223> OTHER INFORMATION: RNAi Agent

<400> SEQUENCE: 130
cauccagaag ccaaacugg                                                    19

<210> SEQ ID NO 131
<211> LENGTH: 19
<212> TYPE: RNA
<213> ORGANISM: Artificial
<220> FEATURE:
<223> OTHER INFORMATION: RNAi Agent

<400> SEQUENCE: 131
agugacuaca acacgaccu                                                    19

<210> SEQ ID NO 132
<211> LENGTH: 19
<212> TYPE: RNA
<213> ORGANISM: Artificial
<220> FEATURE:
<223> OTHER INFORMATION: RNAi Agent

<400> SEQUENCE: 132 aggucuguu guagucacu                                                     19

<210> SEQ ID NO 133
<211> LENGTH: 19
<212> TYPE: RNA
<213> ORGANISM: Artificial
<220> FEATURE:

```
<223> OTHER INFORMATION: RNAi Agent

<400> SEQUENCE: 133
aauaucaccc ugagcagga                                              19

<210> SEQ ID NO 134
<211> LENGTH: 19
<212> TYPE: RNA
<213> ORGANISM: Artificial
<220> FEATURE:
<223> OTHER INFORMATION: RNAi Agent

<400> SEQUENCE: 134
uccugcucag ggugauauu                                              19

<210> SEQ ID NO 135
<211> LENGTH: 19
<212> TYPE: RNA
<213> ORGANISM: Artificial
<220> FEATURE:
<223> OTHER INFORMATION: RNAi Agent

<400> SEQUENCE: 135
ccugcaggcc accaacauc                                              19

<210> SEQ ID NO 136
<211> LENGTH: 19
<212> TYPE: RNA
<213> ORGANISM: Artificial
<220> FEATURE:
<223> OTHER INFORMATION: RNAi Agent

<400> SEQUENCE: 136
gauguuggug gccugcagg                                              19

<210> SEQ ID NO 137
<211> LENGTH: 19
<212> TYPE: RNA
<213> ORGANISM: Artificial
<220> FEATURE:
<223> OTHER INFORMATION: RNAi Agent

<400> SEQUENCE: 137
aucacccuga gcaggaagg                                              19

<210> SEQ ID NO 138
<211> LENGTH: 19
<212> TYPE: RNA
<213> ORGANISM: Artificial
<220> FEATURE:
<223> OTHER INFORMATION: RNAi Agent

<400> SEQUENCE: 138
ccuuccugcu cagggugau                                              19

<210> SEQ ID NO 139
<211> LENGTH: 19
<212> TYPE: RNA
<213> ORGANISM: Artificial
<220> FEATURE:
<223> OTHER INFORMATION: RNAi Agent

<400> SEQUENCE: 139
gcugggaggu cagcgucuc                                              19

<210> SEQ ID NO 140
```

```
<211> LENGTH: 19
<212> TYPE: RNA
<213> ORGANISM: Artificial
<220> FEATURE:
<223> OTHER INFORMATION: RNAi Agent

<400> SEQUENCE: 140
gagacgcuga ccucccagc                                               19

<210> SEQ ID NO 141
<211> LENGTH: 19
<212> TYPE: RNA
<213> ORGANISM: Artificial
<220> FEATURE:
<223> OTHER INFORMATION: RNAi Agent

<400> SEQUENCE: 141
gagcugggag gucagcguc                                               19

<210> SEQ ID NO 142
<211> LENGTH: 19
<212> TYPE: RNA
<213> ORGANISM: Artificial
<220> FEATURE:
<223> OTHER INFORMATION: RNAi Agent

<400> SEQUENCE: 142
gacgcugacc ucccagcuc                                               19

<210> SEQ ID NO 143
<211> LENGTH: 19
<212> TYPE: RNA
<213> ORGANISM: Artificial
<220> FEATURE:
<223> OTHER INFORMATION: RNAi Agent

<400> SEQUENCE: 143
guggccaguu uggcuucug                                               19

<210> SEQ ID NO 144
<211> LENGTH: 19
<212> TYPE: RNA
<213> ORGANISM: Artificial
<220> FEATURE:
<223> OTHER INFORMATION: RNAi Agent

<400> SEQUENCE: 144
cagaagccaa acuggccac                                               19

<210> SEQ ID NO 145
<211> LENGTH: 19
<212> TYPE: RNA
<213> ORGANISM: Artificial
<220> FEATURE:
<223> OTHER INFORMATION: RNAi Agent

<400> SEQUENCE: 145
caguuuggcu ucuggaugg                                               19

<210> SEQ ID NO 146
<211> LENGTH: 19
<212> TYPE: RNA
<213> ORGANISM: Artificial
<220> FEATURE:
<223> OTHER INFORMATION: RNAi Agent

<400> SEQUENCE: 146
```

```
ccauccagaa gccaaacug                                                        19

<210> SEQ ID NO 147
<211> LENGTH: 19
<212> TYPE: RNA
<213> ORGANISM: Artificial
<220> FEATURE:
<223> OTHER INFORMATION: RNAi Agent

<400> SEQUENCE: 147
ggccaguuug gcuucugga                                                        19

<210> SEQ ID NO 148
<211> LENGTH: 19
<212> TYPE: RNA
<213> ORGANISM: Artificial
<220> FEATURE:
<223> OTHER INFORMATION: RNAi Agent

<400> SEQUENCE: 148
uccagaagcc aaacuggcc                                                        19

<210> SEQ ID NO 149
<211> LENGTH: 19
<212> TYPE: RNA
<213> ORGANISM: Artificial
<220> FEATURE:
<223> OTHER INFORMATION: RNAi Agent

<400> SEQUENCE: 149
cuggguggcc aguuuggcu                                                        19

<210> SEQ ID NO 150
<211> LENGTH: 19
<212> TYPE: RNA
<213> ORGANISM: Artificial
<220> FEATURE:
<223> OTHER INFORMATION: RNAi Agent

<400> SEQUENCE: 150
agccaaacug gccacccag                                                        19

<210> SEQ ID NO 151
<211> LENGTH: 19
<212> TYPE: RNA
<213> ORGANISM: Artificial
<220> FEATURE:
<223> OTHER INFORMATION: RNAi Agent

<400> SEQUENCE: 151
ucuacaguga cuacaacac                                                        19

<210> SEQ ID NO 152
<211> LENGTH: 19
<212> TYPE: RNA
<213> ORGANISM: Artificial
<220> FEATURE:
<223> OTHER INFORMATION: RNAi Agent

<400> SEQUENCE: 152
guguuguagu cacuguaga                                                        19

<210> SEQ ID NO 153
<211> LENGTH: 19
<212> TYPE: RNA
<213> ORGANISM: Artificial
<220> FEATURE:
```

```
<223> OTHER INFORMATION: RNAi Agent

<400> SEQUENCE: 153
gcaugacaga gaaggcacu                                                19

<210> SEQ ID NO 154
<211> LENGTH: 19
<212> TYPE: RNA
<213> ORGANISM: Artificial
<220> FEATURE:
<223> OTHER INFORMATION: RNAi Agent

<400> SEQUENCE: 154
agugccuucu cugucaugc                                                19

<210> SEQ ID NO 155
<211> LENGTH: 19
<212> TYPE: RNA
<213> ORGANISM: Artificial
<220> FEATURE:
<223> OTHER INFORMATION: RNAi Agent

<400> SEQUENCE: 155
auaucacccu gagcaggaa                                                19

<210> SEQ ID NO 156
<211> LENGTH: 19
<212> TYPE: RNA
<213> ORGANISM: Artificial
<220> FEATURE:
<223> OTHER INFORMATION: RNAi Agent

<400> SEQUENCE: 156
uuccugcuca gggugauau                                                19

<210> SEQ ID NO 157
<211> LENGTH: 19
<212> TYPE: RNA
<213> ORGANISM: Artificial
<220> FEATURE:
<223> OTHER INFORMATION: RNAi Agent

<400> SEQUENCE: 157
cuacagugac uacaacacg                                                19

<210> SEQ ID NO 158
<211> LENGTH: 19
<212> TYPE: RNA
<213> ORGANISM: Artificial
<220> FEATURE:
<223> OTHER INFORMATION: RNAi Agent

<400> SEQUENCE: 158
cguguuguag ucacuguag                                                19

<210> SEQ ID NO 159
<211> LENGTH: 19
<212> TYPE: RNA
<213> ORGANISM: Artificial
<220> FEATURE:
<223> OTHER INFORMATION: RNAi Agent

<400> SEQUENCE: 159
uaucacccug agcaggaag                                                19

<210> SEQ ID NO 160
```

```
<211> LENGTH: 19
<212> TYPE: RNA
<213> ORGANISM: Artificial
<220> FEATURE:
<223> OTHER INFORMATION: RNAi Agent

<400> SEQUENCE: 160
cuuccugcuc agggugaua                                                  19

<210> SEQ ID NO 161
<211> LENGTH: 19
<212> TYPE: RNA
<213> ORGANISM: Artificial
<220> FEATURE:
<223> OTHER INFORMATION: RNAi Agent

<400> SEQUENCE: 161
ugcaggccac caacaucuu                                                  19

<210> SEQ ID NO 162
<211> LENGTH: 19
<212> TYPE: RNA
<213> ORGANISM: Artificial
<220> FEATURE:
<223> OTHER INFORMATION: RNAi Agent

<400> SEQUENCE: 162
aagauguugg uggccugca                                                  19

<210> SEQ ID NO 163
<211> LENGTH: 19
<212> TYPE: RNA
<213> ORGANISM: Artificial
<220> FEATURE:
<223> OTHER INFORMATION: RNAi Agent

<400> SEQUENCE: 163
caugacagag aaggcacuu                                                  19

<210> SEQ ID NO 164
<211> LENGTH: 19
<212> TYPE: RNA
<213> ORGANISM: Artificial
<220> FEATURE:
<223> OTHER INFORMATION: RNAi Agent

<400> SEQUENCE: 164
aagugccuuc ucugucaug                                                  19

<210> SEQ ID NO 165
<211> LENGTH: 19
<212> TYPE: RNA
<213> ORGANISM: Artificial
<220> FEATURE:
<223> OTHER INFORMATION: RNAi Agent

<400> SEQUENCE: 165
ugaagaagua ccugcugaa                                                  19

<210> SEQ ID NO 166
<211> LENGTH: 19
<212> TYPE: RNA
<213> ORGANISM: Artificial
<220> FEATURE:
<223> OTHER INFORMATION: RNAi Agent

<400> SEQUENCE: 166
```
uucagcaggu acuucuuca                                                  19

<210> SEQ ID NO 167
<211> LENGTH: 19
<212> TYPE: RNA
<213> ORGANISM: Artificial
<220> FEATURE:
<223> OTHER INFORMATION: RNAi Agent

<400> SEQUENCE: 167
gcugguggag gcccacacc                                                  19

<210> SEQ ID NO 168
<211> LENGTH: 19
<212> TYPE: RNA
<213> ORGANISM: Artificial
<220> FEATURE:
<223> OTHER INFORMATION: RNAi Agent

<400> SEQUENCE: 168
ggugugggcc uccaccagc                                                  19

<210> SEQ ID NO 169
<211> LENGTH: 19
<212> TYPE: RNA
<213> ORGANISM: Artificial
<220> FEATURE:
<223> OTHER INFORMATION: RNAi Agent

<400> SEQUENCE: 169
uacagugacu acaacacga                                                  19

<210> SEQ ID NO 170
<211> LENGTH: 19
<212> TYPE: RNA
<213> ORGANISM: Artificial
<220> FEATURE:
<223> OTHER INFORMATION: RNAi Agent

<400> SEQUENCE: 170
ucguguugua gucacugua                                                  19

<210> SEQ ID NO 171
<211> LENGTH: 19
<212> TYPE: RNA
<213> ORGANISM: Artificial
<220> FEATURE:
<223> OTHER INFORMATION: RNAi Agent

<400> SEQUENCE: 171
acagagaagg cacuuccuu                                                  19

<210> SEQ ID NO 172
<211> LENGTH: 19
<212> TYPE: RNA
<213> ORGANISM: Artificial
<220> FEATURE:
<223> OTHER INFORMATION: RNAi Agent

<400> SEQUENCE: 172
aaggaagugc cuucucugu                                                  19

<210> SEQ ID NO 173
<211> LENGTH: 19
<212> TYPE: RNA
<213> ORGANISM: Artificial
<220> FEATURE:

```
<223> OTHER INFORMATION: RNAi Agent

<400> SEQUENCE: 173
acagugacua caacacgac                                            19

<210> SEQ ID NO 174
<211> LENGTH: 19
<212> TYPE: RNA
<213> ORGANISM: Artificial
<220> FEATURE:
<223> OTHER INFORMATION: RNAi Agent

<400> SEQUENCE: 174
gucguguugu agucacugu                                            19

<210> SEQ ID NO 175
<211> LENGTH: 19
<212> TYPE: RNA
<213> ORGANISM: Artificial
<220> FEATURE:
<223> OTHER INFORMATION: RNAi Agent

<400> SEQUENCE: 175
ugagcuggga ggucagcgu                                            19

<210> SEQ ID NO 176
<211> LENGTH: 19
<212> TYPE: RNA
<213> ORGANISM: Artificial
<220> FEATURE:
<223> OTHER INFORMATION: RNAi Agent

<400> SEQUENCE: 176
acgcugaccu cccagcuca                                            19

<210> SEQ ID NO 177
<211> LENGTH: 19
<212> TYPE: RNA
<213> ORGANISM: Artificial
<220> FEATURE:
<223> OTHER INFORMATION: RNAi Agent

<400> SEQUENCE: 177
uggccaguuu ggcuucugg                                            19

<210> SEQ ID NO 178
<211> LENGTH: 19
<212> TYPE: RNA
<213> ORGANISM: Artificial
<220> FEATURE:
<223> OTHER INFORMATION: RNAi Agent

<400> SEQUENCE: 178
ccagaagcca aacuggcca                                            19

<210> SEQ ID NO 179
<211> LENGTH: 19
<212> TYPE: RNA
<213> ORGANISM: Artificial
<220> FEATURE:
<223> OTHER INFORMATION: RNAi Agent

<400> SEQUENCE: 179
ugucucagga gcgggacca                                            19

<210> SEQ ID NO 180
```

```
<211> LENGTH: 19
<212> TYPE: RNA
<213> ORGANISM: Artificial
<220> FEATURE:
<223> OTHER INFORMATION: RNAi Agent

<400> SEQUENCE: 180
uggucccgcu ccugagaca                                              19

<210> SEQ ID NO 181
<211> LENGTH: 19
<212> TYPE: RNA
<213> ORGANISM: Artificial
<220> FEATURE:
<223> OTHER INFORMATION: RNAi Agent

<400> SEQUENCE: 181
guggaggccc acaccaacu                                              19

<210> SEQ ID NO 182
<211> LENGTH: 19
<212> TYPE: RNA
<213> ORGANISM: Artificial
<220> FEATURE:
<223> OTHER INFORMATION: RNAi Agent

<400> SEQUENCE: 182
aguuggugug ggccuccac                                              19

<210> SEQ ID NO 183
<211> LENGTH: 19
<212> TYPE: RNA
<213> ORGANISM: Artificial
<220> FEATURE:
<223> OTHER INFORMATION: RNAi Agent

<400> SEQUENCE: 183
ggguggccag uuuggcuuc                                              19

<210> SEQ ID NO 184
<211> LENGTH: 19
<212> TYPE: RNA
<213> ORGANISM: Artificial
<220> FEATURE:
<223> OTHER INFORMATION: RNAi Agent

<400> SEQUENCE: 184
gaagccaaac uggccaccc                                              19

<210> SEQ ID NO 185
<211> LENGTH: 19
<212> TYPE: RNA
<213> ORGANISM: Artificial
<220> FEATURE:
<223> OTHER INFORMATION: RNAi Agent

<400> SEQUENCE: 185
gguggccagu uuggcuucu                                              19

<210> SEQ ID NO 186
<211> LENGTH: 19
<212> TYPE: RNA
<213> ORGANISM: Artificial
<220> FEATURE:
<223> OTHER INFORMATION: RNAi Agent

<400> SEQUENCE: 186
```
agaagccaaa cuggccacc                                                      19

<210> SEQ ID NO 187
<211> LENGTH: 19
<212> TYPE: RNA
<213> ORGANISM: Artificial
<220> FEATURE:
<223> OTHER INFORMATION: RNAi Agent

<400> SEQUENCE: 187
ucacccugag caggaaggg                                                      19

<210> SEQ ID NO 188
<211> LENGTH: 19
<212> TYPE: RNA
<213> ORGANISM: Artificial
<220> FEATURE:
<223> OTHER INFORMATION: RNAi Agent

<400> SEQUENCE: 188
cccuuccugc ucaggguga                                                      19

<210> SEQ ID NO 189
<211> LENGTH: 19
<212> TYPE: RNA
<213> ORGANISM: Artificial
<220> FEATURE:
<223> OTHER INFORMATION: RNAi Agent

<400> SEQUENCE: 189
gccaguuugg cuucuggau                                                      19

<210> SEQ ID NO 190
<211> LENGTH: 19
<212> TYPE: RNA
<213> ORGANISM: Artificial
<220> FEATURE:
<223> OTHER INFORMATION: RNAi Agent

<400> SEQUENCE: 190
auccagaagc caaacuggc                                                      19

<210> SEQ ID NO 191
<211> LENGTH: 19
<212> TYPE: RNA
<213> ORGANISM: Artificial
<220> FEATURE:
<223> OTHER INFORMATION: RNAi Agent

<400> SEQUENCE: 191
agcuggugga ggcccacac                                                      19

<210> SEQ ID NO 192
<211> LENGTH: 19
<212> TYPE: RNA
<213> ORGANISM: Artificial
<220> FEATURE:
<223> OTHER INFORMATION: RNAi Agent

<400> SEQUENCE: 192
gugugggccu ccaccagcu                                                      19

<210> SEQ ID NO 193
<211> LENGTH: 19
<212> TYPE: RNA
<213> ORGANISM: Artificial
<220> FEATURE:

```
<223> OTHER INFORMATION: RNAi Agent

<400> SEQUENCE: 193
aucuccaugg cugacuggc                                                   19

<210> SEQ ID NO 194
<211> LENGTH: 19
<212> TYPE: RNA
<213> ORGANISM: Artificial
<220> FEATURE:
<223> OTHER INFORMATION: RNAi Agent

<400> SEQUENCE: 194
gccagucagc cauggagau                                                   19

<210> SEQ ID NO 195
<211> LENGTH: 19
<212> TYPE: RNA
<213> ORGANISM: Artificial
<220> FEATURE:
<223> OTHER INFORMATION: RNAi Agent

<400> SEQUENCE: 195
ggcaugacag agaaggcac                                                   19

<210> SEQ ID NO 196
<211> LENGTH: 19
<212> TYPE: RNA
<213> ORGANISM: Artificial
<220> FEATURE:
<223> OTHER INFORMATION: RNAi Agent

<400> SEQUENCE: 196
gugccuucuc ugucaugcc                                                   19

<210> SEQ ID NO 197
<211> LENGTH: 19
<212> TYPE: RNA
<213> ORGANISM: Artificial
<220> FEATURE:
<223> OTHER INFORMATION: RNAi Agent

<400> SEQUENCE: 197
ggagaaauac ugcaacaac                                                   19

<210> SEQ ID NO 198
<211> LENGTH: 19
<212> TYPE: RNA
<213> ORGANISM: Artificial
<220> FEATURE:
<223> OTHER INFORMATION: RNAi Agent

<400> SEQUENCE: 198
guuguugcag uauuucucc                                                   19

<210> SEQ ID NO 199
<211> LENGTH: 19
<212> TYPE: RNA
<213> ORGANISM: Artificial
<220> FEATURE:
<223> OTHER INFORMATION: RNAi Agent

<400> SEQUENCE: 199
uggguggcca guuuggcuu                                                   19

<210> SEQ ID NO 200
```

```
<211> LENGTH: 19
<212> TYPE: RNA
<213> ORGANISM: Artificial
<220> FEATURE:
<223> OTHER INFORMATION: RNAi Agent

<400> SEQUENCE: 200
aagccaaacu ggccaccca                                                   19

<210> SEQ ID NO 201
<211> LENGTH: 19
<212> TYPE: RNA
<213> ORGANISM: Artificial
<220> FEATURE:
<223> OTHER INFORMATION: RNAi Agent

<400> SEQUENCE: 201
gagcuggugg aggcccaca                                                   19

<210> SEQ ID NO 202
<211> LENGTH: 19
<212> TYPE: RNA
<213> ORGANISM: Artificial
<220> FEATURE:
<223> OTHER INFORMATION: RNAi Agent

<400> SEQUENCE: 202
ugugggccuc caccagcuc                                                   19

<210> SEQ ID NO 203
<211> LENGTH: 19
<212> TYPE: RNA
<213> ORGANISM: Artificial
<220> FEATURE:
<223> OTHER INFORMATION: RNAi Agent

<400> SEQUENCE: 203
gacagagaag gcacuuccu                                                   19

<210> SEQ ID NO 204
<211> LENGTH: 19
<212> TYPE: RNA
<213> ORGANISM: Artificial
<220> FEATURE:
<223> OTHER INFORMATION: RNAi Agent

<400> SEQUENCE: 204
aggaagugcc uucucuguc                                                   19

<210> SEQ ID NO 205
<211> LENGTH: 19
<212> TYPE: RNA
<213> ORGANISM: Artificial
<220> FEATURE:
<223> OTHER INFORMATION: RNAi Agent

<400> SEQUENCE: 205
aguuuggcuu cuggaugggg                                                  19

<210> SEQ ID NO 206
<211> LENGTH: 19
<212> TYPE: RNA
<213> ORGANISM: Artificial
<220> FEATURE:
<223> OTHER INFORMATION: RNAi Agent

<400> SEQUENCE: 206
```
cccauccaga agccaaacu                                    19

<210> SEQ ID NO 207
<211> LENGTH: 19
<212> TYPE: RNA
<213> ORGANISM: Artificial
<220> FEATURE:
<223> OTHER INFORMATION: RNAi Agent

<400> SEQUENCE: 207
ugacagagaa ggcacuucc                                    19

<210> SEQ ID NO 208
<211> LENGTH: 19
<212> TYPE: RNA
<213> ORGANISM: Artificial
<220> FEATURE:
<223> OTHER INFORMATION: RNAi Agent

<400> SEQUENCE: 208
ggaagugccu ucucuguca                                    19

<210> SEQ ID NO 209
<211> LENGTH: 19
<212> TYPE: RNA
<213> ORGANISM: Artificial
<220> FEATURE:
<223> OTHER INFORMATION: RNAi Agent

<400> SEQUENCE: 209
gaagaaguac cugcugaag                                    19

<210> SEQ ID NO 210
<211> LENGTH: 19
<212> TYPE: RNA
<213> ORGANISM: Artificial
<220> FEATURE:
<223> OTHER INFORMATION: RNAi Agent

<400> SEQUENCE: 210
cuucagcagg uacuucuuc                                    19

<210> SEQ ID NO 211
<211> LENGTH: 19
<212> TYPE: RNA
<213> ORGANISM: Artificial
<220> FEATURE:
<223> OTHER INFORMATION: RNAi Agent

<400> SEQUENCE: 211
ucuccauggc ugacuggcc                                    19

<210> SEQ ID NO 212
<211> LENGTH: 19
<212> TYPE: RNA
<213> ORGANISM: Artificial
<220> FEATURE:
<223> OTHER INFORMATION: RNAi Agent

<400> SEQUENCE: 212
ggccagucag ccauggaga                                    19

<210> SEQ ID NO 213
<211> LENGTH: 19
<212> TYPE: RNA
<213> ORGANISM: Artificial
<220> FEATURE:

<223> OTHER INFORMATION: RNAi Agent

<400> SEQUENCE: 213
cugguggagg cccacacca         19

<210> SEQ ID NO 214
<211> LENGTH: 19
<212> TYPE: RNA
<213> ORGANISM: Artificial
<220> FEATURE:
<223> OTHER INFORMATION: RNAi Agent

<400> SEQUENCE: 214 uguguggc cuccaccag         19

<210> SEQ ID NO 215
<211> LENGTH: 19
<212> TYPE: RNA
<213> ORGANISM: Artificial
<220> FEATURE:
<223> OTHER INFORMATION: RNAi Agent

<400> SEQUENCE: 215
cagagaaggc acuccuuc         19

<210> SEQ ID NO 216
<211> LENGTH: 19
<212> TYPE: RNA
<213> ORGANISM: Artificial
<220> FEATURE:
<223> OTHER INFORMATION: RNAi Agent

<400> SEQUENCE: 216
gaaggaagug ccuucucug         19

<210> SEQ ID NO 217
<211> LENGTH: 19
<212> TYPE: RNA
<213> ORGANISM: Artificial
<220> FEATURE:
<223> OTHER INFORMATION: RNAi Agent

<400> SEQUENCE: 217
cugcaggcca ccaacaucu         19

<210> SEQ ID NO 218
<211> LENGTH: 19
<212> TYPE: RNA
<213> ORGANISM: Artificial
<220> FEATURE:
<223> OTHER INFORMATION: RNAi Agent

<400> SEQUENCE: 218
agauguuggu ggccugcag         19

<210> SEQ ID NO 219
<211> LENGTH: 19
<212> TYPE: RNA
<213> ORGANISM: Artificial
<220> FEATURE:
<223> OTHER INFORMATION: RNAi Agent

<400> SEQUENCE: 219
gggcaugaca gagaaggca         19

<210> SEQ ID NO 220

```
<211> LENGTH: 19
<212> TYPE: RNA
<213> ORGANISM: Artificial
<220> FEATURE:
<223> OTHER INFORMATION: RNAi Agent

<400> SEQUENCE: 220
ugccuucucu gucaugccc                                                    19

<210> SEQ ID NO 221
<211> LENGTH: 2280
<212> TYPE: DNA
<213> ORGANISM: Cynomolgus

<400> SEQUENCE: 221
ggtacccagc ttgcttgttc tttttgcaga agctcagaat aaacgctcaa ctttggcaga         60
tcaattcccc ggggatccga attcgccacc atgcacgtga agaagtacct gctgaagtgc        120
ctgcaccggc tgcagaaggg ccccggctac acgtacaagg agctgctggt gtggactgc         180 gataacacca cacccacgg ccccaagcgt atcatctgcg aggggcccaa gaagaaagcc         240
gtgtggttcc tgctcaccct gctcttcact gctctcgtct gctggcagtg ggcatcttc         300 atcaggacct acttgagctg ggaggtcagc gtctccctct ccgtaggctt caagaccatg        360
gacttccccg ccgtcaccat ctgcaatgct agccccttca gtattccaa agtcaagcat         420 ttgctgaagg acctggatga gctgatggaa gctgtcctgg agagaatcct ggctcctgag        480
ctaagccatg ccaatgccac caggaccctg aactcttcca tctggaacca cacaccactg       540
gtccttattg atgaacggaa ccccaccac cccatggtcc tcgatctctt tggagataac         600
cacaatggct taacaaacag ctcagcatca gaaaagatct gtaatgccca tgggtgcaaa        660
atggccatga gactatgtag cctcaacggg acccagtgca ccttccggaa cttcaccagc        720
gctaccaggg cagtgacaga gtggtacagc ctgcaggcca ccaacatctt gcgcaggtg         780 ccgcagcagg agctggtgga gatgagctac cccggcgagc agatgatcct ggcctgcctg        840
tttggagctg agccctgcaa ctaccggaac ttcacgtcca tcttctaccc tcactatggc        900
aactgttaca tcttcaactg gggcatgaca gagaaggcac ttccttcggc caaccctgga       960
cctgaatttg gcctgaagtt gatcctggac ataggccagg aagactacgt ccccttcctc      1020
gcgtccacgg ctggggtcag gctgatgctt cacgagcaga ggtcataccc cttcatcaga      1080
gacgagggca tctatgccat gtcggggaca gagacgtcca tcggggtact cgtggacaag      1140
cttcagcgca tggggagcc ctacagcccg tgcaccgtga atggctccga ggtccccgtc       1200
caaaacttct acagtgacta caacacgacc tactccatcc aggcctgtct tcgctcctgc      1260
ttccaagacc acatgatccg tagctgcaag tgtgggcact acctctaccc actgccccgt      1320
ggggagaaat actgcaacaa ccgggacttc ccagactggg cccattgcta ctcagatctg      1380
cagatgagcg tggcgcagag agagacctgc attggcatgt gcaaggaatc ctgcaatgac      1440
acccagtaca gatgactat ctccatggct gactggcctt ctgaggcctc tgaggactgg       1500
attttccacg tcttgtctca ggagcgggac caaagcacca atatcaccct gagcaggaag      1560
ggaattgtca agctcaacat ctacttccaa gaatttaact atcgcaccat tgaagaatca      1620
gcagccaata acctcgtctg gctgctctca aatctgggtg gccagtttgg cttctgatg       1680 gggggctctg tgctgtgcct catcgagttt ggggagatca tcatcgactt tgtgtggatc      1740
accatcatca gctggtggc cttggccaag agcctccggc agcggcgagc ccaagccagc      1800
tactccggcc caccgccac ggtggctgag ctggtggagg cccacaccaa cttcggctac      1860
```

| | | |
|---|---|---|
| cagcctgaca cggccccccg cagccccaac accgggccct accccagtga gcaggccctg | 1920 | |
| cccatcccgg gcacccgcc ccccaactat gactccctgc gtctgcagcc actggacgtc | 1980 | |
| atcgagtctg acagtgaggg tgatgccatc taagcggccg cctagaaata gcttgatctg | 2040 | |
| gttaccacta aaccagcctc aagaacaccc gaatggagtc tctaagctac ataataccaa | 2100 | |
| cttacacttt acaaaatgtt gtcccccaaa atgtagccat tcgtatctgc tcctaataaa | 2160 | |
| aagaaagttt cttcacattc taaaaaaaaa aaaaaaaaaa aaaaaaaaaa aaaaaccccc | 2220 | |
| ccccccccc ccctgcagag atctgctagc ttgagtattc tatagagtca cctaaatact | 2280 | |

<210> SEQ ID NO 222
<211> LENGTH: 2597
<212> TYPE: DNA
<213> ORGANISM: Homo sapien

<400> SEQUENCE: 222

| | | |
|---|---|---|
| gtgcttcccc gcccctgaac ctgctccctc ccagtcggtc tcgccgcgct cgccgggtgt | 60 | |
| cccagtgtca ccaacactcg gccgccgccg ccagcttggc gcgcaccgcc gcctccgcca | 120 | |
| ccgccgacag cgcgcatcct ccgtgtcccc gctccgccgc ccgagcaggt gccactatgc | 180 | |
| acgtgaagaa gtacctgctg aagggcctgc atcggctgca aagggccccc ggctacacgt | 240 | |
| acaaggagct gctggtgtgg tactgcgaca caccaacac ccacggcccc aagcgcatca | 300 | |
| tctgtgaggg gcccaagaag aaagccatgt ggttcctgct caccctgctc ttcgccgccc | 360 | |
| tcgtctgctg gcagtggggc atcttcatca ggacctactt gagctgggag gtcagcgtct | 420 | |
| ccctctccgt aggcttcaag accatggact ccctgccgt caccatctgc aatgctagcc | 480 | |
| ccttcaagta ttccaaaatc aagcatttgc tgaaggacct ggatgagctg atggaagctg | 540 | |
| tcctggagag aatcctggct cctgagctaa gccatgccaa tgccaccagg aacctgaact | 600 | |
| tctccatctg gaaccacaca ccctggtcc ttattgatga acggaacccc caccacccca | 660 | |
| tggtccttga tctctttgga gacaaccaca atggcttaac aagcagctca gcatcagaaa | 720 | |
| agatctgtaa tgcccacggg tgcaaaatgg ccatgagact atgtagcctc aacaggaccc | 780 | |
| agtgtacctt ccggaacttc accagtgcta cccaggcatt gacagagtgg tacatcctgc | 840 | |
| aggccaccaa catctttgca caggtgccac agcaggagct agtagagatg agctaccccg | 900 | |
| gcgagcagat gatcctggcc tgcctattcg gagctgagcc ctgcaactac cggaacttca | 960 | |
| cgtccatctt ctaccctcac tatggcaact gttacatctt caactggggc atgacagaga | 1020 | |
| aggcacttcc ttcggccaac cctggaactg aattcggcct gaagttgatc ctggacatag | 1080 | |
| gccaggaaga ctacgtcccc ttccttgcgt ccacggccgg ggtcaggctg atgcttcacg | 1140 | |
| agcagaggtc atacccttc atcagagatg agggcatcta cgccatgtcg gggacagaga | 1200 | |
| cgtccatcgg ggtactcgtg acaagcttc agcgcatggg ggagccctac agcccgtgca | 1260 | |
| ccgtgaatgg ttctgaggtc cccgtccaaa acttctacag tgactacaac acgacctact | 1320 | |
| ccatccaggc ctgtcttcgc tcctgcttcc aagaccacat gatccgtaac tgcaactgtg | 1380 | |
| gccactacct gtaccactg cccgtggggg agaaatactg caacaaccgg acttcccag | 1440 | |
| actgggccca ttgctactca gatctacaga tgagcgtggc gcagagagag acctgcattg | 1500 | |
| gcatgtgcaa ggagtcctgc aatgacaccc agtacaagat gaccatctcc atggctgact | 1560 | |
| ggccttctga ggcctccgag gactggattt tccacgtctt gtctcaggag cgggaccaaa | 1620 | |
| gcaccaatat caccctgagc aggaagggaa ttgtcaagct caacatctac ttccaagaat | 1680 | |
| ttaactatcg caccattgaa gaatcagcag ccaataacat cgtctggctg ctctcgaatc | 1740 | |

-continued

```
tgggtggcca gtttggcttc tggatggggg gctctgtgct gtgcctcatc gagtttgggg    1800
agatcatcat cgactttgtg tggatcacca tcatcaagct ggtggccttg gccaagagcc    1860
tacggcagcg gcgagcccaa gccagctacg ctggcccacc gcccaccgtg gccgagctgg    1920
tggaggccca caccaacttt ggcttccagc ctgacacggc cccccgcagc ccaacactg     1980 ggccctaccc cagtgagcag gccctgccca tcccaggcac cccgcccccc aactatgact    2040
ccctgcgtct gcagccgctg gacgtcatcg agtctgacag tgagggtgat gccatctaac    2100
cctgcccctg cccaccccgg gcggctgaaa ctcactgagc agccaagact gttgcccgag    2160
gcctcactgt atggtgccct ctccaaaggg tcgggagggt agctctccag gccagagctt    2220
gtgtccttca acagagaggc cagcggcaac tggtccgtta ctggccaagg gctctgtaga    2280
atcacggtgc tggtacagga tgcaggaata aattgtatct tcacctggtt cctaccctcg    2340
tccctacctg tcctgatcct ggtcctgaag accccctcgga cacccctctc ctggtggcag    2400
gccacttccc tcccagtgcc agtctccatc caccccagag aggaacaggc gggtgggcca    2460
tgtggttttc tccttcctgg ccttggctgg cctctggggc aggggtggtg gagagatgga    2520
agggcatcag gtgtagggac cctgccaagt ggcacctgat ttactctaga aaataaaagt    2580
agaaaatact gagtcca                                                   2597
```

```
<210> SEQ ID NO 223
<211> LENGTH: 12
<212> TYPE: RNA
<213> ORGANISM: Artificial
<220> FEATURE:
<223> OTHER INFORMATION: RNAi Agent

<400> SEQUENCE: 223
ugaagaagua cc                                                        12

<210> SEQ ID NO 224
<211> LENGTH: 12
<212> TYPE: RNA
<213> ORGANISM: Artificial
<220> FEATURE:
<223> OTHER INFORMATION: RNAi Agent

<400> SEQUENCE: 224
gguacuucuu ca                                                        12

<210> SEQ ID NO 225
<211> LENGTH: 12
<212> TYPE: RNA
<213> ORGANISM: Artificial
<220> FEATURE:
<223> OTHER INFORMATION: RNAi Agent

<400> SEQUENCE: 225
gaagaaguac cu                                                        12

<210> SEQ ID NO 226
<211> LENGTH: 12
<212> TYPE: RNA
<213> ORGANISM: Artificial
<220> FEATURE:
<223> OTHER INFORMATION: RNAi Agent

<400> SEQUENCE: 226
agguacuucu uc                                                        12

<210> SEQ ID NO 227
```

```
<211> LENGTH: 12
<212> TYPE: RNA
<213> ORGANISM: Artificial
<220> FEATURE:
<223> OTHER INFORMATION: RNAi Agent

<400> SEQUENCE: 227
aagaaguacc ug                                                           12

<210> SEQ ID NO 228
<211> LENGTH: 12
<212> TYPE: RNA
<213> ORGANISM: Artificial
<220> FEATURE:
<223> OTHER INFORMATION: RNAi Agent

<400> SEQUENCE: 228
cagguacuuc uu                                                           12

<210> SEQ ID NO 229
<211> LENGTH: 12
<212> TYPE: RNA
<213> ORGANISM: Artificial
<220> FEATURE:
<223> OTHER INFORMATION: RNAi Agent

<400> SEQUENCE: 229
agaaguaccu gc                                                           12

<210> SEQ ID NO 230
<211> LENGTH: 12
<212> TYPE: RNA
<213> ORGANISM: Artificial
<220> FEATURE:
<223> OTHER INFORMATION: RNAi Agent

<400> SEQUENCE: 230
gcagguacuu cu                                                           12

<210> SEQ ID NO 231
<211> LENGTH: 12
<212> TYPE: RNA
<213> ORGANISM: Artificial
<220> FEATURE:
<223> OTHER INFORMATION: RNAi Agent

<400> SEQUENCE: 231
gaaguaccug cu                                                           12

<210> SEQ ID NO 232
<211> LENGTH: 12
<212> TYPE: RNA
<213> ORGANISM: Artificial
<220> FEATURE:
<223> OTHER INFORMATION: RNAi Agent

<400> SEQUENCE: 232
agcagguacu uc                                                           12

<210> SEQ ID NO 233
<211> LENGTH: 12
<212> TYPE: RNA
<213> ORGANISM: Artificial
<220> FEATURE:
<223> OTHER INFORMATION: RNAi Agent

<400> SEQUENCE: 233
```
aaguaccugc ug                                                              12

<210> SEQ ID NO 234
<211> LENGTH: 12
<212> TYPE: RNA
<213> ORGANISM: Artificial
<220> FEATURE:
<223> OTHER INFORMATION: RNAi Agent

<400> SEQUENCE: 234
cagcagguac uu                                                              12

<210> SEQ ID NO 235
<211> LENGTH: 12
<212> TYPE: RNA
<213> ORGANISM: Artificial
<220> FEATURE:
<223> OTHER INFORMATION: RNAi Agent

<400> SEQUENCE: 235
aguaccugcu ga                                                              12

<210> SEQ ID NO 236
<211> LENGTH: 12
<212> TYPE: RNA
<213> ORGANISM: Artificial
<220> FEATURE:
<223> OTHER INFORMATION: RNAi Agent

<400> SEQUENCE: 236
ucagcaggua cu                                                              12

<210> SEQ ID NO 237
<211> LENGTH: 12
<212> TYPE: RNA
<213> ORGANISM: Artificial
<220> FEATURE:
<223> OTHER INFORMATION: RNAi Agent

<400> SEQUENCE: 237
guaccugcug aa                                                              12

<210> SEQ ID NO 238
<211> LENGTH: 12
<212> TYPE: RNA
<213> ORGANISM: Artificial
<220> FEATURE:
<223> OTHER INFORMATION: RNAi Agent

<400> SEQUENCE: 238
uucagcaggu ac                                                              12

<210> SEQ ID NO 239
<211> LENGTH: 12
<212> TYPE: RNA
<213> ORGANISM: Artificial
<220> FEATURE:
<223> OTHER INFORMATION: RNAi Agent

<400> SEQUENCE: 239
gagcugggag gu                                                              12

<210> SEQ ID NO 240
<211> LENGTH: 12
<212> TYPE: RNA
<213> ORGANISM: Artificial
<220> FEATURE:

```
<223> OTHER INFORMATION: RNAi Agent

<400> SEQUENCE: 240
accucccagc uc                                                         12

<210> SEQ ID NO 241
<211> LENGTH: 12
<212> TYPE: RNA
<213> ORGANISM: Artificial
<220> FEATURE:
<223> OTHER INFORMATION: RNAi Agent

<400> SEQUENCE: 241
agcugggagg uc                                                         12

<210> SEQ ID NO 242
<211> LENGTH: 12
<212> TYPE: RNA
<213> ORGANISM: Artificial
<220> FEATURE:
<223> OTHER INFORMATION: RNAi Agent

<400> SEQUENCE: 242
gaccucccag cu                                                         12

<210> SEQ ID NO 243
<211> LENGTH: 12
<212> TYPE: RNA
<213> ORGANISM: Artificial
<220> FEATURE:
<223> OTHER INFORMATION: RNAi Agent

<400> SEQUENCE: 243
gcugggaggu ca                                                         12

<210> SEQ ID NO 244
<211> LENGTH: 12
<212> TYPE: RNA
<213> ORGANISM: Artificial
<220> FEATURE:
<223> OTHER INFORMATION: RNAi Agent

<400> SEQUENCE: 244
ugaccuccca gc                                                         12

<210> SEQ ID NO 245
<211> LENGTH: 12
<212> TYPE: RNA
<213> ORGANISM: Artificial
<220> FEATURE:
<223> OTHER INFORMATION: RNAi Agent

<400> SEQUENCE: 245
cugggagguc ag                                                         12

<210> SEQ ID NO 246
<211> LENGTH: 12
<212> TYPE: RNA
<213> ORGANISM: Artificial
<220> FEATURE:
<223> OTHER INFORMATION: RNAi Agent

<400> SEQUENCE: 246
cugaccuccc ag                                                         12

<210> SEQ ID NO 247
```

```
<211> LENGTH: 12
<212> TYPE: RNA
<213> ORGANISM: Artificial
<220> FEATURE:
<223> OTHER INFORMATION: RNAi Agent

<400> SEQUENCE: 247
ugggagguca gc                                                              12

<210> SEQ ID NO 248
<211> LENGTH: 12
<212> TYPE: RNA
<213> ORGANISM: Artificial
<220> FEATURE:
<223> OTHER INFORMATION: RNAi Agent

<400> SEQUENCE: 248
gcugaccucc ca                                                              12

<210> SEQ ID NO 249
<211> LENGTH: 12
<212> TYPE: RNA
<213> ORGANISM: Artificial
<220> FEATURE:
<223> OTHER INFORMATION: RNAi Agent

<400> SEQUENCE: 249
gggaggucag cg                                                              12

<210> SEQ ID NO 250
<211> LENGTH: 12
<212> TYPE: RNA
<213> ORGANISM: Artificial
<220> FEATURE:
<223> OTHER INFORMATION: RNAi Agent

<400> SEQUENCE: 250
cgcugaccuc cc                                                              12

<210> SEQ ID NO 251
<211> LENGTH: 12
<212> TYPE: RNA
<213> ORGANISM: Artificial
<220> FEATURE:
<223> OTHER INFORMATION: RNAi Agent

<400> SEQUENCE: 251
ggaggucagc gu                                                              12

<210> SEQ ID NO 252
<211> LENGTH: 12
<212> TYPE: RNA
<213> ORGANISM: Artificial
<220> FEATURE:
<223> OTHER INFORMATION: RNAi Agent

<400> SEQUENCE: 252
acgcugaccu cc                                                              12

<210> SEQ ID NO 253
<211> LENGTH: 12
<212> TYPE: RNA
<213> ORGANISM: Artificial
<220> FEATURE:
<223> OTHER INFORMATION: RNAi Agent

<400> SEQUENCE: 253
```
gaggucagcg uc                                                           12

<210> SEQ ID NO 254
<211> LENGTH: 12
<212> TYPE: RNA
<213> ORGANISM: Artificial
<220> FEATURE:
<223> OTHER INFORMATION: RNAi Agent

<400> SEQUENCE: 254
gacgcugacc uc                                                           12

<210> SEQ ID NO 255
<211> LENGTH: 12
<212> TYPE: RNA
<213> ORGANISM: Artificial
<220> FEATURE:
<223> OTHER INFORMATION: RNAi Agent

<400> SEQUENCE: 255
aggucagcgu cu                                                           12

<210> SEQ ID NO 256
<211> LENGTH: 12
<212> TYPE: RNA
<213> ORGANISM: Artificial
<220> FEATURE:
<223> OTHER INFORMATION: RNAi Agent

<400> SEQUENCE: 256
agacgcugac cu                                                           12

<210> SEQ ID NO 257
<211> LENGTH: 12
<212> TYPE: RNA
<213> ORGANISM: Artificial
<220> FEATURE:
<223> OTHER INFORMATION: RNAi Agent

<400> SEQUENCE: 257
cugcaggcca cc                                                           12

<210> SEQ ID NO 258
<211> LENGTH: 12
<212> TYPE: RNA
<213> ORGANISM: Artificial
<220> FEATURE:
<223> OTHER INFORMATION: RNAi Agent

<400> SEQUENCE: 258
gguggccugc ag                                                           12

<210> SEQ ID NO 259
<211> LENGTH: 12
<212> TYPE: RNA
<213> ORGANISM: Artificial
<220> FEATURE:
<223> OTHER INFORMATION: RNAi Agent

<400> SEQUENCE: 259
ugcaggccac ca                                                           12

<210> SEQ ID NO 260
<211> LENGTH: 12
<212> TYPE: RNA
<213> ORGANISM: Artificial
<220> FEATURE:

-continued

<223> OTHER INFORMATION: RNAi Agent

<400> SEQUENCE: 260
ugguggccug ca                                                          12

<210> SEQ ID NO 261
<211> LENGTH: 12
<212> TYPE: RNA
<213> ORGANISM: Artificial
<220> FEATURE:
<223> OTHER INFORMATION: RNAi Agent

<400> SEQUENCE: 261
gcaggccacc aa                                                          12

<210> SEQ ID NO 262
<211> LENGTH: 12
<212> TYPE: RNA
<213> ORGANISM: Artificial
<220> FEATURE:
<223> OTHER INFORMATION: RNAi Agent

<400> SEQUENCE: 262
uugguggccu gc                                                          12

<210> SEQ ID NO 263
<211> LENGTH: 12
<212> TYPE: RNA
<213> ORGANISM: Artificial
<220> FEATURE:
<223> OTHER INFORMATION: RNAi Agent

<400> SEQUENCE: 263
caggccacca ac                                                          12

<210> SEQ ID NO 264
<211> LENGTH: 12
<212> TYPE: RNA
<213> ORGANISM: Artificial
<220> FEATURE:
<223> OTHER INFORMATION: RNAi Agent

<400> SEQUENCE: 264
guugguggcc ug                                                          12

<210> SEQ ID NO 265
<211> LENGTH: 12
<212> TYPE: RNA
<213> ORGANISM: Artificial
<220> FEATURE:
<223> OTHER INFORMATION: RNAi Agent

<400> SEQUENCE: 265
aggccaccaa ca                                                          12

<210> SEQ ID NO 266
<211> LENGTH: 12
<212> TYPE: RNA
<213> ORGANISM: Artificial
<220> FEATURE:
<223> OTHER INFORMATION: RNAi Agent

<400> SEQUENCE: 266
uguugguggc cu                                                          12

<210> SEQ ID NO 267

```
<211> LENGTH: 12
<212> TYPE: RNA
<213> ORGANISM: Artificial
<220> FEATURE:
<223> OTHER INFORMATION: RNAi Agent

<400> SEQUENCE: 267
ggccaccaac au                                                          12

<210> SEQ ID NO 268
<211> LENGTH: 12
<212> TYPE: RNA
<213> ORGANISM: Artificial
<220> FEATURE:
<223> OTHER INFORMATION: RNAi Agent

<400> SEQUENCE: 268
auguuggugg cc                                                          12

<210> SEQ ID NO 269
<211> LENGTH: 12
<212> TYPE: RNA
<213> ORGANISM: Artificial
<220> FEATURE:
<223> OTHER INFORMATION: RNAi Agent

<400> SEQUENCE: 269
gccaccaaca uc                                                          12

<210> SEQ ID NO 270
<211> LENGTH: 12
<212> TYPE: RNA
<213> ORGANISM: Artificial
<220> FEATURE:
<223> OTHER INFORMATION: RNAi Agent

<400> SEQUENCE: 270
gauguuggug gc                                                          12

<210> SEQ ID NO 271
<211> LENGTH: 12
<212> TYPE: RNA
<213> ORGANISM: Artificial
<220> FEATURE:
<223> OTHER INFORMATION: RNAi Agent

<400> SEQUENCE: 271
ccaccaacau cu                                                          12

<210> SEQ ID NO 272
<211> LENGTH: 12
<212> TYPE: RNA
<213> ORGANISM: Artificial
<220> FEATURE:
<223> OTHER INFORMATION: RNAi Agent

<400> SEQUENCE: 272
agauguuggu gg                                                          12

<210> SEQ ID NO 273
<211> LENGTH: 12
<212> TYPE: RNA
<213> ORGANISM: Artificial
<220> FEATURE:
<223> OTHER INFORMATION: RNAi Agent

<400> SEQUENCE: 273
```

```
ggcaugacag ag                                                    12

<210> SEQ ID NO 274
<211> LENGTH: 12
<212> TYPE: RNA
<213> ORGANISM: Artificial
<220> FEATURE:
<223> OTHER INFORMATION: RNAi Agent

<400> SEQUENCE: 274
cucugucaug cc                                                    12

<210> SEQ ID NO 275
<211> LENGTH: 12
<212> TYPE: RNA
<213> ORGANISM: Artificial
<220> FEATURE:
<223> OTHER INFORMATION: RNAi Agent

<400> SEQUENCE: 275
gcaugacaga ga                                                    12

<210> SEQ ID NO 276
<211> LENGTH: 12
<212> TYPE: RNA
<213> ORGANISM: Artificial
<220> FEATURE:
<223> OTHER INFORMATION: RNAi Agent

<400> SEQUENCE: 276
ucucugucau gc                                                    12

<210> SEQ ID NO 277
<211> LENGTH: 12
<212> TYPE: RNA
<213> ORGANISM: Artificial
<220> FEATURE:
<223> OTHER INFORMATION: RNAi Agent

<400> SEQUENCE: 277
caugacagag aa                                                    12

<210> SEQ ID NO 278
<211> LENGTH: 12
<212> TYPE: RNA
<213> ORGANISM: Artificial
<220> FEATURE:
<223> OTHER INFORMATION: RNAi Agent

<400> SEQUENCE: 278
uucucuguca ug                                                    12

<210> SEQ ID NO 279
<211> LENGTH: 12
<212> TYPE: RNA
<213> ORGANISM: Artificial
<220> FEATURE:
<223> OTHER INFORMATION: RNAi Agent

<400> SEQUENCE: 279
augacagaga ag                                                    12

<210> SEQ ID NO 280
<211> LENGTH: 12
<212> TYPE: RNA
<213> ORGANISM: Artificial
<220> FEATURE:
```

```
<223> OTHER INFORMATION: RNAi Agent

<400> SEQUENCE: 280
cuucucuguc au                                                              12

<210> SEQ ID NO 281
<211> LENGTH: 12
<212> TYPE: RNA
<213> ORGANISM: Artificial
<220> FEATURE:
<223> OTHER INFORMATION: RNAi Agent

<400> SEQUENCE: 281
ugacagagaa gg                                                              12

<210> SEQ ID NO 282
<211> LENGTH: 12
<212> TYPE: RNA
<213> ORGANISM: Artificial
<220> FEATURE:
<223> OTHER INFORMATION: RNAi Agent

<400> SEQUENCE: 282
ccuucucugu ca                                                              12

<210> SEQ ID NO 283
<211> LENGTH: 12
<212> TYPE: RNA
<213> ORGANISM: Artificial
<220> FEATURE:
<223> OTHER INFORMATION: RNAi Agent

<400> SEQUENCE: 283
gacagagaag gc                                                              12

<210> SEQ ID NO 284
<211> LENGTH: 12
<212> TYPE: RNA
<213> ORGANISM: Artificial
<220> FEATURE:
<223> OTHER INFORMATION: RNAi Agent

<400> SEQUENCE: 284
gccuucucug uc                                                              12

<210> SEQ ID NO 285
<211> LENGTH: 12
<212> TYPE: RNA
<213> ORGANISM: Artificial
<220> FEATURE:
<223> OTHER INFORMATION: RNAi Agent

<400> SEQUENCE: 285
acagagaagg ca                                                              12

<210> SEQ ID NO 286
<211> LENGTH: 12
<212> TYPE: RNA
<213> ORGANISM: Artificial
<220> FEATURE:
<223> OTHER INFORMATION: RNAi Agent

<400> SEQUENCE: 286
ugccuucucu gu                                                              12

<210> SEQ ID NO 287
```

```
<211> LENGTH: 12
<212> TYPE: RNA
<213> ORGANISM: Artificial
<220> FEATURE:
<223> OTHER INFORMATION: RNAi Agent

<400> SEQUENCE: 287
cagagaaggc ac                                                          12

<210> SEQ ID NO 288
<211> LENGTH: 12
<212> TYPE: RNA
<213> ORGANISM: Artificial
<220> FEATURE:
<223> OTHER INFORMATION: RNAi Agent

<400> SEQUENCE: 288
gugccuucuc ug                                                          12

<210> SEQ ID NO 289
<211> LENGTH: 12
<212> TYPE: RNA
<213> ORGANISM: Artificial
<220> FEATURE:
<223> OTHER INFORMATION: RNAi Agent

<400> SEQUENCE: 289
agagaaggca cu                                                          12

<210> SEQ ID NO 290
<211> LENGTH: 12
<212> TYPE: RNA
<213> ORGANISM: Artificial
<220> FEATURE:
<223> OTHER INFORMATION: RNAi Agent

<400> SEQUENCE: 290
agugccuucu cu                                                          12

<210> SEQ ID NO 291
<211> LENGTH: 12
<212> TYPE: RNA
<213> ORGANISM: Artificial
<220> FEATURE:
<223> OTHER INFORMATION: RNAi Agent

<400> SEQUENCE: 291
gagaaggcac uu                                                          12

<210> SEQ ID NO 292
<211> LENGTH: 12
<212> TYPE: RNA
<213> ORGANISM: Artificial
<220> FEATURE:
<223> OTHER INFORMATION: RNAi Agent

<400> SEQUENCE: 292
aagugccuuc uc                                                          12

<210> SEQ ID NO 293
<211> LENGTH: 12
<212> TYPE: RNA
<213> ORGANISM: Artificial
<220> FEATURE:
<223> OTHER INFORMATION: RNAi Agent

<400> SEQUENCE: 293
```
agaaggcacu uc                                                            12

<210> SEQ ID NO 294
<211> LENGTH: 12
<212> TYPE: RNA
<213> ORGANISM: Artificial
<220> FEATURE:
<223> OTHER INFORMATION: RNAi Agent

<400> SEQUENCE: 294
gaagugccuu cu                                                            12

<210> SEQ ID NO 295
<211> LENGTH: 12
<212> TYPE: RNA
<213> ORGANISM: Artificial
<220> FEATURE:
<223> OTHER INFORMATION: RNAi Agent

<400> SEQUENCE: 295
gaaggcacuu cc                                                            12

<210> SEQ ID NO 296
<211> LENGTH: 12
<212> TYPE: RNA
<213> ORGANISM: Artificial
<220> FEATURE:
<223> OTHER INFORMATION: RNAi Agent

<400> SEQUENCE: 296
ggaagugccu uc                                                            12

<210> SEQ ID NO 297
<211> LENGTH: 12
<212> TYPE: RNA
<213> ORGANISM: Artificial
<220> FEATURE:
<223> OTHER INFORMATION: RNAi Agent

<400> SEQUENCE: 297
aaggcacuuc cu                                                            12

<210> SEQ ID NO 298
<211> LENGTH: 12
<212> TYPE: RNA
<213> ORGANISM: Artificial
<220> FEATURE:
<223> OTHER INFORMATION: RNAi Agent

<400> SEQUENCE: 298
aggaagugcc uu                                                            12

<210> SEQ ID NO 299
<211> LENGTH: 12
<212> TYPE: RNA
<213> ORGANISM: Artificial
<220> FEATURE:
<223> OTHER INFORMATION: RNAi Agent

<400> SEQUENCE: 299
aggcacuucc uu                                                            12

<210> SEQ ID NO 300
<211> LENGTH: 12
<212> TYPE: RNA
<213> ORGANISM: Artificial
<220> FEATURE:

```
<223> OTHER INFORMATION: RNAi Agent

<400> SEQUENCE: 300
aaggaagugc cu                                                          12

<210> SEQ ID NO 301
<211> LENGTH: 12
<212> TYPE: RNA
<213> ORGANISM: Artificial
<220> FEATURE:
<223> OTHER INFORMATION: RNAi Agent

<400> SEQUENCE: 301
cuacagugac ua                                                          12

<210> SEQ ID NO 302
<211> LENGTH: 12
<212> TYPE: RNA
<213> ORGANISM: Artificial
<220> FEATURE:
<223> OTHER INFORMATION: RNAi Agent

<400> SEQUENCE: 302
uagucacugu ag                                                          12

<210> SEQ ID NO 303
<211> LENGTH: 12
<212> TYPE: RNA
<213> ORGANISM: Artificial
<220> FEATURE:
<223> OTHER INFORMATION: RNAi Agent

<400> SEQUENCE: 303
uacagugacu ac                                                          12

<210> SEQ ID NO 304
<211> LENGTH: 12
<212> TYPE: RNA
<213> ORGANISM: Artificial
<220> FEATURE:
<223> OTHER INFORMATION: RNAi Agent

<400> SEQUENCE: 304
guagucacug ua                                                          12

<210> SEQ ID NO 305
<211> LENGTH: 12
<212> TYPE: RNA
<213> ORGANISM: Artificial
<220> FEATURE:
<223> OTHER INFORMATION: RNAi Agent

<400> SEQUENCE: 305
acagugacua ca                                                          12

<210> SEQ ID NO 306
<211> LENGTH: 12
<212> TYPE: RNA
<213> ORGANISM: Artificial
<220> FEATURE:
<223> OTHER INFORMATION: RNAi Agent

<400> SEQUENCE: 306
uguagucacu gu                                                          12

<210> SEQ ID NO 307
```

```
<211> LENGTH: 12
<212> TYPE: RNA
<213> ORGANISM: Artificial
<220> FEATURE:
<223> OTHER INFORMATION: RNAi Agent

<400> SEQUENCE: 307
cagugacuac aa                                                          12

<210> SEQ ID NO 308
<211> LENGTH: 12
<212> TYPE: RNA
<213> ORGANISM: Artificial
<220> FEATURE:
<223> OTHER INFORMATION: RNAi Agent

<400> SEQUENCE: 308
uuguagucac ug                                                          12

<210> SEQ ID NO 309
<211> LENGTH: 12
<212> TYPE: RNA
<213> ORGANISM: Artificial
<220> FEATURE:
<223> OTHER INFORMATION: RNAi Agent

<400> SEQUENCE: 309
agugacuaca ac                                                          12

<210> SEQ ID NO 310
<211> LENGTH: 12
<212> TYPE: RNA
<213> ORGANISM: Artificial
<220> FEATURE:
<223> OTHER INFORMATION: RNAi Agent

<400> SEQUENCE: 310
guuguaguca cu                                                          12

<210> SEQ ID NO 311
<211> LENGTH: 12
<212> TYPE: RNA
<213> ORGANISM: Artificial
<220> FEATURE:
<223> OTHER INFORMATION: RNAi Agent

<400> SEQUENCE: 311
gugacuacaa ca                                                          12

<210> SEQ ID NO 312
<211> LENGTH: 12
<212> TYPE: RNA
<213> ORGANISM: Artificial
<220> FEATURE:
<223> OTHER INFORMATION: RNAi Agent

<400> SEQUENCE: 312
uguuguaguc ac                                                          12

<210> SEQ ID NO 313
<211> LENGTH: 12
<212> TYPE: RNA
<213> ORGANISM: Artificial
<220> FEATURE:
<223> OTHER INFORMATION: RNAi Agent

<400> SEQUENCE: 313
```
ugacuacaac ac 12

<210> SEQ ID NO 314
<211> LENGTH: 12
<212> TYPE: RNA
<213> ORGANISM: Artificial
<220> FEATURE:
<223> OTHER INFORMATION: RNAi Agent

<400> SEQUENCE: 314
guguuguagu ca 12

<210> SEQ ID NO 315
<211> LENGTH: 12
<212> TYPE: RNA
<213> ORGANISM: Artificial
<220> FEATURE:
<223> OTHER INFORMATION: RNAi Agent

<400> SEQUENCE: 315
gacuacaaca cg 12

<210> SEQ ID NO 316
<211> LENGTH: 12
<212> TYPE: RNA
<213> ORGANISM: Artificial
<220> FEATURE:
<223> OTHER INFORMATION: RNAi Agent

<400> SEQUENCE: 316
cguguuguag uc 12

<210> SEQ ID NO 317
<211> LENGTH: 12
<212> TYPE: RNA
<213> ORGANISM: Artificial
<220> FEATURE:
<223> OTHER INFORMATION: RNAi Agent

<400> SEQUENCE: 317
acuacaacac ga 12

<210> SEQ ID NO 318
<211> LENGTH: 12
<212> TYPE: RNA
<213> ORGANISM: Artificial
<220> FEATURE:
<223> OTHER INFORMATION: RNAi Agent

<400> SEQUENCE: 318
ucguguugua gu 12

<210> SEQ ID NO 319
<211> LENGTH: 12
<212> TYPE: RNA
<213> ORGANISM: Artificial
<220> FEATURE:
<223> OTHER INFORMATION: RNAi Agent

<400> SEQUENCE: 319
cuacaacacg ac 12

<210> SEQ ID NO 320
<211> LENGTH: 12
<212> TYPE: RNA
<213> ORGANISM: Artificial
<220> FEATURE:

-continued

```
<223> OTHER INFORMATION: RNAi Agent

<400> SEQUENCE: 320
gucguguugu ag                                                              12

<210> SEQ ID NO 321
<211> LENGTH: 12
<212> TYPE: RNA
<213> ORGANISM: Artificial
<220> FEATURE:
<223> OTHER INFORMATION: RNAi Agent

<400> SEQUENCE: 321
uacaacacga cc                                                              12

<210> SEQ ID NO 322
<211> LENGTH: 12
<212> TYPE: RNA
<213> ORGANISM: Artificial
<220> FEATURE:
<223> OTHER INFORMATION: RNAi Agent

<400> SEQUENCE: 322
ggucguguug ua                                                              12

<210> SEQ ID NO 323
<211> LENGTH: 12
<212> TYPE: RNA
<213> ORGANISM: Artificial
<220> FEATURE:
<223> OTHER INFORMATION: RNAi Agent

<400> SEQUENCE: 323
acaacacgac cu                                                              12

<210> SEQ ID NO 324
<211> LENGTH: 12
<212> TYPE: RNA
<213> ORGANISM: Artificial
<220> FEATURE:
<223> OTHER INFORMATION: RNAi Agent

<400> SEQUENCE: 324
aggucguguu gu                                                              12

<210> SEQ ID NO 325
<211> LENGTH: 12
<212> TYPE: RNA
<213> ORGANISM: Artificial
<220> FEATURE:
<223> OTHER INFORMATION: RNAi Agent

<400> SEQUENCE: 325
ggagaaauac ug                                                              12

<210> SEQ ID NO 326
<211> LENGTH: 12
<212> TYPE: RNA
<213> ORGANISM: Artificial
<220> FEATURE:
<223> OTHER INFORMATION: RNAi Agent

<400> SEQUENCE: 326
caguauuucu cc                                                              12

<210> SEQ ID NO 327
```

```
<211> LENGTH: 12
<212> TYPE: RNA
<213> ORGANISM: Artificial
<220> FEATURE:
<223> OTHER INFORMATION: RNAi Agent

<400> SEQUENCE: 327
gagaaauacu gc                                                          12

<210> SEQ ID NO 328
<211> LENGTH: 12
<212> TYPE: RNA
<213> ORGANISM: Artificial
<220> FEATURE:
<223> OTHER INFORMATION: RNAi Agent

<400> SEQUENCE: 328
gcaguauuuc uc                                                          12

<210> SEQ ID NO 329
<211> LENGTH: 12
<212> TYPE: RNA
<213> ORGANISM: Artificial
<220> FEATURE:
<223> OTHER INFORMATION: RNAi Agent

<400> SEQUENCE: 329
agaaauacug ca                                                          12

<210> SEQ ID NO 330
<211> LENGTH: 12
<212> TYPE: RNA
<213> ORGANISM: Artificial
<220> FEATURE:
<223> OTHER INFORMATION: RNAi Agent

<400> SEQUENCE: 330
ugcaguauuu cu                                                          12

<210> SEQ ID NO 331
<211> LENGTH: 12
<212> TYPE: RNA
<213> ORGANISM: Artificial
<220> FEATURE:
<223> OTHER INFORMATION: RNAi Agent

<400> SEQUENCE: 331
gaaauacugc aa                                                          12

<210> SEQ ID NO 332
<211> LENGTH: 12
<212> TYPE: RNA
<213> ORGANISM: Artificial
<220> FEATURE:
<223> OTHER INFORMATION: RNAi Agent

<400> SEQUENCE: 332
uugcaguauu uc                                                          12

<210> SEQ ID NO 333
<211> LENGTH: 12
<212> TYPE: RNA
<213> ORGANISM: Artificial
<220> FEATURE:
<223> OTHER INFORMATION: RNAi Agent

<400> SEQUENCE: 333
```
aaauacugca ac                                                             12

<210> SEQ ID NO 334
<211> LENGTH: 12
<212> TYPE: RNA
<213> ORGANISM: Artificial
<220> FEATURE:
<223> OTHER INFORMATION: RNAi Agent

<400> SEQUENCE: 334
guugcaguau uu                                                             12

<210> SEQ ID NO 335
<211> LENGTH: 12
<212> TYPE: RNA
<213> ORGANISM: Artificial
<220> FEATURE:
<223> OTHER INFORMATION: RNAi Agent

<400> SEQUENCE: 335
aauacugcaa ca                                                             12

<210> SEQ ID NO 336
<211> LENGTH: 12
<212> TYPE: RNA
<213> ORGANISM: Artificial
<220> FEATURE:
<223> OTHER INFORMATION: RNAi Agent

<400> SEQUENCE: 336
uguugcagua uu                                                             12

<210> SEQ ID NO 337
<211> LENGTH: 12
<212> TYPE: RNA
<213> ORGANISM: Artificial
<220> FEATURE:
<223> OTHER INFORMATION: RNAi Agent

<400> SEQUENCE: 337
auacugcaac aa                                                             12

<210> SEQ ID NO 338
<211> LENGTH: 12
<212> TYPE: RNA
<213> ORGANISM: Artificial
<220> FEATURE:
<223> OTHER INFORMATION: RNAi Agent

<400> SEQUENCE: 338
uuguugcagu au                                                             12

<210> SEQ ID NO 339
<211> LENGTH: 12
<212> TYPE: RNA
<213> ORGANISM: Artificial
<220> FEATURE:
<223> OTHER INFORMATION: RNAi Agent

<400> SEQUENCE: 339
ucuccauggc ug                                                             12

<210> SEQ ID NO 340
<211> LENGTH: 12
<212> TYPE: RNA
<213> ORGANISM: Artificial
<220> FEATURE:

```
<223> OTHER INFORMATION: RNAi Agent

<400> SEQUENCE: 340
cagccaugga ga                                                            12

<210> SEQ ID NO 341
<211> LENGTH: 12
<212> TYPE: RNA
<213> ORGANISM: Artificial
<220> FEATURE:
<223> OTHER INFORMATION: RNAi Agent

<400> SEQUENCE: 341
cuccauggcu ga                                                            12

<210> SEQ ID NO 342
<211> LENGTH: 12
<212> TYPE: RNA
<213> ORGANISM: Artificial
<220> FEATURE:
<223> OTHER INFORMATION: RNAi Agent

<400> SEQUENCE: 342
ucagccaugg ag                                                            12

<210> SEQ ID NO 343
<211> LENGTH: 12
<212> TYPE: RNA
<213> ORGANISM: Artificial
<220> FEATURE:
<223> OTHER INFORMATION: RNAi Agent

<400> SEQUENCE: 343
uccauggcug ac                                                            12

<210> SEQ ID NO 344
<211> LENGTH: 12
<212> TYPE: RNA
<213> ORGANISM: Artificial
<220> FEATURE:
<223> OTHER INFORMATION: RNAi Agent

<400> SEQUENCE: 344
gucagccaug ga                                                            12

<210> SEQ ID NO 345
<211> LENGTH: 12
<212> TYPE: RNA
<213> ORGANISM: Artificial
<220> FEATURE:
<223> OTHER INFORMATION: RNAi Agent

<400> SEQUENCE: 345
ccauggcuga cu                                                            12

<210> SEQ ID NO 346
<211> LENGTH: 12
<212> TYPE: RNA
<213> ORGANISM: Artificial
<220> FEATURE:
<223> OTHER INFORMATION: RNAi Agent

<400> SEQUENCE: 346
agucagccau gg                                                            12

<210> SEQ ID NO 347
```

```
<211> LENGTH: 12
<212> TYPE: RNA
<213> ORGANISM: Artificial
<220> FEATURE:
<223> OTHER INFORMATION: RNAi Agent

<400> SEQUENCE: 347
cauggcugac ug                                                             12

<210> SEQ ID NO 348
<211> LENGTH: 12
<212> TYPE: RNA
<213> ORGANISM: Artificial
<220> FEATURE:
<223> OTHER INFORMATION: RNAi Agent

<400> SEQUENCE: 348
cagucagcca ug                                                             12

<210> SEQ ID NO 349
<211> LENGTH: 12
<212> TYPE: RNA
<213> ORGANISM: Artificial
<220> FEATURE:
<223> OTHER INFORMATION: RNAi Agent

<400> SEQUENCE: 349
auggcugacu gg                                                             12

<210> SEQ ID NO 350
<211> LENGTH: 12
<212> TYPE: RNA
<213> ORGANISM: Artificial
<220> FEATURE:
<223> OTHER INFORMATION: RNAi Agent

<400> SEQUENCE: 350
ccagucagcc au                                                             12

<210> SEQ ID NO 351
<211> LENGTH: 12
<212> TYPE: RNA
<213> ORGANISM: Artificial
<220> FEATURE:
<223> OTHER INFORMATION: RNAi Agent

<400> SEQUENCE: 351
uggcugacug gc                                                             12

<210> SEQ ID NO 352
<211> LENGTH: 12
<212> TYPE: RNA
<213> ORGANISM: Artificial
<220> FEATURE:
<223> OTHER INFORMATION: RNAi Agent

<400> SEQUENCE: 352
gccagucagc ca                                                             12

<210> SEQ ID NO 353
<211> LENGTH: 12
<212> TYPE: RNA
<213> ORGANISM: Artificial
<220> FEATURE:
<223> OTHER INFORMATION: RNAi Agent

<400> SEQUENCE: 353
```

| | |
|---|---|
| auaucacccu ga | 12 |

<210> SEQ ID NO 354
<211> LENGTH: 12
<212> TYPE: RNA
<213> ORGANISM: Artificial
<220> FEATURE:
<223> OTHER INFORMATION: RNAi Agent

<400> SEQUENCE: 354

| | |
|---|---|
| ucagggugau au | 12 |

<210> SEQ ID NO 355
<211> LENGTH: 12
<212> TYPE: RNA
<213> ORGANISM: Artificial
<220> FEATURE:
<223> OTHER INFORMATION: RNAi Agent

<400> SEQUENCE: 355

| | |
|---|---|
| uaucacccug ag | 12 |

<210> SEQ ID NO 356
<211> LENGTH: 12
<212> TYPE: RNA
<213> ORGANISM: Artificial
<220> FEATURE:
<223> OTHER INFORMATION: RNAi Agent

<400> SEQUENCE: 356

| | |
|---|---|
| cucaggguga ua | 12 |

<210> SEQ ID NO 357
<211> LENGTH: 12
<212> TYPE: RNA
<213> ORGANISM: Artificial
<220> FEATURE:
<223> OTHER INFORMATION: RNAi Agent

<400> SEQUENCE: 357

| | |
|---|---|
| aucacccuga gc | 12 |

<210> SEQ ID NO 358
<211> LENGTH: 12
<212> TYPE: RNA
<213> ORGANISM: Artificial
<220> FEATURE:
<223> OTHER INFORMATION: RNAi Agent

<400> SEQUENCE: 358

| | |
|---|---|
| gcucagggug au | 12 |

<210> SEQ ID NO 359
<211> LENGTH: 12
<212> TYPE: RNA
<213> ORGANISM: Artificial
<220> FEATURE:
<223> OTHER INFORMATION: RNAi Agent

<400> SEQUENCE: 359

| | |
|---|---|
| ucacccugag ca | 12 |

<210> SEQ ID NO 360
<211> LENGTH: 12
<212> TYPE: RNA
<213> ORGANISM: Artificial
<220> FEATURE:

-continued

<223> OTHER INFORMATION: RNAi Agent

<400> SEQUENCE: 360
ugcucagggu ga                                                              12

<210> SEQ ID NO 361
<211> LENGTH: 12
<212> TYPE: RNA
<213> ORGANISM: Artificial
<220> FEATURE:
<223> OTHER INFORMATION: RNAi Agent

<400> SEQUENCE: 361
cacccugagc ag                                                              12

<210> SEQ ID NO 362
<211> LENGTH: 12
<212> TYPE: RNA
<213> ORGANISM: Artificial
<220> FEATURE:
<223> OTHER INFORMATION: RNAi Agent

<400> SEQUENCE: 362
cugcucaggg ug                                                              12

<210> SEQ ID NO 363
<211> LENGTH: 12
<212> TYPE: RNA
<213> ORGANISM: Artificial
<220> FEATURE:
<223> OTHER INFORMATION: RNAi Agent

<400> SEQUENCE: 363
acccugagca gg                                                              12

<210> SEQ ID NO 364
<211> LENGTH: 12
<212> TYPE: RNA
<213> ORGANISM: Artificial
<220> FEATURE:
<223> OTHER INFORMATION: RNAi Agent

<400> SEQUENCE: 364
ccugcucagg gu                                                              12

<210> SEQ ID NO 365
<211> LENGTH: 12
<212> TYPE: RNA
<213> ORGANISM: Artificial
<220> FEATURE:
<223> OTHER INFORMATION: RNAi Agent

<400> SEQUENCE: 365
cccugagcag ga                                                              12

<210> SEQ ID NO 366
<211> LENGTH: 12
<212> TYPE: RNA
<213> ORGANISM: Artificial
<220> FEATURE:
<223> OTHER INFORMATION: RNAi Agent

<400> SEQUENCE: 366
uccugcucag gg                                                              12

<210> SEQ ID NO 367

```
<211> LENGTH: 12
<212> TYPE: RNA
<213> ORGANISM: Artificial
<220> FEATURE:
<223> OTHER INFORMATION: RNAi Agent

<400> SEQUENCE: 367
ccugagcagg aa                                                           12

<210> SEQ ID NO 368
<211> LENGTH: 12
<212> TYPE: RNA
<213> ORGANISM: Artificial
<220> FEATURE:
<223> OTHER INFORMATION: RNAi Agent

<400> SEQUENCE: 368
uuccugcuca gg                                                           12

<210> SEQ ID NO 369
<211> LENGTH: 12
<212> TYPE: RNA
<213> ORGANISM: Artificial
<220> FEATURE:
<223> OTHER INFORMATION: RNAi Agent

<400> SEQUENCE: 369
cugagcagga ag                                                           12

<210> SEQ ID NO 370
<211> LENGTH: 12
<212> TYPE: RNA
<213> ORGANISM: Artificial
<220> FEATURE:
<223> OTHER INFORMATION: RNAi Agent

<400> SEQUENCE: 370
cuuccugcuc ag                                                           12

<210> SEQ ID NO 371
<211> LENGTH: 12
<212> TYPE: RNA
<213> ORGANISM: Artificial
<220> FEATURE:
<223> OTHER INFORMATION: RNAi Agent

<400> SEQUENCE: 371
ugagcaggaa gg                                                           12

<210> SEQ ID NO 372
<211> LENGTH: 12
<212> TYPE: RNA
<213> ORGANISM: Artificial
<220> FEATURE:
<223> OTHER INFORMATION: RNAi Agent

<400> SEQUENCE: 372
ccuuccugcu ca                                                           12

<210> SEQ ID NO 373
<211> LENGTH: 12
<212> TYPE: RNA
<213> ORGANISM: Artificial
<220> FEATURE:
<223> OTHER INFORMATION: RNAi Agent

<400> SEQUENCE: 373
```
uggguggcca gu                                           12

<210> SEQ ID NO 374
<211> LENGTH: 12
<212> TYPE: RNA
<213> ORGANISM: Artificial
<220> FEATURE:
<223> OTHER INFORMATION: RNAi Agent

<400> SEQUENCE: 374
acuggccacc ca                                           12

<210> SEQ ID NO 375
<211> LENGTH: 12
<212> TYPE: RNA
<213> ORGANISM: Artificial
<220> FEATURE:
<223> OTHER INFORMATION: RNAi Agent

<400> SEQUENCE: 375 gggguggccag uu                                          12

<210> SEQ ID NO 376
<211> LENGTH: 12
<212> TYPE: RNA
<213> ORGANISM: Artificial
<220> FEATURE:
<223> OTHER INFORMATION: RNAi Agent

<400> SEQUENCE: 376
aacuggccac cc                                           12

<210> SEQ ID NO 377
<211> LENGTH: 12
<212> TYPE: RNA
<213> ORGANISM: Artificial
<220> FEATURE:
<223> OTHER INFORMATION: RNAi Agent

<400> SEQUENCE: 377
gguggccagu uu                                           12

<210> SEQ ID NO 378
<211> LENGTH: 12
<212> TYPE: RNA
<213> ORGANISM: Artificial
<220> FEATURE:
<223> OTHER INFORMATION: RNAi Agent

<400> SEQUENCE: 378
aaacuggcca cc                                           12

<210> SEQ ID NO 379
<211> LENGTH: 12
<212> TYPE: RNA
<213> ORGANISM: Artificial
<220> FEATURE:
<223> OTHER INFORMATION: RNAi Agent

<400> SEQUENCE: 379
guggccaguu ug                                           12

<210> SEQ ID NO 380
<211> LENGTH: 12
<212> TYPE: RNA
<213> ORGANISM: Artificial
<220> FEATURE:

<223> OTHER INFORMATION: RNAi Agent

<400> SEQUENCE: 380
caaacuggcc ac                                                              12

<210> SEQ ID NO 381
<211> LENGTH: 12
<212> TYPE: RNA
<213> ORGANISM: Artificial
<220> FEATURE:
<223> OTHER INFORMATION: RNAi Agent

<400> SEQUENCE: 381
uggccaguuu gg                                                              12

<210> SEQ ID NO 382
<211> LENGTH: 12
<212> TYPE: RNA
<213> ORGANISM: Artificial
<220> FEATURE:
<223> OTHER INFORMATION: RNAi Agent

<400> SEQUENCE: 382
ccaaacuggc ca                                                              12

<210> SEQ ID NO 383
<211> LENGTH: 12
<212> TYPE: RNA
<213> ORGANISM: Artificial
<220> FEATURE:
<223> OTHER INFORMATION: RNAi Agent

<400> SEQUENCE: 383
ggccaguuug gc                                                              12

<210> SEQ ID NO 384
<211> LENGTH: 12
<212> TYPE: RNA
<213> ORGANISM: Artificial
<220> FEATURE:
<223> OTHER INFORMATION: RNAi Agent

<400> SEQUENCE: 384
gccaaacugg cc                                                              12

<210> SEQ ID NO 385
<211> LENGTH: 12
<212> TYPE: RNA
<213> ORGANISM: Artificial
<220> FEATURE:
<223> OTHER INFORMATION: RNAi Agent

<400> SEQUENCE: 385
gccaguuugg cu                                                              12

<210> SEQ ID NO 386
<211> LENGTH: 12
<212> TYPE: RNA
<213> ORGANISM: Artificial
<220> FEATURE:
<223> OTHER INFORMATION: RNAi Agent

<400> SEQUENCE: 386
agccaaacug gc                                                              12

<210> SEQ ID NO 387

```
<211> LENGTH: 12
<212> TYPE: RNA
<213> ORGANISM: Artificial
<220> FEATURE:
<223> OTHER INFORMATION: RNAi Agent

<400> SEQUENCE: 387
ccaguuuggc uu                                                           12

<210> SEQ ID NO 388
<211> LENGTH: 12
<212> TYPE: RNA
<213> ORGANISM: Artificial
<220> FEATURE:
<223> OTHER INFORMATION: RNAi Agent

<400> SEQUENCE: 388
aagccaaacu gg                                                           12

<210> SEQ ID NO 389
<211> LENGTH: 12
<212> TYPE: RNA
<213> ORGANISM: Artificial
<220> FEATURE:
<223> OTHER INFORMATION: RNAi Agent

<400> SEQUENCE: 389
caguuuggcu uc                                                           12

<210> SEQ ID NO 390
<211> LENGTH: 12
<212> TYPE: RNA
<213> ORGANISM: Artificial
<220> FEATURE:
<223> OTHER INFORMATION: RNAi Agent

<400> SEQUENCE: 390
gaagccaaac ug                                                           12

<210> SEQ ID NO 391
<211> LENGTH: 12
<212> TYPE: RNA
<213> ORGANISM: Artificial
<220> FEATURE:
<223> OTHER INFORMATION: RNAi Agent

<400> SEQUENCE: 391
aguuuggcuu cu                                                           12

<210> SEQ ID NO 392
<211> LENGTH: 12
<212> TYPE: RNA
<213> ORGANISM: Artificial
<220> FEATURE:
<223> OTHER INFORMATION: RNAi Agent

<400> SEQUENCE: 392
agaagccaaa cu                                                           12

<210> SEQ ID NO 393
<211> LENGTH: 12
<212> TYPE: RNA
<213> ORGANISM: Artificial
<220> FEATURE:
<223> OTHER INFORMATION: RNAi Agent

<400> SEQUENCE: 393
```
guuuggcuuc ug                                                       12

<210> SEQ ID NO 394
<211> LENGTH: 12
<212> TYPE: RNA
<213> ORGANISM: Artificial
<220> FEATURE:
<223> OTHER INFORMATION: RNAi Agent

<400> SEQUENCE: 394
cagaagccaa ac                                                       12

<210> SEQ ID NO 395
<211> LENGTH: 12
<212> TYPE: RNA
<213> ORGANISM: Artificial
<220> FEATURE:
<223> OTHER INFORMATION: RNAi Agent

<400> SEQUENCE: 395
uuuggcuucu gg                                                       12

<210> SEQ ID NO 396
<211> LENGTH: 12
<212> TYPE: RNA
<213> ORGANISM: Artificial
<220> FEATURE:
<223> OTHER INFORMATION: RNAi Agent

<400> SEQUENCE: 396
ccagaagcca aa                                                       12

<210> SEQ ID NO 397
<211> LENGTH: 12
<212> TYPE: RNA
<213> ORGANISM: Artificial
<220> FEATURE:
<223> OTHER INFORMATION: RNAi Agent

<400> SEQUENCE: 397
uuggcuucug ga                                                       12

<210> SEQ ID NO 398
<211> LENGTH: 12
<212> TYPE: RNA
<213> ORGANISM: Artificial
<220> FEATURE:
<223> OTHER INFORMATION: RNAi Agent

<400> SEQUENCE: 398
uccagaagcc aa                                                       12

<210> SEQ ID NO 399
<211> LENGTH: 12
<212> TYPE: RNA
<213> ORGANISM: Artificial
<220> FEATURE:
<223> OTHER INFORMATION: RNAi Agent

<400> SEQUENCE: 399
uggcuucugg au                                                       12

<210> SEQ ID NO 400
<211> LENGTH: 12
<212> TYPE: RNA
<213> ORGANISM: Artificial
<220> FEATURE:

```
<223> OTHER INFORMATION: RNAi Agent

<400> SEQUENCE: 400
auccagaagc ca                                                        12

<210> SEQ ID NO 401
<211> LENGTH: 12
<212> TYPE: RNA
<213> ORGANISM: Artificial
<220> FEATURE:
<223> OTHER INFORMATION: RNAi Agent

<400> SEQUENCE: 401
ggcuucugga ug                                                        12

<210> SEQ ID NO 402
<211> LENGTH: 12
<212> TYPE: RNA
<213> ORGANISM: Artificial
<220> FEATURE:
<223> OTHER INFORMATION: RNAi Agent

<400> SEQUENCE: 402
cauccagaag cc                                                        12

<210> SEQ ID NO 403
<211> LENGTH: 12
<212> TYPE: RNA
<213> ORGANISM: Artificial
<220> FEATURE:
<223> OTHER INFORMATION: RNAi Agent

<400> SEQUENCE: 403
gcuucuggau gg                                                        12

<210> SEQ ID NO 404
<211> LENGTH: 12
<212> TYPE: RNA
<213> ORGANISM: Artificial
<220> FEATURE:
<223> OTHER INFORMATION: RNAi Agent

<400> SEQUENCE: 404
ccauccagaa gc                                                        12

<210> SEQ ID NO 405
<211> LENGTH: 12
<212> TYPE: RNA
<213> ORGANISM: Artificial
<220> FEATURE:
<223> OTHER INFORMATION: RNAi Agent

<400> SEQUENCE: 405
agcuggugga gg                                                        12

<210> SEQ ID NO 406
<211> LENGTH: 12
<212> TYPE: RNA
<213> ORGANISM: Artificial
<220> FEATURE:
<223> OTHER INFORMATION: RNAi Agent

<400> SEQUENCE: 406
ccuccaccag cu                                                        12

<210> SEQ ID NO 407
```

```
<211> LENGTH: 12
<212> TYPE: RNA
<213> ORGANISM: Artificial
<220> FEATURE:
<223> OTHER INFORMATION: RNAi Agent

<400> SEQUENCE: 407
gcugguggag gc                                                            12

<210> SEQ ID NO 408
<211> LENGTH: 12
<212> TYPE: RNA
<213> ORGANISM: Artificial
<220> FEATURE:
<223> OTHER INFORMATION: RNAi Agent

<400> SEQUENCE: 408
gccuccacca gc                                                            12

<210> SEQ ID NO 409
<211> LENGTH: 12
<212> TYPE: RNA
<213> ORGANISM: Artificial
<220> FEATURE:
<223> OTHER INFORMATION: RNAi Agent

<400> SEQUENCE: 409
cugguggagg cc                                                            12

<210> SEQ ID NO 410
<211> LENGTH: 12
<212> TYPE: RNA
<213> ORGANISM: Artificial
<220> FEATURE:
<223> OTHER INFORMATION: RNAi Agent

<400> SEQUENCE: 410
ggccuccacc ag                                                            12

<210> SEQ ID NO 411
<211> LENGTH: 12
<212> TYPE: RNA
<213> ORGANISM: Artificial
<220> FEATURE:
<223> OTHER INFORMATION: RNAi Agent

<400> SEQUENCE: 411
ugguggaggc cc                                                            12

<210> SEQ ID NO 412
<211> LENGTH: 12
<212> TYPE: RNA
<213> ORGANISM: Artificial
<220> FEATURE:
<223> OTHER INFORMATION: RNAi Agent

<400> SEQUENCE: 412
gggccuccac ca                                                            12

<210> SEQ ID NO 413
<211> LENGTH: 12
<212> TYPE: RNA
<213> ORGANISM: Artificial
<220> FEATURE:
<223> OTHER INFORMATION: RNAi Agent

<400> SEQUENCE: 413
```
gguggaggcc ca                                                      12

<210> SEQ ID NO 414
<211> LENGTH: 12
<212> TYPE: RNA
<213> ORGANISM: Artificial
<220> FEATURE:
<223> OTHER INFORMATION: RNAi Agent

<400> SEQUENCE: 414
ugggccucca cc                                                      12

<210> SEQ ID NO 415
<211> LENGTH: 12
<212> TYPE: RNA
<213> ORGANISM: Artificial
<220> FEATURE:
<223> OTHER INFORMATION: RNAi Agent

<400> SEQUENCE: 415
guggaggccc ac                                                      12

<210> SEQ ID NO 416
<211> LENGTH: 12
<212> TYPE: RNA
<213> ORGANISM: Artificial
<220> FEATURE:
<223> OTHER INFORMATION: RNAi Agent

<400> SEQUENCE: 416
gugggccucc ac                                                      12

<210> SEQ ID NO 417
<211> LENGTH: 12
<212> TYPE: RNA
<213> ORGANISM: Artificial
<220> FEATURE:
<223> OTHER INFORMATION: RNAi Agent

<400> SEQUENCE: 417
uggaggccca ca                                                      12

<210> SEQ ID NO 418
<211> LENGTH: 12
<212> TYPE: RNA
<213> ORGANISM: Artificial
<220> FEATURE:
<223> OTHER INFORMATION: RNAi Agent

<400> SEQUENCE: 418
ugugggccuc ca                                                      12

<210> SEQ ID NO 419
<211> LENGTH: 12
<212> TYPE: RNA
<213> ORGANISM: Artificial
<220> FEATURE:
<223> OTHER INFORMATION: RNAi Agent

<400> SEQUENCE: 419
ggaggcccac ac                                                      12

<210> SEQ ID NO 420
<211> LENGTH: 12
<212> TYPE: RNA
<213> ORGANISM: Artificial
<220> FEATURE:

```
<223> OTHER INFORMATION: RNAi Agent

<400> SEQUENCE: 420 guguggccu cc                                                         12

<210> SEQ ID NO 421
<211> LENGTH: 12
<212> TYPE: RNA
<213> ORGANISM: Artificial
<220> FEATURE:
<223> OTHER INFORMATION: RNAi Agent

<400> SEQUENCE: 421
gaggcccaca cc                                                        12

<210> SEQ ID NO 422
<211> LENGTH: 12
<212> TYPE: RNA
<213> ORGANISM: Artificial
<220> FEATURE:
<223> OTHER INFORMATION: RNAi Agent

<400> SEQUENCE: 422
ggugugggcc uc                                                        12

<210> SEQ ID NO 423
<211> LENGTH: 12
<212> TYPE: RNA
<213> ORGANISM: Artificial
<220> FEATURE:
<223> OTHER INFORMATION: RNAi Agent

<400> SEQUENCE: 423
aggcccacac ca                                                        12

<210> SEQ ID NO 424
<211> LENGTH: 12
<212> TYPE: RNA
<213> ORGANISM: Artificial
<220> FEATURE:
<223> OTHER INFORMATION: RNAi Agent

<400> SEQUENCE: 424 ugguguggc cu                                                         12

<210> SEQ ID NO 425
<211> LENGTH: 12
<212> TYPE: RNA
<213> ORGANISM: Artificial
<220> FEATURE:
<223> OTHER INFORMATION: RNAi Agent

<400> SEQUENCE: 425
ggcccacacc aa                                                        12

<210> SEQ ID NO 426
<211> LENGTH: 12
<212> TYPE: RNA
<213> ORGANISM: Artificial
<220> FEATURE:
<223> OTHER INFORMATION: RNAi Agent

<400> SEQUENCE: 426 uuggguggg cc                                                         12

<210> SEQ ID NO 427
```

```
<211> LENGTH: 12
<212> TYPE: RNA
<213> ORGANISM: Artificial
<220> FEATURE:
<223> OTHER INFORMATION: RNAi Agent

<400> SEQUENCE: 427
gcccacacca ac                                                          12

<210> SEQ ID NO 428
<211> LENGTH: 12
<212> TYPE: RNA
<213> ORGANISM: Artificial
<220> FEATURE:
<223> OTHER INFORMATION: RNAi Agent

<400> SEQUENCE: 428
guuggugugg gc                                                          12

<210> SEQ ID NO 429
<211> LENGTH: 19
<212> TYPE: RNA
<213> ORGANISM: Artificial
<220> FEATURE:
<223> OTHER INFORMATION: RNAi Agent

<400> SEQUENCE: 429
cagugacuac aacacgacc                                                   19

<210> SEQ ID NO 430
<211> LENGTH: 19
<212> TYPE: RNA
<213> ORGANISM: Artificial
<220> FEATURE:
<223> OTHER INFORMATION: RNAi Agent

<400> SEQUENCE: 430
ggucguguug uagucacug                                                   19
```